US010745759B2

(12) United States Patent
Carroll et al.

(10) Patent No.: US 10,745,759 B2
(45) Date of Patent: Aug. 18, 2020

(54) METHODS AND COMPOSITIONS FOR THE PROGNOSIS AND TREATMENT OF RELAPSED LEUKEMIA

(71) Applicant: New York University, New York, NY (US)

(72) Inventors: William L. Carroll, Irvington, NY (US); Julia A. Meyer, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/399,467

(22) PCT Filed: May 7, 2013

(86) PCT No.: PCT/US2013/039942
§ 371 (c)(1),
(2) Date: Nov. 6, 2014

(87) PCT Pub. No.: WO2013/169771
PCT Pub. Date: Nov. 14, 2013

(65) Prior Publication Data

US 2015/0148307 A1 May 28, 2015

Related U.S. Application Data

(60) Provisional application No. 61/643,489, filed on May 7, 2012.

(51) Int. Cl.

| | |
|---|---|
| ***C12Q 1/68*** | (2018.01) |
| ***C12Q 1/6886*** | (2018.01) |
| ***A61K 31/52*** | (2006.01) |
| ***A61K 31/573*** | (2006.01) |
| ***A61K 31/704*** | (2006.01) |
| ***A61K 31/7068*** | (2006.01) |
| ***A61K 45/06*** | (2006.01) |

(52) U.S. Cl.
CPC ............ *C12Q 1/6886* (2013.01); *A61K 31/52* (2013.01); *A61K 31/573* (2013.01); *A61K 31/704* (2013.01); *A61K 31/7068* (2013.01); *A61K 45/06* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2003/0092019 A1* 5/2003 Meyer .................... C07K 14/47
435/6.14
2012/0072124 A1 3/2012 Radich et al.
2015/0299801 A1 10/2015 Ferrando et al.

FOREIGN PATENT DOCUMENTS

WO 2010-138843 A2 12/2010

OTHER PUBLICATIONS

Gallier et al. (PLOS computational biology Dec. 2011 vol. 7 e1002295).*
Jordheim (Blood 2007 vol. 110 4294.*
Jordheim et al. (Drug Metabolism and disposition 2008 vol. 36 p. 2419-2423).*
Fyrberg et al. (Cancer Research Abstract 2757 AACR 101st Annual Meeting Apr. 17-21, 2010).*
Mascheretti et al. (Pharmacogenetics 2002 vol. 12 p. 509).*
Juppner (Bone 1995 vol. 17 No. 2 Supplement 39S-42S).*
Mummidi et al. (Journal of Biological Chemistry 2000 vol. 275 No. 25 p. 18946-18961).*
Mitra et al., "Genetic Variants in Cytosolic 5'-Nucleotidase II Are Associated With Its Expression and Cytarabine Sensitivity in HapMap Cell Lines and in Patients With Acute Myeloid Leukemia," The Journal of Pharmacology and Experimental Therapeutics 339(1):9-23 (2011).
Galmarini et al., "Nucleoside Analogues and Nucleobases in Cancer Treatment," The Lancet Oncology 3 (7):415-424 (2002).
Meyer et al., "Relapse-specific Mutations in NT5C2 in Childhood Acute Lymphoblastic Leukemia," Nature Genetics 45(3):290-294 (2013).
International Search Report and Written Opinion for PCT/US2013/039942 filed May 7, 2013 (dated Feb. 4, 2014).
Gallier et al., "Structural Insights into the Inhibition of Cytosolic 5'-Nucleotidase II (cN-II) by Ribonucleoside 5'-Monophosphate Analogues," PLoS Computational Biology 7(12):e1002295 (2011).
Hogan et al., "Integrated Genomic Analysis of Relapsed Childhood Acute Lymphoblastic Leukemia Reveals Therapeutic Strategies," Blood 118(19):5218-5226 (2011).
Meyer et al., "Screening for Gene Mutations: Will Identification of NT5C2 Mutations Help Predict the Chance of Relapse in Acute Lymphoblastic Leukemia?" Expert. Rev. Hematol. 6(3):223-224 (2013).
Carson et al., "Deoxyadenosine-resistant Human T Lymphoblasts with Elevated 5'-nucleotidase Activity," Biochim Biophys Acta. 1091(1):22-8 (1991).
Schirmer et al., "Lack of Cross-resistance with Gemcitabine and Cytarabine in Cladribine-resistant HL60 Cells with Elevated 5'-nucleotidase Activity," Exp Hematol. 26(13):1223-8 (1998).
Lotfi et al., "Pharmacological Basis for Cladribine Resistance in a Human Acute T Lymphoblastic Leukaemia Cell Line Selected for Resistance to Etoposide," Br J Haematol. 113(2):339-46 (2001).
Galmarini et al., "Deoxycytidine Kinase and cN-II Nucleotidase Expression in Blast Cells Predict Survival in Acute Myeloid Leukaemia Patients Treated with Cytarabine," Br J Haematol. 122(1):53-60 (2003).

(Continued)

*Primary Examiner* — Katherine D Salmon
(74) *Attorney, Agent, or Firm* — Pepper Hamilton LLP

(57) ABSTRACT

The present invention is directed to methods of prognosing relapsed leukemia in a subject. These methods are based on the detection of one or more relapse-specific gene mutations in a patient sample. The present invention further relates to methods of preventing and treating relapse leukemia in a subject based on the determined prognosis of the subject.

17 Claims, 14 Drawing Sheets

Specification includes a Sequence Listing.

(56) References Cited

OTHER PUBLICATIONS

Yamamoto et al., "Fludarabine-mediated Circumvention of Cytarabine Resistance is Associated with Fludarabine Triphosphate Accumulation in Cytarabine-resistant Leukemic Cells," Int J Hematol. 85(2):108-15 (2007).
Wallden et al., "Crystal Structure of Human Cytosolic 5'-Nucleotidase II: Insights into Allosteric Regulation and Substrate Recognition," J. Biol. Chem. 282(24):17828-17836 (2007).
Tzoneva et al., "Activating Mutations in the NT5C2 Nucleotidase Gene Drive Chemotherapy Resistance in Relapsed ALL," Nat Med. 19(3):368-71 (2013).
Walldén et al., "Crystal Structure of Human Cytosolic 5'-nucleotidase II: Insights Into Allosteric Regulation and Substrate Recognition," J Biol Chem. 282(24):17828-36 (2007).

* cited by examiner

C

D

SEQUENCE LISTING

```
<160> NUMBER OF SEQ ID NOS: 79

<210> SEQ ID NO 1
<211> LENGTH: 1686
<212> TYPE: DNA
<213> ORGANISM: Homo sapiens

<400> SEQUENCE: 1

atgtcaacct cctggagtga tcggttacag aatgcagcag atatgcctgc taacatggat     60

aagcatgccc tgaaaaagta tcgtcgagaa gcctatcatc gggtgtttgt gaaccgaagt    120

ttagcaatgg aaaagataaa gtgttttggt tttgatatgg attataccct tgctgtgtac    180

aagtccccag agtatgagtc ccttggtttt gagcttactg tggagagatt agtttctatt    240

ggctatcccc aggagttgct cagctttgct tatgattcta cattccctac caggggactt    300

gtctttgaca cactgtatgg aaatcttttg aaagtcgatg cctatggaaa cctcttggtc    360

tgtgcacatg gatttaactt tataagggga ccagaaacta gagaacagta tccaaataaa    420

tttatccagc gagatgatac tgaaagattt tacattctga acacactatt caacctacca    480

gagacctacc tgttggcctg cctagtagat ttttttacta attgtcccag atataccagt    540

tgtgaaacag gatttaaaga tggggacctc ttcatgtcct accggagtat gttccaggat    600

gtaagagatg ctgttgactg ggttcattac aagggctccc ttaaggaaaa gacagttgaa    660

aatcttgaga agtatgtagt caaagatgga aaactgcctt tgcttctgag ccggatgaag    720

gaagtaggga aagtatttct tgctaccaac agtgactata aatatacaga taaaattatg    780

acttacctgt ttgacttccc acatggcccc aagcctggga gctcccatcg accatggcag    840

tcctactttg acttgatctt ggtggatgca cggaaaccac tctttttgg agaaggcaca    900

gtactgcgtc aggtggatac taaaactggc aagctgaaaa ttggtaccta cacagggccc    960

ctacagcatg gtatcgtcta ctcaggaggt tcttctgata cgatctgtga cctgttggga   1020

gccaagggaa aagacatttt gtatattgga gatcacattt ttggggacat tttaaaatca   1080

aagaaacggc aagggtggcg aactttttg gtgattcctg aactcgcaca ggagctacat   1140

gtctggactg acaagagttc acttttcgaa gaacttcaga gcttggatat tttcttggct   1200

gaactctaca agcatcttga cagcagtagc aatgagcgtc cagacatcag ttccatccag   1260

agacgtatta agaaagtaac tcatgacatg gacatgtgct atgggatgat gggaagcctg   1320

tttcgcagtg gctcccggca gaccctttt gccagtcaag tgatgcgtta tgctgacctc   1380
```

```
tatgcagcat ctttcatcaa cctgctgtat taccctttca gctacctctt cagggctgcc   1440

catgtcttga tgcctcatga atcaacggtg gagcacacac acgtagatat caatgagatg   1500

gagtctcctc ttgccacccg gaaccgcaca tcagtggatt tcaaagacac tgactacaag   1560

cggcaccagc tgacacggtc aattagtgag attaaacctc ccaacctctt cccactggcc   1620

ccccaggaaa ttacacactg ccatgacgaa gatgatgatg aagaggagga ggaggaggaa   1680

gaataa                                                              1686


<210> SEQ ID NO 2
<211> LENGTH: 561
<212> TYPE: PRT
<213> ORGANISM: Homo sapiens

<400> SEQUENCE: 2

Met Ser Thr Ser Trp Ser Asp Arg Leu Gln Asn Ala Ala Asp Met Pro
1               5                   10                  15

Ala Asn Met Asp Lys His Ala Leu Lys Lys Tyr Arg Arg Glu Ala Tyr
            20                  25                  30

His Arg Val Phe Val Asn Arg Ser Leu Ala Met Glu Lys Ile Lys Cys
        35                  40                  45

Phe Gly Phe Asp Met Asp Tyr Thr Leu Ala Val Tyr Lys Ser Pro Glu
    50                  55                  60

Tyr Glu Ser Leu Gly Phe Glu Leu Thr Val Glu Arg Leu Val Ser Ile
65                  70                  75                  80

Gly Tyr Pro Gln Glu Leu Leu Ser Phe Ala Tyr Asp Ser Thr Phe Pro
                85                  90                  95

Thr Arg Gly Leu Val Phe Asp Thr Leu Tyr Gly Asn Leu Leu Lys Val
            100                 105                 110

Asp Ala Tyr Gly Asn Leu Leu Val Cys Ala His Gly Phe Asn Phe Ile
        115                 120                 125

Arg Gly Pro Glu Thr Arg Glu Gln Tyr Pro Asn Lys Phe Ile Gln Arg
    130                 135                 140

Asp Asp Thr Glu Arg Phe Tyr Ile Leu Asn Thr Leu Phe Asn Leu Pro
145                 150                 155                 160

Glu Thr Tyr Leu Leu Ala Cys Leu Val Asp Phe Phe Thr Asn Cys Pro
                165                 170                 175

Arg Tyr Thr Ser Cys Glu Thr Gly Phe Lys Asp Gly Asp Leu Phe Met
            180                 185                 190

Ser Tyr Arg Ser Met Phe Gln Asp Val Arg Asp Ala Val Asp Trp Val
        195                 200                 205

His Tyr Lys Gly Ser Leu Lys Glu Lys Thr Val Glu Asn Leu Glu Lys
    210                 215                 220

Tyr Val Val Lys Asp Gly Lys Leu Pro Leu Leu Leu Ser Arg Met Lys
225                 230                 235                 240

Glu Val Gly Lys Val Phe Leu Ala Thr Asn Ser Asp Tyr Lys Tyr Thr
                245                 250                 255

Asp Lys Ile Met Thr Tyr Leu Phe Asp Phe Pro His Gly Pro Lys Pro
            260                 265                 270

Gly Ser Ser His Arg Pro Trp Gln Ser Tyr Phe Asp Leu Ile Leu Val
        275                 280                 285

Asp Ala Arg Lys Pro Leu Phe Phe Gly Glu Gly Thr Val Leu Arg Gln
    290                 295                 300

Val Asp Thr Lys Thr Gly Lys Leu Lys Ile Gly Thr Tyr Thr Gly Pro
305                 310                 315                 320
```

```
Leu Gln His Gly Ile Val Tyr Ser Gly Gly Ser Ser Asp Thr Ile Cys
                325                 330                 335

Asp Leu Leu Gly Ala Lys Gly Lys Asp Ile Leu Tyr Ile Gly Asp His
            340                 345                 350

Ile Phe Gly Asp Ile Leu Lys Ser Lys Lys Arg Gln Gly Trp Arg Thr
        355                 360                 365

Phe Leu Val Ile Pro Glu Leu Ala Gln Glu Leu His Val Trp Thr Asp
    370                 375                 380

Lys Ser Ser Leu Phe Glu Glu Leu Gln Ser Leu Asp Ile Phe Leu Ala
385                 390                 395                 400

Glu Leu Tyr Lys His Leu Asp Ser Ser Ser Asn Glu Arg Pro Asp Ile
                405                 410                 415

Ser Ser Ile Gln Arg Arg Ile Lys Lys Val Thr His Asp Met Asp Met
            420                 425                 430

Cys Tyr Gly Met Met Gly Ser Leu Phe Arg Ser Gly Ser Arg Gln Thr
        435                 440                 445

Leu Phe Ala Ser Gln Val Met Arg Tyr Ala Asp Leu Tyr Ala Ala Ser
    450                 455                 460

Phe Ile Asn Leu Leu Tyr Tyr Pro Phe Ser Tyr Leu Phe Arg Ala Ala
465                 470                 475                 480

His Val Leu Met Pro His Glu Ser Thr Val Glu His Thr His Val Asp
                485                 490                 495

Ile Asn Glu Met Glu Ser Pro Leu Ala Thr Arg Asn Arg Thr Ser Val
            500                 505                 510

Asp Phe Lys Asp Thr Asp Tyr Lys Arg His Gln Leu Thr Arg Ser Ile
        515                 520                 525

Ser Glu Ile Lys Pro Pro Asn Leu Phe Pro Leu Ala Pro Gln Glu Ile
    530                 535                 540

Thr His Cys His Asp Glu Asp Asp Asp Glu Glu Glu Glu Glu Glu Glu
545                 550                 555                 560

Glu
```

<210> SEQ ID NO 3
<211> LENGTH: 4131
<212> TYPE: DNA
<213> ORGANISM: Homo sapiens

<400> SEQUENCE: 3

```
atgtttagag ctggggaggc ctccaaacgc ccattgcctg ggccgtcgcc cccaagggtg      60

cggagtgtgg aggttgcccg ggggagggcc ggctacggat tcacgctttc gggacaggca     120

ccctgtgtgc tcagctgcgt catgagaggg agccctgcgg atttcgtggg cctccgagct     180

ggagaccaga tacttgctgt caatgaaatc aacgtgaaaa aagcatctca tgaagatgta     240

gtgaaattaa ttgggaagtg ctctggtgtc cttcacatgg tgattgctga aggcgtcggc     300

cgcttcgaat cctgttccag tgatgaagaa gggggactct atgaaggaaa aggctggctg     360

aagcccaagc tggattctaa agcactaggt ataaacagag cagagcgagt cgtggaggaa     420

atgcagtctg gtggaatttt caatatgatt tttgaaaacc cgagcctttg tgcgagcaat     480

tcagagccct tgaaattgaa acaaagatcc ctttcagagt cggccgcaac tcgatttgat     540

gttggacatg aaagtataaa taatccaaat cccaacatgc tttctaagga ggaaatatca     600

aaagttattc atgatgattc ggttttcagc attggactag aaagtcatga cgattttgca     660

ttggatgcaa gtattttaaa cgtggcgatg atcgtgggct acttaggctc cattgagctt     720
```

-continued

```
ccttccacga gctccaacct ggagtccgac agcttgcaag ccatccgcgg ctgcatgcgg    780
cgcctgcggg cagagcagaa aatccactcg ctggtgacca tgaagatcat gcacgactgt    840
gtgcagctga gcactgacaa ggctggagtc gtggccgagt acccggccga gaagctggcc    900
ttcagcgccg tgtgcccgga cgaccggcga tttttcgggt tggttaccat gcagacgaat    960
gacgacggga gcctggccca ggaggaggag ggcgccctgc ggacttcctg ccacgtgttc   1020
atggtggacc cagacttgtt taatcacaag atccaccaag gcattgctcg gcggtttggg   1080
tttgagtgca cggccgaccc agacaccaat ggctgtctgg aattcccggc gtcctccctc   1140
cccgtcctgc agttcatctc tgtcctgtac cgagacatgg gtgagctgat tgagggcatg   1200
cgggcccgcg cctttctgga cggggacgcc gatgcccacc agaacaacag caccagcagc   1260
aacagtgaca gcggcattgg gaacttccac caggaggaga agagcaaccg ggtccttgtg   1320
gtggacctgg gtgggagctc gagcagacac ggccccggag gcagcgcgtg ggacggtgtg   1380
ggtgggaggg gtgcccagcc ctggggtgct ccctggactg ggcccttctg tccggacccc   1440
gaagggagcc ccccatttga ggccgctcat cagactgaca ggttctggga cctaaacaag   1500
cacctagggc cagcctctcc tgtggaggtg cccccagctt ccttgaggag ctcagtcccc   1560
ccttccaaga ggggcaccgt gggtgctggc tgtggtttca accagcgctg gctcccggtc   1620
cacgtgctcc gggagtggca gtgcggacac accagcgacc aggactctta cacagattcc   1680
accgatggct ggtccagcat caactgcggc acactgcccc ctcctatgag caagatcccc   1740
gcagaccgct acagggtgga gggcagcttc gcgcagcccc cgctgaatgc cccgaagagg   1800
gagtggtcca ggaaggcctt tggaatgcaa agcatttttg gtccccatcg aaatgttcga   1860
aagactaagg aagataaaaa gggctcaaaa tttgggcggg gaactggact cactcagcct   1920
tctcaacgca cgtctgctcg gagatcattt gggagatcca agagattcag tatcactcgc   1980
tcccttgatg atcttgagtc tgcaactgtg tctgatggcg agttgacggg cgccgacctg   2040
aaggactgcg tcagcaacaa cagcctgagc agcaatgcca gcctccccag cgtgcagagc   2100
tgccggcgcc tgcgtgagag gagggtcgcc agctgggccg tgtcctttga gcgcctgctg   2160
caggaccccg tcggtgtccg ctacttctct gattttctaa ggaaagaatt cagtgaagaa   2220
aacattttat tctggcaggc ctgtgaatat tttaatcatg ttcctgcaca tgacaaaaag   2280
gagctttcct acagggcccg ggagattttc agtaagtttc tctgcagcaa agccaccacc   2340
ccggtcaaca tcgacagcca ggcccagcta gcagacgacg tcctccgcgc acctcaccca   2400
gacatgttca aggagcagca gctgcagatc ttcaatctca tgaagtttga tagctacact   2460
cgctttctga agtccccgct gtaccaggaa tgcatcctgg cggaagtgga gggccgtgca   2520
ctcccggact cgcagcaggt ccccagcagc ccggcttcca agcacagcct cggttcagac   2580
cactccagtg tgtccacgcc aaaaaagtta agtggaaaat caaaatccgg ccgatccctg   2640
aatgaagagc tgggggatga ggacagcgag aagaagcgga aaggcgcgtt tttctcgtgg   2700
tcgcggacca ggagcaccgg gaggtcccag aaaaagaggg agcacgggga ccacgcagac   2760
gacgccctgc atgccaatgg aggcctgtgt cgccgagagt cgcagggctc tgtgtcctct   2820
gcggggagcc tggacctgtc ggaggcctgc aggactttgg cacccgagaa ggacaaggcc   2880
accaagcact gctgcattca tctcccggat gggacatcct gcgtggtggc tgtcaaggcg   2940
ggcttctcca tcaaagacat cctgtccgga ctctgtgagc ggcatggcat caacggggcg   3000
gccgcggacc tcttcctggt gggcggggac aagcctctgg tgctgcacca agacagtagc   3060
```

-continued

```
atcttggagt caagggacct gcgcctagaa aagcgcacct tgtttcggct ggatcttgtt   3120

ccgattaacc ggtcagtggg actcaaggcc aagcccacca agcccgtcac ggaggtgctg   3180

cggcccgtgg tggccagata cggcctggac ctcagtggcc tgctggtgag gctgagtgga   3240

gagaaggagc ccctggacct tggcgcccct atatcgagtc tggacggaca gcgggttgtc   3300

ttggaggaga aggatccttc cagaggaaag gcatccgcag ataaacagaa aggtgtgcca   3360

gtgaaacaga acacagctgt aaattccagc tccagaaacc actcggctac gggagaggaa   3420

agaacactag gcaagtctaa ttctattaaa ataaaaggag aaaatggaaa aaatgctagg   3480

gatccccggc tttcaaagag agaagaatct attgcaaaga ttgggaaaaa aaaatatcag   3540

aaaattaatt tggacgaagc agaggagttt tttgagctta tttccaaagc tcagagcaac   3600

agagcagatg accaacgtgg gctgctaagg aaggaagacc tggtgttgcc agagttcctc   3660

cgtttacctc ctggttccac agaactcacc ctccccactc cagctgctgt ggccaagggc   3720

tttagcaaga gaagcgccac aggcaacggc cgggagagcg cctcccagcc tggcgagcag   3780

tgggagccag tccaggagag cagcgacagc ccgtccacca gcccgggctc agcctccagc   3840

ccccctggac ctcctgggac gacccccccc gggcagaagt ctcccagcgg gcccttctgc   3900

actccccagt cccccgtctc cctcgcgcag gagggcaccg cccagatctg gaagaggcag   3960

tctcaggaag tggaggccgg gggcatccag acggtggagg atgagcacgt ggccgagctg   4020

accctgatgg gggaggggga catcagcagc cccaacagca ccttgctgcc gccgccctcc   4080

accccccagg aagtgccagg accttccaga ccaggtacct ccaggttctg a            4131
```

<210> SEQ ID NO 4
<211> LENGTH: 1447
<212> TYPE: PRT
<213> ORGANISM: Homo sapiens

<400> SEQUENCE: 4

```
Met Phe Arg Ala Gly Glu Ala Ser Lys Arg Pro Leu Pro Gly Pro Ser
1               5                   10                  15

Pro Pro Arg Val Arg Ser Val Glu Val Ala Arg Gly Arg Ala Gly Tyr
            20                  25                  30

Gly Phe Thr Leu Ser Gly Gln Ala Pro Cys Val Leu Ser Cys Val Met
        35                  40                  45

Arg Gly Ser Pro Ala Asp Phe Val Gly Leu Arg Ala Gly Asp Gln Ile
    50                  55                  60

Leu Ala Val Asn Glu Ile Asn Val Lys Lys Ala Ser His Glu Asp Val
65                  70                  75                  80

Val Lys Leu Ile Gly Lys Cys Ser Gly Val Leu His Met Val Ile Ala
                85                  90                  95

Glu Gly Val Gly Arg Phe Glu Ser Cys Ser Ser Asp Glu Glu Gly Gly
            100                 105                 110

Leu Tyr Glu Gly Lys Gly Trp Leu Lys Pro Lys Leu Asp Ser Lys Ala
        115                 120                 125

Leu Gly Ile Asn Arg Ala Glu Arg Val Val Glu Glu Met Gln Ser Gly
    130                 135                 140

Gly Ile Phe Asn Met Ile Phe Glu Asn Pro Ser Leu Cys Ala Ser Asn
145                 150                 155                 160

Ser Glu Pro Leu Lys Leu Lys Gln Arg Ser Leu Ser Glu Ser Ala Ala
                165                 170                 175

Thr Arg Phe Asp Val Gly His Glu Ser Ile Asn Asn Pro Asn Pro Asn
            180                 185                 190
```

```
Met Leu Ser Lys Glu Glu Ile Ser Lys Val Ile His Asp Asp Ser Val
        195                 200                 205

Phe Ser Ile Gly Leu Glu Ser His Asp Asp Phe Ala Leu Asp Ala Ser
    210                 215                 220

Ile Leu Asn Val Ala Met Ile Val Gly Tyr Leu Gly Ser Ile Glu Leu
225                 230                 235                 240

Pro Ser Thr Ser Ser Asn Leu Glu Ser Asp Ser Leu Gln Ala Ile Arg
                245                 250                 255

Gly Cys Met Arg Arg Leu Arg Ala Glu Gln Lys Ile His Ser Leu Val
            260                 265                 270

Thr Met Lys Ile Met His Asp Cys Val Gln Leu Ser Thr Asp Lys Ala
        275                 280                 285

Gly Val Val Ala Glu Tyr Pro Ala Glu Lys Leu Ala Phe Ser Ala Val
    290                 295                 300

Cys Pro Asp Asp Arg Arg Phe Phe Gly Leu Val Thr Met Gln Thr Asn
305                 310                 315                 320

Asp Asp Gly Ser Leu Ala Gln Glu Glu Glu Gly Ala Leu Arg Thr Ser
                325                 330                 335

Cys His Val Phe Met Val Asp Pro Asp Leu Phe Asn His Lys Ile His
            340                 345                 350

Gln Gly Ile Ala Arg Arg Phe Gly Phe Glu Cys Thr Ala Asp Pro Asp
        355                 360                 365

Thr Asn Gly Cys Leu Glu Phe Pro Ala Ser Ser Leu Pro Val Leu Gln
    370                 375                 380

Phe Ile Ser Val Leu Tyr Arg Asp Met Gly Glu Leu Ile Glu Gly Met
385                 390                 395                 400

Arg Ala Arg Ala Phe Leu Asp Gly Asp Ala Asp Ala His Gln Asn Asn
                405                 410                 415

Ser Thr Ser Ser Asn Ser Asp Ser Gly Ile Gly Asn Phe His Gln Glu
            420                 425                 430

Glu Lys Ser Asn Arg Val Leu Val Val Asp Leu Gly Gly Ser Ser Ser
        435                 440                 445

Arg His Gly Pro Gly Gly Ser Ala Trp Asp Gly Val Gly Gly Arg Gly
    450                 455                 460

Ala Gln Pro Trp Gly Ala Pro Trp Thr Gly Pro Phe Cys Pro Asp Pro
465                 470                 475                 480

Glu Gly Ser Pro Pro Phe Glu Ala Ala His Gln Thr Asp Arg Phe Trp
                485                 490                 495

Asp Leu Asn Lys His Leu Gly Pro Ala Ser Pro Val Glu Val Pro Pro
            500                 505                 510

Ala Ser Leu Arg Ser Ser Val Pro Pro Ser Lys Arg Gly Thr Val Gly
        515                 520                 525

Ala Gly Cys Gly Phe Asn Gln Arg Trp Leu Pro Val His Val Leu Arg
    530                 535                 540

Glu Trp Gln Cys Gly His Thr Ser Asp Gln Asp Ser Tyr Thr Asp Ser
545                 550                 555                 560

Thr Asp Gly Trp Ser Ser Ile Asn Cys Gly Thr Leu Pro Pro Pro Met
                565                 570                 575

Ser Lys Ile Pro Ala Asp Arg Tyr Arg Val Glu Gly Ser Phe Ala Gln
            580                 585                 590

Pro Pro Leu Asn Ala Pro Lys Arg Glu Trp Ser Arg Lys Ala Phe Gly
        595                 600                 605
```

```
Met Gln Ser Ile Phe Gly Pro His Arg Asn Val Arg Lys Thr Lys Glu
    610                 615                 620

Asp Lys Lys Gly Ser Lys Phe Gly Arg Gly Thr Gly Leu Thr Gln Pro
625                 630                 635                 640

Ser Gln Arg Thr Ser Ala Arg Arg Ser Phe Gly Arg Ser Lys Arg Phe
                645                 650                 655

Ser Ile Thr Arg Ser Leu Asp Asp Leu Glu Ser Ala Thr Val Ser Asp
            660                 665                 670

Gly Glu Leu Thr Gly Ala Asp Leu Lys Asp Cys Val Ser Asn Asn Ser
        675                 680                 685

Leu Ser Ser Asn Ala Ser Leu Pro Ser Val Gln Ser Cys Arg Arg Leu
    690                 695                 700

Arg Glu Arg Arg Val Ala Ser Trp Ala Val Ser Phe Glu Arg Leu Leu
705                 710                 715                 720

Gln Asp Pro Val Gly Val Arg Tyr Phe Ser Asp Phe Leu Arg Lys Glu
                725                 730                 735

Phe Ser Glu Glu Asn Ile Leu Phe Trp Gln Ala Cys Glu Tyr Phe Asn
            740                 745                 750

His Val Pro Ala His Asp Lys Lys Glu Leu Ser Tyr Arg Ala Arg Glu
        755                 760                 765

Ile Phe Ser Lys Phe Leu Cys Ser Lys Ala Thr Thr Pro Val Asn Ile
    770                 775                 780

Asp Ser Gln Ala Gln Leu Ala Asp Asp Val Leu Arg Ala Pro His Pro
785                 790                 795                 800

Asp Met Phe Lys Glu Gln Gln Leu Gln Ile Phe Asn Leu Met Lys Phe
                805                 810                 815

Asp Ser Tyr Thr Arg Phe Leu Lys Ser Pro Leu Tyr Gln Glu Cys Ile
            820                 825                 830

Leu Ala Glu Val Glu Gly Arg Ala Leu Pro Asp Ser Gln Gln Val Pro
        835                 840                 845

Ser Ser Pro Ala Ser Lys His Ser Leu Gly Ser Asp His Ser Ser Val
    850                 855                 860

Ser Thr Pro Lys Lys Leu Ser Gly Lys Ser Lys Ser Gly Arg Ser Leu
865                 870                 875                 880

Asn Glu Glu Leu Gly Asp Glu Asp Ser Glu Lys Lys Arg Lys Gly Ala
                885                 890                 895

Phe Phe Ser Trp Ser Arg Thr Arg Ser Thr Gly Arg Ser Gln Lys Lys
            900                 905                 910

Arg Glu His Gly Asp His Ala Asp Asp Ala Leu His Ala Asn Gly Gly
        915                 920                 925

Leu Cys Arg Arg Glu Ser Gln Gly Ser Val Ser Ser Ala Gly Ser Leu
    930                 935                 940

Asp Leu Ser Glu Ala Cys Arg Thr Leu Ala Pro Glu Lys Asp Lys Ala
945                 950                 955                 960

Thr Lys His Cys Cys Ile His Leu Pro Asp Gly Thr Ser Cys Val Val
                965                 970                 975

Ala Val Lys Ala Gly Phe Ser Ile Lys Asp Ile Leu Ser Gly Leu Cys
            980                 985                 990

Glu Arg His Gly Ile Asn Gly Ala  Ala Ala Asp Leu Phe  Leu Val Gly
        995                 1000                1005

Gly Asp  Lys Pro Leu Val Leu  His Gln Asp Ser Ser  Ile Leu Glu
    1010                1015                1020

Ser Arg  Asp Leu Arg Leu Glu  Lys Arg Thr Leu Phe  Arg Leu Asp
```

```
    1025                1030                1035

Leu Val  Pro Ile Asn Arg Ser  Val Gly Leu Lys Ala  Lys Pro Thr
    1040                1045                1050

Lys Pro  Val Thr Glu Val Leu  Arg Pro Val Val Ala  Arg Tyr Gly
    1055                1060                1065

Leu Asp  Leu Ser Gly Leu Leu  Val Arg Leu Ser Gly  Glu Lys Glu
    1070                1075                1080

Pro Leu  Asp Leu Gly Ala Pro  Ile Ser Ser Leu Asp  Gly Gln Arg
    1085                1090                1095

Val Val  Leu Glu Glu Lys Asp  Pro Ser Arg Gly Lys  Ala Ser Ala
    1100                1105                1110

Asp Lys  Gln Lys Gly Val Pro  Val Lys Gln Asn Thr  Ala Val Asn
    1115                1120                1125

Ser Ser  Ser Arg Asn His Ser  Ala Thr Gly Glu Glu  Arg Thr Leu
    1130                1135                1140

Gly Lys  Ser Asn Ser Ile Lys  Ile Lys Gly Glu Asn  Gly Lys Asn
    1145                1150                1155

Ala Arg  Asp Pro Arg Leu Ser  Lys Arg Glu Glu Ser  Ile Ala Lys
    1160                1165                1170

Ile Gly  Lys Lys Lys Tyr Gln  Lys Ile Asn Leu Asp  Glu Ala Glu
    1175                1180                1185

Glu Phe  Phe Glu Leu Ile Ser  Lys Ala Gln Ser Asn  Arg Ala Asp
    1190                1195                1200

Asp Gln  Arg Gly Leu Leu Arg  Lys Glu Asp Leu Val  Leu Pro Glu
    1205                1210                1215

Phe Leu  Arg Leu Pro Pro Gly  Ser Thr Glu Leu Thr  Leu Pro Thr
    1220                1225                1230

Pro Ala  Ala Val Ala Lys Gly  Phe Ser Lys Arg Ser  Ala Thr Gly
    1235                1240                1245

Asn Gly  Arg Glu Ser Ala Ser  Gln Pro Gly Glu Gln  Trp Glu Pro
    1250                1255                1260

Val Gln  Glu Ser Ser Asp Ser  Pro Ser Thr Ser Pro  Gly Ser Ala
    1265                1270                1275

Ser Ser  Pro Pro Gly Pro Pro  Gly Thr Thr Pro Pro  Gly Gln Lys
    1280                1285                1290

Ser Pro  Ser Gly Pro Phe Cys  Thr Pro Gln Ser Pro  Val Ser Leu
    1295                1300                1305

Ala Gln  Glu Gly Thr Ala Gln  Ile Trp Lys Arg Gln  Ser Gln Glu
    1310                1315                1320

Val Glu  Ala Gly Gly Ile Gln  Thr Val Glu Asp Glu  His Val Ala
    1325                1330                1335

Glu Leu  Thr Leu Met Gly Glu  Gly Asp Ile Ser Ser  Pro Asn Ser
    1340                1345                1350

Thr Leu  Leu Pro Pro Pro Ser  Thr Pro Gln Glu Val  Pro Gly Pro
    1355                1360                1365

Ser Arg  Pro Gly Ser Gly Thr  His Gly Ser Arg Asp  Leu Pro Val
    1370                1375                1380

Asn Arg  Ile Ile Asp Val Asp  Leu Val Thr Gly Ser  Ala Pro Gly
    1385                1390                1395

Arg Asp  Gly Gly Ile Ala Gly  Ala Gln Ala Gly Pro  Gly Arg Ser
    1400                1405                1410

Gln Ala  Ser Gly Gly Pro Pro  Thr Ser Asp Leu Pro  Gly Leu Gly
    1415                1420                1425
```

Pro Val Pro Gly Glu Pro Ala Lys Pro Lys Thr Ser Ala His His
1430 1435 1440

Ala Thr Phe Val
1445

<210> SEQ ID NO 5
<211> LENGTH: 4425
<212> TYPE: DNA
<213> ORGANISM: Home sapiens

<400> SEQUENCE: 5
atggcccgcc tagccgcagt gctctggaat ctgtgtgtca ccgccgtcct ggtcacctcg 60
gccacccaag gcctgagccg ggccgggctc ccgttcgggc tgatgcgccg ggagctggcg 120
tgtgaaggct accccatcga gctgcggtgc cccggcagcg acgtcatcat ggtggagaat 180
gccaactacg ggcgcacgga cgacaagatt tgcgatgctg acccttttcca gatggagaat 240 gtgcagtgct acctgccgga cgccttcaag atcatgtcac agaggtgtaa caaccgcacc 300
cagtgcgtgg tggtcgccgg ctcggatgcc tttcctgacc cctgtcctgg gacctacaag 360
tacctggagg tgcagtacga ctgtgtcccc tacaaagtgg agcagaaagt cttcgtgtgc 420
ccagggaccc tgcagaaggt gctggagccc acctcgacac acgagtcaga gcaccagtct 480
ggcgcatggt gcaaggaccc gctgcaggcg ggtgaccgca tctacgtgat gccctggatc 540
ccctaccgca cggacacact gactgagtat gcctcgtggg aggactacgt ggccgcccgc 600
cacaccacca cctaccgcct gcccaaccgc gtggatggca caggctttgt ggtctacgat 660
ggtgccgtct tctacaacaa ggagcgcacg cgcaacatcg tcaagtatga cctacggacg 720
cgcatcaaga gcggggagac ggtcatcaat accgccaact accatgacac ctcgccctac 780
cgctggggcg gaaagaccga cattgacctg gcggtggacg agaacgggct gtgggtcatc 840
tacgccactg agggcaacaa cgggcggctg gtggtgagcc agctgaaccc ctacacactg 900
cgctttgagg gcacgtggga gacgggttac gacaagcgct cggcatccaa cgccttcatg 960
gtgtgtgggg tcctgtacgt cctgcgttcc gtgtacgtgg atgatgacag cgaggcggct 1020
ggcaaccgcg tggactatgc cttcaacacc aatgccaacc gcgaggagcc tgtcagcctc 1080
accttcccca accccctacca gttcatctcc tccgttgact acaaccctcg cgacaaccag 1140
ctgtacgtct ggaacaacta tttcgtggtg cgctacagcc tggagttcgg gccgcccgac 1200
cccagtgctg gcccagccac ttccccaccc ctcagcacga ccaccacagc caggcccacg 1260
cccctcacca gcacagcctc gcccgcagcc accaccccgc tccgccgggc acccctcacc 1320
acgcacccag tgggtgccat caaccagctg ggacctgatc tgcctccagc cacagcccca 1380
gtccccagca cccggcggcc cccagccccg aatctacacg tgtcccctga gctcttctgc 1440
gagccccgag aggtacggcg ggtccagtgg ccggccaccc agcagggcat gctggtggag 1500
aggccctgcc ccaaggggac tcgaggaatt gcctccttcc agtgtctacc agccttgggg 1560
ctctggaacc cccggggccc tgacctcagc aactgcacct cccccctgggt caaccaggtg 1620 gcccagaaga tcaagagtgg ggagaacgcg gccaacatcg ccagcgagct ggcccgacac 1680
acccggggct ccatctacgc gggggacgtc tcctcctctg tgaagctgat ggagcagctg 1740
ctggacatcc tggatgccca gctgcaggcc ctgcggccca tcgagcgcga gtcagccggc 1800
aagaactaca acaagatgca caagcgagag agaacttgta aggattatat caaggccgtg 1860
gtggagacag tggacaatct gctccggcca gaagctctgg agtcctggaa ggacatgaat 1920

-continued gccacggagc aggtgcacac ggccaccatg ctcctcgacg tcctggagga gggcgccttc 1980
ctgctggccg acaatgtcag ggagcctgcc cgcttcctgg ctgccaagga gaacgtggtc 2040
ctggaggtca cagtcctgaa cacagagggc caggtgcagg agctggtgtt cccccaggag 2100
gagtacccga gaaagaactc catccagctg tctgccaaaa ccatcaagca gaacagccgc 2160
aatggggtgg tcaaagttgt cttcatcctc tacaacaacc tgggcctctt cctgtccacg 2220
gagaatgcca cagtgaagct ggccggcgaa gcaggcccgg gtggccctgg gggcgcctct 2280
ctagtggtga actcacaggt catcgcagca tccatcaaca aggagtccag ccgcgtcttc 2340
ctcatggacc ctgtcatctt caccgtggcc cacctggagg acaagaacca cttcaatgct 2400
aactgctcct tctggaacta ctcggagcgt tccatgctgg gctactggtc gacccaaggc 2460
tgccgcctgg tggagtccaa caagacccat accacgtgtg cctgcagcca cctcaccaac 2520
ttcgctgtgc tcatggctca ccgtgagatc taccagggcc gcatcaacga gctgctgctg 2580
tcggtcatca cctgggtggg cattgtgatc tccctggtct gcttggccat ctgcatctcc 2640
accttctgct tcctgcgggg gctgcagacc gaccgcaaca ccatccacaa gaacctgtgc 2700
atcaacctct tcctggctga gctgctcttc ctggtcggga tcgacaagac tcagtatgag 2760
attgcctgcc ccatcttcgc cggcctgctg cactatttct tcctggctgc cttctcctgg 2820
ctgtgcctgg agggcgtgca cctctacctg ctactagtgg aggtgtttga gagcgagtat 2880
tcccgcacca agtactacta cctgggtggc tactgcttcc cggccctggt ggtgggcatc 2940
gcggctgcca ttgactaccg cagctacggc accgagaagg cctgctggct ccgagtggac 3000
aattacttca tctggagttt catcgggcca gtctccttcg ttatcgtggt caacctggtg 3060
ttcctcatgg tgaccctgca caagatgatc cgaagctcat ctgtgctcaa gcccgactcc 3120
agccgcctgg acaacattaa atcctgggcg ctgggggcca tcgcgctgct gttcctgctg 3180
ggcctcacct gggctttcgg cctcctcttc atcaacaagg agtcggtggt catggcctat 3240
ctcttcacca ccttcaacgc cttccagggg gtcttcatct tcgtctttca ctgcgcctta 3300
cagaagaagg tgcacaagga gtacagcaag tgcctgcgtc actcctactg ctgcatccgc 3360
tccccacccg ggggcactca cggatccctc aagacctcag ccatgcgaag caacacccgc 3420
tactacacag ggacccagag ccgaattcgg aggatgtgga atgacactgt gaggaaacag 3480
acggagtcct ccttcatggc gggtgacatc aacagcaccc ccaccctgaa ccgaggtacc 3540
atggggaacc acctgctgac caaccccgtg ctgcagcccc gtgggggcac cagtccctac 3600
aacaccctca tcgccgagtc agtgggcttc aatccctcct cgccccctgt cttcaactcc 3660
ccagggagct accgggaacc caagcacccc ttgggaggcc gggaagcctg tggcatggac 3720
accctgcccc tgaacggcaa cttcaataac agttactcct tgcgaagtgg ggatttccct 3780
cccggggatg gggccctga gccgccccga ggccggaacc tagccgatgc ggcggccttt 3840
gagaagatga tcatctcaga gctggtgcac aacaacctgc gggggagcag cagcgcggcc 3900
aagggccctc caccgcctga gccccctgtg ccacctgtgc caggggggcgg gggcgaggaa 3960 gaggcgggcg ggcccggggg tgctgaccgg gccgagattg aacttctcta taaggccctg 4020
gaggagcctc tgctgctgcc ccgggcccag tcggtgctgt accagagcga tctggacgag 4080
tcggagagct gcacggccga ggacggcgcc accagccggc ccctctcctc ccctcctggc 4140
cgggactccc tctatgccag cggggccaac ctgcgggact caccctccta cccggacagc 4200
agccctgagg ggcccagtga ggccctgccc ccaccccctc ccgcaccccc cggcccccc 4260 gaaatctact acacctcgcg cccgccagcc ctggtggccc ggaatcccct gcagggctac 4320

```
taccaggtgc ggcgtcctag ccacgagggc tacctggcag ccccaggcct tgaggggcca   4380

gggcccgatg gggacgggca gatgcagctg gtcaccagtc tctga                   4425


<210> SEQ ID NO 6
<211> LENGTH: 1474
<212> TYPE: PRT
<213> ORGANISM: Homo sapiens

<400> SEQUENCE: 6

Met Ala Arg Leu Ala Ala Val Leu Trp Asn Leu Cys Val Thr Ala Val
1               5                   10                  15

Leu Val Thr Ser Ala Thr Gln Gly Leu Ser Arg Ala Gly Leu Pro Phe
            20                  25                  30

Gly Leu Met Arg Arg Glu Leu Ala Cys Glu Gly Tyr Pro Ile Glu Leu
        35                  40                  45

Arg Cys Pro Gly Ser Asp Val Ile Met Val Glu Asn Ala Asn Tyr Gly
    50                  55                  60

Arg Thr Asp Asp Lys Ile Cys Asp Ala Asp Pro Phe Gln Met Glu Asn
65                  70                  75                  80

Val Gln Cys Tyr Leu Pro Asp Ala Phe Lys Ile Met Ser Gln Arg Cys
                85                  90                  95

Asn Asn Arg Thr Gln Cys Val Val Val Ala Gly Ser Asp Ala Phe Pro
            100                 105                 110

Asp Pro Cys Pro Gly Thr Tyr Lys Tyr Leu Glu Val Gln Tyr Asp Cys
        115                 120                 125

Val Pro Tyr Lys Val Glu Gln Lys Val Phe Val Cys Pro Gly Thr Leu
    130                 135                 140

Gln Lys Val Leu Glu Pro Thr Ser Thr His Glu Ser Glu His Gln Ser
145                 150                 155                 160

Gly Ala Trp Cys Lys Asp Pro Leu Gln Ala Gly Asp Arg Ile Tyr Val
                165                 170                 175

Met Pro Trp Ile Pro Tyr Arg Thr Asp Thr Leu Thr Glu Tyr Ala Ser
            180                 185                 190

Trp Glu Asp Tyr Val Ala Ala Arg His Thr Thr Thr Tyr Arg Leu Pro
        195                 200                 205

Asn Arg Val Asp Gly Thr Gly Phe Val Val Tyr Asp Gly Ala Val Phe
    210                 215                 220

Tyr Asn Lys Glu Arg Thr Arg Asn Ile Val Lys Tyr Asp Leu Arg Thr
225                 230                 235                 240

Arg Ile Lys Ser Gly Glu Thr Val Ile Asn Thr Ala Asn Tyr His Asp
                245                 250                 255

Thr Ser Pro Tyr Arg Trp Gly Gly Lys Thr Asp Ile Asp Leu Ala Val
            260                 265                 270

Asp Glu Asn Gly Leu Trp Val Ile Tyr Ala Thr Glu Gly Asn Asn Gly
        275                 280                 285

Arg Leu Val Val Ser Gln Leu Asn Pro Tyr Thr Leu Arg Phe Glu Gly
    290                 295                 300

Thr Trp Glu Thr Gly Tyr Asp Lys Arg Ser Ala Ser Asn Ala Phe Met
305                 310                 315                 320

Val Cys Gly Val Leu Tyr Val Leu Arg Ser Val Tyr Val Asp Asp Asp
                325                 330                 335

Ser Glu Ala Ala Gly Asn Arg Val Asp Tyr Ala Phe Asn Thr Asn Ala
            340                 345                 350
```

```
Asn Arg Glu Glu Pro Val Ser Leu Thr Phe Pro Asn Pro Tyr Gln Phe
        355                 360                 365

Ile Ser Ser Val Asp Tyr Asn Pro Arg Asp Asn Gln Leu Tyr Val Trp
    370                 375                 380

Asn Asn Tyr Phe Val Val Arg Tyr Ser Leu Glu Phe Gly Pro Pro Asp
385                 390                 395                 400

Pro Ser Ala Gly Pro Ala Thr Ser Pro Pro Leu Ser Thr Thr Thr Thr
                405                 410                 415

Ala Arg Pro Thr Pro Leu Thr Ser Thr Ala Ser Pro Ala Ala Thr Thr
            420                 425                 430

Pro Leu Arg Arg Ala Pro Leu Thr Thr His Pro Val Gly Ala Ile Asn
        435                 440                 445

Gln Leu Gly Pro Asp Leu Pro Pro Ala Thr Ala Pro Val Pro Ser Thr
    450                 455                 460

Arg Arg Pro Pro Ala Pro Asn Leu His Val Ser Pro Glu Leu Phe Cys
465                 470                 475                 480

Glu Pro Arg Glu Val Arg Arg Val Gln Trp Pro Ala Thr Gln Gln Gly
                485                 490                 495

Met Leu Val Glu Arg Pro Cys Pro Lys Gly Thr Arg Gly Ile Ala Ser
            500                 505                 510

Phe Gln Cys Leu Pro Ala Leu Gly Leu Trp Asn Pro Arg Gly Pro Asp
        515                 520                 525

Leu Ser Asn Cys Thr Ser Pro Trp Val Asn Gln Val Ala Gln Lys Ile
    530                 535                 540

Lys Ser Gly Glu Asn Ala Ala Asn Ile Ala Ser Glu Leu Ala Arg His
545                 550                 555                 560

Thr Arg Gly Ser Ile Tyr Ala Gly Asp Val Ser Ser Ser Val Lys Leu
                565                 570                 575

Met Glu Gln Leu Leu Asp Ile Leu Asp Ala Gln Leu Gln Ala Leu Arg
            580                 585                 590

Pro Ile Glu Arg Glu Ser Ala Gly Lys Asn Tyr Asn Lys Met His Lys
        595                 600                 605

Arg Glu Arg Thr Cys Lys Asp Tyr Ile Lys Ala Val Val Glu Thr Val
    610                 615                 620

Asp Asn Leu Leu Arg Pro Glu Ala Leu Glu Ser Trp Lys Asp Met Asn
625                 630                 635                 640

Ala Thr Glu Gln Val His Thr Ala Thr Met Leu Leu Asp Val Leu Glu
                645                 650                 655

Glu Gly Ala Phe Leu Leu Ala Asp Asn Val Arg Glu Pro Ala Arg Phe
            660                 665                 670

Leu Ala Ala Lys Glu Asn Val Val Leu Glu Val Thr Val Leu Asn Thr
        675                 680                 685

Glu Gly Gln Val Gln Glu Leu Val Phe Pro Gln Glu Glu Tyr Pro Arg
    690                 695                 700

Lys Asn Ser Ile Gln Leu Ser Ala Lys Thr Ile Lys Gln Asn Ser Arg
705                 710                 715                 720

Asn Gly Val Val Lys Val Val Phe Ile Leu Tyr Asn Asn Leu Gly Leu
                725                 730                 735

Phe Leu Ser Thr Glu Asn Ala Thr Val Lys Leu Ala Gly Glu Ala Gly
            740                 745                 750

Pro Gly Gly Pro Gly Gly Ala Ser Leu Val Val Asn Ser Gln Val Ile
        755                 760                 765

Ala Ala Ser Ile Asn Lys Glu Ser Ser Arg Val Phe Leu Met Asp Pro
```

```
    770                 775                 780

Val Ile Phe Thr Val Ala His Leu Glu Asp Lys Asn His Phe Asn Ala
785                 790                 795                 800

Asn Cys Ser Phe Trp Asn Tyr Ser Glu Arg Ser Met Leu Gly Tyr Trp
                805                 810                 815

Ser Thr Gln Gly Cys Arg Leu Val Glu Ser Asn Lys Thr His Thr Thr
            820                 825                 830

Cys Ala Cys Ser His Leu Thr Asn Phe Ala Val Leu Met Ala His Arg
        835                 840                 845

Glu Ile Tyr Gln Gly Arg Ile Asn Glu Leu Leu Leu Ser Val Ile Thr
    850                 855                 860

Trp Val Gly Ile Val Ile Ser Leu Val Cys Leu Ala Ile Cys Ile Ser
865                 870                 875                 880

Thr Phe Cys Phe Leu Arg Gly Leu Gln Thr Asp Arg Asn Thr Ile His
                885                 890                 895

Lys Asn Leu Cys Ile Asn Leu Phe Leu Ala Glu Leu Leu Phe Leu Val
            900                 905                 910

Gly Ile Asp Lys Thr Gln Tyr Glu Ile Ala Cys Pro Ile Phe Ala Gly
        915                 920                 925

Leu Leu His Tyr Phe Phe Leu Ala Ala Phe Ser Trp Leu Cys Leu Glu
    930                 935                 940

Gly Val His Leu Tyr Leu Leu Leu Val Glu Val Phe Glu Ser Glu Tyr
945                 950                 955                 960

Ser Arg Thr Lys Tyr Tyr Tyr Leu Gly Gly Tyr Cys Phe Pro Ala Leu
                965                 970                 975

Val Val Gly Ile Ala Ala Ala Ile Asp Tyr Arg Ser Tyr Gly Thr Glu
            980                 985                 990

Lys Ala Cys Trp Leu Arg Val Asp  Asn Tyr Phe Ile Trp  Ser Phe Ile
        995                 1000                1005

Gly Pro  Val Ser Phe Val Ile  Val Val Asn Leu Val  Phe Leu Met
    1010                1015                1020

Val Thr  Leu His Lys Met Ile  Arg Ser Ser Ser Val  Leu Lys Pro
    1025                1030                1035

Asp Ser  Ser Arg Leu Asp Asn  Ile Lys Ser Trp Ala  Leu Gly Ala
    1040                1045                1050

Ile Ala  Leu Leu Phe Leu Leu  Gly Leu Thr Trp Ala  Phe Gly Leu
    1055                1060                1065

Leu Phe  Ile Asn Lys Glu Ser  Val Val Met Ala Tyr  Leu Phe Thr
    1070                1075                1080

Thr Phe  Asn Ala Phe Gln Gly  Val Phe Ile Phe Val  Phe His Cys
    1085                1090                1095

Ala Leu  Gln Lys Lys Val His  Lys Glu Tyr Ser Lys  Cys Leu Arg
    1100                1105                1110

His Ser  Tyr Cys Cys Ile Arg  Ser Pro Pro Gly Gly  Thr His Gly
    1115                1120                1125

Ser Leu  Lys Thr Ser Ala Met  Arg Ser Asn Thr Arg  Tyr Tyr Thr
    1130                1135                1140

Gly Thr  Gln Ser Arg Ile Arg  Arg Met Trp Asn Asp  Thr Val Arg
    1145                1150                1155

Lys Gln  Thr Glu Ser Ser Phe  Met Ala Gly Asp Ile  Asn Ser Thr
    1160                1165                1170

Pro Thr  Leu Asn Arg Gly Thr  Met Gly Asn His Leu  Leu Thr Asn
    1175                1180                1185
```

```
Pro Val  Leu Gln Pro Arg Gly  Gly Thr Ser Pro Tyr  Asn Thr Leu
    1190                 1195                 1200

Ile Ala  Glu Ser Val Gly Phe  Asn Pro Ser Ser Pro  Pro Val Phe
    1205                 1210                 1215

Asn Ser  Pro Gly Ser Tyr Arg  Glu Pro Lys His Pro  Leu Gly Gly
    1220                 1225                 1230

Arg Glu  Ala Cys Gly Met Asp  Thr Leu Pro Leu Asn  Gly Asn Phe
    1235                 1240                 1245

Asn Asn  Ser Tyr Ser Leu Arg  Ser Gly Asp Phe Pro  Pro Gly Asp
    1250                 1255                 1260

Gly Gly  Pro Glu Pro Pro Arg  Gly Arg Asn Leu Ala  Asp Ala Ala
    1265                 1270                 1275

Ala Phe  Glu Lys Met Ile Ile  Ser Glu Leu Val His  Asn Asn Leu
    1280                 1285                 1290

Arg Gly  Ser Ser Ser Ala Ala  Lys Gly Pro Pro Pro  Pro Glu Pro
    1295                 1300                 1305

Pro Val  Pro Pro Val Pro Gly  Gly Gly Gly Glu Glu  Glu Ala Gly
    1310                 1315                 1320

Gly Pro  Gly Gly Ala Asp Arg  Ala Glu Ile Glu Leu  Leu Tyr Lys
    1325                 1330                 1335

Ala Leu  Glu Glu Pro Leu Leu  Leu Pro Arg Ala Gln  Ser Val Leu
    1340                 1345                 1350

Tyr Gln  Ser Asp Leu Asp Glu  Ser Glu Ser Cys Thr  Ala Glu Asp
    1355                 1360                 1365

Gly Ala  Thr Ser Arg Pro Leu  Ser Ser Pro Pro Gly  Arg Asp Ser
    1370                 1375                 1380

Leu Tyr  Ala Ser Gly Ala Asn  Leu Arg Asp Ser Pro  Ser Tyr Pro
    1385                 1390                 1395

Asp Ser  Ser Pro Glu Gly Pro  Ser Glu Ala Leu Pro  Pro Pro Pro
    1400                 1405                 1410

Pro Ala  Pro Pro Gly Pro Pro  Glu Ile Tyr Tyr Thr  Ser Arg Pro
    1415                 1420                 1425

Pro Ala  Leu Val Ala Arg Asn  Pro Leu Gln Gly Tyr  Tyr Gln Val
    1430                 1435                 1440

Arg Arg  Pro Ser His Glu Gly  Tyr Leu Ala Ala Pro  Gly Leu Glu
    1445                 1450                 1455

Gly Pro  Gly Pro Asp Gly Asp  Gly Gln Met Gln Leu  Val Thr Ser
    1460                 1465                 1470

Leu


<210> SEQ ID NO 7
<211> LENGTH: 3693
<212> TYPE: DNA
<213> ORGANISM: Homo sapiens

<400> SEQUENCE: 7

atggcgagcg cctcgtacca catttccaat ttgctggaaa aaatgacatc cagcgacaag      60

gactttaggt ttatggctac aaatgatttg atgacggaac tgcagaaaga ttccatcaag     120

ttggatgatg atagtgaaag gaaagtagtg aaaatgattt tgaagttatt ggaagataaa     180

aatggagagg tacagaattt agctgtcaaa tgtcttggtc ctttagtgag taaagtgaaa     240

gaataccaag tagagacaat tgtagatacc ctctgcacta acatgctttc tgataaagaa     300

caacttcgag acatttcaag tattggtctt aaaacagtaa ttggagaact tcctccagct     360
```

```
tccagtggct ctgcattagc tgctaatgta tgtaaaaaga ttactggacg tcttacaagt    420
gcaatagcaa aacaggaaga tgtctctgtt cagctagaag ccttggatat tatggctgat    480
atgttgagca ggcaaggagg acttcttgtt aatttccatc cttcaattct gacctgtcta    540
cttccccagt tgaccagccc tagacttgca gtgaggaaaa gaaccattat cgctcttggc    600
catctggtta tgagctgtgg aaatatagtt tttgtagatc ttattgaaca tctgttgtca    660
gagttgtcca aaaatgattc tatgtcaaca acaagaacct acatacaatg tattgctgct    720
attagtaggc aagctggtca tagaataggt gaataccttg agaagataat tcctttggtg    780
gtaaaatttt gcaatgtaga tgatgatgaa ttaagagagt actgtattca agcctttgaa    840
tcatttgtaa gaagatgtcc taaggaagta tatcctcatg tttctaccat tataaatatt    900
tgtcttaaat atcttaccta tgatccaaat tataattacg atgatgaaga tgaagatgaa    960
aatgcaatgg atgctgatgg tggtgatgat gatgatcaag ggagtgatga tgaatacagt   1020
gatgatgatg acatgagttg gaaagtgaga cgtgcagctg cgaagtgctt ggatgctgta   1080
gttagcacaa ggcatgaaat gcttccagaa ttctacaaga ccgtctctcc tgcactaata   1140
tccagattta aagagcgtga agagaatgta aaggcagatg tttttcacgc ataccttttct  1200
cttttgaagc aaactcgtcc tgtacaaagt tggctatgtg accctgatgc aatggagcag   1260
ggagaaacac ctttaacaat gcttcagagt caggttccca acattgttaa agctcttcac   1320
aaacagatga aagaaaaaag tgtgaagacc cgacagtgtt gttttaacat gttaactgag   1380
ctggtaaatg tattacctgg ggccctaact caacacattc ctgtacttgt accaggaatc   1440
attttctcac tgaatgataa atcaagctca tcgaatttga agatcgatgc tttgtcatgt   1500
ctatacgtaa tcctctgtaa ccattctcct caagtcttcc atcctcacgt tcaggctttg   1560
gttcctccag tggtggcttg tgttggagac ccattttaca aaattacatc tgaagcactt   1620
cttgttactc aacagcttgt caaagtaatt cgtcctttag atcagccttc ctcgtttgat   1680
gcaactcctt atatcaaaga tctatttacc tgtaccatta agagattaaa agcagctgac   1740
attgatcagg aagtcaagga aagggctatt tcctgtatgg gacaaattat ttgcaacctt   1800
ggagacaatt tgggttctga cttgcctaat acacttcaga ttttcttgga gagactaaag   1860
aatgaaatta ccaggttaac tacagtaaag gcattgacac tgattgctgg gtcacctttg   1920
aagatagatt tgaggcctgt tctgggagaa ggggttccta tccttgcttc atttcttaga   1980
aaaaaccaga gagctttgaa actgggtact ctttctgccc ttgatattct aataaaaaac   2040
tatagtgaca gcttgacagc tgccatgatt gatgcagttc tagatgagct cccacctctt   2100
atcagcgaaa gtgatatgca tgtttcacaa atggccatca gttttcttac cactttggca   2160
aaagtatatc cctcctccct ttcaaagata agtggatcca ttctcaatga acttattgga   2220
cttgtgagat caccccttatt gcaggggggga gctcttagtg ccatgctaga ctttttccaa  2280
gctctggttg tcactggaac aaataattta ggatacatgg atttgttgcg catgctgact   2340
ggtccagttt actctcagag cacagctctt actcataagc agtcttatta ttccattgcc   2400
aaatgtgtag ctgcccttac tcgagcatgc cctaaagagg gaccagctgt agtaggtcag   2460
tttattcaag atgtcaagaa ctcaaggtct acagattcca ttcgtctctt agctctactt   2520
tctcttggag aagttgggca tcatattgac ttaagtggac agttggaact aaaatctgta   2580
atactagaag ctttctcatc tcctagtgaa gaagtcaaat cagctgcatc ctatgcatta   2640
ggcagcatta gtgtgggcaa ccttcctgaa tatctgccgt ttgtcctgca agaaataact   2700
```

-continued

```
agtcaaccca aaaggcagta tcttttactt cattccttga aggaaattat tagctctgca   2760

tcagtggtgg gccttaaacc atatgttgaa aacatctggg ccttattact aaagcactgt   2820

gagtgtgcag aggaaggaac cagaaatgtt gttgctgaat gtctaggaaa actcactcta   2880

attgatccag aaactctcct tccacggctt aaggggtact tgatatcagg ctcatcatat   2940

gcccgaagct cagtggttac ggctgtgaaa tttacaattt ctgaccatcc acaacctatt   3000

gatccactgt taaagaactg cataggtgat ttcctaaaaa ctttggaaga cccagatttg   3060

aatgtgagaa gagtagcctt ggtcacattt aattcagcag cacataacaa gccatcatta   3120

ataagggatc tattggatac tgttcttcca catctttaca atgaaacaaa agttagaaag   3180

gagcttataa gagaggtaga aatgggtcca tttaaacata cggttgatga tggtctggat   3240

attagaaagg cagcatttga gtgtatgtac acacttctag acagttgtct tgatagactt   3300

gatatctttg aatttctaaa tcatgttgaa gatggtttga aggaccatta tgatattaag   3360

atgctgacat tttaatgtt ggtgagactg tctacccttt gtccaagtgc agtactgcag   3420

aggttggacc gacttgttga gccattacgt gcaacatgta caactaaggt aaaggcaaac   3480

tcagtaaagc aggagtttga aaaacaagat gaattaaagc gatctgccat gagagcagta   3540

gcagcactgc taaccattcc agaagcagag aagagtccac tgatgagtga attccagtca   3600

cagatcagtt ctaaccctga gctggcggct atctttgaaa gtatccagaa agattcatca   3660

tctactaact tggaatcaat ggacactagt tag                                3693
```

<210> SEQ ID NO 8
<211> LENGTH: 1230
<212> TYPE: PRT
<213> ORGANISM: Homo sapiens

<400> SEQUENCE: 8

```
Met Ala Ser Ala Ser Tyr His Ile Ser Asn Leu Leu Glu Lys Met Thr
1               5                   10                  15

Ser Ser Asp Lys Asp Phe Arg Phe Met Ala Thr Asn Asp Leu Met Thr
            20                  25                  30

Glu Leu Gln Lys Asp Ser Ile Lys Leu Asp Asp Asp Ser Glu Arg Lys
        35                  40                  45

Val Val Lys Met Ile Leu Lys Leu Leu Glu Asp Lys Asn Gly Glu Val
    50                  55                  60

Gln Asn Leu Ala Val Lys Cys Leu Gly Pro Leu Val Ser Lys Val Lys
65                  70                  75                  80

Glu Tyr Gln Val Glu Thr Ile Val Asp Thr Leu Cys Thr Asn Met Leu
                85                  90                  95

Ser Asp Lys Glu Gln Leu Arg Asp Ile Ser Ser Ile Gly Leu Lys Thr
            100                 105                 110

Val Ile Gly Glu Leu Pro Pro Ala Ser Ser Gly Ser Ala Leu Ala Ala
        115                 120                 125

Asn Val Cys Lys Lys Ile Thr Gly Arg Leu Thr Ser Ala Ile Ala Lys
    130                 135                 140

Gln Glu Asp Val Ser Val Gln Leu Glu Ala Leu Asp Ile Met Ala Asp
145                 150                 155                 160

Met Leu Ser Arg Gln Gly Gly Leu Leu Val Asn Phe His Pro Ser Ile
                165                 170                 175

Leu Thr Cys Leu Leu Pro Gln Leu Thr Ser Pro Arg Leu Ala Val Arg
            180                 185                 190

Lys Arg Thr Ile Ile Ala Leu Gly His Leu Val Met Ser Cys Gly Asn
```

-continued

```
        195                 200                 205

Ile Val Phe Val Asp Leu Ile Glu His Leu Leu Ser Glu Leu Ser Lys
    210                 215                 220

Asn Asp Ser Met Ser Thr Thr Arg Thr Tyr Ile Gln Cys Ile Ala Ala
225                 230                 235                 240

Ile Ser Arg Gln Ala Gly His Arg Ile Gly Glu Tyr Leu Glu Lys Ile
                245                 250                 255

Ile Pro Leu Val Val Lys Phe Cys Asn Val Asp Asp Asp Glu Leu Arg
            260                 265                 270

Glu Tyr Cys Ile Gln Ala Phe Glu Ser Phe Val Arg Arg Cys Pro Lys
        275                 280                 285

Glu Val Tyr Pro His Val Ser Thr Ile Ile Asn Ile Cys Leu Lys Tyr
    290                 295                 300

Leu Thr Tyr Asp Pro Asn Tyr Asn Tyr Asp Asp Glu Asp Glu Asp Glu
305                 310                 315                 320

Asn Ala Met Asp Ala Asp Gly Gly Asp Asp Asp Asp Gln Gly Ser Asp
                325                 330                 335

Asp Glu Tyr Ser Asp Asp Asp Asp Met Ser Trp Lys Val Arg Arg Ala
            340                 345                 350

Ala Ala Lys Cys Leu Asp Ala Val Val Ser Thr Arg His Glu Met Leu
        355                 360                 365

Pro Glu Phe Tyr Lys Thr Val Ser Pro Ala Leu Ile Ser Arg Phe Lys
    370                 375                 380

Glu Arg Glu Glu Asn Val Lys Ala Asp Val Phe His Ala Tyr Leu Ser
385                 390                 395                 400

Leu Leu Lys Gln Thr Arg Pro Val Gln Ser Trp Leu Cys Asp Pro Asp
                405                 410                 415

Ala Met Glu Gln Gly Glu Thr Pro Leu Thr Met Leu Gln Ser Gln Val
            420                 425                 430

Pro Asn Ile Val Lys Ala Leu His Lys Gln Met Lys Glu Lys Ser Val
        435                 440                 445

Lys Thr Arg Gln Cys Cys Phe Asn Met Leu Thr Glu Leu Val Asn Val
    450                 455                 460

Leu Pro Gly Ala Leu Thr Gln His Ile Pro Val Leu Val Pro Gly Ile
465                 470                 475                 480

Ile Phe Ser Leu Asn Asp Lys Ser Ser Ser Ser Asn Leu Lys Ile Asp
                485                 490                 495

Ala Leu Ser Cys Leu Tyr Val Ile Leu Cys Asn His Ser Pro Gln Val
            500                 505                 510

Phe His Pro His Val Gln Ala Leu Val Pro Pro Val Val Ala Cys Val
        515                 520                 525

Gly Asp Pro Phe Tyr Lys Ile Thr Ser Glu Ala Leu Leu Val Thr Gln
    530                 535                 540

Gln Leu Val Lys Val Ile Arg Pro Leu Asp Gln Pro Ser Ser Phe Asp
545                 550                 555                 560

Ala Thr Pro Tyr Ile Lys Asp Leu Phe Thr Cys Thr Ile Lys Arg Leu
                565                 570                 575

Lys Ala Ala Asp Ile Asp Gln Glu Val Lys Glu Arg Ala Ile Ser Cys
            580                 585                 590

Met Gly Gln Ile Ile Cys Asn Leu Gly Asp Asn Leu Gly Ser Asp Leu
        595                 600                 605

Pro Asn Thr Leu Gln Ile Phe Leu Glu Arg Leu Lys Asn Glu Ile Thr
    610                 615                 620
```

```
Arg Leu Thr Thr Val Lys Ala Leu Thr Leu Ile Ala Gly Ser Pro Leu
625                 630                 635                 640

Lys Ile Asp Leu Arg Pro Val Leu Gly Glu Gly Val Pro Ile Leu Ala
                645                 650                 655

Ser Phe Leu Arg Lys Asn Gln Arg Ala Leu Lys Leu Gly Thr Leu Ser
            660                 665                 670

Ala Leu Asp Ile Leu Ile Lys Asn Tyr Ser Asp Ser Leu Thr Ala Ala
        675                 680                 685

Met Ile Asp Ala Val Leu Asp Glu Leu Pro Pro Leu Ile Ser Glu Ser
    690                 695                 700

Asp Met His Val Ser Gln Met Ala Ile Ser Phe Leu Thr Thr Leu Ala
705                 710                 715                 720

Lys Val Tyr Pro Ser Ser Leu Ser Lys Ile Ser Gly Ser Ile Leu Asn
                725                 730                 735

Glu Leu Ile Gly Leu Val Arg Ser Pro Leu Leu Gln Gly Gly Ala Leu
            740                 745                 750

Ser Ala Met Leu Asp Phe Phe Gln Ala Leu Val Val Thr Gly Thr Asn
        755                 760                 765

Asn Leu Gly Tyr Met Asp Leu Leu Arg Met Leu Thr Gly Pro Val Tyr
    770                 775                 780

Ser Gln Ser Thr Ala Leu Thr His Lys Gln Ser Tyr Tyr Ser Ile Ala
785                 790                 795                 800

Lys Cys Val Ala Ala Leu Thr Arg Ala Cys Pro Lys Glu Gly Pro Ala
                805                 810                 815

Val Val Gly Gln Phe Ile Gln Asp Val Lys Asn Ser Arg Ser Thr Asp
            820                 825                 830

Ser Ile Arg Leu Leu Ala Leu Leu Ser Leu Gly Glu Val Gly His His
        835                 840                 845

Ile Asp Leu Ser Gly Gln Leu Glu Leu Lys Ser Val Ile Leu Glu Ala
    850                 855                 860

Phe Ser Ser Pro Ser Glu Glu Val Lys Ser Ala Ala Ser Tyr Ala Leu
865                 870                 875                 880

Gly Ser Ile Ser Val Gly Asn Leu Pro Glu Tyr Leu Pro Phe Val Leu
                885                 890                 895

Gln Glu Ile Thr Ser Gln Pro Lys Arg Gln Tyr Leu Leu Leu His Ser
            900                 905                 910

Leu Lys Glu Ile Ile Ser Ser Ala Ser Val Val Gly Leu Lys Pro Tyr
        915                 920                 925

Val Glu Asn Ile Trp Ala Leu Leu Leu Lys His Cys Glu Cys Ala Glu
    930                 935                 940

Glu Gly Thr Arg Asn Val Val Ala Glu Cys Leu Gly Lys Leu Thr Leu
945                 950                 955                 960

Ile Asp Pro Glu Thr Leu Leu Pro Arg Leu Lys Gly Tyr Leu Ile Ser
                965                 970                 975

Gly Ser Ser Tyr Ala Arg Ser Ser Val Val Thr Ala Val Lys Phe Thr
            980                 985                 990

Ile Ser Asp His Pro Gln Pro Ile  Asp Pro Leu Leu Lys  Asn Cys Ile
        995                 1000                1005

Gly Asp  Phe Leu Lys Thr Leu  Glu Asp Pro Asp Leu  Asn Val Arg
    1010                1015                1020

Arg Val  Ala Leu Val Thr Phe  Asn Ser Ala Ala His  Asn Lys Pro
    1025                1030                1035
```

```
Ser Leu  Ile Arg Asp Leu Leu  Asp Thr Val Leu Pro  His Leu Tyr
    1040                 1045                 1050

Asn Glu  Thr Lys Val Arg Lys  Glu Leu Ile Arg Glu  Val Glu Met
    1055                 1060                 1065

Gly Pro  Phe Lys His Thr Val  Asp Asp Gly Leu Asp  Ile Arg Lys
    1070                 1075                 1080

Ala Ala  Phe Glu Cys Met Tyr  Thr Leu Leu Asp Ser  Cys Leu Asp
    1085                 1090                 1095

Arg Leu  Asp Ile Phe Glu Phe  Leu Asn His Val Glu  Asp Gly Leu
    1100                 1105                 1110

Lys Asp  His Tyr Asp Ile Lys  Met Leu Thr Phe Leu  Met Leu Val
    1115                 1120                 1125

Arg Leu  Ser Thr Leu Cys Pro  Ser Ala Val Leu Gln  Arg Leu Asp
    1130                 1135                 1140

Arg Leu  Val Glu Pro Leu Arg  Ala Thr Cys Thr Thr  Lys Val Lys
    1145                 1150                 1155

Ala Asn  Ser Val Lys Gln Glu  Phe Glu Lys Gln Asp  Glu Leu Lys
    1160                 1165                 1170

Arg Ser  Ala Met Arg Ala Val  Ala Ala Leu Leu Thr  Ile Pro Glu
    1175                 1180                 1185

Ala Glu  Lys Ser Pro Leu Met  Ser Glu Phe Gln Ser  Gln Ile Ser
    1190                 1195                 1200

Ser Asn  Pro Glu Leu Ala Ala  Ile Phe Glu Ser Ile  Gln Lys Asp
    1205                 1210                 1215

Ser Ser  Ser Thr Asn Leu Glu  Ser Met Asp Thr Ser
    1220                 1225                 1230


<210> SEQ ID NO 9
<211> LENGTH: 1302
<212> TYPE: DNA
<213> ORGANISM: Homo sapiens

<400> SEQUENCE: 9

atggcaacat caggtgactg tcccagaagt gaatcgcagg gagaagagcc tgctgagtgc     60

agtgaggccg gtctcctgca ggagggagta cagccagagg agtttgtggc catcgcggac    120

tacgctgcca ccgatgagac ccagctcagt tttttgagag gagaaaaaat tcttatcctg    180

agacaaacca ctgcagattg gtggtggggt gagcgtgcgg gctgctgtgg gtacattccg    240

gcaaaccatg tggggaagca cgtggatgag tacgaccccg aggacacgtg gcaggatgaa    300

gagtacttcg gcagctatgg aactctgaaa ctccacttgg agatgttggc agaccagcca    360

cgaacaacta aataccacag tgtcatcctg cagaataaag aatccctgac ggataaagtc    420

atcctggacg tgggctgtgg gactgggatc atcagtctct tctgtgcaca ctatgcgcgg    480

cctagagcgg tgtacgcggt ggaggccagt gagatggcac agcacacggg gcagctggtc    540

ctgcagaacg gctttgctga catcatcacc gtgtaccagc agaaggtgga ggatgtggtg    600

ctgcccgaga aggtggacgt gctggtgtct gagtggatgg ggacctgcct gctgtttgag    660

ttcatgatcg agtccatcct gtatgcccgg gatgcctggc tgaaggagga cggggtcatt    720

tggcccacca tggctgcgtt gcaccttgtg ccctgcagtg ctgataagga ttatcgtagc    780

aaggtgctct tctgggacaa cgcgtacgag ttcaacctca gcgctctgaa atctttagca    840

gttaaggagt ttttttcaaa gcccaagtat aaccacattt tgaaaccaga agactgtctc    900

tctgaaccgt gcactatatt gcagttggac atgagaaccg tgcaaatttc tgatctagag    960
```

-continued

```
accctgaggg gcgagctgcg cttcgacatc aggaaggcgg ggaccctgca cggcttcacg   1020

gcctggttta gcgtccactt ccagagcctg caggaggggc agccgccgca ggtgctcagc   1080

accgggccct tccaccccac cacacactgg aagcagacgc tgttcatgat ggacgaccca   1140

gtccctgtcc atacaggaga cgtggtcacg ggttcagttg tgttgcagag aaacccagtg   1200

tggagaaggc acatgtctgt ggctctgagc tgggctgtca cttccagaca agaccccaca   1260

tctcaaaaag ttggagaaaa agtcttcccc atctggagat ga                      1302


<210> SEQ ID NO 10
<211> LENGTH: 433
<212> TYPE: PRT
<213> ORGANISM: Homo sapiens

<400> SEQUENCE: 10

Met Ala Thr Ser Gly Asp Cys Pro Arg Ser Glu Ser Gln Gly Glu Glu
1               5                   10                  15

Pro Ala Glu Cys Ser Glu Ala Gly Leu Leu Gln Glu Gly Val Gln Pro
            20                  25                  30

Glu Glu Phe Val Ala Ile Ala Asp Tyr Ala Ala Thr Asp Glu Thr Gln
        35                  40                  45

Leu Ser Phe Leu Arg Gly Glu Lys Ile Leu Ile Leu Arg Gln Thr Thr
    50                  55                  60

Ala Asp Trp Trp Trp Gly Glu Arg Ala Gly Cys Cys Gly Tyr Ile Pro
65                  70                  75                  80

Ala Asn His Val Gly Lys His Val Asp Glu Tyr Asp Pro Glu Asp Thr
                85                  90                  95

Trp Gln Asp Glu Glu Tyr Phe Gly Ser Tyr Gly Thr Leu Lys Leu His
            100                 105                 110

Leu Glu Met Leu Ala Asp Gln Pro Arg Thr Thr Lys Tyr His Ser Val
        115                 120                 125

Ile Leu Gln Asn Lys Glu Ser Leu Thr Asp Lys Val Ile Leu Asp Val
    130                 135                 140

Gly Cys Gly Thr Gly Ile Ile Ser Leu Phe Cys Ala His Tyr Ala Arg
145                 150                 155                 160

Pro Arg Ala Val Tyr Ala Val Glu Ala Ser Glu Met Ala Gln His Thr
                165                 170                 175

Gly Gln Leu Val Leu Gln Asn Gly Phe Ala Asp Ile Ile Thr Val Tyr
            180                 185                 190

Gln Gln Lys Val Glu Asp Val Val Leu Pro Glu Lys Val Asp Val Leu
        195                 200                 205

Val Ser Glu Trp Met Gly Thr Cys Leu Leu Phe Glu Phe Met Ile Glu
    210                 215                 220

Ser Ile Leu Tyr Ala Arg Asp Ala Trp Leu Lys Glu Asp Gly Val Ile
225                 230                 235                 240

Trp Pro Thr Met Ala Ala Leu His Leu Val Pro Cys Ser Ala Asp Lys
                245                 250                 255

Asp Tyr Arg Ser Lys Val Leu Phe Trp Asp Asn Ala Tyr Glu Phe Asn
            260                 265                 270

Leu Ser Ala Leu Lys Ser Leu Ala Val Lys Glu Phe Phe Ser Lys Pro
        275                 280                 285

Lys Tyr Asn His Ile Leu Lys Pro Glu Asp Cys Leu Ser Glu Pro Cys
    290                 295                 300

Thr Ile Leu Gln Leu Asp Met Arg Thr Val Gln Ile Ser Asp Leu Glu
305                 310                 315                 320
```

```
Thr Leu Arg Gly Glu Leu Arg Phe Asp Ile Arg Lys Ala Gly Thr Leu
                325                 330                 335

His Gly Phe Thr Ala Trp Phe Ser Val His Phe Gln Ser Leu Gln Glu
            340                 345                 350

Gly Gln Pro Pro Gln Val Leu Ser Thr Gly Pro Phe His Pro Thr Thr
        355                 360                 365

His Trp Lys Gln Thr Leu Phe Met Met Asp Asp Pro Val Pro Val His
    370                 375                 380

Thr Gly Asp Val Val Thr Gly Ser Val Val Leu Gln Arg Asn Pro Val
385                 390                 395                 400

Trp Arg Arg His Met Ser Val Ala Leu Ser Trp Ala Val Thr Ser Arg
                405                 410                 415

Gln Asp Pro Thr Ser Gln Lys Val Gly Glu Lys Val Phe Pro Ile Trp
            420                 425                 430

Arg
```

<210> SEQ ID NO 11
<211> LENGTH: 855
<212> TYPE: DNA
<213> ORGANISM: Homo sapiens

<400> SEQUENCE: 11

```
atggctccgc ggctgtgcag catctctgtg acggcgcggc ggctgctggg gggcccgggg      60

cctcgcgctg gggacgttgc gtctgcagct gcggcgcgtt tctattccaa ggacaatgaa     120

ggcagctggt tccgctccct ctttgttcac aaagtggatc cccggaagga tgcccactcc     180

accctgctgt ccaagaagga aaccagcaac ctctataaga tccagtttca caatgtaaag     240

cctgaatacc tggatgccta caacagcctc acggaggctg tgctgcccaa gcttcacctg     300

gatgaggact acccatgctc actcgtgggc aactggaaca cgtggtatgg ggagcaggac     360

caggcagtgc acctgtggcg attctcaggt ggctacccag ccctcatgga ctgcatgaac     420

aagctcaaaa acaataagga gtacctggag ttccgaaggg agcggagcca gatgctgctg     480

tccaggagaa accagctgct cctcgagttc agcttctgga atgagccaca gcccagaatg     540

ggtcccaaca tctatgagct gaggacatac aagctcaagc caggaaccat gatcgagtgg     600

gggaacaact gggctcgggc catcaagtac cggcaggaga accaggaggc agtgggcggc     660

ttcttctcac agataggaga gctctacgtg gtgcaccatc tctgggccta taaagacctg     720

cagtctcggg aggagactcg aaacgctgcc tggaggaaga gaggctggga tgaaaatgtc     780

tactatacag tcccccctggt gcgacacatg gagtctagga tcatgatccc cttgaagatc     840

tcgcctctgc agtga                                                      855
```

<210> SEQ ID NO 12
<211> LENGTH: 284
<212> TYPE: PRT
<213> ORGANISM: Homo sapiens

<400> SEQUENCE: 12

```
Met Ala Pro Arg Leu Cys Ser Ile Ser Val Thr Ala Arg Arg Leu Leu
1               5                   10                  15

Gly Gly Pro Gly Pro Arg Ala Gly Asp Val Ala Ser Ala Ala Ala Ala
            20                  25                  30

Arg Phe Tyr Ser Lys Asp Asn Glu Gly Ser Trp Phe Arg Ser Leu Phe
        35                  40                  45
```

-continued

```
Val His Lys Val Asp Pro Arg Lys Asp Ala His Ser Thr Leu Leu Ser
    50                  55                  60

Lys Lys Glu Thr Ser Asn Leu Tyr Lys Ile Gln Phe His Asn Val Lys
65                  70                  75                  80

Pro Glu Tyr Leu Asp Ala Tyr Asn Ser Leu Thr Glu Ala Val Leu Pro
                85                  90                  95

Lys Leu His Leu Asp Glu Asp Tyr Pro Cys Ser Leu Val Gly Asn Trp
            100                 105                 110

Asn Thr Trp Tyr Gly Glu Gln Asp Gln Ala Val His Leu Trp Arg Phe
        115                 120                 125

Ser Gly Gly Tyr Pro Ala Leu Met Asp Cys Met Asn Lys Leu Lys Asn
    130                 135                 140

Asn Lys Glu Tyr Leu Glu Phe Arg Arg Glu Arg Ser Gln Met Leu Leu
145                 150                 155                 160

Ser Arg Arg Asn Gln Leu Leu Leu Glu Phe Ser Phe Trp Asn Glu Pro
                165                 170                 175

Gln Pro Arg Met Gly Pro Asn Ile Tyr Glu Leu Arg Thr Tyr Lys Leu
            180                 185                 190

Lys Pro Gly Thr Met Ile Glu Trp Gly Asn Asn Trp Ala Arg Ala Ile
        195                 200                 205

Lys Tyr Arg Gln Glu Asn Gln Glu Ala Val Gly Gly Phe Phe Ser Gln
    210                 215                 220

Ile Gly Glu Leu Tyr Val Val His His Leu Trp Ala Tyr Lys Asp Leu
225                 230                 235                 240

Gln Ser Arg Glu Glu Thr Arg Asn Ala Ala Trp Arg Lys Arg Gly Trp
                245                 250                 255

Asp Glu Asn Val Tyr Tyr Thr Val Pro Leu Val Arg His Met Glu Ser
            260                 265                 270

Arg Ile Met Ile Pro Leu Lys Ile Ser Pro Leu Gln
        275                 280
```

```
<210> SEQ ID NO 13
<211> LENGTH: 3309
<212> TYPE: DNA
<213> ORGANISM: Homo sapiens

<400> SEQUENCE: 13

atgaaccacc agcagcagca gcagcagcag aaagcgggcg agcagcagtt gagcgagccc      60

gaggacatgg agatggaagc gggagataca gatgacccac caagaattac tcagaaccct     120

gtgatcaatg ggaatgtggc cctgagtgat ggacacaaca ccgcggagga ggacatggag     180

gatgacacca gttggcgctc cgaggcaacc tttcagttca ctgtggagcg cttcagcaga     240

ctgagtgagt cggtccttag ccctccgtgt tttgtgcgaa atctgccatg gaagattatg     300

gtgatgccac gcttttatcc agacagacca caccaaaaaa gcgtaggatt ctttctccag     360

tgcaatgctg aatctgattc cacgtcatgg tcttgccatg cacaagcagt gctgaagata     420

ataaattaca gagatgatga aaagtcgttc agtcgtcgta ttagtcattt gttcttccat     480

aaagaaaatg attggggatt ttccaatttt atggcctgga gtgaagtgac cgatcctgag     540

aaaggattta tagatgatga caaagttacc tttgaagtct ttgtacaggc ggatgctccc     600

catggagttg cgtgggattc aaagaagcac acaggctacg tcggcttaaa gaatcaggga     660

gcgacttgtt acatgaacag cctgctacag acgttatttt tcacgaatca gctacgaaag     720

gctgtgtaca tgatgccaac cgagggggat gattcgtcta aaagcgtccc tttagcatta     780
```

-continued caaagagtgt tctatgaatt acagcatagt gataaacctg taggaacaaa aaagttaaca 840
aagtcatttg ggtgggaaac tttagatagc ttcatgcaac atgatgttca ggagctttgt 900
cgagtgttgc tcgataatgt ggaaaataag atgaaaggca cctgtgtaga gggcaccata 960
cccaaattat tccgcggcaa aatggtgtcc tatatccagt gtaaagaagt agactatcgg 1020
tctgatagaa gagaagatta ttatgatatc cagctaagta tcaaaggaaa gaaaaatata 1080
tttgaatcat ttgtggatta tgtggcagta gaacagctcg atggggacaa taaatacgac 1140
gctggggaac atggcttaca ggaagcagag aaaggtgtga aattcctaac attgccacca 1200
gtgttacatc tacaactgat gagatttatg tatgaccctc agacggacca aaatatcaag 1260
atcaatgata ggtttgaatt cccagagcag ttaccacttg atgaattttt gcaaaaaaca 1320
gatcctaagg accctgcaaa ttatattctt catgcagtcc tggttcatag tggagataat 1380
catggtggac attatgtggt ttatctaaac cccaaagggg atggcaaatg gtgtaaattt 1440
gatgacgacg tggtgtcaag gtgtactaaa gaggaagcaa ttgagcacaa ttatgggggt 1500
cacgatgacg acctgtctgt tcgacactgc actaatgctt acatgttagt ctacatcagg 1560
gaatcaaaac tgagtgaagt tttacaggcg gtcaccgacc atgatattcc tcagcagttg 1620
gtggagcgat tacaagaaga gaaaaggatc gaggctcaga agcggaagga gcggcaggaa 1680
gcccatctct atatgcaagt gcagatagtc gcagaggacc agttttgtgg ccaccaaggg 1740
aatgacatgt acgatgaaga aaaagtgaaa tacactgtgt tcaaagtatt gaagaactcc 1800
tcgcttgctg agtttgttca gagcctctct cagaccatgg gatttccaca agatcaaatt 1860
cgattgtggc ccatgcaagc aaggagtaat ggaacaaaac gaccagcaat gttagataat 1920
gaagccgacg gcaataaaac aatgattgag ctcagtgata atgaaaaccc ttggacaata 1980
ttcctggaaa cagttgatcc cgagctggct gctagtggag cgaccttacc caagtttgat 2040
aaagatcatg atgtaatgtt atttttgaag atgtatgatc ccaaaacgcg gagcttgaat 2100
tactgtgggc atatctacac accaatatcc tgtaaaatac gtgacttgct cccagttatg 2160
tgtgacagag caggatttat tcaagatact agccttatcc tctatgagga agttaaaccg 2220
aatttaacag agagaattca ggactatgac gtgtctcttg ataaagccct tgatgaacta 2280
atggatggtg acatcatagt atttcagaag gatgaccctg aaaatgataa cagtgaatta 2340
cccaccgcaa aggagtattt ccgagatctc taccaccgcg ttgatgtcat tttctgtgat 2400
aaaacaatcc ctaatgatcc tggatttgtg gttacgttat caaatagaat gaattatttt 2460
caggttgcaa agacagttgc acagaggctc aacacagatc caatgttgct gcagtttttc 2520
aagtctcaag gttataggga tggcccaggt aatcctctta gacataatta tgaaggtact 2580
ttaagagatc ttctacagtt cttcaagcct agacaaccta agaaacttta ctatcagcag 2640
cttaagatga aaatcacaga ctttgagaac aggcgaagtt ttaaatgtat atggttaaac 2700
agccaattta gggaagagga aataacacta tatccagaca agcatgggtg tgtccgggac 2760
ctgttagaag aatgtaaaaa ggccgtggag cttggggaga aagcatcagg gaaacttagg 2820
ctgctagaaa ttgtaagcta caaaatcatt ggtgttcatc aagaagatga actattagaa 2880
tgtttatctc ctgcaacgag ccggacgttt cgaatagagg aaatcccttt ggaccaggtg 2940
gacatagaca aagagaatga gatgcttgtc acagtggcgc atttccacaa agaggtcttc 3000
ggaacgttcg gaatcccgtt tttgctgagg atacaccagg gcgagcattt tcgagaagtg 3060
atgaagcgaa tccagagcct gctggacatc caggagaagg agtttgagaa gtttaaattt 3120
gcaattgtaa tgatgggccg acaccagtac ataaatgaag acgagtatga agtaaatttg 3180

-continued aaagactttg agccacagcc cggtaatatg tctcatcctc ggccttggct agggctcgac 3240
cacttcaaca aagccccaaa gaggagtcgc tacacttacc ttgaaaaggc cattaaaatc 3300
cataactga 3309

<210> SEQ ID NO 14
<211> LENGTH: 1102
<212> TYPE: PRT
<213> ORGANISM: Homo sapiens

<400> SEQUENCE: 14

Met Asn His Gln Gln Gln Gln Gln Gln Gln Lys Ala Gly Glu Gln Gln
1 5 10 15

Leu Ser Glu Pro Glu Asp Met Glu Met Glu Ala Gly Asp Thr Asp Asp
20 25 30

Pro Pro Arg Ile Thr Gln Asn Pro Val Ile Asn Gly Asn Val Ala Leu
35 40 45

Ser Asp Gly His Asn Thr Ala Glu Glu Asp Met Glu Asp Asp Thr Ser
50 55 60

Trp Arg Ser Glu Ala Thr Phe Gln Phe Thr Val Glu Arg Phe Ser Arg
65 70 75 80

Leu Ser Glu Ser Val Leu Ser Pro Pro Cys Phe Val Arg Asn Leu Pro
85 90 95

Trp Lys Ile Met Val Met Pro Arg Phe Tyr Pro Asp Arg Pro His Gln
100 105 110

Lys Ser Val Gly Phe Phe Leu Gln Cys Asn Ala Glu Ser Asp Ser Thr
115 120 125

Ser Trp Ser Cys His Ala Gln Ala Val Leu Lys Ile Ile Asn Tyr Arg
130 135 140

Asp Asp Glu Lys Ser Phe Ser Arg Arg Ile Ser His Leu Phe Phe His
145 150 155 160

Lys Glu Asn Asp Trp Gly Phe Ser Asn Phe Met Ala Trp Ser Glu Val
165 170 175

Thr Asp Pro Glu Lys Gly Phe Ile Asp Asp Asp Lys Val Thr Phe Glu
180 185 190

Val Phe Val Gln Ala Asp Ala Pro His Gly Val Ala Trp Asp Ser Lys
195 200 205

Lys His Thr Gly Tyr Val Gly Leu Lys Asn Gln Gly Ala Thr Cys Tyr
210 215 220

Met Asn Ser Leu Leu Gln Thr Leu Phe Phe Thr Asn Gln Leu Arg Lys
225 230 235 240

Ala Val Tyr Met Met Pro Thr Glu Gly Asp Asp Ser Ser Lys Ser Val
245 250 255

Pro Leu Ala Leu Gln Arg Val Phe Tyr Glu Leu Gln His Ser Asp Lys
260 265 270

Pro Val Gly Thr Lys Lys Leu Thr Lys Ser Phe Gly Trp Glu Thr Leu
275 280 285

Asp Ser Phe Met Gln His Asp Val Gln Glu Leu Cys Arg Val Leu Leu
290 295 300

Asp Asn Val Glu Asn Lys Met Lys Gly Thr Cys Val Glu Gly Thr Ile
305 310 315 320

Pro Lys Leu Phe Arg Gly Lys Met Val Ser Tyr Ile Gln Cys Lys Glu
325 330 335

Val Asp Tyr Arg Ser Asp Arg Arg Glu Asp Tyr Tyr Asp Ile Gln Leu

```
            340                 345                 350

Ser Ile Lys Gly Lys Lys Asn Ile Phe Glu Ser Phe Val Asp Tyr Val
        355                 360                 365

Ala Val Glu Gln Leu Asp Gly Asp Asn Lys Tyr Asp Ala Gly Glu His
    370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
        435                 440                 445

Ile Leu His Ala Val Leu Val His Ser Gly Asp Asn His Gly Gly His
    450                 455                 460

Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Asp Leu Ser Val Arg His Cys Thr Asn
            500                 505                 510

Ala Tyr Met Leu Val Tyr Ile Arg Glu Ser Lys Leu Ser Glu Val Leu
        515                 520                 525

Gln Ala Val Thr Asp His Asp Ile Pro Gln Gln Leu Val Glu Arg Leu
    530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
    610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
    690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765
```

```
Gln Lys Asp Asp Pro Glu Asn Asp Asn Ser Glu Leu Pro Thr Ala Lys
    770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830

Asp Pro Met Leu Leu Gln Phe Phe Lys Ser Gln Gly Tyr Arg Asp Gly
        835                 840                 845

Pro Gly Asn Pro Leu Arg His Asn Tyr Glu Gly Thr Leu Arg Asp Leu
    850                 855                 860

Leu Gln Phe Phe Lys Pro Arg Gln Pro Lys Lys Leu Tyr Tyr Gln Gln
865                 870                 875                 880

Leu Lys Met Lys Ile Thr Asp Phe Glu Asn Arg Arg Ser Phe Lys Cys
                885                 890                 895

Ile Trp Leu Asn Ser Gln Phe Arg Glu Glu Glu Ile Thr Leu Tyr Pro
            900                 905                 910

Asp Lys His Gly Cys Val Arg Asp Leu Leu Glu Glu Cys Lys Lys Ala
        915                 920                 925

Val Glu Leu Gly Glu Lys Ala Ser Gly Lys Leu Arg Leu Leu Glu Ile
    930                 935                 940

Val Ser Tyr Lys Ile Ile Gly Val His Gln Glu Asp Glu Leu Leu Glu
945                 950                 955                 960

Cys Leu Ser Pro Ala Thr Ser Arg Thr Phe Arg Ile Glu Glu Ile Pro
                965                 970                 975

Leu Asp Gln Val Asp Ile Asp Lys Glu Asn Glu Met Leu Val Thr Val
            980                 985                 990

Ala His Phe His Lys Glu Val Phe  Gly Thr Phe Gly Ile  Pro Phe Leu
        995                 1000                1005

Leu Arg  Ile His Gln Gly Glu  His Phe Arg Glu Val  Met Lys Arg
    1010                1015                1020

Ile Gln  Ser Leu Leu Asp Ile  Gln Glu Lys Glu Phe  Glu Lys Phe
    1025                1030                1035

Lys Phe  Ala Ile Val Met Met  Gly Arg His Gln Tyr  Ile Asn Glu
    1040                1045                1050

Asp Glu  Tyr Glu Val Asn Leu  Lys Asp Phe Glu Pro  Gln Pro Gly
    1055                1060                1065

Asn Met  Ser His Pro Arg Pro  Trp Leu Gly Leu Asp  His Phe Asn
    1070                1075                1080

Lys Ala  Pro Lys Arg Ser Arg  Tyr Thr Tyr Leu Glu  Lys Ala Ile
    1085                1090                1095

Lys Ile  His Asn
    1100
```

<210> SEQ ID NO 15
<211> LENGTH: 4632
<212> TYPE: DNA
<213> ORGANISM: Homo sapiens

<400> SEQUENCE: 15

```
atgtatgcag cagtggaaca tgggcctgtg ctttgcagcg attccaacat cctgtgcctg      60

tcctggaagg ggcgtgtccc caagagtgag aaggagaagc ctgtgtgcag gagacgctac     120
```

-continued

```
tatgaggaag gctggctggc cacgggcaac gggcgaggag tggttggggt gactttcacc    180
tctagtcact gtcgcaggga caggagtact ccacagagga taaatttcaa cctccggggc    240
cacaatagcg aggttgtgct ggtgaggtgg aatgagccct accagaaact ggccacgtgc    300
gatgcggacg gaggcatatt cgtgtggatt cagtacgagg gcaggtggtc tgtggagctg    360
gtcaacgacc gcggggcgca ggtgagtgat ttcacgtgga gccatgatgg aactcaagca    420
cttatttcct atcgagatgg gtttgtcctg gttgggtctg tcagtggaca aagacactgg    480
tcatccgaaa tcaacttgga aagtcaaatt acgtgtggca tatggactcc tgacgaccaa    540
caggtgctgt ttggcacggc cgatgggcag gtgattgtca tggattgcca cggcagaatg    600
ctggcccacg tcctcttgca cgagtcagac ggtgtcctcg gcatgtcctg gaactacccg    660
atcttcctgg tggaggacag cagcgagagc gacacggact cagatgacta cgcccctccc    720
caagatggtc cggcagcata tcccatccca gtgcagaaca tcaagcctct gctcaccgtc    780
agcttcacct cgggagacat cagcttaatg aacaactacg atgacttgtc tcccacggtc    840
atccgctcag ggctgaaaga ggtggtagcc cagtggtgca cacaggggga cttgctggca    900
gtcgctggga tggaacggca gacccagctt ggtgagcttc ccaatggtcc ccttctgaag    960
agtgccatgg tcaagttcta caatgttcgt ggggagcaca tcttcacact ggacactctc   1020
gtgcagcgcc ccatcatctc catctgctgg ggtcaccggg attcgaggct gttgatggca   1080
tcaggaccag ccctgtacgt ggtgcgtgtg gagcaccggg tgtccagcct gcagctgctg   1140
tgccagcagg ccatcgccag caccttgcgt gaggacaagg acgtcagcaa gctgactctg   1200
ccccccgcc tctgctccta cctctccact gccttcatcc ccaccatcaa gcccccaatt    1260
ccagatccga acaacatgag agactttgtc agctacccat cagccggcaa cgagcggctg   1320
cactgcacca tgaagcgcac agaggacgac ccggaggtgg gcggcccgtg ctacacgctc   1380
tacctggagt acctgggcgg gcttgtgccc atcctcaaag ggcggcgcat cagcaagctg   1440
cggccagagt tcgtcatcat ggacccgcgg acagatagca aaccagatga aatctatggg   1500
aacagcttga tttctactgt gatcgacagc tgcaactgct cagactccag tgacattgag   1560
ctgagtgatg actgggctgc caagaaatct cccaaaatct ccagagctag caaatcaccc   1620
aaactcccaa ggatcagcat tgaggcccgc aagtcaccca agctgccccg ggctgctcag   1680
gagctctccc ggtccccacg gttgcccctg cgcaagccct ctgtgggctc gcccagcctg   1740
actcggagag agtttccttt tgaagacatc actcagcaca actatcttgc tcaggtcacg   1800
tctaatatct ggggaaccaa atttaagatt gtgggcttgg ctgctttcct gccaaccaac   1860
ctcggtgcag taatctataa aaccagcctc ctgcatctcc agccgcggca gatgaccatt   1920
tatctcccag aagttcggaa aatttccatg gactatatta atttacctgt cttcaaccca   1980
aatgttttca gtgaagatga agatgattta ccagtgacag gagcatctgg tgtccctgag   2040
aacagcccac cttgtaccgt gaacatccct attgcaccga tccacagctc ggctcaggct   2100
atgtccccca cgcagagcat agggctggtg cagtccctac tggccaatca gaatgtgcag   2160
ctagatgtcc tgaccaacca gacgacagct gtagggacag cagaacatgc aggtgacagt   2220
gccacccagt acccagtctc caaccggtac tccaatcctg gacaggtgat tttcggaagc   2280
gtggaaatgg gccgcatcat tcagaacccc cctccactgt ccctgcctcc cccgccgcag   2340
gggcccatgc agctgtccac ggtgggccat ggagaccgag accacgaaca cctgcagaag   2400
tcagccaagg ccctgcggcc aacaccgcag ctggcagctg agggggacgc agtggtcttt   2460
agtgcccccc aggaggtcca ggtgacgaag ataaaccctc cacccccgta cccaggaacc   2520
```

```
atccccgctg cccccaccac agcagcaccc ccgccccctc tgccgccccc acagccccca   2580
gtggatgtgt gcttgaagaa gggcgacttc tccctctacc ccacgtcagt gcactaccag   2640
accccccctgg gctatgagag gatcaccacc ttcgacagca gtggcaacgt ggaggaggtg   2700
tgccggcccc gcacccggat gctgtgctcc cagaacacgt acaccctccc cggcccgggt   2760
agctctgcca ccttgaggct cacggccact gagaagaagg tccctcagcc ctgcagcagt   2820
gccaccctga accgcctgac cgtccctcgc tactccatcc ccaccgggga cccacccccg   2880
tatcctgaaa ttgccagcca gctggcccag gggcgggggg ctgcccagag gtccgacaat   2940
agcctcatcc acgctaccct gcggaggaac aaccgtgagg ctacgctcaa gatggcccag   3000
ctggccgaca gcccgcgggc ccccctgcag cccctggcca agtccaaggg cgggcccggg   3060
ggggtggtga cacagctccc agcgcggccc ccacctgccc tgtacacctg cagtcagtgc   3120
agtggcacag ggcccagctc acagcccgga gcctccctgg cccataccgc cagcgcctcc   3180
ccgttggcct cccagtcctc ctacagcctc ctgagcccac ccgacagcgc ccgcgaccgc   3240
accgactacg tcaactcggc cttcacggag gacgaggccc tgtcccagca ctgtcagctt   3300
gagaagccct tgaggcaccc tcccctgcct gaagctgctg tcaccctgaa acggccaccc   3360
ccttaccagt gggaccccat gctgggtgag gatgtttggg ttcctcaaga aaggacagca   3420
cagacttcag ggcccaaccc cttaaaactg tcctctctga tgctgagtca gggccagcac   3480
ctggacgtgt cccgactgcc cttcatctcc cccaagtctc ctgccagccc cactgccact   3540
ttccaaacag gctatgggat gggagtgcca tatccaggaa gctataacaa ccccccctttg   3600
cctggagtgc aggctccctg ctctcccaaa gatgccctgt ccccaacgca gtttgcacaa   3660
caggagcctg ctgtggtcct tcagccgctg tacccaccca gcctctccta ttgcaccctg   3720
ccccccatgt acccaggaag cagcacgtgc tctagtttac agctgccacc tgtcgccttg   3780
catccatgga gttcctacag cgcctgcccg cccatgcaga acccccaggg cactctcccc   3840
ccaaagccac acttggtggt ggagaagccc cttgtgtccc caccacctgc cgacctccaa   3900
agccacttgg gcacagaggt gatggtagag actgcagaca acttccagga agtcctctcc   3960
ctgaccgaaa gcccagtccc ccagcggaca gaaaaatttg gaaagaagaa ccggaagcgc   4020
ctggacagcc gagcagaaga aggcagcgtt caggccatca ctgagggcaa agtgaagaag   4080
gaggctagga ctttgagtga ctttaattcc ctaatctcca gcccacacct ggggagagag   4140
aagaagaaag tgaagagtca gaaagaccaa ctgaagtcaa agaagttgaa taagacaaac   4200
gagttccagg acagctccga gagcgagcct gagctgttca tcagcgggga tgagctcatg   4260
aaccagagcc agggcagcag aaagggctgg aaaagcaagc gctccccacg ggccgccggc   4320
gagctggagg aggccaagtg ccggcgggcc agtgagaagg aggacgggcg gctgggcagc   4380
caaggcttcg tgtacgtgat ggccaacaag cagccgctgt ggaacgaggc cacccaggtc   4440
taccagctgg acttcggggg gcgggtgacc caggagtccg ccaagaactt ccagattgag   4500
ttagaggggc ggcaggtgat gcagtttgga cggattgatg gcagtgcgta cattctagac   4560
ttccagtatc cgttctcagc cgtgcaggcc tttgcagttg ccctggccaa cgtgactcag   4620
cgcctcaaat ga                                                       4632
```

<210> SEQ ID NO 16
<211> LENGTH: 1543
<212> TYPE: PRT
<213> ORGANISM: Homo sapiens

<400> SEQUENCE: 16

Met Tyr Ala Ala Val Glu His Gly Pro Val Leu Cys Ser Asp Ser Asn
1 5 10 15

Ile Leu Cys Leu Ser Trp Lys Gly Arg Val Pro Lys Ser Glu Lys Glu
20 25 30

Lys Pro Val Cys Arg Arg Arg Tyr Tyr Glu Glu Gly Trp Leu Ala Thr
35 40 45

Gly Asn Gly Arg Gly Val Val Gly Val Thr Phe Thr Ser Ser His Cys
50 55 60

Arg Arg Asp Arg Ser Thr Pro Gln Arg Ile Asn Phe Asn Leu Arg Gly
65 70 75 80

His Asn Ser Glu Val Val Leu Val Arg Trp Asn Glu Pro Tyr Gln Lys
85 90 95

Leu Ala Thr Cys Asp Ala Asp Gly Gly Ile Phe Val Trp Ile Gln Tyr
100 105 110

Glu Gly Arg Trp Ser Val Glu Leu Val Asn Asp Arg Gly Ala Gln Val
115 120 125

Ser Asp Phe Thr Trp Ser His Asp Gly Thr Gln Ala Leu Ile Ser Tyr
130 135 140

Arg Asp Gly Phe Val Leu Val Gly Ser Val Ser Gly Gln Arg His Trp
145 150 155 160

Ser Ser Glu Ile Asn Leu Glu Ser Gln Ile Thr Cys Gly Ile Trp Thr
165 170 175

Pro Asp Asp Gln Gln Val Leu Phe Gly Thr Ala Asp Gly Gln Val Ile
180 185 190

Val Met Asp Cys His Gly Arg Met Leu Ala His Val Leu Leu His Glu
195 200 205

Ser Asp Gly Val Leu Gly Met Ser Trp Asn Tyr Pro Ile Phe Leu Val
210 215 220

Glu Asp Ser Ser Glu Ser Asp Thr Asp Ser Asp Asp Tyr Ala Pro Pro
225 230 235 240

Gln Asp Gly Pro Ala Ala Tyr Pro Ile Pro Val Gln Asn Ile Lys Pro
245 250 255

Leu Leu Thr Val Ser Phe Thr Ser Gly Asp Ile Ser Leu Met Asn Asn
260 265 270

Tyr Asp Asp Leu Ser Pro Thr Val Ile Arg Ser Gly Leu Lys Glu Val
275 280 285

Val Ala Gln Trp Cys Thr Gln Gly Asp Leu Leu Ala Val Ala Gly Met
290 295 300

Glu Arg Gln Thr Gln Leu Gly Glu Leu Pro Asn Gly Pro Leu Leu Lys
305 310 315 320

Ser Ala Met Val Lys Phe Tyr Asn Val Arg Gly Glu His Ile Phe Thr
325 330 335

Leu Asp Thr Leu Val Gln Arg Pro Ile Ile Ser Ile Cys Trp Gly His
340 345 350

Arg Asp Ser Arg Leu Leu Met Ala Ser Gly Pro Ala Leu Tyr Val Val
355 360 365

Arg Val Glu His Arg Val Ser Ser Leu Gln Leu Leu Cys Gln Gln Ala
370 375 380

Ile Ala Ser Thr Leu Arg Glu Asp Lys Asp Val Ser Lys Leu Thr Leu
385 390 395 400

Pro Pro Arg Leu Cys Ser Tyr Leu Ser Thr Ala Phe Ile Pro Thr Ile
405 410 415

-continued

```
Lys Pro Pro Ile Pro Asp Pro Asn Asn Met Arg Asp Phe Val Ser Tyr
            420                 425                 430

Pro Ser Ala Gly Asn Glu Arg Leu His Cys Thr Met Lys Arg Thr Glu
        435                 440                 445

Asp Asp Pro Glu Val Gly Gly Pro Cys Tyr Thr Leu Tyr Leu Glu Tyr
    450                 455                 460

Leu Gly Gly Leu Val Pro Ile Leu Lys Gly Arg Arg Ile Ser Lys Leu
465                 470                 475                 480

Arg Pro Glu Phe Val Ile Met Asp Pro Arg Thr Asp Ser Lys Pro Asp
                485                 490                 495

Glu Ile Tyr Gly Asn Ser Leu Ile Ser Thr Val Ile Asp Ser Cys Asn
            500                 505                 510

Cys Ser Asp Ser Ser Asp Ile Glu Leu Ser Asp Asp Trp Ala Ala Lys
        515                 520                 525

Lys Ser Pro Lys Ile Ser Arg Ala Ser Lys Ser Pro Lys Leu Pro Arg
    530                 535                 540

Ile Ser Ile Glu Ala Arg Lys Ser Pro Lys Leu Pro Arg Ala Ala Gln
545                 550                 555                 560

Glu Leu Ser Arg Ser Pro Arg Leu Pro Leu Arg Lys Pro Ser Val Gly
                565                 570                 575

Ser Pro Ser Leu Thr Arg Arg Glu Phe Pro Phe Glu Asp Ile Thr Gln
            580                 585                 590

His Asn Tyr Leu Ala Gln Val Thr Ser Asn Ile Trp Gly Thr Lys Phe
        595                 600                 605

Lys Ile Val Gly Leu Ala Ala Phe Leu Pro Thr Asn Leu Gly Ala Val
    610                 615                 620

Ile Tyr Lys Thr Ser Leu Leu His Leu Gln Pro Arg Gln Met Thr Ile
625                 630                 635                 640

Tyr Leu Pro Glu Val Arg Lys Ile Ser Met Asp Tyr Ile Asn Leu Pro
                645                 650                 655

Val Phe Asn Pro Asn Val Phe Ser Glu Asp Glu Asp Asp Leu Pro Val
            660                 665                 670

Thr Gly Ala Ser Gly Val Pro Glu Asn Ser Pro Pro Cys Thr Val Asn
        675                 680                 685

Ile Pro Ile Ala Pro Ile His Ser Ser Ala Gln Ala Met Ser Pro Thr
    690                 695                 700

Gln Ser Ile Gly Leu Val Gln Ser Leu Leu Ala Asn Gln Asn Val Gln
705                 710                 715                 720

Leu Asp Val Leu Thr Asn Gln Thr Thr Ala Val Gly Thr Ala Glu His
                725                 730                 735

Ala Gly Asp Ser Ala Thr Gln Tyr Pro Val Ser Asn Arg Tyr Ser Asn
            740                 745                 750

Pro Gly Gln Val Ile Phe Gly Ser Val Glu Met Gly Arg Ile Ile Gln
        755                 760                 765

Asn Pro Pro Pro Leu Ser Leu Pro Pro Pro Pro Gln Gly Pro Met Gln
    770                 775                 780

Leu Ser Thr Val Gly His Gly Asp Arg Asp His Glu His Leu Gln Lys
785                 790                 795                 800

Ser Ala Lys Ala Leu Arg Pro Thr Pro Gln Leu Ala Ala Glu Gly Asp
                805                 810                 815

Ala Val Val Phe Ser Ala Pro Gln Glu Val Gln Val Thr Lys Ile Asn
            820                 825                 830
```

```
Pro Pro Pro Pro Tyr Pro Gly Thr Ile Pro Ala Ala Pro Thr Thr Ala
        835                 840                 845

Ala Pro Pro Pro Pro Leu Pro Pro Pro Gln Pro Pro Val Asp Val Cys
    850                 855                 860

Leu Lys Lys Gly Asp Phe Ser Leu Tyr Pro Thr Ser Val His Tyr Gln
865                 870                 875                 880

Thr Pro Leu Gly Tyr Glu Arg Ile Thr Thr Phe Asp Ser Ser Gly Asn
                885                 890                 895

Val Glu Glu Val Cys Arg Pro Arg Thr Arg Met Leu Cys Ser Gln Asn
            900                 905                 910

Thr Tyr Thr Leu Pro Gly Pro Gly Ser Ser Ala Thr Leu Arg Leu Thr
        915                 920                 925

Ala Thr Glu Lys Lys Val Pro Gln Pro Cys Ser Ser Ala Thr Leu Asn
    930                 935                 940

Arg Leu Thr Val Pro Arg Tyr Ser Ile Pro Thr Gly Asp Pro Pro Pro
945                 950                 955                 960

Tyr Pro Glu Ile Ala Ser Gln Leu Ala Gln Gly Arg Gly Ala Ala Gln
                965                 970                 975

Arg Ser Asp Asn Ser Leu Ile His Ala Thr Leu Arg Arg Asn Asn Arg
            980                 985                 990

Glu Ala Thr Leu Lys Met Ala Gln  Leu Ala Asp Ser Pro  Arg Ala Pro
        995                 1000                 1005

Leu Gln  Pro Leu Ala Lys Ser  Lys Gly Gly Pro Gly  Gly Val Val
    1010                 1015                 1020

Thr Gln  Leu Pro Ala Arg Pro  Pro Pro Ala Leu Tyr  Thr Cys Ser
    1025                 1030                 1035

Gln Cys  Ser Gly Thr Gly Pro  Ser Ser Gln Pro Gly  Ala Ser Leu
    1040                 1045                 1050

Ala His  Thr Ala Ser Ala Ser  Pro Leu Ala Ser Gln  Ser Ser Tyr
    1055                 1060                 1065

Ser Leu  Leu Ser Pro Pro Asp  Ser Ala Arg Asp Arg  Thr Asp Tyr
    1070                 1075                 1080

Val Asn  Ser Ala Phe Thr Glu  Asp Glu Ala Leu Ser  Gln His Cys
    1085                 1090                 1095

Gln Leu  Glu Lys Pro Leu Arg  His Pro Pro Leu Pro  Glu Ala Ala
    1100                 1105                 1110

Val Thr  Leu Lys Arg Pro Pro  Pro Tyr Gln Trp Asp  Pro Met Leu
    1115                 1120                 1125

Gly Glu  Asp Val Trp Val Pro  Gln Glu Arg Thr Ala  Gln Thr Ser
    1130                 1135                 1140

Gly Pro  Asn Pro Leu Lys Leu  Ser Ser Leu Met Leu  Ser Gln Gly
    1145                 1150                 1155

Gln His  Leu Asp Val Ser Arg  Leu Pro Phe Ile Ser  Pro Lys Ser
    1160                 1165                 1170

Pro Ala  Ser Pro Thr Ala Thr  Phe Gln Thr Gly Tyr  Gly Met Gly
    1175                 1180                 1185

Val Pro  Tyr Pro Gly Ser Tyr  Asn Asn Pro Pro Leu  Pro Gly Val
    1190                 1195                 1200

Gln Ala  Pro Cys Ser Pro Lys  Asp Ala Leu Ser Pro  Thr Gln Phe
    1205                 1210                 1215

Ala Gln  Gln Glu Pro Ala Val  Val Leu Gln Pro Leu  Tyr Pro Pro
    1220                 1225                 1230

Ser Leu  Ser Tyr Cys Thr Leu  Pro Pro Met Tyr Pro  Gly Ser Ser
```

```
    1235                1240                1245

Thr Cys  Ser Ser Leu Gln Leu  Pro Pro Val Ala Leu  His Pro Trp
    1250                1255                1260

Ser Ser  Tyr Ser Ala Cys Pro  Pro Met Gln Asn Pro  Gln Gly Thr
    1265                1270                1275

Leu Pro  Pro Lys Pro His Leu  Val Val Glu Lys Pro  Leu Val Ser
    1280                1285                1290

Pro Pro  Pro Ala Asp Leu Gln  Ser His Leu Gly Thr  Glu Val Met
    1295                1300                1305

Val Glu  Thr Ala Asp Asn Phe  Gln Glu Val Leu Ser  Leu Thr Glu
    1310                1315                1320

Ser Pro  Val Pro Gln Arg Thr  Glu Lys Phe Gly Lys  Lys Asn Arg
    1325                1330                1335

Lys Arg  Leu Asp Ser Arg Ala  Glu Glu Gly Ser Val  Gln Ala Ile
    1340                1345                1350

Thr Glu  Gly Lys Val Lys Lys  Glu Ala Arg Thr Leu  Ser Asp Phe
    1355                1360                1365

Asn Ser  Leu Ile Ser Ser Pro  His Leu Gly Arg Glu  Lys Lys Lys
    1370                1375                1380

Val Lys  Ser Gln Lys Asp Gln  Leu Lys Ser Lys Lys  Leu Asn Lys
    1385                1390                1395

Thr Asn  Glu Phe Gln Asp Ser  Ser Glu Ser Glu Pro  Glu Leu Phe
    1400                1405                1410

Ile Ser  Gly Asp Glu Leu Met  Asn Gln Ser Gln Gly  Ser Arg Lys
    1415                1420                1425

Gly Trp  Lys Ser Lys Arg Ser  Pro Arg Ala Ala Gly  Glu Leu Glu
    1430                1435                1440

Glu Ala  Lys Cys Arg Arg Ala  Ser Glu Lys Glu Asp  Gly Arg Leu
    1445                1450                1455

Gly Ser  Gln Gly Phe Val Tyr  Val Met Ala Asn Lys  Gln Pro Leu
    1460                1465                1470

Trp Asn  Glu Ala Thr Gln Val  Tyr Gln Leu Asp Phe  Gly Gly Arg
    1475                1480                1485

Val Thr  Gln Glu Ser Ala Lys  Asn Phe Gln Ile Glu  Leu Glu Gly
    1490                1495                1500

Arg Gln  Val Met Gln Phe Gly  Arg Ile Asp Gly Ser  Ala Tyr Ile
    1505                1510                1515

Leu Asp  Phe Gln Tyr Pro Phe  Ser Ala Val Gln Ala  Phe Ala Val
    1520                1525                1530

Ala Leu  Ala Asn Val Thr Gln  Arg Leu Lys
    1535                1540
```

<210> SEQ ID NO 17
<211> LENGTH: 552
<212> TYPE: DNA
<213> ORGANISM: Homo sapiens

<400> SEQUENCE: 17

```
atggcctcca acaaaactac attgcaaaaa atgggaaaaa aacagaatgg aaagagtaaa     60

aaagttgaag aggcagagcc tgaagaattt gtcgtggaaa aagtactaga tcgacgtgta    120

gtgaatggga aagtggaata tttcctgaag tggaagggat ttacagatgc tgacaatact    180

tgggaacctg aagaaaattt agattgtcca gaattgattg aagcgtttct taactctcag    240

aaagctggca aagaaaaaga tggtacaaaa agaaaatctt tatctgacag tgaatctgat    300
```

gacagcaaat caaagaagaa aagagatgct gctgacaaac caagaggatt tgccagaggt 360
cttgatcctg aaagaataat tggtgccaca gacagcagtg gagaattgat gtttctcatg 420
aaatggaaag attcagatga ggcagacttg gtgctggcga aagaggcaaa tatgaagtgt 480
cctcaaattg taattgcttt ttatgaagag agactaactt ggcattcttg tccagaagat 540
gaagctcaat aa 552

<210> SEQ ID NO 18
<211> LENGTH: 183
<212> TYPE: PRT
<213> ORGANISM: Homo sapiens

<400> SEQUENCE: 18

Met Ala Ser Asn Lys Thr Thr Leu Gln Lys Met Gly Lys Lys Gln Asn
1 5 10 15

Gly Lys Ser Lys Lys Val Glu Glu Ala Glu Pro Glu Glu Phe Val Val
20 25 30

Glu Lys Val Leu Asp Arg Arg Val Val Asn Gly Lys Val Glu Tyr Phe
35 40 45

Leu Lys Trp Lys Gly Phe Thr Asp Ala Asp Asn Thr Trp Glu Pro Glu
50 55 60

Glu Asn Leu Asp Cys Pro Glu Leu Ile Glu Ala Phe Leu Asn Ser Gln
65 70 75 80

Lys Ala Gly Lys Glu Lys Asp Gly Thr Lys Arg Lys Ser Leu Ser Asp
85 90 95

Ser Glu Ser Asp Asp Ser Lys Ser Lys Lys Lys Arg Asp Ala Ala Asp
100 105 110

Lys Pro Arg Gly Phe Ala Arg Gly Leu Asp Pro Glu Arg Ile Ile Gly
115 120 125

Ala Thr Asp Ser Ser Gly Glu Leu Met Phe Leu Met Lys Trp Lys Asp
130 135 140

Ser Asp Glu Ala Asp Leu Val Leu Ala Lys Glu Ala Asn Met Lys Cys
145 150 155 160

Pro Gln Ile Val Ile Ala Phe Tyr Glu Glu Arg Leu Thr Trp His Ser
165 170 175

Cys Pro Glu Asp Glu Ala Gln
180

<210> SEQ ID NO 19
<211> LENGTH: 1743
<212> TYPE: DNA
<213> ORGANISM: Homo sapiens

<400> SEQUENCE: 19
atgttcgcgg ggctgcagga cctgggcgtg gccaacggcg aggacctgaa ggagaccctg 60
accaactgca cggagccgct caaggccatc gagcagttcc agacagagaa tggtgtgctg 120
ctgccatctc ttcagtcagc cctccccttc ttggacctgc acgggacgcc gcggctggag 180
ttccaccagt cggtattcga tgagctgcgg gacaagctgc tggagcgagt gtcagccatc 240
gcttcggagg ggaaggctga ggaaaggtac aagaagctgg aagaccttct ggagaagagc 300
ttttctctgg tgaagatgcc gtccctgcag cccgtggtga tgtgcgtcat gaagcacctg 360
cccaaggttc cggagaaaaa actgaagctg gttatggctg acaaggagct gtatcgagcc 420
tgcgccgtgg aggtgaagcg gcagatctgg caagacaacc aggccctctt cggggacgag 480
gtttccccac tcctgaagca gtacatcctg gagaaggaga gcgctctctt cagtacagag 540
ctctctgtcc tgcacaactt tttcagtcct tcccccaaga ccaggcgcca gggcgaggtg 600
gtgcagcggc tgacgcggat ggtggggaag aacgtgaagc tgtacgacat ggtgctgcag 660
tttctgcgca cgctcttcct gcgcacgcgg aatgtgcact actgcacgct gcgggctgag 720
ctgctcatgt ccctgcacga cctggacgtg ggtgaaatct gcaccgtgga cccgtgccac 780
aagttcacct ggtgcctgga cgcctgcatc cgagagcggt tcgtggacag caagagggcg 840
cgggagctgc aggggtttct cgatggcgtc aagaagggcc aggagcaggt gctgggggac 900
ctgtccatga tcctgtgtga ccccttcgcc atcaacacgc tggcactgag cacagtcagg 960
cacctgcagg agctggtcgg ccaggagaca ctgcccaggg acagccccga cctcctgctg 1020
ctgctccggc tgctggcgct gggccaggga gcctgggaca tgatcgacag ccaggtcttc 1080
aaggagccca agatggaggt agagctcatc accaggttcc tcccgatgct catgtccttc 1140
ctggtggatg actacacttt caatgtggat cagaaacttc cggctgagga gaaagcccca 1200
gtctcatatc caaacacact tcccgaaagc ttcactaagt ttctgcagga gcagcgcatg 1260
gcctgcgagg tggggctgta ctacgtcctg cacatcacca agcagaggaa caagaacgcg 1320
ctcctccgcc tgctgcccgg gctggtggag acctttggcg acttggcctt tggcgacatc 1380
ttcctccacc tgctcacggg caaccttgcg ctgctggccg acgaatttgc ccttgaggac 1440
ttctgcagca gcctcttcga tggcttcttc ctcaccgcct ctccaaggaa ggagaacgtg 1500
caccggcacg cgctgcggct cctcattcac ctgcacccca gggtggcccc gtctaagctg 1560
gaggcgttgc agaaggccct ggagcctaca ggccagagcg gagaggcagt gaaggagctt 1620
tactcccagc tcggcgagaa gctggaacag ctggatcacc ggaagcccag cccggcacag 1680
gctgcggaga cgccggccct ggagctgccc ctccccagcg tgcccgcccc tgccccgctc 1740
tga 1743

<210> SEQ ID NO 20
<211> LENGTH: 580
<212> TYPE: PRT
<213> ORGANISM: Homo sapiens

<400> SEQUENCE: 20

Met Phe Ala Gly Leu Gln Asp Leu Gly Val Ala Asn Gly Glu Asp Leu
1 5 10 15

Lys Glu Thr Leu Thr Asn Cys Thr Glu Pro Leu Lys Ala Ile Glu Gln
20 25 30

Phe Gln Thr Glu Asn Gly Val Leu Leu Pro Ser Leu Gln Ser Ala Leu
35 40 45

Pro Phe Leu Asp Leu His Gly Thr Pro Arg Leu Glu Phe His Gln Ser
50 55 60

Val Phe Asp Glu Leu Arg Asp Lys Leu Leu Glu Arg Val Ser Ala Ile
65 70 75 80

Ala Ser Glu Gly Lys Ala Glu Glu Arg Tyr Lys Lys Leu Glu Asp Leu
85 90 95

Leu Glu Lys Ser Phe Ser Leu Val Lys Met Pro Ser Leu Gln Pro Val
100 105 110

Val Met Cys Val Met Lys His Leu Pro Lys Val Pro Glu Lys Lys Leu
115 120 125

Lys Leu Val Met Ala Asp Lys Glu Leu Tyr Arg Ala Cys Ala Val Glu
130 135 140

```
Val Lys Arg Gln Ile Trp Gln Asp Asn Gln Ala Leu Phe Gly Asp Glu
145                 150                 155                 160

Val Ser Pro Leu Leu Lys Gln Tyr Ile Leu Glu Lys Glu Ser Ala Leu
                165                 170                 175

Phe Ser Thr Glu Leu Ser Val Leu His Asn Phe Phe Ser Pro Ser Pro
            180                 185                 190

Lys Thr Arg Arg Gln Gly Glu Val Val Gln Arg Leu Thr Arg Met Val
        195                 200                 205

Gly Lys Asn Val Lys Leu Tyr Asp Met Val Leu Gln Phe Leu Arg Thr
    210                 215                 220

Leu Phe Leu Arg Thr Arg Asn Val His Tyr Cys Thr Leu Arg Ala Glu
225                 230                 235                 240

Leu Leu Met Ser Leu His Asp Leu Asp Val Gly Glu Ile Cys Thr Val
                245                 250                 255

Asp Pro Cys His Lys Phe Thr Trp Cys Leu Asp Ala Cys Ile Arg Glu
            260                 265                 270

Arg Phe Val Asp Ser Lys Arg Ala Arg Glu Leu Gln Gly Phe Leu Asp
        275                 280                 285

Gly Val Lys Lys Gly Gln Glu Gln Val Leu Gly Asp Leu Ser Met Ile
    290                 295                 300

Leu Cys Asp Pro Phe Ala Ile Asn Thr Leu Ala Leu Ser Thr Val Arg
305                 310                 315                 320

His Leu Gln Glu Leu Val Gly Gln Glu Thr Leu Pro Arg Asp Ser Pro
                325                 330                 335

Asp Leu Leu Leu Leu Leu Arg Leu Leu Ala Leu Gly Gln Gly Ala Trp
            340                 345                 350

Asp Met Ile Asp Ser Gln Val Phe Lys Glu Pro Lys Met Glu Val Glu
        355                 360                 365

Leu Ile Thr Arg Phe Leu Pro Met Leu Met Ser Phe Leu Val Asp Asp
    370                 375                 380

Tyr Thr Phe Asn Val Asp Gln Lys Leu Pro Ala Glu Glu Lys Ala Pro
385                 390                 395                 400

Val Ser Tyr Pro Asn Thr Leu Pro Glu Ser Phe Thr Lys Phe Leu Gln
                405                 410                 415

Glu Gln Arg Met Ala Cys Glu Val Gly Leu Tyr Tyr Val Leu His Ile
            420                 425                 430

Thr Lys Gln Arg Asn Lys Asn Ala Leu Leu Arg Leu Leu Pro Gly Leu
        435                 440                 445

Val Glu Thr Phe Gly Asp Leu Ala Phe Gly Asp Ile Phe Leu His Leu
    450                 455                 460

Leu Thr Gly Asn Leu Ala Leu Leu Ala Asp Glu Phe Ala Leu Glu Asp
465                 470                 475                 480

Phe Cys Ser Ser Leu Phe Asp Gly Phe Phe Leu Thr Ala Ser Pro Arg
                485                 490                 495

Lys Glu Asn Val His Arg His Ala Leu Arg Leu Leu Ile His Leu His
            500                 505                 510

Pro Arg Val Ala Pro Ser Lys Leu Glu Ala Leu Gln Lys Ala Leu Glu
        515                 520                 525

Pro Thr Gly Gln Ser Gly Glu Ala Val Lys Glu Leu Tyr Ser Gln Leu
    530                 535                 540

Gly Glu Lys Leu Glu Gln Leu Asp His Arg Lys Pro Ser Pro Ala Gln
545                 550                 555                 560

Ala Ala Glu Thr Pro Ala Leu Glu Leu Pro Leu Pro Ser Val Pro Ala
```

```
            565                 570                 575

Pro Ala Pro Leu
            580


<210> SEQ ID NO 21
<211> LENGTH: 636
<212> TYPE: DNA
<213> ORGANISM: Homo sapiens

<400> SEQUENCE: 21

atggctgtag tacctctgct gttgttgggg ggtttgtgga gcgctgtggg agcgtccagc     60

ctgggtgtcg ttacttgcgg ctccgtggtg aagctactca atacgcgcca caacgtccga    120

ctgcactcac acgacgtgcg ctatgggtca ggtagtgggc agcagtcagt gacaggtgta    180

acctctgtgg atgacagcaa cagttactgg aggatacggg ggaagagtgc cacagtgtgt    240

gagaggggaa cccccatcaa gtgtggccag cccatccggc tgacacatgt caacactggc    300

cgaaacctcc atagtcacca cttcacttca cctctttctg gaaaccagga agtgagtgct    360

tttggtgagg aaggtgaagg tgattatctg gatgactgga cagtgctctg taatggaccc    420

tactgggtga gagatggtga ggtgcggttc aaacactctt ccactgaggt actgctgtct    480

gtcacaggag aacaatatgg tcgacctatc agtgggcaaa aagaggtgca tggcatggcc    540

cagccaagtc agaacaacta ctggaaagcc atggaaggca tcttcatgaa gcccagtgag    600

ttgttgaagg cagaagccca ccatgcagag ctgtga                              636


<210> SEQ ID NO 22
<211> LENGTH: 211
<212> TYPE: PRT
<213> ORGANISM: Homo sapiens

<400> SEQUENCE: 22

Met Ala Val Val Pro Leu Leu Leu Leu Gly Gly Leu Trp Ser Ala Val
1               5                   10                  15

Gly Ala Ser Ser Leu Gly Val Val Thr Cys Gly Ser Val Val Lys Leu
            20                  25                  30

Leu Asn Thr Arg His Asn Val Arg Leu His Ser His Asp Val Arg Tyr
        35                  40                  45

Gly Ser Gly Ser Gly Gln Gln Ser Val Thr Gly Val Thr Ser Val Asp
    50                  55                  60

Asp Ser Asn Ser Tyr Trp Arg Ile Arg Gly Lys Ser Ala Thr Val Cys
65                  70                  75                  80

Glu Arg Gly Thr Pro Ile Lys Cys Gly Gln Pro Ile Arg Leu Thr His
                85                  90                  95

Val Asn Thr Gly Arg Asn Leu His Ser His His Phe Thr Ser Pro Leu
            100                 105                 110

Ser Gly Asn Gln Glu Val Ser Ala Phe Gly Glu Glu Gly Glu Gly Asp
        115                 120                 125

Tyr Leu Asp Asp Trp Thr Val Leu Cys Asn Gly Pro Tyr Trp Val Arg
    130                 135                 140

Asp Gly Glu Val Arg Phe Lys His Ser Ser Thr Glu Val Leu Leu Ser
145                 150                 155                 160

Val Thr Gly Glu Gln Tyr Gly Arg Pro Ile Ser Gly Gln Lys Glu Val
                165                 170                 175

His Gly Met Ala Gln Pro Ser Gln Asn Asn Tyr Trp Lys Ala Met Glu
            180                 185                 190
```

```
Gly Ile Phe Met Lys Pro Ser Glu Leu Leu Lys Ala Glu Ala His His
        195                 200                 205

Ala Glu Leu
    210


<210> SEQ ID NO 23
<211> LENGTH: 1248
<212> TYPE: DNA
<213> ORGANISM: Homo sapiens

<400> SEQUENCE: 23

atggcggcca tggagaccga gacggcgccg ctgaccctag agtcgctgcc caccgatccc      60

ctgctcctca tcttatcctt tttggactat cgggatctaa tcaactgttg ttatgtcagt     120

cgaagactta gccagctatc aagtcatgat ccgctgtgga gaagacattg caaaaaatac     180

tggctgatat ctgaggaaga gaaaacacag aagaatcagt gttggaaatc tctcttcata     240

gatacttact ctgatgtagg aagatacatt gaccattatg ctgctattaa aaaggcctgg     300

gatgatctca agaaatattt ggagcccagg tgtcctcgga tggtttttatc tctgaaagag     360

ggtgctcgag aggaagacct cgatgctgtg gaagcgcaga ttggctgcaa gcttcctgac     420

gattatcgat gttcataccg aattcacaat ggacagaagt tagtggttcc tgggttattg     480

ggaagcatgg cactgtctaa tcactatcgt tctgaagatt tgttagacgt cgatacagct     540

gccggaggat tccagcagag acagggactg aaatactgtc tccctttaac tttttgcata     600

catactggtt tgagtcagta catagcagtg gaagctgcag agggccgaaa caaaaatgaa     660

gttttctacc aatgtccaga ccaaatggct cgaaatccag ctgctattga catgtttatt     720

ataggtgcta cttttactga ctggtttacc tcttatgtca aaaatgttgt atcaggtggc     780

ttccccatca tcagagacca aattttcaga tatgttcacg atccagaatg tgtagcaaca     840

actggggata ttactgtgtc agtttccaca tcgtttctgc cagaacttag ctctgtacat     900

ccaccccact atttcttcac ataccgaatc aggattgaaa tgtcaaaaga tgcacttcct     960

gagaaggcct gtcagttgga cagtcgctat tggagaataa caaatgctaa gggtgacgtg    1020

gaagaagttc aaggacctgg agtagttggt gaatttccaa tcatcagccc aggtcgggta    1080

tatgaataca caagctgtac cacattctct acaacatcag gatacatgga aggatattat    1140

accttccatt ttctttactt taaagacaag atctttaatg ttgccattcc ccgattccat    1200

atggcatgtc caacattcag ggtgtctata gcccgattgg taagttaa                 1248


<210> SEQ ID NO 24
<211> LENGTH: 415
<212> TYPE: PRT
<213> ORGANISM: Homo sapiens

<400> SEQUENCE: 24

Met Ala Ala Met Glu Thr Glu Thr Ala Pro Leu Thr Leu Glu Ser Leu
1               5                   10                  15

Pro Thr Asp Pro Leu Leu Leu Ile Leu Ser Phe Leu Asp Tyr Arg Asp
            20                  25                  30

Leu Ile Asn Cys Cys Tyr Val Ser Arg Arg Leu Ser Gln Leu Ser Ser
        35                  40                  45

His Asp Pro Leu Trp Arg Arg His Cys Lys Lys Tyr Trp Leu Ile Ser
    50                  55                  60

Glu Glu Glu Lys Thr Gln Lys Asn Gln Cys Trp Lys Ser Leu Phe Ile
65                  70                  75                  80
```

-continued

```
Asp Thr Tyr Ser Asp Val Gly Arg Tyr Ile Asp His Tyr Ala Ala Ile
                85                  90                  95

Lys Lys Ala Trp Asp Asp Leu Lys Lys Tyr Leu Glu Pro Arg Cys Pro
            100                 105                 110

Arg Met Val Leu Ser Leu Lys Glu Gly Ala Arg Glu Glu Asp Leu Asp
        115                 120                 125

Ala Val Glu Ala Gln Ile Gly Cys Lys Leu Pro Asp Asp Tyr Arg Cys
    130                 135                 140

Ser Tyr Arg Ile His Asn Gly Gln Lys Leu Val Val Pro Gly Leu Leu
145                 150                 155                 160

Gly Ser Met Ala Leu Ser Asn His Tyr Arg Ser Glu Asp Leu Leu Asp
                165                 170                 175

Val Asp Thr Ala Ala Gly Gly Phe Gln Gln Arg Gln Gly Leu Lys Tyr
            180                 185                 190

Cys Leu Pro Leu Thr Phe Cys Ile His Thr Gly Leu Ser Gln Tyr Ile
        195                 200                 205

Ala Val Glu Ala Ala Glu Gly Arg Asn Lys Asn Glu Val Phe Tyr Gln
    210                 215                 220

Cys Pro Asp Gln Met Ala Arg Asn Pro Ala Ala Ile Asp Met Phe Ile
225                 230                 235                 240

Ile Gly Ala Thr Phe Thr Asp Trp Phe Thr Ser Tyr Val Lys Asn Val
                245                 250                 255

Val Ser Gly Gly Phe Pro Ile Ile Arg Asp Gln Ile Phe Arg Tyr Val
            260                 265                 270

His Asp Pro Glu Cys Val Ala Thr Thr Gly Asp Ile Thr Val Ser Val
        275                 280                 285

Ser Thr Ser Phe Leu Pro Glu Leu Ser Ser Val His Pro Pro His Tyr
    290                 295                 300

Phe Phe Thr Tyr Arg Ile Arg Ile Glu Met Ser Lys Asp Ala Leu Pro
305                 310                 315                 320

Glu Lys Ala Cys Gln Leu Asp Ser Arg Tyr Trp Arg Ile Thr Asn Ala
                325                 330                 335

Lys Gly Asp Val Glu Glu Val Gln Gly Pro Gly Val Val Gly Glu Phe
            340                 345                 350

Pro Ile Ile Ser Pro Gly Arg Val Tyr Glu Tyr Thr Ser Cys Thr Thr
        355                 360                 365

Phe Ser Thr Thr Ser Gly Tyr Met Glu Gly Tyr Tyr Thr Phe His Phe
    370                 375                 380

Leu Tyr Phe Lys Asp Lys Ile Phe Asn Val Ala Ile Pro Arg Phe His
385                 390                 395                 400

Met Ala Cys Pro Thr Phe Arg Val Ser Ile Ala Arg Leu Val Ser
                405                 410                 415
```

<210> SEQ ID NO 25
<211> LENGTH: 1014
<212> TYPE: DNA
<213> ORGANISM: Homo sapiens

<400> SEQUENCE: 25

```
atggggctgg ggctgctgct cccgctgctg ctgctctgga ctcgggggac tcaggggtcc      60

gagctggacc ccaaagggca gcacgtctgt gtggccagca gcccctctgc tgagctgcag     120

tgctgcgcag gctggaggca gaaggatcaa gaatgcacca tccccatctg tgaggggccg     180

gacgcctgcc agaaagacga ggtgtgtgtg aagccgggcc tctgtcgatg caagcctgga     240
```

-continued

```
ttctttgggg cccactgcag ctcccgctgc ccgggccagt actggggccc cgactgccgt    300

gagagctgcc cctgccaccc gcacggccag tgcgagccag ccacgggcgc gtgccagtgc    360

caggccgacc gctggggagc ccgctgcgag ttcccgtgcg cctgcggccc ccacgggcgc    420

tgcgaccccg cgaccggcgt gtgccactgc gaacccggct ggtggtcgtc cacgtgccgc    480

cgcccgtgcc agtgcaacac cgcggcggcg cgctgcgagc aggccacggg cgcctgcgtg    540

tgcaagccgg gctggtgggg gcgccgctgc agcttccgct gcaactgcca cggctccccg    600

tgcgagcagg actccggccg ctgcgcctgc cggccgggct ggtggggtcc cgaatgccag    660

cagcagtgcg agtgtgtgcg gggccgctgc agcgccgcct ccggcgagtg cacctgcccg    720

cccggcttcc gcggagcgcg ctgcgagctg ccctgcccgg caggcagcca cggggtgcag    780

tgcgcacaca gctgtggccg ctgcaaacac aatgagccgt gctctccaga cacaggcagc    840

tgtgagtcct gcgagccggg ctggaacggg acccagtgcc agcagccctg cctgcctggc    900

acctttggcg agagctgcga acagcagtgc cctcactgcc gacatgggga ggcctgtgag    960

ccagatactg gccactgtca gcgctgtgac cctggctggc tggggcccag gtga         1014
```

<210> SEQ ID NO 26
<211> LENGTH: 337
<212> TYPE: PRT
<213> ORGANISM: Homo sapiens

<400> SEQUENCE: 26

```
Met Gly Leu Gly Leu Leu Leu Pro Leu Leu Leu Leu Trp Thr Arg Gly
1               5                   10                  15

Thr Gln Gly Ser Glu Leu Asp Pro Lys Gly Gln His Val Cys Val Ala
            20                  25                  30

Ser Ser Pro Ser Ala Glu Leu Gln Cys Cys Ala Gly Trp Arg Gln Lys
        35                  40                  45

Asp Gln Glu Cys Thr Ile Pro Ile Cys Glu Gly Pro Asp Ala Cys Gln
    50                  55                  60

Lys Asp Glu Val Cys Val Lys Pro Gly Leu Cys Arg Cys Lys Pro Gly
65                  70                  75                  80

Phe Phe Gly Ala His Cys Ser Ser Arg Cys Pro Gly Gln Tyr Trp Gly
                85                  90                  95

Pro Asp Cys Arg Glu Ser Cys Pro Cys His Pro His Gly Gln Cys Glu
            100                 105                 110

Pro Ala Thr Gly Ala Cys Gln Cys Gln Ala Asp Arg Trp Gly Ala Arg
        115                 120                 125

Cys Glu Phe Pro Cys Ala Cys Gly Pro His Gly Arg Cys Asp Pro Ala
    130                 135                 140

Thr Gly Val Cys His Cys Glu Pro Gly Trp Trp Ser Ser Thr Cys Arg
145                 150                 155                 160

Arg Pro Cys Gln Cys Asn Thr Ala Ala Ala Arg Cys Glu Gln Ala Thr
                165                 170                 175

Gly Ala Cys Val Cys Lys Pro Gly Trp Trp Gly Arg Arg Cys Ser Phe
            180                 185                 190

Arg Cys Asn Cys His Gly Ser Pro Cys Glu Gln Asp Ser Gly Arg Cys
        195                 200                 205

Ala Cys Arg Pro Gly Trp Trp Gly Pro Glu Cys Gln Gln Gln Cys Glu
    210                 215                 220

Cys Val Arg Gly Arg Cys Ser Ala Ala Ser Gly Glu Cys Thr Cys Pro
225                 230                 235                 240
```

```
Pro Gly Phe Arg Gly Ala Arg Cys Glu Leu Pro Cys Pro Ala Gly Ser
                245                 250                 255

His Gly Val Gln Cys Ala His Ser Cys Gly Arg Cys Lys His Asn Glu
            260                 265                 270

Pro Cys Ser Pro Asp Thr Gly Ser Cys Glu Ser Cys Glu Pro Gly Trp
        275                 280                 285

Asn Gly Thr Gln Cys Gln Gln Pro Cys Leu Pro Gly Thr Phe Gly Glu
    290                 295                 300

Ser Cys Glu Gln Gln Cys Pro His Cys Arg His Gly Glu Ala Cys Glu
305                 310                 315                 320

Pro Asp Thr Gly His Cys Gln Arg Cys Asp Pro Gly Trp Leu Gly Pro
                325                 330                 335

Arg


<210> SEQ ID NO 27
<211> LENGTH: 1065
<212> TYPE: DNA
<213> ORGANISM: Homo sapiens

<400> SEQUENCE: 27

atggacatga tgctgttggt gcagggtgct tgttgctcga accagtggct ggcggcggtg      60

ctcctcagcc tgtgctgcct gctaccctcc tgcctcccgg ctggacagag tgtggacttc     120

ccctgggcgg ccgtggacaa catgatggtc agaaaagggg acacggcggt gcttaggtgt     180

tatttggaag atggagcttc aaagggtgcc tggctgaacc ggtcaagtat tatttttgcg     240

ggaggtgata agtggtcagt ggatcctcga gtttcaattt caacattgaa taaaagggac     300

tacagcctcc agatacagaa tgtagatgtg acagatgatg gcccatacac gtgttctgtt     360

cagactcaac atacacccag aacaatgcag gtgcatctaa ctgtgcaagt tcctcctaag     420

atatatgaca tctcaaatga tatgaccgtc aatgaaggaa ccaacgtcac tcttacttgt     480

ttggccactg ggaaaccaga gccttccatt tcttggcgac acatctcccc atcagcaaaa     540

ccatttgaaa atggacaata tttggacatt tatggaatta caagggacca ggctggggaa     600

tatgaatgca gtgcggaaaa tgatgtgtca ttcccagatg tgaggaaagt aaaagttgtt     660

gtcaactttg ctcctactat tcaggaaatt aaatctggca ccgtgacccc cggacgcagt     720

ggcctgataa gatgtgaagg tgcaggtgtg ccgcctccag cctttgaatg gtacaaagga     780

gagaagaagc tcttcaatgg ccaacaagga attattattc aaaattttag cacaagatcc     840

attctcactg ttaccaacgt gacacaggag cacttcggca attatacctg tgtggctgcc     900

aacaagctag gcacaaccaa tgcgagcctg cctcttaacc ctccaagtac agcccagtat     960

ggaattaccg ggagcgctga tgttcttttc tcctgctggt accttgtgtt gacactgtcc    1020

tctttcacca gcatattcta cctgaagaat gccattctac aataa                    1065


<210> SEQ ID NO 28
<211> LENGTH: 354
<212> TYPE: PRT
<213> ORGANISM: Homo sapiens

<400> SEQUENCE: 28

Met Asp Met Met Leu Leu Val Gln Gly Ala Cys Cys Ser Asn Gln Trp
1               5                   10                  15

Leu Ala Ala Val Leu Leu Ser Leu Cys Cys Leu Leu Pro Ser Cys Leu
            20                  25                  30

Pro Ala Gly Gln Ser Val Asp Phe Pro Trp Ala Ala Val Asp Asn Met
```

```
        35                  40                  45

Met Val Arg Lys Gly Asp Thr Ala Val Leu Arg Cys Tyr Leu Glu Asp
    50                  55                  60

Gly Ala Ser Lys Gly Ala Trp Leu Asn Arg Ser Ser Ile Ile Phe Ala
65                  70                  75                  80

Gly Gly Asp Lys Trp Ser Val Asp Pro Arg Val Ser Ile Ser Thr Leu
                85                  90                  95

Asn Lys Arg Asp Tyr Ser Leu Gln Ile Gln Asn Val Asp Val Thr Asp
            100                 105                 110

Asp Gly Pro Tyr Thr Cys Ser Val Gln Thr Gln His Thr Pro Arg Thr
        115                 120                 125

Met Gln Val His Leu Thr Val Gln Val Pro Pro Lys Ile Tyr Asp Ile
    130                 135                 140

Ser Asn Asp Met Thr Val Asn Glu Gly Thr Asn Val Thr Leu Thr Cys
145                 150                 155                 160

Leu Ala Thr Gly Lys Pro Glu Pro Ser Ile Ser Trp Arg His Ile Ser
                165                 170                 175

Pro Ser Ala Lys Pro Phe Glu Asn Gly Gln Tyr Leu Asp Ile Tyr Gly
            180                 185                 190

Ile Thr Arg Asp Gln Ala Gly Glu Tyr Glu Cys Ser Ala Glu Asn Asp
        195                 200                 205

Val Ser Phe Pro Asp Val Arg Lys Val Lys Val Val Val Asn Phe Ala
    210                 215                 220

Pro Thr Ile Gln Glu Ile Lys Ser Gly Thr Val Thr Pro Gly Arg Ser
225                 230                 235                 240

Gly Leu Ile Arg Cys Glu Gly Ala Gly Val Pro Pro Pro Ala Phe Glu
                245                 250                 255

Trp Tyr Lys Gly Glu Lys Lys Leu Phe Asn Gly Gln Gln Gly Ile Ile
            260                 265                 270

Ile Gln Asn Phe Ser Thr Arg Ser Ile Leu Thr Val Thr Asn Val Thr
        275                 280                 285

Gln Glu His Phe Gly Asn Tyr Thr Cys Val Ala Ala Asn Lys Leu Gly
    290                 295                 300

Thr Thr Asn Ala Ser Leu Pro Leu Asn Pro Pro Ser Thr Ala Gln Tyr
305                 310                 315                 320

Gly Ile Thr Gly Ser Ala Asp Val Leu Phe Ser Cys Trp Tyr Leu Val
                325                 330                 335

Leu Thr Leu Ser Ser Phe Thr Ser Ile Phe Tyr Leu Lys Asn Ala Ile
            340                 345                 350

Leu Gln


<210> SEQ ID NO 29
<211> LENGTH: 858
<212> TYPE: DNA
<213> ORGANISM: Homo sapiens

<400> SEQUENCE: 29

atgctttatc tcatcgggtt gggcctggga gatgccaagg acatcacagt caagggcctg      60

gaagttgtta gacgctgcag tcgagtgtat ctggaagcct acacctcagt cctaactgta     120

gggaaggaag ccttggaaga gttttatgga agaaaattgg ttgttgctga tagagaagaa     180

gtggaacaag aagcagataa tattttaaag gatgctgata tcagtgatgt tgcattcctt     240

gtggttggtg atccatttgg ggccacaaca cacagtgatc ttgttctaag agcaacaaag     300
```

ctgggaattc cttatagagt tattcacaat gcctccataa tgaatgctgt aggctgctgt 360
ggtttacagt tatataagtt tggagagaca gtttctattg ttttttggac agacacttgg 420
agaccagaaa gcttctttga caaagtgaag aagaacagac aaaatggcat gcacacatta 480
tgtttactag acatcaaagt aaaggagcag tctttggaaa atctaatcaa gggaaggaag 540
atctatgaac ctccacggta tatgagtgta aaccaagcag cccagcagct tctggagatt 600
gttcaaaatc aaagaatacg aggagaagaa ccagcagtta ccgaggagac actttgtgtt 660
ggcttagcca gggttggagc cgacgaccag aaaattgcag caggcacttt aaggcaaatg 720
tgcactgtgg acttgggaga accattgcat tccttgatca tcacaggagg cagcatacat 780
ccaatggaga tggagatgct aagtctgttt tccataccag aaaatagctc agaatctcaa 840
agcatcaatg gactttga 858

<210> SEQ ID NO 30
<211> LENGTH: 285
<212> TYPE: PRT
<213> ORGANISM: Homo sapiens

<400> SEQUENCE: 30

Met Leu Tyr Leu Ile Gly Leu Gly Leu Gly Asp Ala Lys Asp Ile Thr
1 5 10 15

Val Lys Gly Leu Glu Val Val Arg Arg Cys Ser Arg Val Tyr Leu Glu
20 25 30

Ala Tyr Thr Ser Val Leu Thr Val Gly Lys Glu Ala Leu Glu Glu Phe
35 40 45

Tyr Gly Arg Lys Leu Val Val Ala Asp Arg Glu Glu Val Glu Gln Glu
50 55 60

Ala Asp Asn Ile Leu Lys Asp Ala Asp Ile Ser Asp Val Ala Phe Leu
65 70 75 80

Val Val Gly Asp Pro Phe Gly Ala Thr Thr His Ser Asp Leu Val Leu
85 90 95

Arg Ala Thr Lys Leu Gly Ile Pro Tyr Arg Val Ile His Asn Ala Ser
100 105 110

Ile Met Asn Ala Val Gly Cys Cys Gly Leu Gln Leu Tyr Lys Phe Gly
115 120 125

Glu Thr Val Ser Ile Val Phe Trp Thr Asp Thr Trp Arg Pro Glu Ser
130 135 140

Phe Phe Asp Lys Val Lys Lys Asn Arg Gln Asn Gly Met His Thr Leu
145 150 155 160

Cys Leu Leu Asp Ile Lys Val Lys Glu Gln Ser Leu Glu Asn Leu Ile
165 170 175

Lys Gly Arg Lys Ile Tyr Glu Pro Pro Arg Tyr Met Ser Val Asn Gln
180 185 190

Ala Ala Gln Gln Leu Leu Glu Ile Val Gln Asn Gln Arg Ile Arg Gly
195 200 205

Glu Glu Pro Ala Val Thr Glu Glu Thr Leu Cys Val Gly Leu Ala Arg
210 215 220

Val Gly Ala Asp Asp Gln Lys Ile Ala Ala Gly Thr Leu Arg Gln Met
225 230 235 240

Cys Thr Val Asp Leu Gly Glu Pro Leu His Ser Leu Ile Ile Thr Gly
245 250 255

Gly Ser Ile His Pro Met Glu Met Glu Met Leu Ser Leu Phe Ser Ile
260 265 270

-continued

```
Pro Glu Asn Ser Ser Glu Ser Gln Ser Ile Asn Gly Leu
        275                 280                 285
```

<210> SEQ ID NO 31
<211> LENGTH: 2295
<212> TYPE: DNA
<213> ORGANISM: Homo sapiens

<400> SEQUENCE: 31

```
atgtcggata cgcggcggcg agtgaaggtc tataccctga acgaagaccg gcaatgggac     60

gaccgaggca ccgggcacgt ctcctccact tacgtggagg agctcaaggg gatgtcgctg    120

ctggttcggg cagagtccga cggatcacta ctcttggaat caaagataaa tccaaatact    180

gcatatcaga aacaacagga tacattaatt gtttggtcag aagcagagaa ctatgatttg    240

gctctgagtt ttcaggagaa agctggctgt gatgagatct gggaaaaaat ttgtcaggtt    300

caaggtaaag acccatcagt ggaagtcaca caggacctca ttgatgaatc tgaagaagaa    360

cgatttgaag aaatgcctga aactagtcat ctgattgacc tgcccacatg tgaactcaat    420

aaacttgaag agattgctga cttagttacc tcagtgctct cctcacctat ccgtagggaa    480

aagctggctc tcgccttgga aaatgaaggc tatattaaaa aactattgca gctgttccaa    540

gcttgcgaga acctagaaaa cactgaaggc ttacaccatt tgtatgaaat tattagagga    600

atcttattcc taaataaggc aactcttttt gaggtaatgt tttctgatga gtgtatcatg    660

gatgtcgtgg gatgccttga atatgaccct gctttggctc agccaaaaag acatagagaa    720

ttcttgacca aaactgcaaa gttcaaggaa gttataccaa taacagactc tgaactaagg    780

caaaaaatac atcagactta cagggtacag tacattcagg acatcatttt gcccacacca    840

tctgtttttg aagagaattt tctttctact cttacgtctt ttattttctt caacaaagtt    900

gagatagtca gcatgttgca ggaagatgag aagtttttgt ctgaagtttt tgcacaatta    960

acagatgagg ctacagatga tgataaacgg cgtgaattgg ttaatttttt caaggagttt   1020

tgtgcatttt ctcagacatt acaacctcaa aacagggatg catttttcaa aacattggca   1080

aaattgggaa ttcttcctgc tcttgaaatt gtaatgggca tggatgattt gcaagtcaga   1140

tcagctgcta cagatatatt ttcttatcta gtagaattta gtccatctat ggtccgagag   1200

tttgtaatgc aagaagctca gcagagtgat gacgatattc ttcttattaa tgtggtaatt   1260

gaacaaatga tctgtgatac tgatcctgag ctaggaggcg ctgttcagtt aatgggactt   1320

cttcgtactc taattgatcc agagaacatg ctggctacaa ctaataaaac cgaaaaaagt   1380

gaatttctaa atttttcta caaccattgt atgcatgttc tcacagcacc acttttgacc   1440

aatacttcag aagacaaatg tgaaaaggat aatatagttg gatcaaacaa aaacaacaca   1500

atttgtcccg gtgcccttcg ctttatgagg cggataattg gacttaaaga tgaattttat   1560

aatcgttaca tcaccaaggg aaatcttttt gagccagtta taaatgcact tctggataat   1620

ggaactcggt ataatctgtt gaattcagct gttattgagt tgtttgaatt tataagagtg   1680

gaagatatca agtctcttac tgcccatata gttgaaaact tttataaagc acttgaatcg   1740

attgaatatg ttcagacatt caaaggattg aagactaaat atgagcaaga aaaagacaga   1800

caaaatcaga aactgaacag tgtaccatct atattgcgta gtaacagatt tcgcagagat   1860

gcaaaagcct tggaagagga tgaagaaatg tggtttaatg aagatgaaga agaggaagga   1920

aaagcagttg tggcaccagt ggaaaaacct aagccagaag atgattttcc agataattat   1980

gaaaagttta tggagactaa aaaagcaaaa gaaagtgaag acaaggaaaa ccttcccaaa   2040
```

```
aggacatctc ctggtggctt caaatttact ttctcccact ctgccagtgc tgctaatgga   2100

acaaacagta aatctgtagt ggctcagata ccaccagcaa cttctaatgg atcctcttcc   2160

aaaaccacaa acttgcctac gtcagtaaca gccaccaagg gaagtttggt tggcttagtg   2220

gattatccag atgatgaaga ggaagatgaa gaagaagaat cgtcccccag gaaaagacct   2280

cgtcttggct cataa                                                    2295


<210> SEQ ID NO 32
<211> LENGTH: 764
<212> TYPE: PRT
<213> ORGANISM: Homo sapiens

<400> SEQUENCE: 32

Met Ser Asp Thr Arg Arg Arg Val Lys Val Tyr Thr Leu Asn Glu Asp
1               5                   10                  15

Arg Gln Trp Asp Asp Arg Gly Thr Gly His Val Ser Ser Thr Tyr Val
            20                  25                  30

Glu Glu Leu Lys Gly Met Ser Leu Leu Val Arg Ala Glu Ser Asp Gly
        35                  40                  45

Ser Leu Leu Leu Glu Ser Lys Ile Asn Pro Asn Thr Ala Tyr Gln Lys
    50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Val Gln Gly Lys Asp Pro Ser Val Glu Val Thr Gln Asp
            100                 105                 110

Leu Ile Asp Glu Ser Glu Glu Glu Arg Phe Glu Glu Met Pro Glu Thr
        115                 120                 125

Ser His Leu Ile Asp Leu Pro Thr Cys Glu Leu Asn Lys Leu Glu Glu
    130                 135                 140

Ile Ala Asp Leu Val Thr Ser Val Leu Ser Ser Pro Ile Arg Arg Glu
145                 150                 155                 160

Lys Leu Ala Leu Ala Leu Glu Asn Glu Gly Tyr Ile Lys Lys Leu Leu
                165                 170                 175

Gln Leu Phe Gln Ala Cys Glu Asn Leu Glu Asn Thr Glu Gly Leu His
            180                 185                 190

His Leu Tyr Glu Ile Ile Arg Gly Ile Leu Phe Leu Asn Lys Ala Thr
        195                 200                 205

Leu Phe Glu Val Met Phe Ser Asp Glu Cys Ile Met Asp Val Val Gly
    210                 215                 220

Cys Leu Glu Tyr Asp Pro Ala Leu Ala Gln Pro Lys Arg His Arg Glu
225                 230                 235                 240

Phe Leu Thr Lys Thr Ala Lys Phe Lys Glu Val Ile Pro Ile Thr Asp
                245                 250                 255

Ser Glu Leu Arg Gln Lys Ile His Gln Thr Tyr Arg Val Gln Tyr Ile
            260                 265                 270

Gln Asp Ile Ile Leu Pro Thr Pro Ser Val Phe Glu Glu Asn Phe Leu
        275                 280                 285

Ser Thr Leu Thr Ser Phe Ile Phe Phe Asn Lys Val Glu Ile Val Ser
    290                 295                 300

Met Leu Gln Glu Asp Glu Lys Phe Leu Ser Glu Val Phe Ala Gln Leu
305                 310                 315                 320

Thr Asp Glu Ala Thr Asp Asp Asp Lys Arg Arg Glu Leu Val Asn Phe
```

-continued

```
                325                 330                 335

Phe Lys Glu Phe Cys Ala Phe Ser Gln Thr Leu Gln Pro Gln Asn Arg
            340                 345                 350

Asp Ala Phe Phe Lys Thr Leu Ala Lys Leu Gly Ile Leu Pro Ala Leu
        355                 360                 365

Glu Ile Val Met Gly Met Asp Asp Leu Gln Val Arg Ser Ala Ala Thr
    370                 375                 380

Asp Ile Phe Ser Tyr Leu Val Glu Phe Ser Pro Ser Met Val Arg Glu
385                 390                 395                 400

Phe Val Met Gln Glu Ala Gln Gln Ser Asp Asp Asp Ile Leu Leu Ile
                405                 410                 415

Asn Val Val Ile Glu Gln Met Ile Cys Asp Thr Asp Pro Glu Leu Gly
            420                 425                 430

Gly Ala Val Gln Leu Met Gly Leu Leu Arg Thr Leu Ile Asp Pro Glu
        435                 440                 445

Asn Met Leu Ala Thr Thr Asn Lys Thr Glu Lys Ser Glu Phe Leu Asn
    450                 455                 460

Phe Phe Tyr Asn His Cys Met His Val Leu Thr Ala Pro Leu Leu Thr
465                 470                 475                 480

Asn Thr Ser Glu Asp Lys Cys Glu Lys Asp Asn Ile Val Gly Ser Asn
                485                 490                 495

Lys Asn Asn Thr Ile Cys Pro Gly Ala Leu Arg Phe Met Arg Arg Ile
            500                 505                 510

Ile Gly Leu Lys Asp Glu Phe Tyr Asn Arg Tyr Ile Thr Lys Gly Asn
        515                 520                 525

Leu Phe Glu Pro Val Ile Asn Ala Leu Leu Asp Asn Gly Thr Arg Tyr
    530                 535                 540

Asn Leu Leu Asn Ser Ala Val Ile Glu Leu Phe Glu Phe Ile Arg Val
545                 550                 555                 560

Glu Asp Ile Lys Ser Leu Thr Ala His Ile Val Glu Asn Phe Tyr Lys
                565                 570                 575

Ala Leu Glu Ser Ile Glu Tyr Val Gln Thr Phe Lys Gly Leu Lys Thr
            580                 585                 590

Lys Tyr Glu Gln Glu Lys Asp Arg Gln Asn Gln Lys Leu Asn Ser Val
        595                 600                 605

Pro Ser Ile Leu Arg Ser Asn Arg Phe Arg Arg Asp Ala Lys Ala Leu
    610                 615                 620

Glu Glu Asp Glu Glu Met Trp Phe Asn Glu Asp Glu Glu Glu Glu Gly
625                 630                 635                 640

Lys Ala Val Val Ala Pro Val Glu Lys Pro Lys Pro Glu Asp Asp Phe
                645                 650                 655

Pro Asp Asn Tyr Glu Lys Phe Met Glu Thr Lys Lys Ala Lys Glu Ser
            660                 665                 670

Glu Asp Lys Glu Asn Leu Pro Lys Arg Thr Ser Pro Gly Gly Phe Lys
        675                 680                 685

Phe Thr Phe Ser His Ser Ala Ser Ala Ala Asn Gly Thr Asn Ser Lys
    690                 695                 700

Ser Val Val Ala Gln Ile Pro Pro Ala Thr Ser Asn Gly Ser Ser Ser
705                 710                 715                 720

Lys Thr Thr Asn Leu Pro Thr Ser Val Thr Ala Thr Lys Gly Ser Leu
                725                 730                 735

Val Gly Leu Val Asp Tyr Pro Asp Asp Glu Glu Glu Asp Glu Glu Glu
            740                 745                 750
```

Glu Ser Ser Pro Arg Lys Arg Pro Arg Leu Gly Ser
755 760

<210> SEQ ID NO 33
<211> LENGTH: 1650
<212> TYPE: DNA
<213> ORGANISM: Homo sapiens

<400> SEQUENCE: 33
atggcggagg cttcttttgg aagttcgagc ccagttgggt ctttgtcttc tgaggatcat 60
gattttgacc ccactgctga gatgttggtc catgactatg atgatgaaag aactcttgaa 120
gaagaggaaa tgatggatga gggtaaaaac ttcagttcag aaattgaaga cttagaaaag 180
gaaggaacca tgcctctaga agatttactg gcattctatg gctatgaacc tacaattcca 240
gcagttgcaa attccagtgc aaatagttcc ccaagtgaac tggcagatga actaccagac 300
atgacactag acaaagagga aatagcaaaa gacctgttgt caggtgatga cgaggaaact 360
cagtcttctg cggatgatct gacgccatct gtgacttccc atgaaacttc tgatttcttc 420
cctaggcctt tacgatcaaa tactgcatgt gatggtgata aggaatcaga ggttgaagat 480
gttgaaacag acagtggtaa ttcacctgaa gatttgagga aggaaataat gattggttta 540
caatatcagg cagagattcc cccttatctt ggagagtacg atggtaatga gaaagtatat 600
gaaaacgaag accagttact ttggtgtcct gatgtggttt tggagagcaa agttaaggaa 660
taccttgttg agacttcatt aaggactggc agtgaaaaaa taatggatag gatttctgca 720
ggaacacaca caagggacaa tgaacaggca ttatatgaac ttctcaagtg taaccacaat 780
ataaaggaag caatcgaaag atactgctgc aatggaaagg cctctcaagg aatgactgca 840
tggacggaag aagaatgccg aagctttgaa catgcactca tgcttttttgg aaaagatttt 900 catcttatac agaagaataa ggtgagaact aggacagttg ctgagtgtgt agcattctac 960
tatatgtgga agaaatctga acgttatgat tactttgctc aacagacaag atttgggaaa 1020
aaaagatata accatcaccc tggagttacg gactatatgg atcgtttagt agatgaaaca 1080
gaagctttgg gtgggacggt aaatgcttca gccttaactt ctaaccggcc tgagcctatt 1140
cctgatcaac agctaaacat tctcaactcc ttcactgcca gtgacttgac agctttgacc 1200
aacagtgtag caaccgtctg cgaccccaca gatgtgaatt gtttggatga tagctttcct 1260
ccactgggca acacaccccg tggacaagtt aatcatgtgc ctgttgtaac agaagagtta 1320
ctcaccctgc ccagcaatgg ggaaagtgat tgttttaatt tatttgagac tggattttat 1380
cactcggagc taaaccctat gaacatgtgc agtgaagagt cagagagacc agcaaaaaga 1440
ttgaaaatgg gcattgccgt ccctgaatcc tttatgaatg aagtttctgt aaataacctg 1500
ggtgtggact ttgaaaatca cacacatcac atcaccagtg ccaaaatggc tgtttctgtg 1560
gctgactttg gcagtctctc tgccaacgag accaatggtt tcatcagtgc ccatgctctg 1620
catcagcacg cggccctaca ctctgagtga 1650

<210> SEQ ID NO 34
<211> LENGTH: 549
<212> TYPE: PRT
<213> ORGANISM: Homo sapiens

<400> SEQUENCE: 34

Met Ala Glu Ala Ser Phe Gly Ser Ser Ser Pro Val Gly Ser Leu Ser
1 5 10 15

-continued

```
Ser Glu Asp His Asp Phe Asp Pro Thr Ala Glu Met Leu Val His Asp
            20                  25                  30

Tyr Asp Asp Glu Arg Thr Leu Glu Glu Glu Met Met Asp Glu Gly
        35                  40                  45

Lys Asn Phe Ser Ser Glu Ile Glu Asp Leu Glu Lys Glu Gly Thr Met
    50                  55                  60

Pro Leu Glu Asp Leu Leu Ala Phe Tyr Gly Tyr Glu Pro Thr Ile Pro
65                  70                  75                  80

Ala Val Ala Asn Ser Ser Ala Asn Ser Ser Pro Ser Glu Leu Ala Asp
                85                  90                  95

Glu Leu Pro Asp Met Thr Leu Asp Lys Glu Glu Ile Ala Lys Asp Leu
            100                 105                 110

Leu Ser Gly Asp Asp Glu Glu Thr Gln Ser Ser Ala Asp Asp Leu Thr
        115                 120                 125

Pro Ser Val Thr Ser His Glu Thr Ser Asp Phe Phe Pro Arg Pro Leu
    130                 135                 140

Arg Ser Asn Thr Ala Cys Asp Gly Asp Lys Glu Ser Glu Val Glu Asp
145                 150                 155                 160

Val Glu Thr Asp Ser Gly Asn Ser Pro Glu Asp Leu Arg Lys Glu Ile
                165                 170                 175

Met Ile Gly Leu Gln Tyr Gln Ala Glu Ile Pro Pro Tyr Leu Gly Glu
            180                 185                 190

Tyr Asp Gly Asn Glu Lys Val Tyr Glu Asn Glu Asp Gln Leu Leu Trp
        195                 200                 205

Cys Pro Asp Val Val Leu Glu Ser Lys Val Lys Glu Tyr Leu Val Glu
    210                 215                 220

Thr Ser Leu Arg Thr Gly Ser Glu Lys Ile Met Asp Arg Ile Ser Ala
225                 230                 235                 240

Gly Thr His Thr Arg Asp Asn Glu Gln Ala Leu Tyr Glu Leu Leu Lys
                245                 250                 255

Cys Asn His Asn Ile Lys Glu Ala Ile Glu Arg Tyr Cys Cys Asn Gly
            260                 265                 270

Lys Ala Ser Gln Gly Met Thr Ala Trp Thr Glu Glu Glu Cys Arg Ser
        275                 280                 285

Phe Glu His Ala Leu Met Leu Phe Gly Lys Asp Phe His Leu Ile Gln
    290                 295                 300

Lys Asn Lys Val Arg Thr Arg Thr Val Ala Glu Cys Val Ala Phe Tyr
305                 310                 315                 320

Tyr Met Trp Lys Lys Ser Glu Arg Tyr Asp Tyr Phe Ala Gln Gln Thr
                325                 330                 335

Arg Phe Gly Lys Lys Arg Tyr Asn His His Pro Gly Val Thr Asp Tyr
            340                 345                 350

Met Asp Arg Leu Val Asp Glu Thr Glu Ala Leu Gly Gly Thr Val Asn
        355                 360                 365

Ala Ser Ala Leu Thr Ser Asn Arg Pro Glu Pro Ile Pro Asp Gln Gln
    370                 375                 380

Leu Asn Ile Leu Asn Ser Phe Thr Ala Ser Asp Leu Thr Ala Leu Thr
385                 390                 395                 400

Asn Ser Val Ala Thr Val Cys Asp Pro Thr Asp Val Asn Cys Leu Asp
                405                 410                 415

Asp Ser Phe Pro Pro Leu Gly Asn Thr Pro Arg Gly Gln Val Asn His
            420                 425                 430

Val Pro Val Val Thr Glu Glu Leu Leu Thr Leu Pro Ser Asn Gly Glu
```

```
        435                 440                 445

Ser Asp Cys Phe Asn Leu Phe Glu Thr Gly Phe Tyr His Ser Glu Leu
    450                 455                 460

Asn Pro Met Asn Met Cys Ser Glu Glu Ser Glu Arg Pro Ala Lys Arg
465                 470                 475                 480

Leu Lys Met Gly Ile Ala Val Pro Glu Ser Phe Met Asn Glu Val Ser
                485                 490                 495

Val Asn Asn Leu Gly Val Asp Phe Glu Asn His Thr His His Ile Thr
            500                 505                 510

Ser Ala Lys Met Ala Val Ser Val Ala Asp Phe Gly Ser Leu Ser Ala
        515                 520                 525

Asn Glu Thr Asn Gly Phe Ile Ser Ala His Ala Leu His Gln His Ala
    530                 535                 540

Ala Leu His Ser Glu
545


<210> SEQ ID NO 35
<211> LENGTH: 7398
<212> TYPE: DNA
<213> ORGANISM: Homo sapiens

<400> SEQUENCE: 35

atgaacacag aagagctgga gttattgagt gactccaaat acagaaacta tgtagcagca     60

attgacaaag cactaaagaa ttttgaatac tccagtgaat gggcagattt gatatcagca    120

cttggaaaac ttaataaggt tttacaaaat aatgcaaagt accaagtagt acccaaaaag    180

ctgaccatag gcaaacgcct agctcaatgt ctacatccag cattaccagg tggagttcat    240

cggaaggcgc ttgaaacata tgaaattatc ttcaaaataa ttggacctaa gcgacttgcc    300

aaagatcttt ttttatatag ttctggatta tttcctcttc ttgcaaatgc tgccatgtct    360

gtgaaaccaa cattgctcag tttgtatgag atatattatc tgcctttggg taaaacactg    420

aaacctggtc tacagggatt gcttactggt attcttcctg gcttagaaga aggatcagag    480

tactatgaga gaacaaatat gttgttggaa aaggttgctg ctgctgtgga ccagtcagca    540

ttctacagtg ccctgtgggg tagtcttctc accagtcctg ctgtgcgttt acctggaatc    600

acgtatgttc ttgcccattt aaacaggaag ctttctatgg aagatcaact ttatataatt    660

ggcagtgata ttgagctaat ggtagaagca gtaagtactt cagtgcagga ctcaagtgta    720

cttgtacaga gaagcacact ggacctcata ctcttctgtt ttccattcca catgagtcag    780

gccactcgac cggatatgat caggatcttg tcagcagccc ttcatgtagt gctaaggagg    840

gatatgtctc tgaatcgaag actttatgca tggcttcttg gttttgataa caacggtgct    900

atcataggac ccagaagcac aagacacagt aatcctgaag aacatgccac ttactatttc    960

actacctttt caaaagaatt attagtccag gcaatggtgg gaatcttaca agtgaatgga   1020

tttggagaag agaacactct aatgcaggat ctaaagcctt ttcgcatttt aatcagttta   1080

ctggacaaac ctgagctagg acctgtaatt ctagaagatg tcctgattga agtgtttaga   1140

acattatatt ctcaatgcaa agcagagttg gatcttcaaa ctgaaccacc cttcagcaag   1200

gatcatgctc agttaagcag taaattaaga gaaaataaga aaacagcaga gctgattaaa   1260

actgctaacc ttctctttaa ttccttcgaa ccttattata tgtgggatta tgttgcacgc   1320

tggtttgaag aatgttgtag gaggacactg catgtgagac ttcagattgg acctggagat   1380

agtaatgact catctgaatt acagctgacc aatttctgct tactggtgga ttttttgttg   1440
```

```
gacatagttt ctttgcctac tagaagtatg agggtgctgt gtcaggagac ttacattgaa   1500
atccagacag aacacttgcc ccagttgctg ctcagaatga tttctgcctt gacaagccat   1560
ctccagacat tgcacttatc tgaactcaca gattctctca gactctgctc aaagatcctt   1620
agcaaggttc agcctccact gttatctgct agcactggag gtgttttgca gtttccaagt   1680
gggcagaaca attcagtcaa agagtgggaa gacaaaaagg tatcatcagt ttctcatgaa   1740
aatcctactg aagtgtttga agatggagaa aatccaccaa gtagtcgatc atcagagagt   1800
ggattcactg agtttataca atatcaagca gaccgaactg atgatattga cagagaactg   1860
agtgagggcc agggggcagc tgccatccca attggtagca catcctctga gacagaaaca   1920
gcatccactg tgggatctga agaaaccatc atccagaccc cttccgtagt cactcagggg   1980
acagcaaccc gaagtaggaa gacagcccaa aagactgcaa tgcagtgctg cttggagtat   2040
gtccaacagt ttcttaccag acttatcaac ctctacatca ttcagaataa ctctttttct   2100
cagtctttgg ctacagaaca tcaaggggat cttggtcgag aacaaggaga gacttcaaaa   2160
tgggacagaa attcacaagg agatgtaaaa gagaaaaaca taagtaaaca aaaaacttct   2220
aaagaatacc tgtctgcctt ccttgctgcc tgtcagctct tcctagagtg ctcaagtttc   2280
ccagtttaca ttgctgaggg gaaccataca tcagagttac gttctgaaaa attggagact   2340
gactgtgagc atgtgcagcc tccacagtgg ctccagactc tgatgaatgc ttgcagccaa   2400
gcaagtgatt tcagtgttca gagtgttgct atttcactag ttatggacct ggtgggactg   2460
acacagtctg tggccatggt cactggggaa aacatcaaca gtgtagagcc tgcacaaccc   2520
ttaagtccaa accagggaag agtagctgtg gttattagac ctcccctcac tcagggcaat   2580
ctgaggtaca tagctgagaa gactgaattt ttcaagcatg tagctttaac attgtgggac   2640
cagttgggag atgggacacc tcagcatcac cagaagagtg tggaactatt ttatcaatta   2700
cataacttag ttccttcttc tagcatctgt gaggatgtta taagtcagca gttaacccat   2760
aaagataaga aaataaggat ggaagcacat gccaagtttg cagttctttg gcatctaacg   2820
agagatctcc atataaataa atcttcatct tttgtacgtt cttttgacag gtcactgttc   2880
atcatgttag atagccttaa cagtctcgat ggttctacta gctctgtggg acaagcctgg   2940
ctgaaccaag tcctacaaag acatgatatt gcacgagttt tggaaccatt gctattgctc   3000
ctgcttcatc caaaaactca gagggtttca gtacagcgtg tacaagcaga acgttattgg   3060
aataagtctc cctgttatcc aggagaggag agtgacaagc atttcatgca aaattttgcc   3120
tgcagcaatg tgagccaagt acaactcatc acatcaaaag gaaatggtga aaagccactt   3180
accatggatg aaatagagaa ctttagtctc actgtgaatc cattaagtga cagactttcc   3240
ctcctaagta ccagcagtga gacaattcca atggttgtgt ctgattttga tcttccagac   3300
caacagatag aaatacttca gagttctgac tcgggatgtt cacagtcctc tgctggggac   3360
aacttgagtt acgaagttga tcctgaaacc gtgaatgccc aagaggattc tcaaatgccc   3420
aaggaaagct ccccagatga tgatgttcaa caggtagtat ttgacctgat atgtaaagtt   3480
gtaagtggcc tcgaagtgga atctgcatca gttacatctc aattagaaat tgaagctatg   3540
cccccaaagt gcagtgatat agatccagat gaagagacga ttaaaattga agatgactcc   3600
attcaacaga gtcagaatgc tttgctgagt aatgaaagtt ctcagtttct gtctgtgtct   3660
gcagagggag gccatgagtg tgtggcaaat ggaatctcca ggaatagctc ctcaccttgt   3720
atttcaggaa ccacacacac tcttcatgac tcttctgttg cttccataga aaccaaatct   3780
agacaaagga gtcacagtag tattcaattc agcttcaaag aaaaattatc agaaaaagtt   3840
```

```
tcggagaagg aaacaatagt taaggagtca ggtaaacaac caggagcaaa acctaaagta   3900
aaacttgcca gaaaaaagga tgatgacaag aaaaaatctt caaatgaaaa actcaaacaa   3960
accagtgtat tcttcagtga tggtctggat ttagagaact ggtatagctg tggagaggga   4020
gacatttctg aaattgagag tgacatgggt tctccaggat ctcgaaaatc tcccaatttc   4080
aacattcatc ctctctatca acatgtgctc ctgtatctcc agttgtatga ttcatccagg   4140
actttgtatg ctttctctgc catcaaagcc atcttgaaaa ctaaccctat agcttttgta   4200
aatgccattt caactactag tgtaaataat gcatatactc ctcagttgtc tctccttcag   4260
aatctattgg ccagacaccg gatttctgtt atgggcaaag atttttatag tcacattcca   4320
gtggactcaa atcataactt ccggagttct atgtacatag aaattcttat ttctctctgc   4380
ttatattaca tgcgtagcca ttacccaact catgtcaagg ttactgcaca agatttaata   4440
ggcaatcgaa acatgcaaat gatgagcata gaaattctga cactactctt cactgagctg   4500
gcaaaagtaa tagaaagctc agcgaagggt ttccctagtt ttatttctga tatgttatct   4560
aagtgcaaag ttcagaaagt gattcttcat tgtttgctgt catctatctt tagtgctcag   4620
aaatggcata gtgaaaaaat ggcaggtaag aacctggttg ctgtggaaga aggtttctca   4680
gaggacagcc ttattaattt ctcagaggat gaatttgaca atggcagcac gttgcagtca   4740
caacttctta aggtgcttca gaggctgatt gttctagaac acagagtaat gactattcct   4800
gaagagaatg aaacaggttt tgattttgtt gtatctgact tagaacacat cagtccccat   4860
caacccatga cttctcttca gtatttgcat gctcagccaa tcacatgtca aggcatgttc   4920
ctctgtgcag tgatacgagc tttgcatcag cactgtgcat gtaagatgca cccacaatgg   4980
attggtttaa tcacatctac tctgccttac atgggaaaag ttctgcagag agtggttgtt   5040
tctgtgacac tacaactgtg cagaaattta gataatctaa ttcagcagta caaatacgaa   5100
acaggattat ctgatagtag gcctctgtgg atggcatcaa ttattccacc agatatgatt   5160
cttactcttt tggaagggat tacagccatt atccattact gtttgttgga tccaactaca   5220
cagtatcacc aacttttggt cagtgtagac cagaaacact tgtttgaagc acgcagtgga   5280
atcctctcaa tccttcatat gatcatgtcc tctgtgacac tgctttggag catactgcat   5340
caagctgatt cttcagaaaa gatgactatt gccgcatccg catctcttac cactattaat   5400
cttggagcta caaagaactt gagacaacag attcttgaat tgttgggccc catttcaatg   5460
aatcatggtg ttcactttat ggctgccatt gcatttgtgt ggaatgaaag aagacagaat   5520
aaaacaacca ccaggaccaa ggtcattcct gcagccagtg aagaacagct tttattagtg   5580
gaattggttc gttcaatcag tgtcatgaga gcagaaactg ttatccagac tgtaaaagaa   5640
gttttaaagc agccaccagc catagccaag gacaagaaac atctttcttt ggaagtctgc   5700
atgcttcagt tttctatgc ttatattcaa agaattccag tgcccaattt agtggatagc    5760
tgggcgtcac tgttgatact tctgaaagac tctatacaac tgagtcttcc agctccaggg   5820
cagtttctta tacttggggt tctgaatgag tttattatga aaaaccctag tttggaaaat   5880
aaaaaagacc aaagagacct tcaggatgta actcacaaaa tagtggatgc aattggtgca   5940
attgctggtt cttctctgga acagacaaca tggctgcgac gaaatcttga agttaagcct   6000
tctcccaaaa taatggtaga tggaaccaat ttggaatctg atgttgaaga tatgttatca   6060
cctgcaatgg aaaccgcaaa cataactcct tctgtatata gtgtccatgc attgacatta   6120
ctctctgagg ttttggctca tcttttggat atggttttct atagtgatga aaaggagcgg   6180
```

```
gttattcctt tacttgtaaa tattatgcat tatgttgtgc cctacctcag aaatcacagt   6240
gcacataatg cccctagtta tcgagcttgt gtccagctgc tcagcagtct tagtgggtat   6300
cagtacacac ggagagcttg gaaaaaagaa gcttttgacc tctttatgga tcccagtttc   6360
tttcagatgg atgcctcttg tgttaatcat tggagagcaa ttatggacaa tctgatgaca   6420
catgataaaa caacatttag agatttgatg actcgtgtag cagtggctca aagcagttca   6480
cttaatctct ttgcaaaccg tgatgtggag ctagaacaga gagctatgct tcttaaaaga   6540
ttagcatttg ctatttttag cagtgaaatt gaccagtacc agaaatatct tccagatata   6600
caagagagat tggttgagag tctccgtttg ccacaggtgc caactctcca ttctcaagtg   6660
ttcctgtttt tcagagtgtt acttttaaga atgtctcccc aacatcttac ctcactctgg   6720
cctaccatga ttacagaact tgtacaagta tttttactga tggagcagga actcactgct   6780
gatgaagata tttcacggac ttcagggccc tctgtggctg gtctggagac aacgtacaca   6840
ggaggtaatg gcttctctac ttcatataac agccagcggt ggttaaacct ctatctctct   6900
gcttgcaaat ttttggattt ggctctcgca ttgccctctg aaaaccttcc tcagtttcag   6960
atgtaccgat gggcctttat tccagaagcc tcagatgatt caggtttgga agtcagaagg   7020
cagggtatac atcaacgaga atttaaacct tacgtggtac gactagcaaa acttcttcgg   7080
aaaagagcaa agaaaaatcc agaggaagac aactcaggga gaacattggg ttgggagcca   7140
gggcacttgc tgctcaccat ctgcaccgtg cgcagtatgg agcagctcct gccgttcttc   7200
aatgtgctca gtcaagtctt caacagcaaa gtcacaagcc gatgtggagg acactcaggg   7260
agtcctatcc tctactcaaa tgccttccct aataaggaca tgaaactgga gaaccacaaa   7320
ccatgttcca gcaaagccag gcaaaaaata gaagagatgg tagaaaaaga ttttctggaa   7380
gggatgataa aaacttga                                                 7398
```

<210> SEQ ID NO 36
<211> LENGTH: 2465
<212> TYPE: PRT
<213> ORGANISM: Homo sapiens

<400> SEQUENCE: 36

```
Met Asn Thr Glu Glu Leu Glu Leu Leu Ser Asp Ser Lys Tyr Arg Asn
1               5                   10                  15

Tyr Val Ala Ala Ile Asp Lys Ala Leu Lys Asn Phe Glu Tyr Ser Ser
            20                  25                  30

Glu Trp Ala Asp Leu Ile Ser Ala Leu Gly Lys Leu Asn Lys Val Leu
        35                  40                  45

Gln Asn Asn Ala Lys Tyr Gln Val Val Pro Lys Lys Leu Thr Ile Gly
    50                  55                  60

Lys Arg Leu Ala Gln Cys Leu His Pro Ala Leu Pro Gly Gly Val His
65                  70                  75                  80

Arg Lys Ala Leu Glu Thr Tyr Glu Ile Ile Phe Lys Ile Ile Gly Pro
                85                  90                  95

Lys Arg Leu Ala Lys Asp Leu Phe Leu Tyr Ser Ser Gly Leu Phe Pro
            100                 105                 110

Leu Leu Ala Asn Ala Ala Met Ser Val Lys Pro Thr Leu Leu Ser Leu
        115                 120                 125

Tyr Glu Ile Tyr Tyr Leu Pro Leu Gly Lys Thr Leu Lys Pro Gly Leu
    130                 135                 140

Gln Gly Leu Leu Thr Gly Ile Leu Pro Gly Leu Glu Glu Gly Ser Glu
145                 150                 155                 160
```

```
Tyr Tyr Glu Arg Thr Asn Met Leu Leu Glu Lys Val Ala Ala Ala Val
                165                 170                 175

Asp Gln Ser Ala Phe Tyr Ser Ala Leu Trp Gly Ser Leu Leu Thr Ser
            180                 185                 190

Pro Ala Val Arg Leu Pro Gly Ile Thr Tyr Val Leu Ala His Leu Asn
        195                 200                 205

Arg Lys Leu Ser Met Glu Asp Gln Leu Tyr Ile Ile Gly Ser Asp Ile
    210                 215                 220

Glu Leu Met Val Glu Ala Val Ser Thr Ser Val Gln Asp Ser Ser Val
225                 230                 235                 240

Leu Val Gln Arg Ser Thr Leu Asp Leu Ile Leu Phe Cys Phe Pro Phe
                245                 250                 255

His Met Ser Gln Ala Thr Arg Pro Asp Met Ile Arg Ile Leu Ser Ala
            260                 265                 270

Ala Leu His Val Val Leu Arg Arg Asp Met Ser Leu Asn Arg Arg Leu
        275                 280                 285

Tyr Ala Trp Leu Leu Gly Phe Asp Asn Asn Gly Ala Ile Ile Gly Pro
    290                 295                 300

Arg Ser Thr Arg His Ser Asn Pro Glu Glu His Ala Thr Tyr Tyr Phe
305                 310                 315                 320

Thr Thr Phe Ser Lys Glu Leu Leu Val Gln Ala Met Val Gly Ile Leu
                325                 330                 335

Gln Val Asn Gly Phe Gly Glu Glu Asn Thr Leu Met Gln Asp Leu Lys
            340                 345                 350

Pro Phe Arg Ile Leu Ile Ser Leu Leu Asp Lys Pro Glu Leu Gly Pro
        355                 360                 365

Val Ile Leu Glu Asp Val Leu Ile Glu Val Phe Arg Thr Leu Tyr Ser
    370                 375                 380

Gln Cys Lys Ala Glu Leu Asp Leu Gln Thr Glu Pro Pro Phe Ser Lys
385                 390                 395                 400

Asp His Ala Gln Leu Ser Ser Lys Leu Arg Glu Asn Lys Lys Thr Ala
                405                 410                 415

Glu Leu Ile Lys Thr Ala Asn Leu Leu Phe Asn Ser Phe Glu Pro Tyr
            420                 425                 430

Tyr Met Trp Asp Tyr Val Ala Arg Trp Phe Glu Glu Cys Cys Arg Arg
        435                 440                 445

Thr Leu His Val Arg Leu Gln Ile Gly Pro Gly Asp Ser Asn Asp Ser
    450                 455                 460

Ser Glu Leu Gln Leu Thr Asn Phe Cys Leu Leu Val Asp Phe Leu Leu
465                 470                 475                 480

Asp Ile Val Ser Leu Pro Thr Arg Ser Met Arg Val Leu Cys Gln Glu
                485                 490                 495

Thr Tyr Ile Glu Ile Gln Thr Glu His Leu Pro Gln Leu Leu Leu Arg
            500                 505                 510

Met Ile Ser Ala Leu Thr Ser His Leu Gln Thr Leu His Leu Ser Glu
        515                 520                 525

Leu Thr Asp Ser Leu Arg Leu Cys Ser Lys Ile Leu Ser Lys Val Gln
    530                 535                 540

Pro Pro Leu Leu Ser Ala Ser Thr Gly Gly Val Leu Gln Phe Pro Ser
545                 550                 555                 560

Gly Gln Asn Asn Ser Val Lys Glu Trp Glu Asp Lys Lys Val Ser Ser
                565                 570                 575
```

```
Val Ser His Glu Asn Pro Thr Glu Val Phe Glu Asp Gly Glu Asn Pro
            580                 585                 590

Pro Ser Ser Arg Ser Ser Glu Ser Gly Phe Thr Glu Phe Ile Gln Tyr
        595                 600                 605

Gln Ala Asp Arg Thr Asp Asp Ile Asp Arg Glu Leu Ser Glu Gly Gln
    610                 615                 620

Gly Ala Ala Ala Ile Pro Ile Gly Ser Thr Ser Ser Glu Thr Glu Thr
625                 630                 635                 640

Ala Ser Thr Val Gly Ser Glu Glu Thr Ile Ile Gln Thr Pro Ser Val
                645                 650                 655

Val Thr Gln Gly Thr Ala Thr Arg Ser Arg Lys Thr Ala Gln Lys Thr
            660                 665                 670

Ala Met Gln Cys Cys Leu Glu Tyr Val Gln Gln Phe Leu Thr Arg Leu
        675                 680                 685

Ile Asn Leu Tyr Ile Ile Gln Asn Asn Ser Phe Ser Gln Ser Leu Ala
    690                 695                 700

Thr Glu His Gln Gly Asp Leu Gly Arg Glu Gln Gly Glu Thr Ser Lys
705                 710                 715                 720

Trp Asp Arg Asn Ser Gln Gly Asp Val Lys Glu Lys Asn Ile Ser Lys
                725                 730                 735

Gln Lys Thr Ser Lys Glu Tyr Leu Ser Ala Phe Leu Ala Ala Cys Gln
            740                 745                 750

Leu Phe Leu Glu Cys Ser Ser Phe Pro Val Tyr Ile Ala Glu Gly Asn
        755                 760                 765

His Thr Ser Glu Leu Arg Ser Glu Lys Leu Glu Thr Asp Cys Glu His
    770                 775                 780

Val Gln Pro Pro Gln Trp Leu Gln Thr Leu Met Asn Ala Cys Ser Gln
785                 790                 795                 800

Ala Ser Asp Phe Ser Val Gln Ser Val Ala Ile Ser Leu Val Met Asp
                805                 810                 815

Leu Val Gly Leu Thr Gln Ser Val Ala Met Val Thr Gly Glu Asn Ile
            820                 825                 830

Asn Ser Val Glu Pro Ala Gln Pro Leu Ser Pro Asn Gln Gly Arg Val
        835                 840                 845

Ala Val Val Ile Arg Pro Pro Leu Thr Gln Gly Asn Leu Arg Tyr Ile
    850                 855                 860

Ala Glu Lys Thr Glu Phe Phe Lys His Val Ala Leu Thr Leu Trp Asp
865                 870                 875                 880

Gln Leu Gly Asp Gly Thr Pro Gln His His Gln Lys Ser Val Glu Leu
                885                 890                 895

Phe Tyr Gln Leu His Asn Leu Val Pro Ser Ser Ser Ile Cys Glu Asp
            900                 905                 910

Val Ile Ser Gln Gln Leu Thr His Lys Asp Lys Lys Ile Arg Met Glu
        915                 920                 925

Ala His Ala Lys Phe Ala Val Leu Trp His Leu Thr Arg Asp Leu His
    930                 935                 940

Ile Asn Lys Ser Ser Ser Phe Val Arg Ser Phe Asp Arg Ser Leu Phe
945                 950                 955                 960

Ile Met Leu Asp Ser Leu Asn Ser Leu Asp Gly Ser Thr Ser Ser Val
                965                 970                 975

Gly Gln Ala Trp Leu Asn Gln Val Leu Gln Arg His Asp Ile Ala Arg
            980                 985                 990

Val Leu Glu Pro Leu Leu Leu Leu  Leu Leu His Pro Lys  Thr Gln Arg
```

```
        995                 1000                1005

Val Ser  Val Gln Arg Val Gln  Ala Glu Arg Tyr Trp  Asn Lys Ser
    1010                 1015                 1020

Pro Cys  Tyr Pro Gly Glu Glu  Ser Asp Lys His Phe  Met Gln Asn
    1025                 1030                 1035

Phe Ala  Cys Ser Asn Val Ser  Gln Val Gln Leu Ile  Thr Ser Lys
    1040                 1045                 1050

Gly Asn  Gly Glu Lys Pro Leu  Thr Met Asp Glu Ile  Glu Asn Phe
    1055                 1060                 1065

Ser Leu  Thr Val Asn Pro Leu  Ser Asp Arg Leu Ser  Leu Leu Ser
    1070                 1075                 1080

Thr Ser  Ser Glu Thr Ile Pro  Met Val Val Ser Asp  Phe Asp Leu
    1085                 1090                 1095

Pro Asp  Gln Gln Ile Glu Ile  Leu Gln Ser Ser Asp  Ser Gly Cys
    1100                 1105                 1110

Ser Gln  Ser Ser Ala Gly Asp  Asn Leu Ser Tyr Glu  Val Asp Pro
    1115                 1120                 1125

Glu Thr  Val Asn Ala Gln Glu  Asp Ser Gln Met Pro  Lys Glu Ser
    1130                 1135                 1140

Ser Pro  Asp Asp Asp Val Gln  Gln Val Val Phe Asp  Leu Ile Cys
    1145                 1150                 1155

Lys Val  Val Ser Gly Leu Glu  Val Glu Ser Ala Ser  Val Thr Ser
    1160                 1165                 1170

Gln Leu  Glu Ile Glu Ala Met  Pro Pro Lys Cys Ser  Asp Ile Asp
    1175                 1180                 1185

Pro Asp  Glu Glu Thr Ile Lys  Ile Glu Asp Asp Ser  Ile Gln Gln
    1190                 1195                 1200

Ser Gln  Asn Ala Leu Leu Ser  Asn Glu Ser Ser Gln  Phe Leu Ser
    1205                 1210                 1215

Val Ser  Ala Glu Gly Gly His  Glu Cys Val Ala Asn  Gly Ile Ser
    1220                 1225                 1230

Arg Asn  Ser Ser Ser Pro Cys  Ile Ser Gly Thr Thr  His Thr Leu
    1235                 1240                 1245

His Asp  Ser Ser Val Ala Ser  Ile Glu Thr Lys Ser  Arg Gln Arg
    1250                 1255                 1260

Ser His  Ser Ser Ile Gln Phe  Ser Phe Lys Glu Lys  Leu Ser Glu
    1265                 1270                 1275

Lys Val  Ser Glu Lys Glu Thr  Ile Val Lys Glu Ser  Gly Lys Gln
    1280                 1285                 1290

Pro Gly  Ala Lys Pro Lys Val  Lys Leu Ala Arg Lys  Lys Asp Asp
    1295                 1300                 1305

Asp Lys  Lys Lys Ser Ser Asn  Glu Lys Leu Lys Gln  Thr Ser Val
    1310                 1315                 1320

Phe Phe  Ser Asp Gly Leu Asp  Leu Glu Asn Trp Tyr  Ser Cys Gly
    1325                 1330                 1335

Glu Gly  Asp Ile Ser Glu Ile  Glu Ser Asp Met Gly  Ser Pro Gly
    1340                 1345                 1350

Ser Arg  Lys Ser Pro Asn Phe  Asn Ile His Pro Leu  Tyr Gln His
    1355                 1360                 1365

Val Leu  Leu Tyr Leu Gln Leu  Tyr Asp Ser Ser Arg  Thr Leu Tyr
    1370                 1375                 1380

Ala Phe  Ser Ala Ile Lys Ala  Ile Leu Lys Thr Asn  Pro Ile Ala
    1385                 1390                 1395
```

Phe Val Asn Ala Ile Ser Thr Thr Ser Val Asn Asn Ala Tyr Thr
1400 1405 1410

Pro Gln Leu Ser Leu Leu Gln Asn Leu Leu Ala Arg His Arg Ile
1415 1420 1425

Ser Val Met Gly Lys Asp Phe Tyr Ser His Ile Pro Val Asp Ser
1430 1435 1440

Asn His Asn Phe Arg Ser Ser Met Tyr Ile Glu Ile Leu Ile Ser
1445 1450 1455

Leu Cys Leu Tyr Tyr Met Arg Ser His Tyr Pro Thr His Val Lys
1460 1465 1470

Val Thr Ala Gln Asp Leu Ile Gly Asn Arg Asn Met Gln Met Met
1475 1480 1485

Ser Ile Glu Ile Leu Thr Leu Leu Phe Thr Glu Leu Ala Lys Val
1490 1495 1500

Ile Glu Ser Ser Ala Lys Gly Phe Pro Ser Phe Ile Ser Asp Met
1505 1510 1515

Leu Ser Lys Cys Lys Val Gln Lys Val Ile Leu His Cys Leu Leu
1520 1525 1530

Ser Ser Ile Phe Ser Ala Gln Lys Trp His Ser Glu Lys Met Ala
1535 1540 1545

Gly Lys Asn Leu Val Ala Val Glu Glu Gly Phe Ser Glu Asp Ser
1550 1555 1560

Leu Ile Asn Phe Ser Glu Asp Glu Phe Asp Asn Gly Ser Thr Leu
1565 1570 1575

Gln Ser Gln Leu Leu Lys Val Leu Gln Arg Leu Ile Val Leu Glu
1580 1585 1590

His Arg Val Met Thr Ile Pro Glu Glu Asn Glu Thr Gly Phe Asp
1595 1600 1605

Phe Val Val Ser Asp Leu Glu His Ile Ser Pro His Gln Pro Met
1610 1615 1620

Thr Ser Leu Gln Tyr Leu His Ala Gln Pro Ile Thr Cys Gln Gly
1625 1630 1635

Met Phe Leu Cys Ala Val Ile Arg Ala Leu His Gln His Cys Ala
1640 1645 1650

Cys Lys Met His Pro Gln Trp Ile Gly Leu Ile Thr Ser Thr Leu
1655 1660 1665

Pro Tyr Met Gly Lys Val Leu Gln Arg Val Val Val Ser Val Thr
1670 1675 1680

Leu Gln Leu Cys Arg Asn Leu Asp Asn Leu Ile Gln Gln Tyr Lys
1685 1690 1695

Tyr Glu Thr Gly Leu Ser Asp Ser Arg Pro Leu Trp Met Ala Ser
1700 1705 1710

Ile Ile Pro Pro Asp Met Ile Leu Thr Leu Leu Glu Gly Ile Thr
1715 1720 1725

Ala Ile Ile His Tyr Cys Leu Leu Asp Pro Thr Thr Gln Tyr His
1730 1735 1740

Gln Leu Leu Val Ser Val Asp Gln Lys His Leu Phe Glu Ala Arg
1745 1750 1755

Ser Gly Ile Leu Ser Ile Leu His Met Ile Met Ser Ser Val Thr
1760 1765 1770

Leu Leu Trp Ser Ile Leu His Gln Ala Asp Ser Ser Glu Lys Met
1775 1780 1785

Thr Ile Ala Ala Ser Ala Ser Leu Thr Thr Ile Asn Leu Gly Ala
1790 1795 1800

Thr Lys Asn Leu Arg Gln Gln Ile Leu Glu Leu Leu Gly Pro Ile
1805 1810 1815

Ser Met Asn His Gly Val His Phe Met Ala Ala Ile Ala Phe Val
1820 1825 1830

Trp Asn Glu Arg Arg Gln Asn Lys Thr Thr Thr Arg Thr Lys Val
1835 1840 1845

Ile Pro Ala Ala Ser Glu Glu Gln Leu Leu Leu Val Glu Leu Val
1850 1855 1860

Arg Ser Ile Ser Val Met Arg Ala Glu Thr Val Ile Gln Thr Val
1865 1870 1875

Lys Glu Val Leu Lys Gln Pro Pro Ala Ile Ala Lys Asp Lys Lys
1880 1885 1890

His Leu Ser Leu Glu Val Cys Met Leu Gln Phe Phe Tyr Ala Tyr
1895 1900 1905

Ile Gln Arg Ile Pro Val Pro Asn Leu Val Asp Ser Trp Ala Ser
1910 1915 1920

Leu Leu Ile Leu Leu Lys Asp Ser Ile Gln Leu Ser Leu Pro Ala
1925 1930 1935

Pro Gly Gln Phe Leu Ile Leu Gly Val Leu Asn Glu Phe Ile Met
1940 1945 1950

Lys Asn Pro Ser Leu Glu Asn Lys Lys Asp Gln Arg Asp Leu Gln
1955 1960 1965

Asp Val Thr His Lys Ile Val Asp Ala Ile Gly Ala Ile Ala Gly
1970 1975 1980

Ser Ser Leu Glu Gln Thr Thr Trp Leu Arg Arg Asn Leu Glu Val
1985 1990 1995

Lys Pro Ser Pro Lys Ile Met Val Asp Gly Thr Asn Leu Glu Ser
2000 2005 2010

Asp Val Glu Asp Met Leu Ser Pro Ala Met Glu Thr Ala Asn Ile
2015 2020 2025

Thr Pro Ser Val Tyr Ser Val His Ala Leu Thr Leu Leu Ser Glu
2030 2035 2040

Val Leu Ala His Leu Leu Asp Met Val Phe Tyr Ser Asp Glu Lys
2045 2050 2055

Glu Arg Val Ile Pro Leu Leu Val Asn Ile Met His Tyr Val Val
2060 2065 2070

Pro Tyr Leu Arg Asn His Ser Ala His Asn Ala Pro Ser Tyr Arg
2075 2080 2085

Ala Cys Val Gln Leu Leu Ser Ser Leu Ser Gly Tyr Gln Tyr Thr
2090 2095 2100

Arg Arg Ala Trp Lys Lys Glu Ala Phe Asp Leu Phe Met Asp Pro
2105 2110 2115

Ser Phe Phe Gln Met Asp Ala Ser Cys Val Asn His Trp Arg Ala
2120 2125 2130

Ile Met Asp Asn Leu Met Thr His Asp Lys Thr Thr Phe Arg Asp
2135 2140 2145

Leu Met Thr Arg Val Ala Val Ala Gln Ser Ser Ser Leu Asn Leu
2150 2155 2160

Phe Ala Asn Arg Asp Val Glu Leu Glu Gln Arg Ala Met Leu Leu
2165 2170 2175

Lys Arg Leu Ala Phe Ala Ile Phe Ser Ser Glu Ile Asp Gln Tyr

```
    2180                2185                2190

Gln Lys  Tyr Leu Pro Asp Ile  Gln Glu Arg Leu Val  Glu Ser Leu
    2195                2200                2205

Arg Leu  Pro Gln Val Pro Thr  Leu His Ser Gln Val  Phe Leu Phe
    2210                2215                2220

Phe Arg  Val Leu Leu Leu Arg  Met Ser Pro Gln His  Leu Thr Ser
    2225                2230                2235

Leu Trp  Pro Thr Met Ile Thr  Glu Leu Val Gln Val  Phe Leu Leu
    2240                2245                2250

Met Glu  Gln Glu Leu Thr Ala  Asp Glu Asp Ile Ser  Arg Thr Ser
    2255                2260                2265

Gly Pro  Ser Val Ala Gly Leu  Glu Thr Thr Tyr Thr  Gly Gly Asn
    2270                2275                2280

Gly Phe  Ser Thr Ser Tyr Asn  Ser Gln Arg Trp Leu  Asn Leu Tyr
    2285                2290                2295

Leu Ser  Ala Cys Lys Phe Leu  Asp Leu Ala Leu Ala  Leu Pro Ser
    2300                2305                2310

Glu Asn  Leu Pro Gln Phe Gln  Met Tyr Arg Trp Ala  Phe Ile Pro
    2315                2320                2325

Glu Ala  Ser Asp Asp Ser Gly  Leu Glu Val Arg Arg  Gln Gly Ile
    2330                2335                2340

His Gln  Arg Glu Phe Lys Pro  Tyr Val Val Arg Leu  Ala Lys Leu
    2345                2350                2355

Leu Arg  Lys Arg Ala Lys Lys  Asn Pro Glu Glu Asp  Asn Ser Gly
    2360                2365                2370

Arg Thr  Leu Gly Trp Glu Pro  Gly His Leu Leu Leu  Thr Ile Cys
    2375                2380                2385

Thr Val  Arg Ser Met Glu Gln  Leu Leu Pro Phe Phe  Asn Val Leu
    2390                2395                2400

Ser Gln  Val Phe Asn Ser Lys  Val Thr Ser Arg Cys  Gly Gly His
    2405                2410                2415

Ser Gly  Ser Pro Ile Leu Tyr  Ser Asn Ala Phe Pro  Asn Lys Asp
    2420                2425                2430

Met Lys  Leu Glu Asn His Lys  Pro Cys Ser Ser Lys  Ala Arg Gln
    2435                2440                2445

Lys Ile  Glu Glu Met Val Glu  Lys Asp Phe Leu Glu  Gly Met Ile
    2450                2455                2460

Lys Thr
    2465
```

<210> SEQ ID NO 37
<211> LENGTH: 1737
<212> TYPE: DNA
<213> ORGANISM: Homo sapiens

<400> SEQUENCE: 37

```
atggctgaag aatcaagaaa gccttcagcc ccatccccac cagaccagac tcctgaagag      60
gatcttgtaa tcgtcaaggt agaggaggat catggttggg accaggaatc tagtctgcat     120
gaaagtaacc ctcttggcca agaagtgttc cgcctgcgct tcaggcagtt acgctaccag     180
gagacactag gaccccgaga agctctgatc caactacggg ccctttgcca tcagtggctg     240
aggccagatt tgaacaccaa ggaacagatc ctggagctgc tggtgctgga gcagttcttg     300
accatcctac ctgaggagct ccagacactg gttaaggaac atcagctaga gaacggagag     360
```

```
gaggtggtga ccctattaga ggatttggaa aggcagattg atatactagg acgaccagtc    420

tcagctcgcg tacatggaca tagggtactc tgggaggagg tagtacattc agcatctgca    480

ccagagcctc caaatactca gctccaatct gaggcaaccc aacataaatc tccagtgccc    540

caagagtcac aagagagagc catgtctact tcccagagtc ctactcgttc ccagaaagga    600

agttctggag accaggaaat gacagctaca cttctcacag cagggttcca gactttggag    660

aagattgaag acatggctgt gtcccttatt cgagaggagt ggcttcttga tccatcacag    720

aaggatctgt gtagagataa caggccagaa aatttcagaa acatgttctc cctgggtggt    780

gagaccagga gtgagaacag ggaattagct tcaaaacagg taatatctac tggaatccag    840

ccacatggag agacagctgc caaatgcaac ggggatgtta tcaggggtct tgagcatgaa    900

gaagcccgag accttctggg cagattagag aggcagcggg gaaatcccac acaagagaga    960

cgacataaat gtgatgaatg tgggaaaagc tttgctcaga gctcaggcct tgttcgccac   1020

tggagaatcc acactgggga gaaaccctat cagtgtaatg tgtgtggtaa agccttcagt   1080

tacaggtcag cccttctttc acatcaggat atccacaaca aagtaaaacg ctatcactgt   1140

aaggagtgtg gcaaagcctt cagtcagaac acaggcctga ttctgcacca gagaatccac   1200

actggggaga agccatatca gtgcaatcag tgtgggaagg ctttcagtca gagtgcgggc   1260

cttattctgc accagagaat ccacagtgga gagagaccct atgaatgtaa tgagtgtggg   1320

aaagctttca gtcatagctc acacctcatt ggacatcaga gaatccacac tggggagaag   1380

ccctatgagt gtgatgagtg tgggaaaacc ttcaggcgga gctcacatct tattggtcat   1440

cagaggagcc acactgggga gaaaccctac aaatgcaatg agtgtgggag ggccttcagt   1500

cagaagtcag gccttattga acatcagaga atccacactg gagaaagacc ctataaatgt   1560

aaagaatgtg ggaaagcttt caatgggaac actggtctca ttcaacacct gagaattcac   1620

acaggggaga agccctacca atgtaatgag tgtgggaaag cctttattca gaggtcaagt   1680

ctcattcgac atcagagaat ccacagtggt gaaaaatctg aatccataag cgtttag      1737
```

<210> SEQ ID NO 38
<211> LENGTH: 578
<212> TYPE: PRT
<213> ORGANISM: Homo sapiens

<400> SEQUENCE: 38

```
Met Ala Glu Glu Ser Arg Lys Pro Ser Ala Pro Ser Pro Pro Asp Gln
1               5                   10                  15

Thr Pro Glu Glu Asp Leu Val Ile Val Lys Val Glu Glu Asp His Gly
            20                  25                  30

Trp Asp Gln Glu Ser Ser Leu His Glu Ser Asn Pro Leu Gly Gln Glu
        35                  40                  45

Val Phe Arg Leu Arg Phe Arg Gln Leu Arg Tyr Gln Glu Thr Leu Gly
    50                  55                  60

Pro Arg Glu Ala Leu Ile Gln Leu Arg Ala Leu Cys His Gln Trp Leu
65                  70                  75                  80

Arg Pro Asp Leu Asn Thr Lys Glu Gln Ile Leu Glu Leu Leu Val Leu
                85                  90                  95

Glu Gln Phe Leu Thr Ile Leu Pro Glu Glu Leu Gln Thr Leu Val Lys
            100                 105                 110

Glu His Gln Leu Glu Asn Gly Glu Glu Val Val Thr Leu Leu Glu Asp
        115                 120                 125

Leu Glu Arg Gln Ile Asp Ile Leu Gly Arg Pro Val Ser Ala Arg Val
```

```
    130                 135                 140

His Gly His Arg Val Leu Trp Glu Glu Val Val His Ser Ala Ser Ala
145                 150                 155                 160

Pro Glu Pro Pro Asn Thr Gln Leu Gln Ser Glu Ala Thr Gln His Lys
                165                 170                 175

Ser Pro Val Pro Gln Glu Ser Gln Glu Arg Ala Met Ser Thr Ser Gln
            180                 185                 190

Ser Pro Thr Arg Ser Gln Lys Gly Ser Ser Gly Asp Gln Glu Met Thr
        195                 200                 205

Ala Thr Leu Leu Thr Ala Gly Phe Gln Thr Leu Glu Lys Ile Glu Asp
    210                 215                 220

Met Ala Val Ser Leu Ile Arg Glu Glu Trp Leu Leu Asp Pro Ser Gln
225                 230                 235                 240

Lys Asp Leu Cys Arg Asp Asn Arg Pro Glu Asn Phe Arg Asn Met Phe
                245                 250                 255

Ser Leu Gly Gly Glu Thr Arg Ser Glu Asn Arg Glu Leu Ala Ser Lys
            260                 265                 270

Gln Val Ile Ser Thr Gly Ile Gln Pro His Gly Glu Thr Ala Ala Lys
        275                 280                 285

Cys Asn Gly Asp Val Ile Arg Gly Leu Glu His Glu Glu Ala Arg Asp
    290                 295                 300

Leu Leu Gly Arg Leu Glu Arg Gln Arg Gly Asn Pro Thr Gln Glu Arg
305                 310                 315                 320

Arg His Lys Cys Asp Glu Cys Gly Lys Ser Phe Ala Gln Ser Ser Gly
                325                 330                 335

Leu Val Arg His Trp Arg Ile His Thr Gly Glu Lys Pro Tyr Gln Cys
            340                 345                 350

Asn Val Cys Gly Lys Ala Phe Ser Tyr Arg Ser Ala Leu Leu Ser His
        355                 360                 365

Gln Asp Ile His Asn Lys Val Lys Arg Tyr His Cys Lys Glu Cys Gly
    370                 375                 380

Lys Ala Phe Ser Gln Asn Thr Gly Leu Ile Leu His Gln Arg Ile His
385                 390                 395                 400

Thr Gly Glu Lys Pro Tyr Gln Cys Asn Gln Cys Gly Lys Ala Phe Ser
                405                 410                 415

Gln Ser Ala Gly Leu Ile Leu His Gln Arg Ile His Ser Gly Glu Arg
            420                 425                 430

Pro Tyr Glu Cys Asn Glu Cys Gly Lys Ala Phe Ser His Ser Ser His
        435                 440                 445

Leu Ile Gly His Gln Arg Ile His Thr Gly Glu Lys Pro Tyr Glu Cys
    450                 455                 460

Asp Glu Cys Gly Lys Thr Phe Arg Arg Ser Ser His Leu Ile Gly His
465                 470                 475                 480

Gln Arg Ser His Thr Gly Glu Lys Pro Tyr Lys Cys Asn Glu Cys Gly
                485                 490                 495

Arg Ala Phe Ser Gln Lys Ser Gly Leu Ile Glu His Gln Arg Ile His
            500                 505                 510

Thr Gly Glu Arg Pro Tyr Lys Cys Lys Glu Cys Gly Lys Ala Phe Asn
        515                 520                 525

Gly Asn Thr Gly Leu Ile Gln His Leu Arg Ile His Thr Gly Glu Lys
    530                 535                 540

Pro Tyr Gln Cys Asn Glu Cys Gly Lys Ala Phe Ile Gln Arg Ser Ser
545                 550                 555                 560
```

```
Leu Ile Arg His Gln Arg Ile His Ser Gly Glu Lys Ser Glu Ser Ile
                565                 570                 575

Ser Val


<210> SEQ ID NO 39
<211> LENGTH: 711
<212> TYPE: DNA
<213> ORGANISM: Homo sapiens

<400> SEQUENCE: 39

atgcccacgg acatggaaca cacaggacat tacctacatc ttgcctttct gatgacaaca     60

gttttttctt tgtctcctgg aacaaaagca aactataccc gtctgtgggc taacagtact    120

tcttcctggg attcagttat tcaaaacaag acaggcagaa accaaaatga aaacattaac    180

acaaacccta taactcctga agtagattat aaaggtaatt ctacaaacat gcctgaaaca    240

tctcacatcg tagctttaac ttctaaatct gaacaggagc tttatatacc ttctgtcgtc    300

agcaacagtc cttcaacagt acagagcatt gaaaacacaa gcaaaagtca tggtgaaatt    360

ttcaaaaagg atgtctgtgc ggaaaacaac aacaacatgg ctatgctaat ttgcttaatt    420

ataattgcag tgctttttct tatctgtacc tttctatttc tatcaactgt ggttttggca    480

aacaaagtct cttctctcag acgatcaaaa caagtaggca agcgtcagcc tagaagcaat    540

ggcgatttc tggcaagcgg tctatggccc gctgaatcag acacttggaa aagaacaaaa    600

cagctcacag gacccaacct agtgatgcaa tctactggag tgctcacagc tacaagggaa    660

agaaaagatg aagaaggaac tgaaaaactt actaacaaac agataggtta g             711


<210> SEQ ID NO 40
<211> LENGTH: 236
<212> TYPE: PRT
<213> ORGANISM: Homo sapiens

<400> SEQUENCE: 40

Met Pro Thr Asp Met Glu His Thr Gly His Tyr Leu His Leu Ala Phe
1               5                   10                  15

Leu Met Thr Thr Val Phe Ser Leu Ser Pro Gly Thr Lys Ala Asn Tyr
            20                  25                  30

Thr Arg Leu Trp Ala Asn Ser Thr Ser Ser Trp Asp Ser Val Ile Gln
        35                  40                  45

Asn Lys Thr Gly Arg Asn Gln Asn Glu Asn Ile Asn Thr Asn Pro Ile
    50                  55                  60

Thr Pro Glu Val Asp Tyr Lys Gly Asn Ser Thr Asn Met Pro Glu Thr
65                  70                  75                  80

Ser His Ile Val Ala Leu Thr Ser Lys Ser Glu Gln Glu Leu Tyr Ile
                85                  90                  95

Pro Ser Val Val Ser Asn Ser Pro Ser Thr Val Gln Ser Ile Glu Asn
            100                 105                 110

Thr Ser Lys Ser His Gly Glu Ile Phe Lys Lys Asp Val Cys Ala Glu
        115                 120                 125

Asn Asn Asn Asn Met Ala Met Leu Ile Cys Leu Ile Ile Ile Ala Val
    130                 135                 140

Leu Phe Leu Ile Cys Thr Phe Leu Phe Leu Ser Thr Val Val Leu Ala
145                 150                 155                 160

Asn Lys Val Ser Ser Leu Arg Arg Ser Lys Gln Val Gly Lys Arg Gln
                165                 170                 175
```

```
Pro Arg Ser Asn Gly Asp Phe Leu Ala Ser Gly Leu Trp Pro Ala Glu
            180                 185                 190

Ser Asp Thr Trp Lys Arg Thr Lys Gln Leu Thr Gly Pro Asn Leu Val
        195                 200                 205

Met Gln Ser Thr Gly Val Leu Thr Ala Thr Arg Glu Arg Lys Asp Glu
    210                 215                 220

Glu Gly Thr Glu Lys Leu Thr Asn Lys Gln Ile Gly
225                 230                 235


<210> SEQ ID NO 41
<211> LENGTH: 1887
<212> TYPE: DNA
<213> ORGANISM: Homo sapiens

<400> SEQUENCE: 41

atggattcgg gcagcagcag cagcgactcg gcgcccgatt gctgggacca ggtggacatg     60

gaatccccgg ggtcggcccc gagcggggat ggagtctcct ctgcggtggc cgaggcccag    120

cgcgagcccc tcagctcggc tttcagccgt aagctcaacg tcaacgccaa gcccttcgtg    180

cctaacgtac acgccgcgga gttcgtgccg tccttcctgc ggggcccgac tcagccgccc    240

accctcccgg ccggctccgg cagcaacgat gaaacctgca ccggcgcggg ataccctcaa    300

ggtaaaagga tgggacgggg ggcacctgtg gaaccttccc gagaggaacc gttagtgtcg    360

cttgaaggtt ccaattcagc cgttaccatg gaactttcag aacctgttgt agaaaatgga    420

gaggtggaaa tggccctaga agaatcatgg gagcacagta aagaagtaag tgaagccgag    480

cctgggggtg gttcctcggg agattcaggg cccccagaag aaagtggcca ggaaatgatg    540

gaggaaaaag aggaaataag aaaatccaaa tctgtgatcg taccctcagg tgcacctaag    600

aaagaacacg taaatgtagt attcattggc catgtagacg ctggcaagtc aaccatcgga    660

ggacagataa tgtttttgac tggaatggtt gacaaaagaa cactggagaa atatgaaaga    720

gaagctaagg aaaaaaacag agaaacctgg tatttgtcct gggccttaga tacaaatcag    780

gaggaacgag acaagggtaa aacagtcgaa gtgggtcgtg cctattttga aacagaaagg    840

aaacatttca caattttaga tgcccctggc cacaagagtt ttgtcccaaa tatgattggt    900

ggtgcttctc aagctgattt ggctgtgctg gtcatctctg ccaggaaagg agagtttgaa    960

actggatttg aaaaaggtgg acagacaaga gaacatgcga tgttggcaaa aacggcaggg   1020

gtaaaacatt taatagtgct tattaataag atggatgatc ccacagtaaa ttggagcatc   1080

gagagatatg aagaatgtaa agaaaaactg gtgccctttt tgaaaaaagt aggcttcagt   1140

ccaaaaaagg acattcactt tatgccctgc tcaggactga ccggagcaaa tattaaagag   1200

cagtcagatt tctgcccttg gtacactgga ttaccattta ttccgtattt ggataacttg   1260

ccaaacttca acagatcaat tgatggacca ataagactgc caattgtgga taagtacaaa   1320

gatatgggca ccgtggtcct gggaaagctg gaatccgggt ccatttttaa aggccagcag   1380

ctcgtgatga tgccaaacaa gcacaatgta gaagttcttg gaatactttc tgatgatact   1440

gaaactgatt ttgtagcccc aggtgaaaac ctcaaaatca gactgaaggg aattgaagaa   1500

gaagagattc ttccaggatt catactttgt gatcctagta acctctgcca ttctggacgc   1560

acgtttgatg ttcagatagt gattattgag cacaaatcca tcatctgccc aggttataat   1620

gcggtgctgc acattcatac ttgtattgag gaagttgaga taacagcgtt aatctccttg   1680

gtagacaaaa aatcaggaga aaaaagtaag acacgacccc gcttcgtgaa acaagatcaa   1740

gtatgcattg ctcgtttaag gacagcagga accatctgcc tcgagacgtt caaagatttt   1800
```

```
cctcagatgg gtcgttttac tttaagagat gagggtaaga ccattgcaat tggaaaagtt   1860

ctgaaattgg tcccagagaa ggactaa                                       1887


<210> SEQ ID NO 42
<211> LENGTH: 628
<212> TYPE: PRT
<213> ORGANISM: Homo sapiens

<400> SEQUENCE: 42

Met Asp Ser Gly Ser Ser Ser Ser Asp Ser Ala Pro Asp Cys Trp Asp
1               5                   10                  15

Gln Val Asp Met Glu Ser Pro Gly Ser Ala Pro Ser Gly Asp Gly Val
            20                  25                  30

Ser Ser Ala Val Ala Glu Ala Gln Arg Glu Pro Leu Ser Ser Ala Phe
        35                  40                  45

Ser Arg Lys Leu Asn Val Asn Ala Lys Pro Phe Val Pro Asn Val His
    50                  55                  60

Ala Ala Glu Phe Val Pro Ser Phe Leu Arg Gly Pro Thr Gln Pro Pro
65                  70                  75                  80

Thr Leu Pro Ala Gly Ser Gly Ser Asn Asp Glu Thr Cys Thr Gly Ala
                85                  90                  95

Gly Tyr Pro Gln Gly Lys Arg Met Gly Arg Gly Ala Pro Val Glu Pro
            100                 105                 110

Ser Arg Glu Glu Pro Leu Val Ser Leu Glu Gly Ser Asn Ser Ala Val
        115                 120                 125

Thr Met Glu Leu Ser Glu Pro Val Val Glu Asn Gly Glu Val Glu Met
    130                 135                 140

Ala Leu Glu Glu Ser Trp Glu His Ser Lys Glu Val Ser Glu Ala Glu
145                 150                 155                 160

Pro Gly Gly Gly Ser Ser Gly Asp Ser Gly Pro Pro Glu Glu Ser Gly
                165                 170                 175

Gln Glu Met Met Glu Glu Lys Glu Glu Ile Arg Lys Ser Lys Ser Val
            180                 185                 190

Ile Val Pro Ser Gly Ala Pro Lys Lys Glu His Val Asn Val Val Phe
        195                 200                 205

Ile Gly His Val Asp Ala Gly Lys Ser Thr Ile Gly Gly Gln Ile Met
    210                 215                 220

Phe Leu Thr Gly Met Val Asp Lys Arg Thr Leu Glu Lys Tyr Glu Arg
225                 230                 235                 240

Glu Ala Lys Glu Lys Asn Arg Glu Thr Trp Tyr Leu Ser Trp Ala Leu
                245                 250                 255

Asp Thr Asn Gln Glu Glu Arg Asp Lys Gly Lys Thr Val Glu Val Gly
            260                 265                 270

Arg Ala Tyr Phe Glu Thr Glu Arg Lys His Phe Thr Ile Leu Asp Ala
        275                 280                 285

Pro Gly His Lys Ser Phe Val Pro Asn Met Ile Gly Gly Ala Ser Gln
    290                 295                 300

Ala Asp Leu Ala Val Leu Val Ile Ser Ala Arg Lys Gly Glu Phe Glu
305                 310                 315                 320

Thr Gly Phe Glu Lys Gly Gly Gln Thr Arg Glu His Ala Met Leu Ala
                325                 330                 335

Lys Thr Ala Gly Val Lys His Leu Ile Val Leu Ile Asn Lys Met Asp
            340                 345                 350
```

```
Asp Pro Thr Val Asn Trp Ser Ile Glu Arg Tyr Glu Glu Cys Lys Glu
            355                 360                 365

Lys Leu Val Pro Phe Leu Lys Lys Val Gly Phe Ser Pro Lys Lys Asp
    370                 375                 380

Ile His Phe Met Pro Cys Ser Gly Leu Thr Gly Ala Asn Ile Lys Glu
385                 390                 395                 400

Gln Ser Asp Phe Cys Pro Trp Tyr Thr Gly Leu Pro Phe Ile Pro Tyr
                405                 410                 415

Leu Asp Asn Leu Pro Asn Phe Asn Arg Ser Ile Asp Gly Pro Ile Arg
                420                 425                 430

Leu Pro Ile Val Asp Lys Tyr Lys Asp Met Gly Thr Val Val Leu Gly
                435                 440                 445

Lys Leu Glu Ser Gly Ser Ile Phe Lys Gly Gln Gln Leu Val Met Met
    450                 455                 460

Pro Asn Lys His Asn Val Glu Val Leu Gly Ile Leu Ser Asp Asp Thr
465                 470                 475                 480

Glu Thr Asp Phe Val Ala Pro Gly Glu Asn Leu Lys Ile Arg Leu Lys
                485                 490                 495

Gly Ile Glu Glu Glu Glu Ile Leu Pro Gly Phe Ile Leu Cys Asp Pro
            500                 505                 510

Ser Asn Leu Cys His Ser Gly Arg Thr Phe Asp Val Gln Ile Val Ile
        515                 520                 525

Ile Glu His Lys Ser Ile Ile Cys Pro Gly Tyr Asn Ala Val Leu His
    530                 535                 540

Ile His Thr Cys Ile Glu Glu Val Glu Ile Thr Ala Leu Ile Ser Leu
545                 550                 555                 560

Val Asp Lys Lys Ser Gly Glu Lys Ser Lys Thr Arg Pro Arg Phe Val
                565                 570                 575

Lys Gln Asp Gln Val Cys Ile Ala Arg Leu Arg Thr Ala Gly Thr Ile
                580                 585                 590

Cys Leu Glu Thr Phe Lys Asp Phe Pro Gln Met Gly Arg Phe Thr Leu
            595                 600                 605

Arg Asp Glu Gly Lys Thr Ile Ala Ile Gly Lys Val Leu Lys Leu Val
610                 615                 620

Pro Glu Lys Asp
625

<210> SEQ ID NO 43
<211> LENGTH: 1320
<212> TYPE: DNA
<213> ORGANISM: Homo sapiens

<400> SEQUENCE: 43

atgcccctca acgttagctt caccaacagg aactatgacc tcgactacga ctcggtgcag      60

ccgtatttct actgcgacga ggaggagaac ttctaccagc agcagcagca gagcgagctg     120

cagcccccgg cgcccagcga ggatatctgg aagaaattcg agctgctgcc caccccgccc     180

ctgtccccta gccgccgctc cgggctctgc tcgccctcct acgttgcggt cacacccttc     240

tcccttcggg gagacaacga cggcggtggc gggagcttct ccacggccga ccagctggag     300

atggtgaccg agctgctggg aggagacatg gtgaaccaga gtttcatctg cgacccggac     360

gacgagacct tcatcaaaaa catcatcatc caggactgta tgtggagcgg cttctcggcc     420

gccgccaagc tcgtctcaga gaagctggcc tcctaccagg ctgcgcgcaa agacagcggc     480

agcccgaacc ccgcccgcgg ccacagcgtc tgctccacct ccagcttgta cctgcaggat     540
```

```
ctgagcgccg ccgcctcaga gtgcatcgac ccctcggtgg tcttccccta ccctctcaac    600

gacagcagct cgcccaagtc ctgcgcctcg caagactcca gcgccttctc tccgtcctcg    660

gattctctgc tctcctcgac ggagtcctcc ccgcagggca gccccgagcc cctggtgctc    720

catgaggaga caccgcccac caccagcagc gactctgagg aggaacaaga agatgaggaa    780

gaaatcgatg ttgtttctgt ggaaaagagg caggctcctg gcaaaaggtc agagtctgga    840

tcaccttctg ctggaggcca cagcaaacct cctcacagcc cactggtcct caagaggtgc    900

cacgtctcca cacatcagca caactacgca gcgcctccct ccactcggaa ggactatcct    960

gctgccaaga gggtcaagtt ggacagtgtc agagtcctga gacagatcag caacaaccga   1020

aaatgcacca gccccaggtc ctcggacacc gaggagaatg tcaagaggcg aacacacaac   1080

gtcttggagc gccagaggag gaacgagcta aaacggagct tttttgccct gcgtgaccag   1140

atcccggagt tggaaaacaa tgaaaaggcc cccaaggtag ttatccttaa aaaagccaca   1200

gcatacatcc tgtccgtcca agcagaggag caaaagctca tttctgaaga ggacttgttg   1260

cggaaacgac gagaacagtt gaaacacaaa cttgaacagc tacggaactc ttgtgcgtaa   1320
```

```
<210> SEQ ID NO 44
<211> LENGTH: 439
<212> TYPE: PRT
<213> ORGANISM: Homo sapiens

<400> SEQUENCE: 44

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
            180                 185                 190

Val Val Phe Pro Tyr Pro Leu Asn Asp Ser Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240
```

```
His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435


<210> SEQ ID NO 45
<211> LENGTH: 24
<212> TYPE: DNA
<213> ORGANISM: Artificial
<220> FEATURE:
<223> OTHER INFORMATION: Primer

<400> SEQUENCE: 45

ttatctttcc ggattgaaat tacc                                          24


<210> SEQ ID NO 46
<211> LENGTH: 25
<212> TYPE: DNA
<213> ORGANISM: Artificial
<220> FEATURE:
<223> OTHER INFORMATION: Primer

<400> SEQUENCE: 46

ccatgtacta gacatacgat ctggg                                         25


<210> SEQ ID NO 47
<211> LENGTH: 24
<212> TYPE: DNA
<213> ORGANISM: Artificial
<220> FEATURE:
<223> OTHER INFORMATION: Primer

<400> SEQUENCE: 47

aaggtaactg tatgggataa tggg                                          24


<210> SEQ ID NO 48
<211> LENGTH: 23
```

<212> TYPE: DNA
<213> ORGANISM: Artificial
<220> FEATURE:
<223> OTHER INFORMATION: Primer

<400> SEQUENCE: 48
aattgaattg cctactgtga acc 23

<210> SEQ ID NO 49
<211> LENGTH: 21
<212> TYPE: DNA
<213> ORGANISM: Artificial
<220> FEATURE:
<223> OTHER INFORMATION: Primer

<400> SEQUENCE: 49
acagaacatg gagtttgagg g 21

<210> SEQ ID NO 50
<211> LENGTH: 21
<212> TYPE: DNA
<213> ORGANISM: Artificial
<220> FEATURE:
<223> OTHER INFORMATION: Primer

<400> SEQUENCE: 50
aagtgggtct tcctcagttg c 21

<210> SEQ ID NO 51
<211> LENGTH: 25
<212> TYPE: DNA
<213> ORGANISM: Artificial
<220> FEATURE:
<223> OTHER INFORMATION: Primer

<400> SEQUENCE: 51
acaaagcttg aattaaatga ggttg 25

<210> SEQ ID NO 52
<211> LENGTH: 26
<212> TYPE: DNA
<213> ORGANISM: Artificial
<220> FEATURE:
<223> OTHER INFORMATION: Primer

<400> SEQUENCE: 52
aactaacctt atgtaaggga atttgc 26

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
ttctgtcttg cacatagcca tc 22

<210> SEQ ID NO 54
<211> LENGTH: 21
<212> TYPE: DNA
<213> ORGANISM: Artificial
<220> FEATURE:
<223> OTHER INFORMATION: Primer

<400> SEQUENCE: 54
actaggcagg ccaacaggta g 21

<210> SEQ ID NO 55
<211> LENGTH: 21
<212> TYPE: DNA
<213> ORGANISM: Artificial
<220> FEATURE:
<223> OTHER INFORMATION: Primer

<400> SEQUENCE: 55
actgatgctt tcccttctgt g 21

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
ctggtgctgt cccatctctc 20

<210> SEQ ID NO 57
<211> LENGTH: 21
<212> TYPE: DNA
<213> ORGANISM: Artificial
<220> FEATURE:
<223> OTHER INFORMATION: Primer

<400> SEQUENCE: 57
agccatttct ggtggtcaaa g 21

<210> SEQ ID NO 58
<211> LENGTH: 20
<212> TYPE: DNA
<213> ORGANISM: Artificial
<220> FEATURE:
<223> OTHER INFORMATION: Primer

<400> SEQUENCE: 58
ttggaaagtt aatgccacgc 20

<210> SEQ ID NO 59
<211> LENGTH: 20
<212> TYPE: DNA
<213> ORGANISM: Artificial
<220> FEATURE:
<223> OTHER INFORMATION: Primer

<400> SEQUENCE: 59
actctagcat gggcaacagg 20

<210> SEQ ID NO 60
<211> LENGTH: 21
<212> TYPE: DNA
<213> ORGANISM: Artificial
<220> FEATURE:
<223> OTHER INFORMATION: Primer

<400> SEQUENCE: 60
cccgacacat actatgccaa g 21

<210> SEQ ID NO 61
<211> LENGTH: 21
<212> TYPE: DNA
<213> ORGANISM: Artificial

<220> FEATURE:
<223> OTHER INFORMATION: Primer

<400> SEQUENCE: 61
tcctgttgtg gacagaaatc c 21

<210> SEQ ID NO 62
<211> LENGTH: 25
<212> TYPE: DNA
<213> ORGANISM: Artificial
<220> FEATURE:
<223> OTHER INFORMATION: Primer

<400> SEQUENCE: 62
aaatttgaga accactgtta tcctg 25

<210> SEQ ID NO 63
<211> LENGTH: 21
<212> TYPE: DNA
<213> ORGANISM: Artificial
<220> FEATURE:
<223> OTHER INFORMATION: Primer

<400> SEQUENCE: 63
taatttctgg cttccactgc c 21

<210> SEQ ID NO 64
<211> LENGTH: 21
<212> TYPE: DNA
<213> ORGANISM: Artificial
<220> FEATURE:
<223> OTHER INFORMATION: Primer

<400> SEQUENCE: 64
ggttctgacc aattctttcc c 21

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
tgtgcctggc tgacacaata c 21

<210> SEQ ID NO 66
<211> LENGTH: 22
<212> TYPE: DNA
<213> ORGANISM: Artificial
<220> FEATURE:
<223> OTHER INFORMATION: Primer

<400> SEQUENCE: 66
gccaaatgaa tggcacttac tc 22

<210> SEQ ID NO 67
<211> LENGTH: 21
<212> TYPE: DNA
<213> ORGANISM: Artificial
<220> FEATURE:
<223> OTHER INFORMATION: Primer

<400> SEQUENCE: 67
ctgtctggcc aagtagcact g 21

<210> SEQ ID NO 68
<211> LENGTH: 21
<212> TYPE: DNA
<213> ORGANISM: Artificial
<220> FEATURE:
<223> OTHER INFORMATION: Primer

<400> SEQUENCE: 68
aactgctcaa acccagactc c 21

<210> SEQ ID NO 69
<211> LENGTH: 21
<212> TYPE: DNA
<213> ORGANISM: Artificial
<220> FEATURE:
<223> OTHER INFORMATION: Primer

<400> SEQUENCE: 69
gtcagcacag tggagctgaa g 21

<210> SEQ ID NO 70
<211> LENGTH: 21
<212> TYPE: DNA
<213> ORGANISM: Artificial
<220> FEATURE:
<223> OTHER INFORMATION: Primer

<400> SEQUENCE: 70
ttgaccacct ctgacttcct g 21

<210> SEQ ID NO 71
<211> LENGTH: 21
<212> TYPE: DNA
<213> ORGANISM: Artificial
<220> FEATURE:
<223> OTHER INFORMATION: Primer

<400> SEQUENCE: 71
tgttgtcaga ctccaagcag g 21

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
gggattactg gcctggaaag 20

<210> SEQ ID NO 73
<211> LENGTH: 21
<212> TYPE: DNA
<213> ORGANISM: Artificial
<220> FEATURE:
<223> OTHER INFORMATION: Primer

<400> SEQUENCE: 73
gctaattagg gtggctgagg c 21

<210> SEQ ID NO 74
<211> LENGTH: 20
<212> TYPE: DNA
<213> ORGANISM: Artificial
<220> FEATURE:
<223> OTHER INFORMATION: Primer -continued

```
<400> SEQUENCE: 74

aaacaggctt cccatcatcc                                                20


<210> SEQ ID NO 75
<211> LENGTH: 21
<212> TYPE: DNA
<213> ORGANISM: Artificial
<220> FEATURE:
<223> OTHER INFORMATION: Primer

<400> SEQUENCE: 75

cgtccagaca tcagttccat c                                              21


<210> SEQ ID NO 76
<211> LENGTH: 20
<212> TYPE: DNA
<213> ORGANISM: Artificial
<220> FEATURE:
<223> OTHER INFORMATION: Primer

<400> SEQUENCE: 76

gtgccatctc acaaaggtgg                                                20


<210> SEQ ID NO 77
<211> LENGTH: 21
<212> TYPE: DNA
<213> ORGANISM: Artificial
<220> FEATURE:
<223> OTHER INFORMATION: Primer

<400> SEQUENCE: 77

agatgtaatt gcatggccac c                                              21


<210> SEQ ID NO 78
<211> LENGTH: 20
<212> TYPE: DNA
<213> ORGANISM: Artificial
<220> FEATURE:
<223> OTHER INFORMATION: Primer

<400> SEQUENCE: 78

agggacctcg tttgttcctg                                                20


<210> SEQ ID NO 79
<211> LENGTH: 5
<212> TYPE: PRT
<213> ORGANISM: Artificial
<220> FEATURE:
<223> OTHER INFORMATION: CNII helix sequence

<400> SEQUENCE: 79

Lys Lys Tyr Arg Arg
1               5
```

METHODS AND COMPOSITIONS FOR THE PROGNOSIS AND TREATMENT OF RELAPSED LEUKEMIA

This application is a national stage application under 35 U.S.C. § 371 from PCT/US2013/039942, filed May 7, 2013, which claims the benefit of U.S. Provisional Patent Application Ser. No. 61/643,489, filed May 7, 2012, which is hereby incorporated by reference in its entirety.

This invention was made with government support under R01CA140729 and R21CA152838-02 awarded by the National Institutes of Health. The government has certain rights in the invention.

FIELD OF THE INVENTION

The present invention is directed to methods of prognosing, preventing, and treating relapsed leukemia in a subject.

BACKGROUND OF THE INVENTION

Acute lymphoblastic leukemia (ALL) is the most common pediatric malignancy, accounting for greater than 25% of all childhood cancers (Li et al., "Cancer Incidence Among Children and Adolescents in the United States, 2001-2003," *Pediatrics* 121:e1470-7 (2008)). Cure rates for ALL have improved dramatically over the past four decades with the development of risk stratification protocols that tailor therapy based on predicted risk of relapse factors, resulting in an overall five year event-free survival now approaching 80% (Escherich et al., "Cooperative Study Group for Childhood Acute Lymphoblastic Leukaemia (COALL): Long-Term Results of Trials 82, 85, 89, 92 and 97," *Leukemia* 24:298-308 (2010) and Gaynon et al., "Long-Term Results of the Children's Cancer Group Studies for Childhood Acute Lymphoblastic *Leukemia* 1983-2002: A Children's Oncology Group Report," *Leukemia* 24:285-97 (2010)). Despite these improvements, up to 20% of patients experience disease recurrence (Pui & Evans, "Treatment of Acute Lymphoblastic Leukemia," *N. Engl. J. Med.* 354:166-78 (2006)). The prognosis for these children is dismal (Chessells et al., "Long-Term Follow-Up of Relapsed Childhood Acute Lymphoblastic Leukaemia," *Br. J. Haematol.* 123: 396-405 (2003)), even with aggressive retrieval strategies involving allogeneic stem cell transplant (Eapen et al., "Outcomes After HLA-Matched Sibling Transplantation or Chemotherapy in Children with B-Precursor Acute Lymphoblastic Leukemia in a Second Remission: A Collaborative Study of the Children's Oncology Group and the Center for International Blood and Marrow Transplant Research," *Blood* 107:4961-7 (2006) and Gaynon et al., "Bone Marrow Transplantation Versus Prolonged Intensive Chemotherapy for Children with Acute Lymphoblastic Leukemia and an Initial Bone Marrow Relapse Within 12 Months of the Completion of Primary Therapy: Children's Oncology Group study CCG-1941," *J. Clin. Oncol.* 24:3150-6 (2006)), and relapsed ALL remains one of the leading causes of mortality for all childhood malignancies.

Differences in gene expression, copy number, and methylation that have evolved with therapy have been profiled to determine biological pathways responsible for treatment failure. These results indicate that a number of pathways are implicated in ALL relapse (Mullighan et al., "CREBBP Mutations in Relapsed Acute Lymphoblastic Leukaemia," *Nature* 471:235-9 (2011); Mullighan et al., "Genomic Analysis of the Clonal Origins of Relapsed Acute Lymphoblastic Leukemia," *Science* 322:1377-80 (2008); and Hogan et al., "Integrated Genomic Analysis of Relapsed Childhood Acute Lymphoblastic Leukemia Reveals Therapeutic Strategies," *Blood* 118(19):5218-26 (2011)). However the evolution of ALL clones has not been analyzed on a whole transcriptome level.

The present invention is directed to overcoming these and other deficiencies in the art.

SUMMARY OF THE INVENTION

A first aspect of the present invention is directed to a method of determining a subject's risk of developing relapse leukemia. This method involves contacting an isolated biological sample from a subject having leukemia with one or more reagents suitable for detecting the presence or absence of one or more mutations in one or more genes selected from the group consisting of NT5C2, RGS12, LPHN1, CAND1, PRMT2, NIPSNAP1, USP7, TULP4, CBX3, COBRA1, SDF2, FBXO3, SCARF1, NEGR1, DPH5, SMEK2, MIER3, DOPEY1, ZNF192, EVI2A, GSPT2, and MYC, and detecting the presence or absence of the one or more mutations in the one or more genes based on said contacting. The subject's prognosis is determined based on said detection, wherein the presence of one or more mutations in the one or more genes predicts an increased likelihood the subject will develop relapse leukemia.

Another aspect of the present invention relates to a method of treating a subject having leukemia. This method involves selecting a subject having leukemia and one or more mutations in one or more genes selected from the group consisting of NT5C2, RGS12, LPHN1, CAND1, PRMT2, NIPSNAP1, USP7, TULP4, CBX3, COBRA1, SDF2, FBXO3, SCARF1, NEGR1, DPH5, SMEK2, MIER3, DOPEY1, ZNF192, EVI2A, GSPT2, and MYC, and administering a therapy suitable for treating relapse leukemia to the selected subject.

Another aspect of the present invention is directed to a method of preventing or treating relapsed leukemia in a subject. This method involves selecting a subject having one or more NT5C2 gene mutations and administering to the selected subject an agent that inhibits NT5C2 gene expression and/or NT5C2 encoded enzyme activity under conditions effective to prevent or treat relapsed leukemia in the subject.

Relapsed childhood acute lymphoblastic leukemia (ALL) carries a poor prognosis, despite intensive retreatment, owing to intrinsic drug resistance (Raetz et al. "Reinduction Platform for Children with First Marrow Relapse in Acute Lymphoblastic Lymphoma," *J. Clin. Oncol.* 26: 3971-3978 (2008), and Klumper et al., "In Vitro Cellular Drug Resistance in Children with Relapsed/Refractory Acute Lymphoblastic Leukemia," *Blood* 86: 3861-3868 (1995), which are hereby incorporated by reference in their entirety). The biological pathways that mediate resistance are unknown. Here, the transcriptome profiles of matched diagnosis and relapse bone marrow specimens from individuals with pediatric B-lymphoblastic leukemia using RNA sequencing are reported. Transcriptome sequencing identified 20 newly acquired, novel nonsynonymous mutations not present at initial diagnosis, with 2 individuals harboring relapse-specific mutations in the same gene, NT5C2, encoding a 5'-nucleotidase. Full exon sequencing of NT5C2 was completed in 61 further relapse specimens, identifying additional mutations in 5 cases. Enzymatic analysis of mutant proteins showed that base substitutions conferred increased enzymatic activity and resistance to treatment with nucleoside analog therapies. Clinically, all individuals who harbored NT5C2 mutations relapsed early, within 36 months of initial diagnosis (P=0.03). These results suggest that mutations in NT5C2 are associated with the outgrowth of drug-resistant clones in ALL.

BRIEF DESCRIPTION OF THE DRAWINGS

FIG. 5A shows the sequencing trace for R238W mutation in Patient #7 samples (i.e., germline, diagnosis, and relapse genomic DNA samples) and FIG. 5B shows the sequencing trace for S445F mutation in Patient #8 samples. FIGS. 5C and 5D show sequencing traces for all NT5C2 mutations in samples from the expanded cohort of patients subject to full exon sequencing. Both forward and reverse traces were available for each mutation but only one trace is shown. Top track shows reference sequence (hg18), middle track shows sample sequence, bottom plot is discordance between reference and sample. Mutations are clearly visible as peaks in bottom track (green line marks threshold for Mutation Surveyor program to automatically call mutations). All SNV sequence traces were manually inspected for mutations that did not meet the automatic threshold.

FIG. 6A shows a dimer of human cytosolic 5'-nucleotidase II (cN-II) subunits. Two such dimers, linked by a different interface, form the tetrameric active form of this enzyme. The backbone traces of the structures are shown as ribbons. The bottom monomer ribbon is colored in a gradient from its N terminus (purple) to its C terminus (red). The location of the active site is indicated by an asterisk. Note that the C terminus of one monomer extends into a groove in the other monomer to form the dimer. The upper monomer ribbon is colored green for contrast. The location of the disordered loop at positions 400-417 is indicated as an orange dashed line in the bottom monomer and as a transparent green U-shaped arrow in the top monomer to show its expected area of interaction. The p.Arg238Trp, p.Arg367Gln and p.Ser445Phe alterations are shown as space-filling spheres colored red for oxygen, blue for nitrogen and white for carbon. The projected locations of the insertion (p.Lys404ins) and point alteration (p.Ser408Arg) in the disordered loop, which is not visible in the crystal structure, are indicated by dashed circles and labeled. A straight transparent green arrow indicates the expected trajectory of the acidic C-terminal tail of the upper monomer, which is not present in the crystal structure, as it lies across the bottom monomer. FIG. 6B is a schematic of NT5C2 coding region annotated with relapse-specific mutations and the encoded protein alterations. Three mutations were found at the same site in exon 9 encoding amino acid 238. FIG. 6C shows an immunoblot analysis of wildtype and mutant cN-II protein induction by IPTG in BL21 cells. Protein lysates (10 mg per lane) were blotted with antibody against cN-II (WT, wild type). In FIG. 6D, equivalent volumes of BL21 protein lysate were subjected to a 5'-nucleotidase assay (Diazyme). Mean activity levels were normalized by protein concentration for each sample. Columns show the mean of three independent experiments ±s.d. P values were calculated using two-sided unpaired Student's t tests (*P≤0.01).

In FIGS. 7A-7F, Reh cells infected with control GFP lentivirus or with virus expressing wild-type (WT) or mutant cN-II were treated with increasing concentrations of 6-thioguanine (FIG. 7A), 6-mercaptopurine (6-MP) (FIG. 7B), cytarabine (FIG. 7C), gemcitabine (FIG. 7D), doxorubicin (FIG. 7E) or prednisolone (FIG. 7F) and assayed for apoptosis. Columns show a mean of three independent determinations ±s.d. from a representative experiment repeated three times with similar results. P values were calculated using two-sided unpaired Student's t tests (*P<0.001). FIG. 7G is an immunoblot of infected Reh cells showing the presence of Flag-tagged cN-II proteins compared to GFP control and Reh cells alone. Actin is shown as a loading control.

FIG. 11A is a mapped RNA sequence read along the EV12A gene from patient #3. Diagnosis shows a mutation at amino acid residue 127 present in a low number of reads (not all sequence coverage is shown). FIG. 11B is a mapped RNA sequence read along the EV12A gene from the same patient at relapse showing outgrowth of the mutation at amino acid position 127. FIG. 11C is a mapped RNA sequence read along the MYC gene from patient #4. Diagnosis shows side-by-side mutations at threonine 58 present in a low number of reads (not all sequence coverage is shown). FIG. 11D is a mapped RNA sequence read along the MYC gene from the same patient at relapse showing outgrowth of this same mutation.

DETAILED DESCRIPTION OF THE INVENTION

Figure 1:
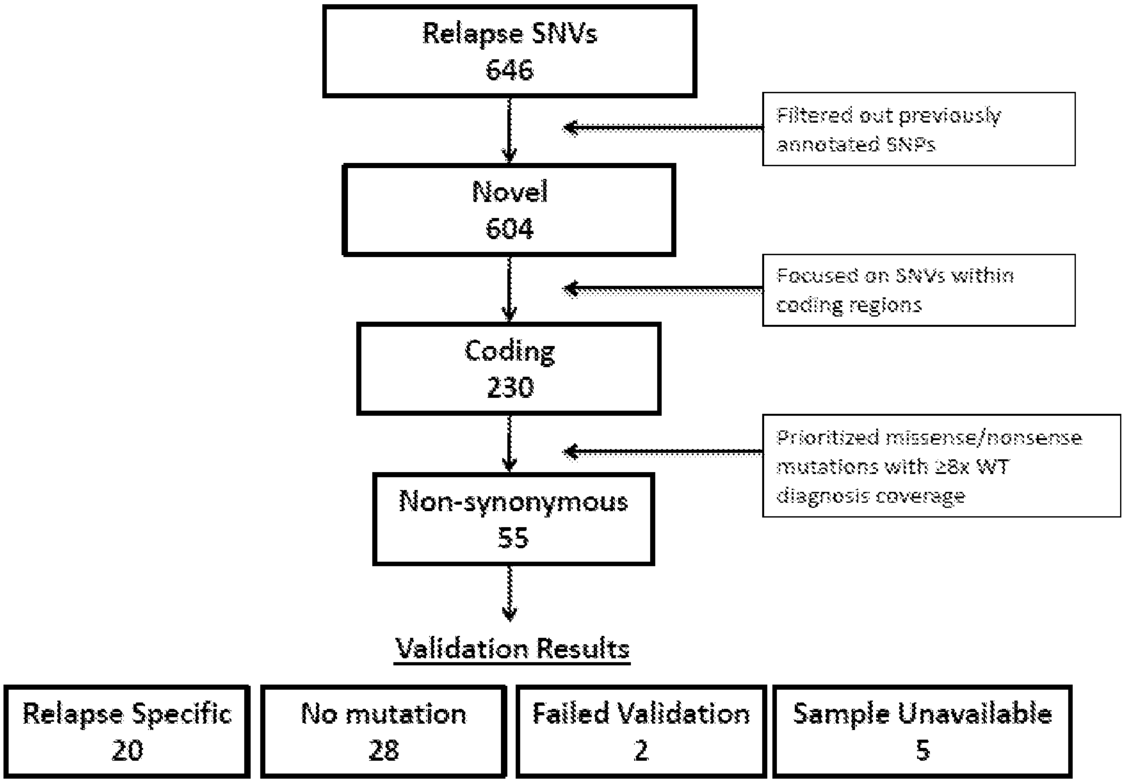
FIG. 1 is flow diagram showing the prioritization scheme for validation of relapse specific single nucleotide variants (SNVs). Total variants were filtered for 8× coverage per site and events that occurred more times at relapse compared to matched diagnosis samples were considered. Variants were then filtered for previously characterized SNV present in dbSNP 135 and 1000 Genome Projects, and prioritization was given to those present in coding regions that resulted in non-synonymous changes. Lastly, all SNVs were then cross checked against reads per site to filter for false positive relapse enriched SNVs that may have been present at low levels in diagnosis samples. In total 50 SNVs were sent for validation from germline, diagnosis, and relapse sample genomic DNA (5 SNVs were present in patients without genomic DNA). Twenty (20) SNVs were validated as relapse specific (not present in germline or diagnosis sample), 28 SNVs did not validate (WT sequence instead at predicted site), and 2 SNVs failed during the validation process and no data was available after Sanger sequencing.

A first aspect of the present invention is directed to a method of determining a subject's risk of developing relapse leukemia. This method involves contacting an isolated biological sample from a subject having leukemia with one or more reagents suitable for detecting the presence or absence of one or more mutations in one or more genes selected from the group consisting of NT5C2, RGS12, LPHN1, CAND1, PRMT2, NIPSNAP1, USP7, TULP4, CBX3, COBRA1, SDF2, FBXO3, SCARF1, NEGR1, DPH5, SMEK2, MIER3, DOPEY1, ZNF192, EVI2A, GSPT2, and MYC, and detecting the presence or absence of the one or more mutations in the one or more genes based on said contacting. The subject's prognosis is determined based on said detection, wherein the presence of one or more mutations in the one or more genes predicts an increased likelihood the subject will develop relapse leukemia.

In accordance with this and all other aspects of the present invention, a "subject" or "patient" encompasses any animal, preferably, a mammal having leukemia. Exemplary mammalian subjects include, without limitation, humans, non-human primates, dogs, cats, rodents, horses, cattle, sheep, and pigs. More preferably, the subject is a human.

Also in accordance with this aspect of the invention, the subject has leukemia, for example, the subject may have acute lymphoblastic leukemia (ALL), i.e., B-cell ALL or T-cell ALL. The subject may be an adult or juvenile (e.g., a child between the ages of 1-10 years old)

The biological sample obtained from the patient is any sample containing leukemic cells. For example, suitable biological samples, include bone marrow or peripheral blood samples.

As described herein, applicants have identified and validated one or more mutations in each of the following genes, NT5C2, RGS12, LPHN1, CAND1, PRMT2, NIPSNAP1, USP7, TULP4, CBX3, COBRA1, SDF2, FBXO3, SCARF1, NEGR1, DPH5, SMEK2, MIER3, DOPEY1, ZNF192, EVI2A, GSPT2, and MYC, that predict a poor prognosis for patients having leukemia. Specifically, detecting the presence of one or more of these mutations, which include non-synonymous single nucleotide base substitutions, insertions, and deletions predicts an increased likelihood that the subject or patient will develop relapse leukemia (i.e., predicts a poor prognosis). Based on the detection of these mutations at diagnosis or sometime thereafter, the patient's course of treatment can be modified and optimized to prevent the onset of relapse disease. In one embodiment of the present invention, the prognosis of a subject or patient having leukemia is monitored after diagnosis by periodically testing a peripheral blood or bone marrow sample from the subject for the presence or absence of mutations in the above identified genes. Based on the detection of a mutation, the subject's current course of treatment is assessed and modified to prevent relapse disease as described infra.

In one embodiment of this aspect of the present invention, the one or more mutations detected in the patient sample include mutations specific to the NT5C2 gene, which encodes cytosolic 5'nucleotidase (cN-II). The mRNA and amino acid sequence for human cN-II are provided below as SEQ ID NOs: 1 and 2, respectively.

```
                                                          SEQ ID NO: 1
Human NT5C2
atgtcaacct cctggagtga tcggttacag aatgcagcag atatgcctgc taacatggat    60

aagcatgccc tgaaaaagta tcgtcgagaa gcctatcatc gggtgtttgt gaaccgaagt   120

ttagcaatgg aaaagataaa gtgttttggt tttgatatgg attataccct tgctgtgtac   180

aagtccccag agtatgagtc ccttggtttt gagcttactg tggagagatt agtttctatt   240

ggctatcccc aggagttgct cagctttgct tatgattcta cattccctac caggggactt   300

gtctttgaca cactgtatgg aaatcttttg aaagtcgatg cctatggaaa cctcttggtc   360

tgtgcacatg gatttaactt tataagggga ccagaaacta gagaacagta tccaaataaa   420

tttatccagc gagatgatac tgaaagattt tacattctga acacactatt caacctacca   480

gagacctacc tgttggcctg cctagtagat ttttttacta attgtcccag atataccagt   540

tgtgaaacag gatttaaaga tggggacctc ttcatgtcct accggagtat gttccaggat   600

gtaagagatg ctgttgactg ggttcattac aagggctccc ttaaggaaaa gacagttgaa   660

aatcttgaga agtatgtagt caaagatgga aaactgcctt tgcttctgag ccggatgaag   720

gaagtaggga aagtatttct tgctaccaac agtgactata aatatacaga taaaattatg   780

acttacctgt ttgacttccc acatggcccc aagcctggga gctcccatcg accatggcag   840

tcctactttg acttgatctt ggtggatgca cggaaaccac tctttttggg agaaggcaca   900

gtactgcgtc aggtggatac taaaactggc aagctgaaaa ttggtaccta cacagggccc   960
```

-continued

```
ctacagcatg gtatcgtcta ctcaggaggt tcttctgata cgatctgtga cctgttggga  1020

gccaagggaa aagacatttt gtatattgga gatcacattt ttggggacat tttaaaatca  1080

aagaaacggc aagggtggcg aacttttttg gtgattcctg aactcgcaca ggagctacat  1140

gtctggactg acaagagttc acttttcgaa gaacttcaga gcttggatat tttcttggct  1200

gaactctaca agcatcttga cagcagtagc aatgagcgtc cagacatcag ttccatccag  1260

agacgtatta agaaagtaac tcatgacatg gacatgtgct atgggatgat gggaagcctg  1320

tttcgcagtg gctcccggca gaccctttttt gccagtcaag tgatgcgtta tgctgacctc  1380

tatgcagcat ctttcatcaa cctgctgtat taccctttca gctacctctt cagggctgcc  1440

catgtcttga tgcctcatga atcaacggtg gagcacacac acgtagatat caatgagatg  1500

gagtctcctc ttgccacccg gaaccgcaca tcagtggatt tcaaagacac tgactacaag  1560

cggcaccagc tgacacggtc aattagtgag attaaacctc ccaacctctt cccactggcc  1620

ccccaggaaa ttacacactg ccatgacgaa gatgatgatg aagaggagga ggaggaggaa  1680

gaataa                                                             1686

                                                      SEQ ID NO: 2
Human cN-II
Met Ser Thr Ser Trp Ser Asp Arg Leu Gln Asn Ala Ala Asp Met Pro
1               5                   10                  15

Ala Asn Met Asp Lys His Ala Leu Lys Lys Tyr Arg Arg Glu Ala Tyr
            20                  25                  30

His Arg Val Phe Val Asn Arg Ser Leu Ala Met Glu Lys Ile Lys Cys
        35                  40                  45

Phe Gly Phe Asp Met Asp Tyr Thr Leu Ala Val Tyr Lys Ser Pro Glu
    50                  55                  60

Tyr Glu Ser Leu Gly Phe Glu Leu Thr Val Glu Arg Leu Val Ser Ile
65                  70                  75                  80

Gly Tyr Pro Gln Glu Leu Leu Ser Phe Ala Tyr Asp Ser Thr Phe Pro
                85                  90                  95

Thr Arg Gly Leu Val Phe Asp Thr Leu Tyr Gly Asn Leu Leu Lys Val
            100                 105                 110

Asp Ala Tyr Gly Asn Leu Leu Val Cys Ala His Gly Phe Asn Phe Ile
        115                 120                 125

Arg Gly Pro Glu Thr Arg Glu Gln Tyr Pro Asn Lys Phe Ile Gln Arg
    130                 135                 140

Asp Asp Thr Glu Arg Phe Tyr Ile Leu Asn Thr Leu Phe Asn Leu Pro
145                 150                 155                 160

Glu Thr Tyr Leu Leu Ala Cys Leu Val Asp Phe Phe Thr Asn Cys Pro
                165                 170                 175

Arg Tyr Thr Ser Cys Glu Thr Gly Phe Lys Asp Gly Asp Leu Phe Met
            180                 185                 190

Ser Tyr Arg Ser Met Phe Gln Asp Val Arg Asp Ala Val Asp Trp Val
        195                 200                 205

His Tyr Lys Gly Ser Leu Lys Glu Lys Thr Val Glu Asn Leu Glu Lys
    210                 215                 220

Tyr Val Val Lys Asp Gly Lys Leu Pro Leu Leu Leu Ser Arg Met Lys
225                 230                 235                 240

Glu Val Gly Lys Val Phe Leu Ala Thr Asn Ser Asp Tyr Lys Tyr Thr
                245                 250                 255

Asp Lys Ile Met Thr Tyr Leu Phe Asp Phe Pro His Gly Pro Lys Pro
            260                 265                 270

Gly Ser Ser His Arg Pro Trp Gln Ser Tyr Phe Asp Leu Ile Leu Val
        275                 280                 285
```

-continued

```
Asp Ala Arg Lys Pro Leu Phe Phe Gly Glu Gly Thr Val Leu Arg Gln
    290                 295                 300

Val Asp Thr Lys Thr Gly Lys Leu Lys Ile Gly Thr Tyr Thr Gly Pro
305                 310                 315                 320

Leu Gln His Gly Ile Val Tyr Ser Gly Gly Ser Ser Asp Thr Ile Cys
                325                 330                 335

Asp Leu Leu Gly Ala Lys Gly Lys Asp Ile Leu Tyr Ile Gly Asp His
            340                 345                 350

Ile Phe Gly Asp Ile Leu Lys Ser Lys Lys Arg Gln Gly Trp Arg Thr
        355                 360                 365

Phe Leu Val Ile Pro Glu Leu Ala Gln Glu Leu His Val Trp Thr Asp
    370                 375                 380

Lys Ser Ser Leu Phe Glu Glu Leu Gln Ser Leu Asp Ile Phe Leu Ala
385                 390                 395                 400

Glu Leu Tyr Lys His Leu Asp Ser Ser Ser Asn Glu Arg Pro Asp Ile
                405                 410                 415

Ser Ser Ile Gln Arg Arg Ile Lys Lys Val Thr His Asp Met Asp Met
            420                 425                 430

Cys Tyr Gly Met Met Gly Ser Leu Phe Arg Ser Gly Ser Arg Gln Thr
        435                 440                 445

Leu Phe Ala Ser Gln Val Met Arg Tyr Ala Asp Leu Tyr Ala Ala Ser
    450                 455                 460

Phe Ile Asn Leu Leu Tyr Tyr Pro Phe Ser Tyr Leu Phe Arg Ala Ala
465                 470                 475                 480

His Val Leu Met Pro His Glu Ser Thr Val Glu His Thr His Val Asp
                485                 490                 495

Ile Asn Glu Met Glu Ser Pro Leu Ala Thr Arg Asn Arg Thr Ser Val
            500                 505                 510

Asp Phe Lys Asp Thr Asp Tyr Lys Arg His Gln Leu Thr Arg Ser Ile
        515                 520                 525

Ser Glu Ile Lys Pro Pro Asn Leu Phe Pro Leu Ala Pro Gln Glu Ile
    530                 535                 540

Thr His Cys His Asp Glu Asp Asp Asp Glu Glu Glu Glu Glu Glu Glu
545                 550                 555                 560

Glu
```

Relapse specific mutations in NT5C2 encode amino acid substitutions at one or more amino acid residues corresponding to amino acid positions 238, 367, 408, and/or 445 of the human cN-II protein (SEQ ID NO: 2). Exemplary mutations encoding these amino acid substitutions include, without limitation, a cytosine (C)→thymine (T) change at a nucleotide position corresponding to position 712 of SEQ ID NO:1, resulting in a arginine to tryptophan substitution at an amino acid position corresponding to position 238 (R238W) of SEQ ID NO:2; a guanine (G)→alanine (A) change at a nucleotide position corresponding to position 1100 of SEQ ID NO:1, resulting in an arginine to glutamine substitution at an amino acid position corresponding to position 367 of SEQ ID NO:2 (R367Q); a C→A change at a nucleotide position corresponding to position 1224 of SEQ ID NO:1, resulting in a serine to arginine substitution at an amino acid position corresponding to position 408 of SEQ ID NO:2 (5408R); and a C→T change at a nucleotide position corresponding to position 1334 of SEQ ID NO:1, resulting in a serine to phenylalanine substitution at an amino acid position corresponding to position 445 of SEQ ID NO:2 (S445F). Alternatively, the mutation in the NT5C2 gene may encode an amino acid insertion, for example, G→AGAC insertion at a nucleotide position corresponding to position 1212 of SEQ ID NO:1, resulting in the insertion of an aspartic acid residue at amino acid position 404 of SEQ ID NO:2 (K404insKD). One of skill in the art appreciates that due to the degeneracy of the genetic code, other nucleotide substitutions, insertions, or deletions besides those specifically identified above can result in the same or similar amino acid changes, and detection of these alternative mutations are also encompassed by the methods described herein.

In another embodiment of this aspect of the present invention, the one or more mutations detected in the patient sample include a mutation in the RGS12 gene encoding the regulator of G-protein signaling-12 protein. This mutation maps to position 3287853 of chromosome 4 of human genome build 18 (hg18). The mRNA sequence for human RGS12 (NCBI Accession No. NM_002926) and corresponding amino acid sequence are provided below as SEQ ID NOs: 3 and 4, respectively. A relapse specific mutation in RGS12 results in an alanine to valine substitution at an amino acid position corresponding to A53 of SEQ ID NO:4 below. An exemplary mutation in RGS12 encoding this amino acid substitution comprises a C→T change at a nucleotide position corresponding to position 158 of SEQ ID NO:3.

SEQ ID NO: 3

Human RGS12

```
atgtttagag ctggggaggc ctccaaacgc ccattgcctg ggccgtcgcc cccaagggtg    60

cggagtgtgg aggttgcccg ggggagggcc ggctacggat tcacgctttc gggacaggca   120

ccctgtgtgc tcagctgcgt catgagaggg agccctgcgg atttcgtggg cctccgagct   180

ggagaccaga tacttgctgt caatgaaatc aacgtgaaaa aagcatctca tgaagatgta   240

gtgaaattaa ttgggaagtg ctctggtgtc cttcacatgg tgattgctga aggcgtcggc   300

cgcttcgaat cctgttccag tgatgaagaa gggggactct atgaaggaaa aggctggctg   360

aagcccaagc tggattctaa agcactaggt ataaacagag cagagcgagt cgtggaggaa   420

atgcagtctg gtggaatttt caatatgatt tttgaaaacc cgagcctttg tgcgagcaat   480

tcagagccct tgaaattgaa acaaagatcc ctttcagagt cggccgcaac tcgatttgat   540

gttggacatg aaagtataaa taatccaaat cccaacatgc tttctaagga ggaaatatca   600

aaagttattc atgatgattc ggttttcagc attggactag aaagtcatga cgattttgca   660

ttggatgcaa gtattttaaa cgtggcgatg atcgtgggct acttaggctc cattgagctt   720

ccttccacga gctccaacct ggagtccgac agcttgcaag ccatccgcgg ctgcatgcgg   780

cgcctgcggg cagagcagaa aatccactcg ctggtgacca tgaagatcat gcacgactgt   840

gtgcagctga gcactgacaa ggctggagtc gtggccgagt acccggccga gaagctggcc   900

ttcagcgccg tgtgcccgga cgaccggcga tttttcgggt tggttaccat gcagacgaat   960

gacgacggga gcctggccca ggaggaggag ggcgccctgc ggacttcctg ccacgtgttc  1020

atggtggacc cagacttgtt taatcacaag atccaccaag gcattgctcg gcggtttggg  1080

tttgagtgca cggccgaccc agacaccaat ggctgtctgg aattcccggc gtcctccctc  1140

cccgtcctgc agttcatctc tgtcctgtac cgagacatgg gtgagctgat tgagggcatg  1200

cgggcccgcg cctttctgga cggggacgcc gatgcccacc agaacaacag caccagcagc  1260

aacagtgaca gcggcattgg gaacttccac caggaggaga agagcaaccg ggtccttgtg  1320

gtggacctgg gtgggagctc gagcagacac ggccccggag gcagcgcgtg ggacggtgtg  1380

ggtgggaggg gtgcccagcc ctggggtgct ccctggactg ggcccttctg tccggacccc  1440

gaagggagcc ccccatttga ggccgctcat cagactgaca ggttctggga cctaaacaag  1500

cacctagggc cagcctctcc tgtggaggtg cccccagctt ccttgaggag ctcagtcccc  1560

ccttccaaga ggggcaccgt gggtgctggc tgtggtttca accagcgctg gctcccggtc  1620

cacgtgctcc gggagtggca gtgcggacac accagcgacc aggactctta cacagattcc  1680

accgatggct ggtccagcat caactgcggc acactgcccc ctcctatgag caagatcccc  1740

gcagaccgct acagggtgga gggcagcttc gcgcagcccc cgctgaatgc cccgaagagg  1800

gagtggtcca ggaaggcctt tggaatgcaa agcatctttg gtccccatcg aaatgttcga  1860

aagactaagg aagataaaaa gggctcaaaa tttgggcggg gaactggact cactcagcct  1920

tctcaacgca cgtctgctcg gagatcattt gggagatcca agagattcag tatcactcgc  1980

tcccttgatg atcttgagtc tgcaactgtg tctgacggcg agttgacggg cgccgacccg  2040

aaggactgcg tcagcaacaa cagcctgagc agcaatgcca gcctccccag cgtgcagagc  2100

tgccggcgcc tgcgcgagag gagggtcgcc agccgggccg Cgtcctttga gcgcccgctg  2160

caggaccccg tcggtgtccg ccacttctcc gatttcctaa ggaaagaatt cagtgaagaa  2220

aacattccat tctggcaggc ctgtgaatat tttaaccatg ctcctgcaca tgacaaaaag  2280

gagctttcct acagggcccg ggagattttc agtaagtttc tctgcagcaa agccaccacc  2340

ccggtcaaca tcgacagcca ggcccagcta gcagazgacg tcctccgcgc acctcaccca  2400
```

-continued

```
gacatgttca aggagcagca gctgcagatc ttcaatctca tgaagtttga tagctacact  2460

cgctttctga agtccccgct gtaccaggaa tgcatzctgg cggaagtgga gggccgtgca  2520

ctcccggact cgcagcaggt ccccagcagc ccggcttcca agcacagcct cggttcagac  2580

cactccagtg tgtccacgcc aaaaaagtta agtggaaaat caaaatccgg ccgatccctg  2640

aatgaagagc tgggggatga ggacagcgag aagaagcgga aaggcgcgtt tttctcgtgg  2700

tcgcggacca ggagcaccgg gaggtcccag aaaaagaggg agcacgggga ccacgcagac  2760

gacgccctgc atgccaatgg aggcctgtgt cgccgagagt cgcagggctc tgtgtcctct  2820

gcggggagcc tggacctgtc ggaggcctgc aggactttgg cacccgagaa ggacaaggcc  2880

accaagcact gctgcattca tctcccggat gggacatcct gcgtggtggc tgtcaaggcg  2940

ggcttctcca tcaaagacat cctgtccgga ctctgtgagc ggcatggcat caacggggcg  3000

gccgcggacc tctccctggt gggcggggac aagcctctgg cgctgcacca agacagtagc  3060

atcttggagt caagggacct gcgcctagaa aagcgcacct tgtttcggct ggatcttgtt  3120

ccgattaacc ggtcagtggg actcaaggcc aagcccacca agcccgtcac ggaggtgctg  3180

cggcccgtgg tggccagata cggcctggac cccagtggcc tgctggtgag gctgagtgga  3240

gagaaggagc ccctggacct tggcgcccct ataccgagtc tggacggaca gcgggttgtc  3300

ttggaggaga aggatccttc cagaggaaag gcatccgcag acaaacagaa aggtgtgcca  3360

gtgaaacaga acacagctgt aaattccagc tccagaaacc actcggctac gggagaggaa  3420

agaacactag gcaagtctaa CCctattaaa ataaaaggag aaaatggaaa aaatgctagg  3480

gatccccggc tttcaaagag agaagaatct attgcaaaga ttgggaaaaa aaaatatcag  3540

aaaattaatt tggacgaagc agaggagttt tttgagctta tttccaaagc tcagagcaac  3600

agagcagatg accaacgtgg gctgctaagg aaggaagacc tggtgttgcc agagttcctc  3660

cgtttacctc ctggttccac agaactcacc ctccccactc cagctgctgt ggccaagggc  3720

tttagcaaga gaagcgccac aggcaacggc cgggagagcg cctcccagcc tggcgagcag  3780

tgggagccag tccaggagag cagcgacagc ccgtccacca gcccgggctc agcctccagc  3840

ccccctggac ctcctgggac gacccccccc gggcagaagt ctcccagcgg gcccttctgc  3900

actccccagt cccccgtctc cctcgcgcag gagggcaccg cccagatctg gaagaggcag  3960

tctcaggaag tggaggccgg gggcatccag acggtggagg atgagcacgt ggccgagctg  4020

accctgatgg gggaggggga catcagcagc cccaacagca ccttgctgcc gccgccctcc  4080

accccccagg aagtgccagg accttccaga ccaggtacct ccaggttctg a           4131
```

SEQ ID NO: 4

```
Human Regulator of G-protein signaling 12
Met Phe Arg Ala Gly Glu Ala Ser Lys Arg Pro Leu Pro Gly Pro Ser
1               5                   10                  15

Pro Pro Arg Val Arg Ser Val Glu Val Ala Arg Gly Arg Ala Gly Tyr
            20                  25                  30

Gly Phe Thr Leu Ser Gly Gln Ala Pro Cys Val Leu Ser Cys Val Met
        35                  40                  45

Arg Gly Ser Pro Ala Asp Phe Val Gly Leu Arg Ala Gly Asp Gln Ile
    50                  55                  60

Leu Ala Val Asn Glu Ile Asn Val Lys Lys Ala Ser His Glu Asp Val
65                  70                  75                  80

Val Lys Leu Ile Gly Lys Cys Ser Gly Val Leu His Met Val Ile Ala
                85                  90                  95

Glu Gly Val Gly Arg Phe Glu Ser Cys Ser Ser Asp Glu Glu Gly Gly
            100                 105                 110
```

-continued

```
Leu Tyr Glu Gly Lys Gly Trp Leu Lys Pro Lys Leu Asp Ser Lys Ala
        115                 120                 125

Leu Gly Ile Asn Arg Ala Glu Arg Val Val Glu Glu Met Gln Ser Gly
    130                 135                 140

Gly Ile Phe Asn Met Ile Phe Glu Asn Pro Ser Leu Cys Ala Ser Asn
145                 150                 155                 160

Ser Glu Pro Leu Lys Leu Lys Gln Arg Ser Leu Ser Glu Ser Ala Ala
                165                 170                 175

Thr Arg Phe Asp Val Gly His Glu Ser Ile Asn Asn Pro Asn Pro Asn
            180                 185                 190

Met Leu Ser Lys Glu Glu Ile Ser Lys Val Ile His Asp Asp Ser Val
        195                 200                 205

Phe Ser Ile Gly Leu Glu Ser His Asp Asp Phe Ala Leu Asp Ala Ser
    210                 215                 220

Ile Leu Asn Val Ala Met Ile Val Gly Tyr Leu Gly Ser Ile Glu Leu
225                 230                 235                 240

Pro Ser Thr Ser Ser Asn Leu Glu Ser Asp Ser Leu Gln Ala Ile Arg
                245                 250                 255

Gly Cys Met Arg Arg Leu Arg Ala Glu Gln Lys Ile His Ser Leu Val
            260                 265                 270

Thr Met Lys Ile Met His Asp Cys Val Gln Leu Ser Thr Asp Lys Ala
        275                 280                 285

Gly Val Val Ala Glu Tyr Pro Ala Glu Lys Leu Ala Phe Ser Ala Val
    290                 295                 300

Cys Pro Asp Asp Arg Arg Phe Phe Gly Leu Val Thr Met Gln Thr Asn
305                 310                 315                 320

Asp Asp Gly Ser Leu Ala Gln Glu Glu Glu Gly Ala Leu Arg Thr Ser
                325                 330                 335

Cys His Val Phe Met Val Asp Pro Asp Leu Phe Asn His Lys Ile His
            340                 345                 350

Gln Gly Ile Ala Arg Arg Phe Gly Phe Glu Cys Thr Ala Asp Pro Asp
        355                 360                 365

Thr Asn Gly Cys Leu Glu Phe Pro Ala Ser Ser Leu Pro Val Leu Gln
    370                 375                 380

Phe Ile Ser Val Leu Tyr Arg Asp Met Gly Glu Leu Ile Glu Gly Met
385                 390                 395                 400

Arg Ala Arg Ala Phe Leu Asp Gly Asp Ala Asp Ala His Gln Asn Asn
                405                 410                 415

Ser Thr Ser Ser Asn Ser Asp Ser Gly Ile Gly Asn Phe His Gln Glu
            420                 425                 430

Glu Lys Ser Asn Arg Val Leu Val Val Asp Leu Gly Gly Ser Ser Ser
        435                 440                 445

Arg His Gly Pro Gly Gly Ser Ala Trp Asp Gly Val Gly Gly Arg Gly
    450                 455                 460

Ala Gln Pro Trp Gly Ala Pro Trp Thr Gly Pro Phe Cys Pro Asp Pro
465                 470                 475                 480

Glu Gly Ser Pro Pro Phe Glu Ala Ala His Gln Thr Asp Arg Phe Trp
                485                 490                 495

Asp Leu Asn Lys His Leu Gly Pro Ala Ser Pro Val Glu Val Pro Pro
            500                 505                 510

Ala Ser Leu Arg Ser Ser Val Pro Pro Ser Lys Arg Gly Thr Val Gly
        515                 520                 525

Ala Gly Cys Gly Phe Asn Gln Arg Trp Leu Pro Val His Val Leu Arg
    530                 535                 540
```

-continued

```
Glu Trp Gln Cys Gly His Thr Ser Asp Gln Asp Ser Tyr Thr Asp Ser
545                 550                 555                 560

Thr Asp Gly Trp Ser Ser Ile Asn Cys Gly Thr Leu Pro Pro Pro Met
                565                 570                 575

Ser Lys Ile Pro Ala Asp Arg Tyr Arg Val Glu Gly Ser Phe Ala Gln
            580                 585                 590

Pro Pro Leu Asn Ala Pro Lys Arg Glu Trp Ser Arg Lys Ala Phe Gly
        595                 600                 605

Met Gln Ser Ile Phe Gly Pro His Arg Asn Val Arg Lys Thr Lys Glu
    610                 615                 620

Asp Lys Lys Gly Ser Lys Phe Gly Arg Gly Thr Gly Leu Thr Gln Pro
625                 630                 635                 640

Ser Gln Arg Thr Ser Ala Arg Arg Ser Phe Gly Arg Ser Lys Arg Phe
                645                 650                 655

Ser Ile Thr Arg Ser Leu Asp Asp Leu Glu Ser Ala Thr Val Ser Asp
            660                 665                 670

Gly Glu Leu Thr Gly Ala Asp Leu Lys Asp Cys Val Ser Asn Asn Ser
        675                 680                 685

Leu Ser Ser Asn Ala Ser Leu Pro Ser Val Gln Ser Cys Arg Arg Leu
    690                 695                 700

Arg Glu Arg Arg Val Ala Ser Trp Ala Val Ser Phe Glu Arg Leu Leu
705                 710                 715                 720

Gln Asp Pro Val Gly Val Arg Tyr Phe Ser Asp Phe Leu Arg Lys Glu
                725                 730                 735

Phe Ser Glu Glu Asn Ile Leu Phe Trp Gln Ala Cys Glu Tyr Phe Asn
            740                 745                 750

His Val Pro Ala His Asp Lys Lys Glu Leu Ser Tyr Arg Ala Arg Glu
        755                 760                 765

Ile Phe Ser Lys Phe Leu Cys Ser Lys Ala Thr Thr Pro Val Asn Ile
    770                 775                 780

Asp Ser Gln Ala Gln Leu Ala Asp Asp Val Leu Arg Ala Pro His Pro
785                 790                 795                 800

Asp Met Phe Lys Glu Gln Gln Leu Gln Ile Phe Asn Leu Met Lys Phe
                805                 810                 815

Asp Ser Tyr Thr Arg Phe Leu Lys Ser Pro Leu Tyr Gln Glu Cys Ile
            820                 825                 830

Leu Ala Glu Val Glu Gly Arg Ala Leu Pro Asp Ser Gln Gln Val Pro
        835                 840                 845

Ser Ser Pro Ala Ser Lys His Ser Leu Gly Ser Asp His Ser Ser Val
    850                 855                 860

Ser Thr Pro Lys Lys Leu Ser Gly Lys Ser Lys Ser Gly Arg Ser Leu
865                 870                 875                 880

Asn Glu Glu Leu Gly Asp Glu Asp Ser Glu Lys Lys Arg Lys Gly Ala
                885                 890                 895

Phe Phe Ser Trp Ser Arg Thr Arg Ser Thr Gly Arg Ser Gln Lys Lys
            900                 905                 910

Arg Glu His Gly Asp His Ala Asp Asp Ala Leu His Ala Asn Gly Gly
        915                 920                 925

Leu Cys Arg Arg Glu Ser Gln Gly Ser Val Ser Ser Ala Gly Ser Leu
    930                 935                 940

Asp Leu Ser Glu Ala Cys Arg Thr Leu Ala Pro Glu Lys Asp Lys Ala
945                 950                 955                 960

Thr Lys His Cys Cys Ile His Leu Pro Asp Gly Thr Ser Cys Val Val
                965                 970                 975
```

-continued

```
Ala Val Lys Ala Gly Phe Ser Ile Lys Asp Ile Leu Ser Gly Leu Cys
            980                 985                 990

Glu Arg His Gly Ile Asn Gly Ala  Ala Ala Asp Leu Phe  Leu Val Gly
        995                 1000                 1005

Gly Asp  Lys Pro Leu Val Leu  His Gln Asp Ser Ser  Ile Leu Glu
    1010                 1015                 1020

Ser Arg  Asp Leu Arg Leu Glu  Lys Arg Thr Leu Phe  Arg Leu Asp
    1025                 1030                 1035

Leu Val  Pro Ile Asn Arg Ser  Val Gly Leu Lys Ala  Lys Pro Thr
    1040                 1045                 1050

Lys Pro  Val Thr Glu Val Leu  Arg Pro Val Val Ala  Arg Tyr Gly
    1055                 1060                 1065

Leu Asp  Leu Ser Gly Leu Leu  Val Arg Leu Ser Gly  Glu Lys Glu
    1070                 1075                 1080

Pro Leu  Asp Leu Gly Ala Pro  Ile Ser Ser Leu Asp  Gly Gln Arg
    1085                 1090                 1095

Val Val  Leu Glu Glu Lys Asp  Pro Ser Arg Gly Lys  Ala Ser Ala
    1100                 1105                 1110

Asp Lys  Gln Lys Gly Val Pro  Val Lys Gln Asn Thr  Ala Val Asn
    1115                 1120                 1125

Ser Ser  Ser Arg Asn His Ser  Ala Thr Gly Glu Glu  Arg Thr Leu
    1130                 1135                 1140

Gly Lys  Ser Asn Ser Ile Lys  Ile Lys Gly Glu Asn  Gly Lys Asn
    1145                 1150                 1155

Ala Arg  Asp Pro Arg Leu Ser  Lys Arg Glu Glu Ser  Ile Ala Lys
    1160                 1165                 1170

Ile Gly  Lys Lys Lys Tyr Gln  Lys Ile Asn Leu Asp  Glu Ala Glu
    1175                 1180                 1185

Glu Phe  Phe Glu Leu Ile Ser  Lys Ala Gln Ser Asn  Arg Ala Asp
    1190                 1195                 1200

Asp Gln  Arg Gly Leu Leu Arg  Lys Glu Asp Leu Val  Leu Pro Glu
    1205                 1210                 1215

Phe Leu  Arg Leu Pro Pro Gly  Ser Thr Glu Leu Thr  Leu Pro Thr
    1220                 1225                 1230

Pro Ala  Ala Val Ala Lys Gly  Phe Ser Lys Arg Ser  Ala Thr Gly
    1235                 1240                 1245

Asn Gly  Arg Glu Ser Ala Ser  Gln Pro Gly Glu Gln  Trp Glu Pro
    1250                 1255                 1260

Val Gln  Glu Ser Ser Asp Ser  Pro Ser Thr Ser Pro  Gly Ser Ala
    1265                 1270                 1275

Ser Ser  Pro Pro Gly Pro Pro  Gly Thr Thr Pro Pro  Gly Gln Lys
    1280                 1285                 1290

Ser Pro  Ser Gly Pro Phe Cys  Thr Pro Gln Ser Pro  Val Ser Leu
    1295                 1300                 1305

Ala Gln  Glu Gly Thr Ala Gln  Ile Trp Lys Arg Gln  Ser Gln Glu
    1310                 1315                 1320

Val Glu  Ala Gly Gly Ile Gln  Thr Val Glu Asp Glu  His Val Ala
    1325                 1330                 1335

Glu Leu  Thr Leu Met Gly Glu  Gly Asp Ile Ser Ser  Pro Asn Ser
    1340                 1345                 1350

Thr Leu  Leu Pro Pro Pro Ser  Thr Pro Gln Glu Val  Pro Gly Pro
    1355                 1360                 1365

Ser Arg  Pro Gly Ser Gly Thr  His Gly Ser Arg Asp  Leu Pro Val
    1370                 1375                 1380
```

-continued

```
Asn Arg  Ile Ile Asp Val Asp  Leu Val Thr Gly Ser  Ala Pro Gly
    1385                 1390                 1395

Arg Asp  Gly Gly Ile Ala Gly  Ala Gln Ala Gly Pro  Gly Arg Ser
    1400                 1405                 1410

Gln Ala  Ser Gly Gly Pro Pro  Thr Ser Asp Leu Pro  Gly Leu Gly
    1415                 1420                 1425

Pro Val  Pro Gly Glu Pro Ala  Lys Pro Lys Thr Ser  Ala His His
    1430                 1435                 1440

Ala Thr  Phe Val
    1445
```

In another embodiment of this aspect of the present invention, the one or more mutations detected in the patient sample include a mutation in the LPHN1 gene encoding latrophilin-1. This mutation maps to position 14134808 on chromosome 19 of hg18. The mRNA sequence for human LPHN1 (NCBI Accession No. NM_001008701) and corresponding amino acid sequence are provided below as SEQ ID NOs: 5 and 6, respectively. A relapse specific mutation in LPHN1 results in a glutamic acid to glutamine substitution at an amino acid position corresponding to E274 of SEQ ID NO:6 below. An exemplary mutation in LPHN1 encoding this amino acid substitution comprises a G→C change at a nucleotide position corresponding to position 822 of SEQ ID NO:5.

SEQ ID NO: 5

```
Human LPHN1
atggcccgcc tagccgcagt gctctggaat ctgtgtgtca ccgccgtcct ggtcacctcg     60

gccacccaag gcctgagccg ggccgggctc ccgttcgggc tgatgcgccg ggagctggcg    120

tgtgaaggct accccatcga gctgcggtgc cccggcagcg acgtcatcat ggtggagaat    180

gccaactacg ggcgcacgga cgacaagatt tgcgatgctg accctttcca gatggagaat    240

gtgcagtgct acctgccgga cgccttcaag atcatgtcac agaggtgtaa caaccgcacc    300

cagtgcgtgg tggtcgccgg ctcggatgcc tttcctgacc cctgtcctgg gacctacaag    360

tacctggagg tgcagtacga ctgtgtcccc tacaaagtgg agcagaaagt cttcgtgtgc    420

ccagggaccc tgcagaaggt gctggagccc acctcgacac acgagtcaga gcaccagtct    480

ggcgcatggt gcaaggaccc gctgcaggcg ggtgaccgca tctacgtgat gccctggatc    540

ccctaccgca cggacacact gactgagtat gcctcgtggg aggactacgt ggccgcccgc    600

cacaccacca cctaccgcct gcccaaccgc gtggatggca caggctttgt ggtctacgat    660

ggtgccgtct tctacaacaa ggagcgcacg cgcaacatcg tcaagtatga cctacggacg    720

cgcatcaaga gcggggagac ggtcatcaat accgccaact accatgacac ctcgccctac    780

cgctggggcg gaaagaccga cattgacctg gcggtggacg agaacgggct gtgggtcatc    840

tacgccactg agggcaacaa cgggcggctg gtggtgagcc agctgaaccc ctacacactg    900

cgctttgagg gcacgtggga gacgggttac gacaagcgct cggcatccaa cgccttcatg    960

gtgtgtgggg tcctgtacgt cctgcgttcc gtgtacgtgg atgatgacag cgaggcggct   1020

ggcaaccgcg tggactatgc cttcaacacc aatgccaacc gcgaggagcc tgtcagcctc   1080

accttcccca accccctacca gttcatctcc tccgtcgact acaaccctcg cgacaaccag  1140

ctgtacgcct ggaacaacta cttcgtggtg cgccacagcc cggagttcgg gccgcccgac   1200

cccagtgctg gcccagccac ccccccaccc ctcagcacga ccaccacagc caggcccacg   1260

cccctcacca gcacagcctc gcccgcagcc accaccccgc cccgccgggc acccctcacc   1320

acgcacccag tgggtgccat caaccagccg ggacctgatc cgcctccagc cacagcccca   1380

gtccccagca cccggcggcc cccagccccg aatctacacg tgtcccctga gctcttctgc   1440

gagccccgag aggtacggcg ggtccagtgg ccggcsaccc agcagggcat gctggtggag   1500

aggccctgcc ccaaggggac tcgaggaatt gcctccttcc agtgtctacc agccttgggg   1560
```

-continued

```
ctctggaacc cccggggccc tgacctcagc aactgcacct cccccctgggt caaccaggtg  1620
gcccagaaga tcaagagtgg ggagaacgcg gccaacatcg ccagcgagct ggcccgacac  1680
acccggggct ccatctacgc gggggacgtc tcctcctctg tgaagctgat ggagcagctg  1740
ctggacatcc tggatgccca gctgcaggcc ctgcggccca tcgagcgcga gtcagccggc  1800
aagaactaca acaagatgca caagcgagag agaacttgta aggattatat caaggccgtg  1860
gtggagacag tggacaatct gctccggcca gaagctctgg agtcctggaa ggacatgaat  1920
gccacggagc aggtgcacac ggccaccatg ctcctsgacg tcctggagga gggcgccttc  1980
ctgctggccg acaatgtcag ggagcctgcc cgcttcctgg ctgccaagga gaacgtggtc  2040
ctggaggtca cagccctgaa cacagagggc caggtgcagg agctggcgtt cccccaggag  2100
gagtacccga gaaagaactc catccagctg tctgccaaaa ccatcaagca gaacagccgc  2160
aatggggtgg tcaaagttgt cttcatcctc tacaaoaacc tgggcctctc cctgtccacg  2220
gagaatgcca cagtgaagct ggccggcgaa gcaggoccgg gcggccctgg gggcgcctct  2280
ctagtggtga actcacaggt catcgcagca tccatoaaca aggagtccag ccgcgtcttc  2340
ctcatggacc ctgtcatctt caccgtggcc cacctggagg acaagaacca cttcaatgct  2400
aactgctcct tctggaacta ctcggagcgt tccatgctgg gctactggtc gacccaaggc  2460
tgccgcctgg tggagtccaa caagacccat accacgtgtg cctgcagcca cctcaccaac  2520
ttcgctgtgc tcatggctca ccgtgagatc taccagggcc gcatcaacga gctgctgctg  2580
tcggtcatca cctgggtggg cattgtgatc tccctggtct gcttggccat ctgcatctcc  2640
accttctgct tcctgcgggg gctgcagacc gaccgcaaca ccatccacaa gaacctgtgc  2700
atcaacctct tcctggctga gctgctcttc ctggtcggga tcgacaagac tcagtatgag  2760
attgcctgcc ccaccttcgc cggcctgctg cactatttct tcctggctgc cttctcctgg  2820
ctgtgcctgg agggcgtgca cctctacctg ctactagtgg aggtgtttga gagcgagtat  2880
tcccgcacca agtactacta cctgggtggc tactgcttcc cggccctggt ggtgggcatc  2940
gcggctgcca ttgactaccg cagctacggc accgagaagg cctgctggct ccgagtggac  3000
aattacttca tctggagttt catcgggcca gtctccttcg ttatcgtggt caacctggtg  3060
ttcctcatgg tgaccctgca caagatgatc cgaagctcat ctgtgctcaa gcccgactcc  3120
agccgcctgg acaacattaa atcctgggcg ctgggggcca tcgcgctgct gttcctgctg  3180
ggcctcacct gggctttcgg cctcctcttc atcaacaagg agtcggtggt catggcctat  3240
ctcttcacca ccttcaacgc cttccagggg gtcttcatct tcgtctttca ctgcgcctta  3300
cagaagaagg tgcacaagga gtacagcaag tgcctgcgtc actcctactg ctgcatccgc  3360
tccccacccg ggggcactca cggatccctc aagacctcag ccatgcgaag caacacccgc  3420
tactacacag ggacccagag ccgaattcgg aggatgtgga atgacactgt gaggaaacag  3480
acggagtcct ccttcatggc gggtgacatc aacagcaccc ccaccctgaa ccgaggtacc  3540
atggggaacc acctgctgac caaccccgtg ctgcagcccc gtgggggcac cagtccctac  3600
aacaccctca tcgccgagtc agtgggcttc aatccctcct cgccccctgt cttcaactcc  3660
ccagggagct accgggaacc caagcacccc ttgggaggcc gggaagcctg tggcatggac  3720
accctgcccc tgaacggcaa cttcaataac agttactcct tgcgaagtgg ggatttccct  3780
cccggggatg ggggccctga gccgccccga ggccggaacc tagccgatgc ggcggccttt  3840
gagaagatga tcatctcaga gctggtgcac aacaacctgc gggggagcag cagcgcggcc  3900
aagggccctc caccgcctga gccccctgtg ccacctgtgc cagggggcgg gggcgaggaa  3960
```

-continued

```
gaggcgggcg ggcccggggg tgctgaccgg gccgagattg aacttctcta taaggccctg  4020

gaggagcctc tgctgctgcc ccgggcccag tcggtgctgt accagagcga tctggacgag  4080

tcggagagct gcacggccga ggacggcgcc accagccggc ccctctcctc ccctcctggc  4140

cgggactccc tctatgccag cggggccaac ctgcgggact caccctccta cccggacagc  4200

agccctgagg ggcccagtga ggccctgccc ccaccccctc ccgcaccccc cggccccccc  4260

gaaatctact acacctcgcg cccgccagcc ctggtggccc ggaatcccct gcagggctac  4320

taccaggtgc ggcgtcctag ccacgagggc tacctggcag ccccaggcct tgaggggcca  4380

gggcccgatg gggacgggca gatgcagctg gtcaccagtc tctga                 4425
```

SEQ ID NO: 6

Human Latrophilin-1

```
Met Ala Arg Leu Ala Ala Val Leu Trp Asn Leu Cys Val Thr Ala Val
1               5                   10                  15

Leu Val Thr Ser Ala Thr Gln Gly Leu Ser Arg Ala Gly Leu Pro Phe
            20                  25                  30

Gly Leu Met Arg Arg Glu Leu Ala Cys Glu Gly Tyr Pro Ile Glu Leu
        35                  40                  45

Arg Cys Pro Gly Ser Asp Val Ile Met Val Glu Asn Ala Asn Tyr Gly
    50                  55                  60

Arg Thr Asp Asp Lys Ile Cys Asp Ala Asp Pro Phe Gln Met Glu Asn
65                  70                  75                  80

Val Gln Cys Tyr Leu Pro Asp Ala Phe Lys Ile Met Ser Gln Arg Cys
                85                  90                  95

Asn Asn Arg Thr Gln Cys Val Val Val Ala Gly Ser Asp Ala Phe Pro
            100                 105                 110

Asp Pro Cys Pro Gly Thr Tyr Lys Tyr Leu Glu Val Gln Tyr Asp Cys
        115                 120                 125

Val Pro Tyr Lys Val Glu Gln Lys Val Phe Val Cys Pro Gly Thr Leu
    130                 135                 140

Gln Lys Val Leu Glu Pro Thr Ser Thr His Glu Ser Glu His Gln Ser
145                 150                 155                 160

Gly Ala Trp Cys Lys Asp Pro Leu Gln Ala Gly Asp Arg Ile Tyr Val
                165                 170                 175

Met Pro Trp Ile Pro Tyr Arg Thr Asp Thr Leu Thr Glu Tyr Ala Ser
            180                 185                 190

Trp Glu Asp Tyr Val Ala Ala Arg His Thr Thr Thr Tyr Arg Leu Pro
        195                 200                 205

Asn Arg Val Asp Gly Thr Gly Phe Val Val Tyr Asp Gly Ala Val Phe
    210                 215                 220

Tyr Asn Lys Glu Arg Thr Arg Asn Ile Val Lys Tyr Asp Leu Arg Thr
225                 230                 235                 240

Arg Ile Lys Ser Gly Glu Thr Val Ile Asn Thr Ala Asn Tyr His Asp
                245                 250                 255

Thr Ser Pro Tyr Arg Trp Gly Gly Lys Thr Asp Ile Asp Leu Ala Val
            260                 265                 270

Asp Glu Asn Gly Leu Trp Val Ile Tyr Ala Thr Glu Gly Asn Asn Gly
        275                 280                 285

Arg Leu Val Val Ser Gln Leu Asn Pro Tyr Thr Leu Arg Phe Glu Gly
    290                 295                 300

Thr Trp Glu Thr Gly Tyr Asp Lys Arg Ser Ala Ser Asn Ala Phe Met
305                 310                 315                 320

Val Cys Gly Val Leu Tyr Val Leu Arg Ser Val Tyr Val Asp Asp Asp
                325                 330                 335
```

-continued

```
Ser Glu Ala Ala Gly Asn Arg Val Asp Tyr Ala Phe Asn Thr Asn Ala
            340                 345                 350

Asn Arg Glu Glu Pro Val Ser Leu Thr Phe Pro Asn Pro Tyr Gln Phe
        355                 360                 365

Ile Ser Ser Val Asp Tyr Asn Pro Arg Asp Asn Gln Leu Tyr Val Trp
    370                 375                 380

Asn Asn Tyr Phe Val Val Arg Tyr Ser Leu Glu Phe Gly Pro Pro Asp
385                 390                 395                 400

Pro Ser Ala Gly Pro Ala Thr Ser Pro Pro Leu Ser Thr Thr Thr Thr
                405                 410                 415

Ala Arg Pro Thr Pro Leu Thr Ser Thr Ala Ser Pro Ala Ala Thr Thr
            420                 425                 430

Pro Leu Arg Arg Ala Pro Leu Thr Thr His Pro Val Gly Ala Ile Asn
        435                 440                 445

Gln Leu Gly Pro Asp Leu Pro Pro Ala Thr Ala Pro Val Pro Ser Thr
    450                 455                 460

Arg Arg Pro Pro Ala Pro Asn Leu His Val Ser Pro Glu Leu Phe Cys
465                 470                 475                 480

Glu Pro Arg Glu Val Arg Arg Val Gln Trp Pro Ala Thr Gln Gln Gly
                485                 490                 495

Met Leu Val Glu Arg Pro Cys Pro Lys Gly Thr Arg Gly Ile Ala Ser
            500                 505                 510

Phe Gln Cys Leu Pro Ala Leu Gly Leu Trp Asn Pro Arg Gly Pro Asp
        515                 520                 525

Leu Ser Asn Cys Thr Ser Pro Trp Val Asn Gln Val Ala Gln Lys Ile
    530                 535                 540

Lys Ser Gly Glu Asn Ala Ala Asn Ile Ala Ser Glu Leu Ala Arg His
545                 550                 555                 560

Thr Arg Gly Ser Ile Tyr Ala Gly Asp Val Ser Ser Ser Val Lys Leu
                565                 570                 575

Met Glu Gln Leu Leu Asp Ile Leu Asp Ala Gln Leu Gln Ala Leu Arg
            580                 585                 590

Pro Ile Glu Arg Glu Ser Ala Gly Lys Asn Tyr Asn Lys Met His Lys
        595                 600                 605

Arg Glu Arg Thr Cys Lys Asp Tyr Ile Lys Ala Val Val Glu Thr Val
    610                 615                 620

Asp Asn Leu Leu Arg Pro Glu Ala Leu Glu Ser Trp Lys Asp Met Asn
625                 630                 635                 640

Ala Thr Glu Gln Val His Thr Ala Thr Met Leu Leu Asp Val Leu Glu
                645                 650                 655

Glu Gly Ala Phe Leu Leu Ala Asp Asn Val Arg Glu Pro Ala Arg Phe
            660                 665                 670

Leu Ala Ala Lys Glu Asn Val Val Leu Glu Val Thr Val Leu Asn Thr
        675                 680                 685

Glu Gly Gln Val Gln Glu Leu Val Phe Pro Gln Glu Glu Tyr Pro Arg
    690                 695                 700

Lys Asn Ser Ile Gln Leu Ser Ala Lys Thr Ile Lys Gln Asn Ser Arg
705                 710                 715                 720

Asn Gly Val Val Lys Val Val Phe Ile Leu Tyr Asn Asn Leu Gly Leu
                725                 730                 735

Phe Leu Ser Thr Glu Asn Ala Thr Val Lys Leu Ala Gly Glu Ala Gly
            740                 745                 750

Pro Gly Gly Pro Gly Gly Ala Ser Leu Val Val Asn Ser Gln Val Ile
        755                 760                 765
```

-continued

```
Ala Ala Ser Ile Asn Lys Glu Ser Ser Arg Val Phe Leu Met Asp Pro
    770                 775                 780

Val Ile Phe Thr Val Ala His Leu Glu Asp Lys Asn His Phe Asn Ala
785                 790                 795                 800

Asn Cys Ser Phe Trp Asn Tyr Ser Glu Arg Ser Met Leu Gly Tyr Trp
                805                 810                 815

Ser Thr Gln Gly Cys Arg Leu Val Glu Ser Asn Lys Thr His Thr Thr
            820                 825                 830

Cys Ala Cys Ser His Leu Thr Asn Phe Ala Val Leu Met Ala His Arg
        835                 840                 845

Glu Ile Tyr Gln Gly Arg Ile Asn Glu Leu Leu Leu Ser Val Ile Thr
    850                 855                 860

Trp Val Gly Ile Val Ile Ser Leu Val Cys Leu Ala Ile Cys Ile Ser
865                 870                 875                 880

Thr Phe Cys Phe Leu Arg Gly Leu Gln Thr Asp Arg Asn Thr Ile His
                885                 890                 895

Lys Asn Leu Cys Ile Asn Leu Phe Leu Ala Glu Leu Leu Phe Leu Val
            900                 905                 910

Gly Ile Asp Lys Thr Gln Tyr Glu Ile Ala Cys Pro Ile Phe Ala Gly
        915                 920                 925

Leu Leu His Tyr Phe Phe Leu Ala Ala Phe Ser Trp Leu Cys Leu Glu
    930                 935                 940

Gly Val His Leu Tyr Leu Leu Leu Val Glu Val Phe Glu Ser Glu Tyr
945                 950                 955                 960

Ser Arg Thr Lys Tyr Tyr Tyr Leu Gly Gly Tyr Cys Phe Pro Ala Leu
                965                 970                 975

Val Val Gly Ile Ala Ala Ala Ile Asp Tyr Arg Ser Tyr Gly Thr Glu
            980                 985                 990

Lys Ala Cys Trp Leu Arg Val Asp  Asn Tyr Phe Ile Trp  Ser Phe Ile
        995                 1000                1005

Gly Pro  Val Ser Phe Val Ile  Val Val Asn Leu Val  Phe Leu Met
    1010                1015                1020

Val Thr  Leu His Lys Met Ile  Arg Ser Ser Ser Val  Leu Lys Pro
    1025                1030                1035

Asp Ser  Ser Arg Leu Asp Asn  Ile Lys Ser Trp Ala  Leu Gly Ala
    1040                1045                1050

Ile Ala  Leu Leu Phe Leu Leu  Gly Leu Thr Trp Ala  Phe Gly Leu
    1055                1060                1065

Leu Phe  Ile Asn Lys Glu Ser  Val Val Met Ala Tyr  Leu Phe Thr
    1070                1075                1080

Thr Phe  Asn Ala Phe Gln Gly  Val Phe Ile Phe Val  Phe His Cys
    1085                1090                1095

Ala Leu  Gln Lys Lys Val His  Lys Glu Tyr Ser Lys  Cys Leu Arg
    1100                1105                1110

His Ser  Tyr Cys Cys Ile Arg  Ser Pro Pro Gly Gly  Thr His Gly
    1115                1120                1125

Ser Leu  Lys Thr Ser Ala Met  Arg Ser Asn Thr Arg  Tyr Tyr Thr
    1130                1135                1140

Gly Thr  Gln Ser Arg Ile Arg  Arg Met Trp Asn Asp  Thr Val Arg
    1145                1150                1155

Lys Gln  Thr Glu Ser Ser Phe  Met Ala Gly Asp Ile  Asn Ser Thr
    1160                1165                1170

Pro Thr  Leu Asn Arg Gly Thr  Met Gly Asn His Leu  Leu Thr Asn
    1175                1180                1185
```

-continued

```
Pro Val  Leu Gln Pro Arg Gly  Gly Thr Ser Pro Tyr  Asn Thr Leu
    1190                 1195                 1200

Ile Ala  Glu Ser Val Gly Phe  Asn Pro Ser Ser Pro  Pro Val Phe
    1205                 1210                 1215

Asn Ser  Pro Gly Ser Tyr Arg  Glu Pro Lys His Pro  Leu Gly Gly
    1220                 1225                 1230

Arg Glu  Ala Cys Gly Met Asp  Thr Leu Pro Leu Asn  Gly Asn Phe
    1235                 1240                 1245

Asn Asn  Ser Tyr Ser Leu Arg  Ser Gly Asp Phe Pro  Pro Gly Asp
    1250                 1255                 1260

Gly Gly  Pro Glu Pro Pro Arg  Gly Arg Asn Leu Ala  Asp Ala Ala
    1265                 1270                 1275

Ala Phe  Glu Lys Met Ile Ile  Ser Glu Leu Val His  Asn Asn Leu
    1280                 1285                 1290

Arg Gly  Ser Ser Ser Ala Ala  Lys Gly Pro Pro Pro  Pro Glu Pro
    1295                 1300                 1305

Pro Val  Pro Pro Val Pro Gly  Gly Gly Gly Glu Glu  Glu Ala Gly
    1310                 1315                 1320

Gly Pro  Gly Gly Ala Asp Arg  Ala Glu Ile Glu Leu  Leu Tyr Lys
    1325                 1330                 1335

Ala Leu  Glu Glu Pro Leu Leu  Leu Pro Arg Ala Gln  Ser Val Leu
    1340                 1345                 1350

Tyr Gln  Ser Asp Leu Asp Glu  Ser Glu Ser Cys Thr  Ala Glu Asp
    1355                 1360                 1365

Gly Ala  Thr Ser Arg Pro Leu  Ser Ser Pro Pro Gly  Arg Asp Ser
    1370                 1375                 1380

Leu Tyr  Ala Ser Gly Ala Asn  Leu Arg Asp Ser Pro  Ser Tyr Pro
    1385                 1390                 1395

Asp Ser  Ser Pro Glu Gly Pro  Ser Glu Ala Leu Pro  Pro Pro Pro
    1400                 1405                 1410

Pro Ala  Pro Pro Gly Pro Pro  Glu Ile Tyr Tyr Thr  Ser Arg Pro
    1415                 1420                 1425

Pro Ala  Leu Val Ala Arg Asn  Pro Leu Gln Gly Tyr  Tyr Gln Val
    1430                 1435                 1440

Arg Arg  Pro Ser His Glu Gly  Tyr Leu Ala Ala Pro  Gly Leu Glu
    1445                 1450                 1455

Gly Pro  Gly Pro Asp Gly Asp  Gly Gln Met Gln Leu  Val Thr Ser
    1460                 1465                 1470

Leu
```

In another embodiment of this aspect of the present invention, the one or more mutations detected in the patient sample include a mutation in the CANDI gene encoding cullin-associated NEDD8-dissociated protein 1. This mutation maps to position 65985593 on chromosome 12 of hg18. The mRNA sequence for human CANDI (NCBI Accession No. NM_018448) and corresponding amino acid sequence are provided below as SEQ ID NOs: 7 and 8, respectively. A relapse specific mutation in CAND1 results in a leucine to phenylalanine substitution at an amino acid position corresponding to L626 of SEQ ID NO: 8 below. An exemplary mutation in CANDI encoding this amino acid substitution comprises a A→C change at a nucleotide position corresponding to position 1878 of SEQ ID NO: 7.

SEQ ID NO: 7

Human CAND1

```
atggcgagcg cctcgtacca catttccaat ttgctggaaa aaatgacatc cagcgacaag    60

gactttaggt ttatggctac aaatgatttg atgacggaac tgcagaaaga ttccatcaag   120

ttggatgatg atagtgaaag gaaagtagtg aaaatgattt tgaagttatt ggaagataaa   180

aatggagagg tacagaattt agctgtcaaa tgtcttggtc ctttagtgag taaagtgaaa   240
```

-continued

```
gaataccaag tagagacaat tgtagatacc ctctgcacta acatgctttc tgataaagaa   300
caacttcgag acatttcaag tattggtctt aaaacagtaa ttggagaact tcctccagct   360
tccagtggct ctgcattagc tgctaatgta tgtaaaaaga ttactggacg tcttacaagt   420
gcaatagcaa aacaggaaga tgtctctgtt cagctagaag ccttggatat tatggctgat   480
atgttgagca ggcaaggagg acttcttgtt aatttccatc cttcaattct gacctgtcta   540
cttccccagt tgaccagccc tagacttgca gtgaggaaaa gaaccattat cgctcttggc   600
catctggtta tgagctgtgg aaatatagtt tttgtagatc ttattgaaca tctgttgtca   660
gagttgtcca aaaatgattc tatgtcaaca acaagaacct acatacaatg tattgctgct   720
attagtaggc aagctggtca tagaataggt gaataccttg agaagataat tcctttggtg   780
gtaaaatttt gcaatgtaga tgatgatgaa ttaagagagt actgtattca agcctttgaa   840
tcatttgtaa gaagatgtcc taaggaagta tatcctcatg tttctaccat tataaatatt   900
tgtcttaaat atcttaccta tgatccaaat tataattacg atgatgaaga tgaagatgaa   960
aatgcaatgg atgctgatgg tggtgatgat gatgatcaag ggagtgatga tgaatacagt  1020
gatgatgatg acatgagttg gaaagtgaga cgtgcagctg cgaagtgctt ggatgctgta  1080
gttagcacaa ggcatgaaat gcttccagaa ttctacaaga ccgtctctcc tgcactaata  1140
tccagattta aagagcgtga agagaatgta aaggcagatg tttttcacgc ataccttttct  1200
cttttgaagc aaactcgtcc tgtacaaagt tggctatgtg accctgatgc aatggagcag  1260
ggagaaacac ctttaacaat gcttcagagt caggttccca acattgttaa agctcttcac  1320
aaacagatga aagaaaaaag tgtgaagacc cgacagtgtt gttttaacat gttaactgag  1380
ctggtaaatg tattacctgg ggccctaact caacacattc ctgtacttgt accaggaatc  1440
attttctcac tgaatgataa atcaagctca tcgaatttga agatcgatgc tttgtcatgt  1500
ctatacgtaa tcctctgtaa ccattctcct caagtcttcc atcctcacgt tcaggctttg  1560
gttcctccag tggtggcttg tgttggagac ccattttaca aaattacatc tgaagcactt  1620
cttgttactc aacagcttgt caaagtaatt cgtcctttag atcagccttc ctcgtttgat  1680
gcaactcctt atatcaaaga tctatttacc tgtaccatta agagattaaa agcagctgac  1740
attgatcagg aagtcaagga aagggctatt tcctgtatgg gacaaattat ttgcaacctt  1800
ggagacaatt tgggttctga cttgcctaat acacttcaga ttttcttgga gagactaaag  1860
aatgaaatta ccaggttaac tacagtaaag gcattgacac tgattgctgg gtcacctttg  1920
aagatagatt tgaggcctgt tctgggagaa ggggttccta tccttgcttc atttcttaga  1980
aaaaaccaga gagctttgaa actgggtact ctttctgccc ttgatattct aataaaaaac  2040
tatagtgaca gcttgacagc tgccatgatt gatgcagttc tagatgagct cccacctctt  2100
atcagcgaaa gtgatatgca tgtttcacaa atggccatca gttttcttac cactttggca  2160
aaagtatatc cctcctccct ttcaaagata agtggatcca ttctcaatga acttattgga  2220
cttgtgagat cacccttatt gcaggggggga gctcttagtg ccatgctaga ctttttccaa  2280
gctctggttg tcactggaac aaataattta ggatacatgg atttgttgcg catgctgact  2340
ggtccagttt actctcagag cacagctctt actcataagc agtcttatta ttccattgcc  2400
aaatgtgtag ctgcccttac tcgagcatgc cctaaagagg gaccagctgt agtaggtcag  2460
tttattcaag atgtcaagaa ctcaaggtct acagattcca ttcgtctctt agctctactt  2520
tctcttggag aagttgggca tcatattgac ttaagtggac agttggaact aaaatctgta  2580
atactagaag ctttctcatc tcctagtgaa gaagtcaaat cagctgcatc ctatgcatta  2640
ggcagcatta gtgtgggcaa ccttcctgaa tatctgccgt ttgtcctgca agaaataact  2700
```

-continued

```
agtcaaccca aaaggcagta tcttttactt cattccttga aggaaattat tagctctgca  2760
tcagtggtgg gccttaaacc atatgttgaa aacatctggg ccttattact aaagcactgt  2820
gagtgtgcag aggaaggaac cagaaatgtt gttgctgaat gtctaggaaa actcactcta  2880
attgatccag aaactctcct tccacggctt aaggggtact tgatatcagg ctcatcatat  2940
gcccgaagct cagtggttac ggctgtgaaa tttacaattt ctgaccatcc acaacctatt  3000
gatccactgt taaagaactg cataggtgat ttcctaaaaa ctttggaaga cccagatttg  3060
aatgtgagaa gagtagcctt ggtcacattt aattcagcag cacataacaa gccatcatta  3120
ataagggatc tattggatac tgttcttcca catctttaca atgaaacaaa agttagaaag  3180
gagcttataa gagaggtaga aatgggtcca tttaaacata cggttgatga tggtctggat  3240
attagaaagg cagcatttga gtgtatgtac acacttctag acagttgtct tgatagactt  3300
gatatctttg aatttctaaa tcatgttgaa gatggtttga aggaccatta tgatattaag  3360
atgctgacat tttaatgtt ggtgagactg tctacccttt gtccaagtgc agtactgcag  3420
aggttggacc gacttgttga gccattacgt gcaacatgta caactaaggt aaaggcaaac  3480
tcagtaaagc aggagtttga aaaacaagat gaattaaagc gatctgccat gagagcagta  3540
gcagcactgc taaccattcc agaagcagag aagagtccac tgatgagtga attccagtca  3600
cagatcagtt ctaaccctga gctggcggct atctttgaaa gtatccagaa agattcatca  3660
tctactaact tggaatcaat ggacactagt tag                               3693
```

SEQ ID NO: 8

Human Cullin-associated NEDD8-dissociated protein 1

```
Met Ala Ser Ala Ser Tyr His Ile Ser Asn Leu Leu Glu Lys Met Thr
1               5                   10                  15

Ser Ser Asp Lys Asp Phe Arg Phe Met Ala Thr Asn Asp Leu Met Thr
            20                  25                  30

Glu Leu Gln Lys Asp Ser Ile Lys Leu Asp Asp Asp Ser Glu Arg Lys
        35                  40                  45

Val Val Lys Met Ile Leu Lys Leu Leu Glu Asp Lys Asn Gly Glu Val
    50                  55                  60

Gln Asn Leu Ala Val Lys Cys Leu Gly Pro Leu Val Ser Lys Val Lys
65                  70                  75                  80

Glu Tyr Gln Val Glu Thr Ile Val Asp Thr Leu Cys Thr Asn Met Leu
                85                  90                  95

Ser Asp Lys Glu Gln Leu Arg Asp Ile Ser Ser Ile Gly Leu Lys Thr
            100                 105                 110

Val Ile Gly Glu Leu Pro Pro Ala Ser Ser Gly Ser Ala Leu Ala Ala
        115                 120                 125

Asn Val Cys Lys Lys Ile Thr Gly Arg Leu Thr Ser Ala Ile Ala Lys
    130                 135                 140

Gln Glu Asp Val Ser Val Gln Leu Glu Ala Leu Asp Ile Met Ala Asp
145                 150                 155                 160

Met Leu Ser Arg Gln Gly Gly Leu Leu Val Asn Phe His Pro Ser Ile
                165                 170                 175

Leu Thr Cys Leu Leu Pro Gln Leu Thr Ser Pro Arg Leu Ala Val Arg
            180                 185                 190

Lys Arg Thr Ile Ile Ala Leu Gly His Leu Val Met Ser Cys Gly Asn
        195                 200                 205

Ile Val Phe Val Asp Leu Ile Glu His Leu Leu Ser Glu Leu Ser Lys
    210                 215                 220

Asn Asp Ser Met Ser Thr Thr Arg Thr Tyr Ile Gln Cys Ile Ala Ala
225                 230                 235                 240
```

-continued

```
Ile Ser Arg Gln Ala Gly His Arg Ile Gly Glu Tyr Leu Glu Lys Ile
                245                 250                 255

Ile Pro Leu Val Val Lys Phe Cys Asn Val Asp Asp Asp Glu Leu Arg
            260                 265                 270

Glu Tyr Cys Ile Gln Ala Phe Glu Ser Phe Val Arg Arg Cys Pro Lys
        275                 280                 285

Glu Val Tyr Pro His Val Ser Thr Ile Ile Asn Ile Cys Leu Lys Tyr
    290                 295                 300

Leu Thr Tyr Asp Pro Asn Tyr Asn Tyr Asp Asp Glu Asp Glu Asp Glu
305                 310                 315                 320

Asn Ala Met Asp Ala Asp Gly Gly Asp Asp Asp Gln Gly Ser Asp
                325                 330                 335

Asp Glu Tyr Ser Asp Asp Asp Asp Met Ser Trp Lys Val Arg Arg Ala
            340                 345                 350

Ala Ala Lys Cys Leu Asp Ala Val Val Ser Thr Arg His Glu Met Leu
        355                 360                 365

Pro Glu Phe Tyr Lys Thr Val Ser Pro Ala Leu Ile Ser Arg Phe Lys
    370                 375                 380

Glu Arg Glu Glu Asn Val Lys Ala Asp Val Phe His Ala Tyr Leu Ser
385                 390                 395                 400

Leu Leu Lys Gln Thr Arg Pro Val Gln Ser Trp Leu Cys Asp Pro Asp
                405                 410                 415

Ala Met Glu Gln Gly Glu Thr Pro Leu Thr Met Leu Gln Ser Gln Val
            420                 425                 430

Pro Asn Ile Val Lys Ala Leu His Lys Gln Met Lys Glu Lys Ser Val
        435                 440                 445

Lys Thr Arg Gln Cys Cys Phe Asn Met Leu Thr Glu Leu Val Asn Val
    450                 455                 460

Leu Pro Gly Ala Leu Thr Gln His Ile Pro Val Leu Val Pro Gly Ile
465                 470                 475                 480

Ile Phe Ser Leu Asn Asp Lys Ser Ser Ser Ser Asn Leu Lys Ile Asp
                485                 490                 495

Ala Leu Ser Cys Leu Tyr Val Ile Leu Cys Asn His Ser Pro Gln Val
            500                 505                 510

Phe His Pro His Val Gln Ala Leu Val Pro Pro Val Val Ala Cys Val
        515                 520                 525

Gly Asp Pro Phe Tyr Lys Ile Thr Ser Glu Ala Leu Leu Val Thr Gln
    530                 535                 540

Gln Leu Val Lys Val Ile Arg Pro Leu Asp Gln Pro Ser Ser Phe Asp
545                 550                 555                 560

Ala Thr Pro Tyr Ile Lys Asp Leu Phe Thr Cys Thr Ile Lys Arg Leu
                565                 570                 575

Lys Ala Ala Asp Ile Asp Gln Glu Val Lys Glu Arg Ala Ile Ser Cys
            580                 585                 590

Met Gly Gln Ile Ile Cys Asn Leu Gly Asp Asn Leu Gly Ser Asp Leu
        595                 600                 605

Pro Asn Thr Leu Gln Ile Phe Leu Glu Arg Leu Lys Asn Glu Ile Thr
    610                 615                 620

Arg Leu Thr Thr Val Lys Ala Leu Thr Leu Ile Ala Gly Ser Pro Leu
625                 630                 635                 640

Lys Ile Asp Leu Arg Pro Val Leu Gly Glu Gly Val Pro Ile Leu Ala
                645                 650                 655

Ser Phe Leu Arg Lys Asn Gln Arg Ala Leu Lys Leu Gly Thr Leu Ser
            660                 665                 670
```

-continued

```
Ala Leu Asp Ile Leu Ile Lys Asn Tyr Ser Asp Ser Leu Thr Ala Ala
        675                 680                 685

Met Ile Asp Ala Val Leu Asp Glu Leu Pro Pro Leu Ile Ser Glu Ser
    690                 695                 700

Asp Met His Val Ser Gln Met Ala Ile Ser Phe Leu Thr Thr Leu Ala
705                 710                 715                 720

Lys Val Tyr Pro Ser Ser Leu Ser Lys Ile Ser Gly Ser Ile Leu Asn
                725                 730                 735

Glu Leu Ile Gly Leu Val Arg Ser Pro Leu Leu Gln Gly Gly Ala Leu
            740                 745                 750

Ser Ala Met Leu Asp Phe Phe Gln Ala Leu Val Val Thr Gly Thr Asn
        755                 760                 765

Asn Leu Gly Tyr Met Asp Leu Leu Arg Met Leu Thr Gly Pro Val Tyr
    770                 775                 780

Ser Gln Ser Thr Ala Leu Thr His Lys Gln Ser Tyr Tyr Ser Ile Ala
785                 790                 795                 800

Lys Cys Val Ala Ala Leu Thr Arg Ala Cys Pro Lys Glu Gly Pro Ala
                805                 810                 815

Val Val Gly Gln Phe Ile Gln Asp Val Lys Asn Ser Arg Ser Thr Asp
            820                 825                 830

Ser Ile Arg Leu Leu Ala Leu Leu Ser Leu Gly Glu Val Gly His His
        835                 840                 845

Ile Asp Leu Ser Gly Gln Leu Glu Leu Lys Ser Val Ile Leu Glu Ala
    850                 855                 860

Phe Ser Ser Pro Ser Glu Glu Val Lys Ser Ala Ala Ser Tyr Ala Leu
865                 870                 875                 880

Gly Ser Ile Ser Val Gly Asn Leu Pro Glu Tyr Leu Pro Phe Val Leu
                885                 890                 895

Gln Glu Ile Thr Ser Gln Pro Lys Arg Gln Tyr Leu Leu Leu His Ser
            900                 905                 910

Leu Lys Glu Ile Ile Ser Ser Ala Ser Val Val Gly Leu Lys Pro Tyr
        915                 920                 925

Val Glu Asn Ile Trp Ala Leu Leu Leu Lys His Cys Glu Cys Ala Glu
    930                 935                 940

Glu Gly Thr Arg Asn Val Val Ala Glu Cys Leu Gly Lys Leu Thr Leu
945                 950                 955                 960

Ile Asp Pro Glu Thr Leu Leu Pro Arg Leu Lys Gly Tyr Leu Ile Ser
                965                 970                 975

Gly Ser Ser Tyr Ala Arg Ser Ser Val Val Thr Ala Val Lys Phe Thr
            980                 985                 990

Ile Ser Asp His Pro Gln Pro Ile  Asp Pro Leu Leu Lys  Asn Cys Ile
        995                 1000                 1005

Gly Asp  Phe Leu Lys Thr Leu  Glu Asp Pro Asp Leu  Asn Val Arg
    1010                 1015                 1020

Arg Val  Ala Leu Val Thr Phe  Asn Ser Ala Ala His  Asn Lys Pro
    1025                 1030                 1035

Ser Leu  Ile Arg Asp Leu Leu  Asp Thr Val Leu Pro  His Leu Tyr
    1040                 1045                 1050

Asn Glu  Thr Lys Val Arg Lys  Glu Leu Ile Arg Glu  Val Glu Met
    1055                 1060                 1065

Gly Pro  Phe Lys His Thr Val  Asp Asp Gly Leu Asp  Ile Arg Lys
    1070                 1075                 1080

Ala Ala  Phe Glu Cys Met Tyr  Thr Leu Leu Asp Ser  Cys Leu Asp
    1085                 1090                 1095
```

-continued

```
Arg Leu  Asp Ile Phe Glu Phe  Leu Asn His Val Glu  Asp Gly Leu
    1100                 1105                 1110

Lys Asp  His Tyr Asp Ile Lys  Met Leu Thr Phe Leu  Met Leu Val
    1115                 1120                 1125

Arg Leu  Ser Thr Leu Cys Pro  Ser Ala Val Leu Gln  Arg Leu Asp
    1130                 1135                 1140

Arg Leu  Val Glu Pro Leu Arg  Ala Thr Cys Thr Thr  Lys Val Lys
    1145                 1150                 1155

Ala Asn  Ser Val Lys Gln Glu  Phe Glu Lys Gln Asp  Glu Leu Lys
    1160                 1165                 1170

Arg Ser  Ala Met Arg Ala Val  Ala Ala Leu Leu Thr  Ile Pro Glu
    1175                 1180                 1185

Ala Glu  Lys Ser Pro Leu Met  Ser Glu Phe Gln Ser  Gln Ile Ser
    1190                 1195                 1200

Ser Asn  Pro Glu Leu Ala Ala  Ile Phe Glu Ser Ile  Gln Lys Asp
    1205                 1210                 1215

Ser Ser  Ser Thr Asn Leu Glu  Ser Met Asp Thr Ser
    1220                 1225                 1230
```

In another embodiment of this aspect of the present invention, the one or more mutations detected in the patient sample include a mutation in the PRMT2 gene encoding protein arginine N-methyltransferase 2. This mutation maps to position 46903160 of chromosome 21 of hg 18. The mRNA sequence for human PRMT2 (NCBI Accession No. NM_001535) and corresponding amino acid sequence are provided below as SEQ ID NOs: 9 and 10, respectively. A relapse specific mutation in PRMT2 results in a methionine to leucine substitution at an amino acid position corresponding to M244 of SEQ ID NO: 10 below. An exemplary mutation in PRMT2 encoding this amino acid substitution comprises a A→C change at a nucleotide position corresponding to position 730 of SEQ ID NO: 9.

```
                                                        SEQ ID NO: 9
Human PRMT2
atggcaacat caggtgactg tcccagaagt gaatcgcagg gagaagagcc tgctgagtgc    60

agtgaggccg gtctcctgca ggagggagta cagccagagg agtttgtggc catcgcggac   120

tacgctgcca ccgatgagac ccagctcagt tttttgagag gagaaaaaat tcttatcctg   180

agacaaacca ctgcagattg gtggtggggt gagcgtgcgg gctgctgtgg gtacattccg   240

gcaaaccatg tggggaagca cgtggatgag tacgaccccg aggacacgtg gcaggatgaa   300

gagtacttcg gcagctatgg aactctgaaa ctccacttgg agatgttggc agaccagcca   360

cgaacaacta aataccacag tgtcatcctg cagaataaag aatccctgac ggataaagtc   420

atcctggacg tgggctgtgg gactgggatc atcagtctct tctgtgcaca ctatgcgcgg   480

cctagagcgg tgtacgcggt ggaggccagt gagatggcac agcacacggg gcagctggtc   540

ctgcagaacg gctttgctga catcatcacc gtgtaccagc agaaggtgga ggatgtggtg   600

ctgcccgaga aggtggacgt gctggtgtct gagtggatgg ggacctgcct gctgtttgag   660

ttcatgatcg agtccatcct gtatgcccgg gatgcctggc tgaaggagga cggggtcatt   720

tggcccacca tggctgcgtt gcaccttgtg ccctgcagtg ctgataagga ttatcgtagc   780

aaggtgctct tctgggacaa cgcgtacgag ttcaacctca gcgctctgaa atctttagca   840

gttaaggagt ttttttcaaa gcccaagtat aaccacattt tgaaaccaga agactgtctc   900

tctgaaccgt gcactatatt gcagttggac atgagaaccg tgcaaatttc tgatctagag   960

accctgaggg gcgagctgcg cttcgacatc aggaaggcgg ggaccctgca cggcttcacg  1020

gcctggttta gcgtccactt ccagagcctg caggaggggc agccgccgca ggtgctcagc  1080

accgggccct tccaccccac cacacactgg aagcagacgc tgttcatgat ggacgaccca  1140

gtccctgtcc atacaggaga cgtggtcacg ggttcagttg tgttgcagag aaacccagtg  1200
```

-continued

```
tggagaaggc acatgtctgt ggctctgagc tgggctgtca cttccagaca agaccccaca  1260

tctcaaaaag ttggagaaaa agtcttcccc atctggagat ga                     1302

                                                        SEQ ID NO: 10
Human Protein arginine N-methyltransferase 2
Met Ala Thr Ser Gly Asp Cys Pro Arg Ser Glu Ser Gln Gly Glu Glu
1               5                   10                  15

Pro Ala Glu Cys Ser Glu Ala Gly Leu Leu Gln Glu Gly Val Gln Pro
            20                  25                  30

Glu Glu Phe Val Ala Ile Ala Asp Tyr Ala Ala Thr Asp Glu Thr Gln
        35                  40                  45

Leu Ser Phe Leu Arg Gly Glu Lys Ile Leu Ile Leu Arg Gln Thr Thr
    50                  55                  60

Ala Asp Trp Trp Trp Gly Glu Arg Ala Gly Cys Cys Gly Tyr Ile Pro
65                  70                  75                  80

Ala Asn His Val Gly Lys His Val Asp Glu Tyr Asp Pro Glu Asp Thr
                85                  90                  95

Trp Gln Asp Glu Glu Tyr Phe Gly Ser Tyr Gly Thr Leu Lys Leu His
            100                 105                 110

Leu Glu Met Leu Ala Asp Gln Pro Arg Thr Thr Lys Tyr His Ser Val
        115                 120                 125

Ile Leu Gln Asn Lys Glu Ser Leu Thr Asp Lys Val Ile Leu Asp Val
    130                 135                 140

Gly Cys Gly Thr Gly Ile Ile Ser Leu Phe Cys Ala His Tyr Ala Arg
145                 150                 155                 160

Pro Arg Ala Val Tyr Ala Val Glu Ala Ser Glu Met Ala Gln His Thr
                165                 170                 175

Gly Gln Leu Val Leu Gln Asn Gly Phe Ala Asp Ile Ile Thr Val Tyr
            180                 185                 190

Gln Gln Lys Val Glu Asp Val Val Leu Pro Glu Lys Val Asp Val Leu
        195                 200                 205

Val Ser Glu Trp Met Gly Thr Cys Leu Leu Phe Glu Phe Met Ile Glu
    210                 215                 220

Ser Ile Leu Tyr Ala Arg Asp Ala Trp Leu Lys Glu Asp Gly Val Ile
225                 230                 235                 240

Trp Pro Thr Met Ala Ala Leu His Leu Val Pro Cys Ser Ala Asp Lys
                245                 250                 255

Asp Tyr Arg Ser Lys Val Leu Phe Trp Asp Asn Ala Tyr Glu Phe Asn
            260                 265                 270

Leu Ser Ala Leu Lys Ser Leu Ala Val Lys Glu Phe Phe Ser Lys Pro
        275                 280                 285

Lys Tyr Asn His Ile Leu Lys Pro Glu Asp Cys Leu Ser Glu Pro Cys
    290                 295                 300

Thr Ile Leu Gln Leu Asp Met Arg Thr Val Gln Ile Ser Asp Leu Glu
305                 310                 315                 320

Thr Leu Arg Gly Glu Leu Arg Phe Asp Ile Arg Lys Ala Gly Thr Leu
                325                 330                 335

His Gly Phe Thr Ala Trp Phe Ser Val His Phe Gln Ser Leu Gln Glu
            340                 345                 350

Gly Gln Pro Pro Gln Val Leu Ser Thr Gly Pro Phe His Pro Thr Thr
        355                 360                 365

His Trp Lys Gln Thr Leu Phe Met Met Asp Asp Pro Val Pro Val His
    370                 375                 380

Thr Gly Asp Val Val Thr Gly Ser Val Val Leu Gln Arg Asn Pro Val
385                 390                 395                 400
```

-continued

```
Trp Arg Arg His Met Ser Val Ala Leu Ser Trp Ala Val Thr Ser Arg
            405                 410                 415

Gln Asp Pro Thr Ser Gln Lys Val Gly Glu Lys Val Phe Pro Ile Trp
            420                 425                 430

Arg
```

In another embodiment of this aspect of the present invention, the one or more mutations detected in the patient sample include a mutation in the NIPSNAP1 gene encoding protein NipSnap homolog 1. This mutation maps to position 28287562 of chromosome 22 of hg 18. The mRNA sequence for human NIPSNAP1 (NCBI Accession No. NM_003634) and corresponding amino acid sequence are provided below as SEQ ID NOs: 11 and 12, respectively. A relapse specific mutation in NIPSNAP1 results in a serine to isoleucine substitution at an amino acid position corresponding to S171 of SEQ ID NO: 12 below. An exemplary mutation in NIPSNAP1 encoding this amino acid substitution comprises a G→T change at a nucleotide position corresponding to position 512 of SEQ ID NO: 11.

```
                                                              SEQ ID NO: 11
Human NIPSNAP1
atggctccgc ggctgtgcag catctctgtg acggcgcggc ggctgctggg gggcccgggg     60

cctcgcgctg gggacgttgc gtctgcagct gcggcgcgtt tctattccaa ggacaatgaa    120

ggcagctggt tccgctccct ctttgttcac aaagtggatc cccggaagga tgcccactcc    180

accctgctgt ccaagaagga aaccagcaac ctctataaga tccagtttca caatgtaaag    240

cctgaatacc tggatgccta caacagcctc acggaggctg tgctgcccaa gcttcacctg    300

gatgaggact acccatgctc actcgtgggc aactggaaca cgtggtatgg ggagcaggac    360

caggcagtgc acctgtggcg attctcaggt ggctacccag ccctcatgga ctgcatgaac    420

aagctcaaaa acaataagga gtacctggag ttccgaaggg agcggagcca gatgctgctg    480

tccaggagaa accagctgct cctcgagttc agcttctgga atgagccaca gcccagaatg    540

ggtcccaaca tctatgagct gaggacatac aagctcaagc caggaaccat gatcgagtgg    600

gggaacaact gggctcgggc catcaagtac cggcaggaga accaggaggc agtgggcggc    660

ttcttctcac agataggaga gctctacgtg gtgcaccatc tctgggccta taaagacctg    720

cagtctcggg aggagactcg aaacgctgcc tggaggaaga gaggctggga tgaaaatgtc    780

tactatacag tccccctggt gcgacacatg gagtctagga tcatgatccc cttgaagatc    840

tcgcctctgc agtga                                                      855
                                                              SEQ ID NO: 12
Human Protein NipSnap homolog 1
Met Ala Pro Arg Leu Cys Ser Ile Ser Val Thr Ala Arg Arg Leu Leu
1               5                   10                  15

Gly Gly Pro Gly Pro Arg Ala Gly Asp Val Ala Ser Ala Ala Ala Ala
            20                  25                  30

Arg Phe Tyr Ser Lys Asp Asn Glu Gly Ser Trp Phe Arg Ser Leu Phe
            35                  40                  45

Val His Lys Val Asp Pro Arg Lys Asp Ala His Ser Thr Leu Leu Ser
50                  55                  60

Lys Lys Glu Thr Ser Asn Leu Tyr Lys Ile Gln Phe His Asn Val Lys
65                  70                  75                  80

Pro Glu Tyr Leu Asp Ala Tyr Asn Ser Leu Thr Glu Ala Val Leu Pro
            85                  90                  95

Lys Leu His Leu Asp Glu Asp Tyr Pro Cys Ser Leu Val Gly Asn Trp
            100                 105                 110

Asn Thr Trp Tyr Gly Glu Gln Asp Gln Ala Val His Leu Trp Arg Phe
            115                 120                 125

Ser Gly Gly Tyr Pro Ala Leu Met Asp Cys Met Asn Lys Leu Lys Asn
            130                 135                 140
```

-continued

```
Asn Lys Glu Tyr Leu Glu Phe Arg Arg Glu Arg Ser Gln Met Leu Leu
145                 150                 155                 160

Ser Arg Arg Asn Gln Leu Leu Leu Glu Phe Ser Phe Trp Asn Glu Pro
                165                 170                 175

Gln Pro Arg Met Gly Pro Asn Ile Tyr Glu Leu Arg Thr Tyr Lys Leu
            180                 185                 190

Lys Pro Gly Thr Met Ile Glu Trp Gly Asn Asn Trp Ala Arg Ala Ile
        195                 200                 205

Lys Tyr Arg Gln Glu Asn Gln Glu Ala Val Gly Gly Phe Phe Ser Gln
    210                 215                 220

Ile Gly Glu Leu Tyr Val Val His His Leu Trp Ala Tyr Lys Asp Leu
225                 230                 235                 240

Gln Ser Arg Glu Glu Thr Arg Asn Ala Ala Trp Arg Lys Arg Gly Trp
                245                 250                 255

Asp Glu Asn Val Tyr Tyr Thr Val Pro Leu Val Arg His Met Glu Ser
            260                 265                 270

Arg Ile Met Ile Pro Leu Lys Ile Ser Pro Leu Gln
        275                 280
```

In another embodiment of this aspect of the present invention, the one or more mutations detected in the patient sample include a mutation in the USP7 gene encoding ubiquitin carboxyl-terminal hydrolase-7. This mutation maps to position 8902368 of chromosome 16 of hg 18. The mRNA sequence for human USP7 (NCBI Accession No. NM_003470) and corresponding amino acid sequence are provided below as SEQ ID NOs: 13 and 14, respectively. A relapse specific mutation in USP7 results in a threonine to serine substitution at an amino acid position corresponding to T730 of SEQ ID NO: 14 below. An exemplary mutation in USP7 encoding this amino acid substitution comprises a A→T change at a nucleotide position corresponding to position 2188 of SEQ ID NO: 13.

```
                                                          SEQ ID NO: 13
Human USP7
atgaaccacc agcagcagca gcagcagcag aaagcgggcg agcagcagtt gagcgagccc     60

gaggacatgg agatggaagc gggagataca gatgacccac caagaattac tcagaaccct    120

gtgatcaatg ggaatgtggc cctgagtgat ggacacaaca ccgcggagga ggacatggag    180

gatgacacca gttggcgctc cgaggcaacc tttcagttca ctgtggagcg cttcagcaga    240

ctgagtgagt cggtccttag ccctccgtgt tttgtgcgaa atctgccatg gaagattatg    300

gtgatgccac gcttttatcc agacagacca caccaaaaaa gcgtaggatt ctttctccag    360

tgcaatgctg aatctgattc cacgtcatgg tcttgccatg cacaagcagt gctgaagata    420

ataaattaca gagatgatga aaagtcgttc agtcgtcgta ttagtcattt gttcttccat    480

aaagaaaatg attggggatt ttccaatttt atggcctgga gtgaagtgac cgatcctgag    540

aaaggattta tagatgatga caaagttacc tttgaagtct ttgtacaggc ggatgctccc    600

catggagttg cgtgggattc aaagaagcac acaggctacg tcggcttaaa gaatcaggga    660

gcgacttgtt acatgaacag cctgctacag acgttatttt tcacgaatca gctacgaaag    720

gctgtgtaca tgatgccaac cgagggggat gattcgtcta aaagcgtccc tttagcatta    780

caaagagtgt tctatgaatt acagcatagt gataaacctg taggaacaaa aaagttaaca    840

aagtcatttg ggtgggaaac tttagatagc ttcatgcaac atgatgttca ggagctttgt    900

cgagtgttgc tcgataatgt ggaaaataag atgaaaggca cctgtgtaga gggcaccata    960

cccaaattat tccgcggcaa aatggtgtcc tatatccagt gtaaagaagt agactatcgg   1020

tctgatagaa gagaagatta ttatgatatc cagctaagta tcaaaggaaa gaaaaatata   1080

tttgaatcat ttgtggatta tgtggcagta gaacagctcg atggggacaa taaatacgac   1140

gctggggaac atggcttaca ggaagcagag aaaggtgtga aattcctaac attgccacca   1200
```

-continued

```
gtgttacatc tacaactgat gagatttatg tatgaccctc agacggacca aaatatcaag  1260
atcaatgata ggtttgaatt cccagagcag ttaccacttg atgaattttt gcaaaaaaca  1320
gatcctaagg accctgcaaa ttatattctt catgcagtcc tggttcatag tggagataat  1380
catggtggac attatgtggt ttatctaaac cccaaagggg atggcaaatg gtgtaaattt  1440
gatgacgacg tggtgtcaag gtgtactaaa gaggaagcaa ttgagcacaa ttatgggggt  1500
cacgatgacg acctgtctgt tcgacactgc actaatgctt acatgttagt ctacatcagg  1560
gaatcaaaac tgagtgaagt tttacaggcg gtcaccgacc atgatattcc tcagcagttg  1620
gtggagcgat tacaagaaga gaaaaggatc gaggctcaga agcggaagga gcggcaggaa  1680
gcccatctct atatgcaagt gcagatagtc gcagaggacc agttttgtgg ccaccaaggg  1740
aatgacatgt acgatgaaga aaaagtgaaa tacactgtgt tcaaagtatt gaagaactcc  1800
tcgcttgctg agtttgttca gagcctctct cagaccatgg gatttccaca agatcaaatt  1860
cgattgtggc ccatgcaagc aaggagtaat ggaacaaaac gaccagcaat gttagataat  1920
gaagccgacg gcaataaaac aatgattgag ctcagtgata atgaaaaccc ttggacaata  1980
ttcctggaaa cagttgatcc cgagctggct gctagtggag cgaccttacc caagtttgat  2040
aaagatcatg atgtaatgtt atttttgaag atgtatgatc ccaaaacgcg gagcttgaat  2100
tactgtgggc atatctacac accaatatcc tgtaaaatac gtgacttgct cccagttatg  2160
tgtgacagag caggatttat tcaagatact agccttatcc tctatgagga agttaaaccg  2220
aatttaacag agagaattca ggactatgac gtgtctcttg ataaagccct tgatgaacta  2280
atggatggtg acatcatagt atttcagaag gatgaccctg aaaatgataa cagtgaatta  2340
cccaccgcaa aggagtattt ccgagatctc taccaccgcg ttgatgtcat tttctgtgat  2400
aaaacaatcc ctaatgatcc tggatttgtg gttacgttat caaatagaat gaattatttt  2460
caggttgcaa agacagttgc acagaggctc aacacagatc caatgttgct gcagtttttc  2520
aagtctcaag gttataggga tggcccaggt aatcctctta gacataatta tgaaggtact  2580
ttaagagatc ttctacagtt cttcaagcct agacaaccta agaaacttta ctatcagcag  2640
cttaagatga aaatcacaga ctttgagaac aggcgaagtt ttaaatgtat atggttaaac  2700
agccaattta gggaagagga aataacacta tatccagaca agcatgggtg tgtccgggac  2760
ctgttagaag aatgtaaaaa ggccgtggag cttggggaga aagcatcagg gaaacttagg  2820
ctgctagaaa ttgtaagcta caaaatcatt ggtgttcatc aagaagatga actattagaa  2880
tgtttatctc ctgcaacgag ccggacgttt cgaatagagg aaatcccttt ggaccaggtg  2940
gacatagaca aagagaatga gatgcttgtc acagtggcgc atttccacaa agaggtcttc  3000
ggaacgttcg gaatcccgtt tttgctgagg atacaccagg gcgagcattt tcgagaagtg  3060
atgaagcgaa tccagagcct gctggacatc caggagaagg agtttgagaa gtttaaattt  3120
gcaattgtaa tgatgggccg acaccagtac ataaatgaag acgagtatga agtaaatttg  3180
aaagactttg agccacagcc cggtaatatg tctcatcctc ggccttggct agggctcgac  3240
cacttcaaca aagccccaaa gaggagtcgc tacacttacc ttgaaaaggc cattaaaatc  3300
cataactga                                                           3309
```

SEQ ID NO: 14

```
Human Ubiquitin carboxyl-terminal hydrolase 7
Met Asn His Gln Gln Gln Gln Gln Gln Gln Lys Ala Gly Glu Gln Gln
1               5                   10                  15

Leu Ser Glu Pro Glu Asp Met Glu Met Glu Ala Gly Asp Thr Asp Asp
            20                  25                  30
```

-continued

```
Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
    50                  55                  60

Trp Arg Ser Glu Ala Thr Phe Gln Phe Thr Val Glu Arg Phe Ser Arg
65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
    130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
    210                 215                 220

Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Ser Lys Ser Val
                245                 250                 255

Pro Leu Ala Leu Gln Arg Val Phe Tyr Glu Leu Gln His Ser Asp Lys
            260                 265                 270

Pro Val Gly Thr Lys Lys Leu Thr Lys Ser Phe Gly Trp Glu Thr Leu
        275                 280                 285

Asp Ser Phe Met Gln His Asp Val Gln Glu Leu Cys Arg Val Leu Leu
    290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
            340                 345                 350

Ser Ile Lys Gly Lys Lys Asn Ile Phe Glu Ser Phe Val Asp Tyr Val
        355                 360                 365

Ala Val Glu Gln Leu Asp Gly Asp Asn Lys Tyr Asp Ala Gly Glu His
    370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
        435                 440                 445

Ile Leu His Ala Val Leu Val His Ser Gly Asp Asn His Gly Gly His
    450                 455                 460
```

-continued

```
Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Asp Leu Ser Val Arg His Cys Thr Asn
            500                 505                 510

Ala Tyr Met Leu Val Tyr Ile Arg Glu Ser Lys Leu Ser Glu Val Leu
        515                 520                 525

Gln Ala Val Thr Asp His Asp Ile Pro Gln Gln Leu Val Glu Arg Leu
    530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
    610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
    690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765

Gln Lys Asp Asp Pro Glu Asn Asp Asn Ser Glu Leu Pro Thr Ala Lys
    770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830

Asp Pro Met Leu Leu Gln Phe Phe Lys Ser Gln Gly Tyr Arg Asp Gly
        835                 840                 845

Pro Gly Asn Pro Leu Arg His Asn Tyr Glu Gly Thr Leu Arg Asp Leu
    850                 855                 860

Leu Gln Phe Phe Lys Pro Arg Gln Pro Lys Lys Leu Tyr Tyr Gln Gln
865                 870                 875                 880

Leu Lys Met Lys Ile Thr Asp Phe Glu Asn Arg Arg Ser Phe Lys Cys
                885                 890                 895
```

-continued

```
Ile Trp Leu Asn Ser Gln Phe Arg Glu Glu Glu Ile Thr Leu Tyr Pro
            900                 905                 910

Asp Lys His Gly Cys Val Arg Asp Leu Leu Glu Glu Cys Lys Lys Ala
        915                 920                 925

Val Glu Leu Gly Glu Lys Ala Ser Gly Lys Leu Arg Leu Leu Glu Ile
    930                 935                 940

Val Ser Tyr Lys Ile Ile Gly Val His Gln Glu Asp Glu Leu Leu Glu
945                 950                 955                 960

Cys Leu Ser Pro Ala Thr Ser Arg Thr Phe Arg Ile Glu Glu Ile Pro
                965                 970                 975

Leu Asp Gln Val Asp Ile Asp Lys Glu Asn Glu Met Leu Val Thr Val
            980                 985                 990

Ala His Phe His Lys Glu Val Phe  Gly Thr Phe Gly Ile  Pro Phe Leu
        995                 1000                1005

Leu Arg  Ile His Gln Gly Glu  His Phe Arg Glu Val  Met Lys Arg
    1010                1015                1020

Ile Gln  Ser Leu Leu Asp Ile  Gln Glu Lys Glu Phe  Glu Lys Phe
    1025                1030                1035

Lys Phe  Ala Ile Val Met Met  Gly Arg His Gln Tyr  Ile Asn Glu
    1040                1045                1050

Asp Glu  Tyr Glu Val Asn Leu  Lys Asp Phe Glu Pro  Gln Pro Gly
    1055                1060                1065

Asn Met  Ser His Pro Arg Pro  Trp Leu Gly Leu Asp  His Phe Asn
    1070                1075                1080

Lys Ala  Pro Lys Arg Ser Arg  Tyr Thr Tyr Leu Glu  Lys Ala Ile
    1085                1090                1095

Lys Ile  His Asn
    1100
```

In another embodiment of this aspect of the present invention, the one or more mutations detected in the patient sample include a mutation in the TULP4 gene encoding tubby-related protein 4. This mutation maps to position 158844705 of chromosome 6 of hg 18. The mRNA sequence for human TULP4 (NCBI Accession No. NM_020245) and corresponding amino acid sequence are provided below as SEQ ID NOs: 15 and 16, respectively. A relapse specific mutation in TULP4 results in a leucine to arginine substitution at an amino acid position corresponding to L1341 of SEQ ID NO: 16 below. An exemplary mutation in TULP4 encoding this amino acid substitution comprises a T G change at a nucleotide position corresponding to position 4022 of SEQ ID NO: 15.

```
                                                          SEQ ID NO: 15
Human TULP4
atgtatgcag cagtggaaca tgggcctgtg ctttgcagcg attccaacat cctgtgcctg    60

tcctggaagg ggcgtgtccc caagagtgag aaggagaagc ctgtgtgcag gagacgctac   120

tatgaggaag gctggctggc cacgggcaac gggcgaggag tggttggggt gactttcacc   180

tctagtcact gtcgcaggga caggagtact ccacagagga taaatttcaa cctccggggc   240

cacaatagcg aggttgtgct ggtgaggtgg aatgagccct accagaaact ggccacgtgc   300

gatgcggacg gaggcatatt cgtgtggatt cagtacgagg gcaggtggtc tgtggagctg   360

gtcaacgacc gcggggcgca ggtgagtgat ttcacgtgga gccatgatgg aactcaagca   420

cttatttcct atcgagatgg gtttgtcctg gttgggtctg tcagtggaca aagacactgg   480

tcatccgaaa tcaacttgga aagtcaaatt acgtgtggca tatggactcc tgacgaccaa   540

caggtgctgt ttggcacggc cgatgggcag gtgattgtca tggattgcca cggcagaatg   600

ctggcccacg tcctcttgca cgagtcagac ggtgtcctcg gcatgtcctg gaactacccg   660

atcttcctgg tggaggacag cagcgagagc gacacggact cagatgacta cgcccctccc   720

caagatggtc cggcagcata tcccatccca gtgcagaaca tcaagcctct gctcaccgtc   780
```

-continued

```
agcttcacct cgggagacat cagcttaatg aacaactacg atgacttgtc tcccacggtc    840
atccgctcag ggctgaaaga ggtggtagcc cagtggtgca cacaggggga cttgctggca    900
gtcgctggga tggaacggca gacccagctt ggtgagcttc ccaatggtcc ccttctgaag    960
agtgccatgg tcaagttcta caatgttcgt ggggagcaca tcttcacact ggacactctc   1020
gtgcagcgcc ccatcatctc catctgctgg ggtcaccggg attcgaggct gttgatggca   1080
tcaggaccag ccctgtacgt ggtgcgtgtg gagcaccggg tgtccagcct gcagctgctg   1140
tgccagcagg ccatcgccag caccttgcgt gaggacaagg acgtcagcaa gctgactctg   1200
ccccccccgcc tctgctccta cctctccact gccttcatcc ccaccatcaa gcccccaatt   1260
ccagatccga acaacatgag agactttgtc agctacccat cagccggcaa cgagcggctg   1320
cactgcacca tgaagcgcac agaggacgac ccggaggtgg gcggcccgtg ctacacgctc   1380
tacctggagt acctgggcgg gcttgtgccc atcctcaaag ggcggcgcat cagcaagctg   1440
cggccagagt tcgtcatcat ggacccgcgg acagatagca aaccagatga aatctatggg   1500
aacagcttga tttctactgt gatcgacagc tgcaactgct cagactccag tgacattgag   1560
ctgagtgatg actgggctgc caagaaatct cccaaaatct ccagagctag caaatcaccc   1620
aaactcccaa ggatcagcat tgaggcccgc aagtcaccca agctgccccg ggctgctcag   1680
gagctctccc ggtccccacg gttgcccctg cgcaagccct ctgtgggctc gcccagcctg   1740
actcggagag agtttccttt tgaagacatc actcagcaca actatcttgc tcaggtcacg   1800
tctaatatct ggggaaccaa atttaagatt gtgggcttgg ctgctttcct gccaaccaac   1860
ctcggtgcag taatctataa aaccagcctc ctgcatctcc agccgcggca gatgaccatt   1920
tatctcccag aagttcggaa aatttccatg gactatatta atttacctgt cttcaaccca   1980
aatgttttca gtgaagatga agatgattta ccagtgacag gagcatctgg tgtccctgag   2040
aacagcccac cttgtaccgt gaacatccct attgcaccga tccacagctc ggctcaggct   2100
atgtccccca cgcagagcat agggctggtg cagtccctac tggccaatca gaatgtgcag   2160
ctagatgtcc tgaccaacca gacgacagct gtagggacag cagaacatgc aggtgacagt   2220
gccacccagt acccagtctc caaccggtac tccaatcctg gacaggtgat tttcggaagc   2280
gtggaaatgg gccgcatcat tcagaacccc cctccactgt ccctgcctcc cccgccgcag   2340
gggcccatgc agctgtccac ggtgggccat ggagaccgag accacgaaca cctgcagaag   2400
tcagccaagg ccctgcggcc aacaccgcag ctggcagctg agggggacgc agtggtcttt   2460
agtgcccccc aggaggtcca ggtgacgaag ataaaccctc cacccccgta cccaggaacc   2520
atccccgctg cccccaccac agcagcaccc ccgccccctc tgccgccccc acagccccca   2580
gtggatgtgt gcttgaagaa gggcgacttc tccctctacc ccacgtcagt gcactaccag   2640
accccccctgg gctatgagag gatcaccacc ttcgacagca gtggcaacgt ggaggaggtg   2700
tgccggcccc gcacccggat gctgtgctcc cagaacacgt acaccctccc cggcccgggt   2760
agctctgcca ccttgaggct cacggccact gagaagaagg tccctcagcc ctgcagcagt   2820
gccaccctga accgcctgac cgtccctcgc tactccatcc ccaccgggga cccacccccg   2880
tatcctgaaa ttgccagcca gctggcccag gggcgggggg ctgcccagag gtccgacaat   2940
agcctcatcc acgctaccct gcggaggaac aaccgtgagg ctacgctcaa gatggcccag   3000
ctggccgaca gcccgcgggc ccccctgcag cccctggcca agtccaaggg cgggcccggg   3060
ggggtggtga cacagctccc agcgcggccc ccacctgccc tgtacacctg cagtcagtgc   3120
agtggcacag ggcccagctc acagcccgga gcctccctgg cccataccgc cagcgcctcc   3180
```

-continued

```
ccgttggcct cccagtcctc ctacagcctc ctgagcccac ccgacagcgc ccgcgaccgc  3240

accgactacg tcaactcggc cttcacggag gacgaggccc tgtcccagca ctgtcagctt  3300

gagaagccct tgaggcaccc tcccctgcct gaagctgctg tcaccctgaa acggccaccc  3360

ccttaccagt gggaccccat gctgggtgag gatgtttggg ttcctcaaga aaggacagca  3420

cagacttcag ggcccaaccc cttaaaactg tcctctctga tgctgagtca gggccagcac  3480

ctggacgtgt cccgactgcc cttcatctcc cccaagtctc ctgccagccc cactgccact  3540

ttccaaacag gctatgggat gggagtgcca tatccaggaa gctataacaa ccccccttttg  3600

cctggagtgc aggctccctg ctctcccaaa gatgccctgt ccccaacgca gtttgcacaa  3660

caggagcctg ctgtggtcct tcagccgctg tacccaccca gcctctccta ttgcaccctg  3720

ccccccatgt acccaggaag cagcacgtgc tctagtttac agctgccacc tgtcgccttg  3780

catccatgga gttcctacag cgcctgcccg cccatgcaga acccccaggg cactctcccc  3840

ccaaagccac acttggtggt ggagaagccc cttgtgtccc caccacctgc cgacctccaa  3900

agccacttgg gcacagaggt gatggtagag actgcagaca acttccagga agtcctctcc  3960

ctgaccgaaa gcccagtccc ccagcggaca gaaaaatttg gaaagaagaa ccggaagcgc  4020

ctggacagcc gagcagaaga aggcagcgtt caggccatca ctgagggcaa agtgaagaag  4080

gaggctagga ctttgagtga ctttaattcc ctaatctcca gcccacacct ggggagagag  4140

aagaagaaag tgaagagtca gaaagaccaa ctgaagtcaa agaagttgaa taagacaaac  4200

gagttccagg acagctccga gagcgagcct gagctgttca tcagcgggga tgagctcatg  4260

aaccagagcc agggcagcag aaagggctgg aaaagcaagc gctccccacg ggccgccggc  4320

gagctggagg aggccaagtg ccggcgggcc agtgagaagg aggacgggcg gctgggcagc  4380

caaggcttcg tgtacgtgat ggccaacaag cagccgctgt ggaacgaggc cacccaggtc  4440

taccagctgg acttcggggg gcgggtgacc caggagtccg ccaagaactt ccagattgag  4500

ttagaggggc ggcaggtgat gcagtttgga cggattgatg gcagtgcgta cattctagac  4560

ttccagtatc cgttctcagc cgtgcaggcc tttgcagttg ccctggccaa cgtgactcag  4620

cgcctcaaat ga                                                      4632
```

SEQ ID NO: 16

Human Tubby-related protein 4

```
Met Tyr Ala Ala Val Glu His Gly Pro Val Leu Cys Ser Asp Ser Asn
1               5                   10                  15

Ile Leu Cys Leu Ser Trp Lys Gly Arg Val Pro Lys Ser Glu Lys Glu
            20                  25                  30

Lys Pro Val Cys Arg Arg Arg Tyr Tyr Glu Glu Gly Trp Leu Ala Thr
        35                  40                  45

Gly Asn Gly Arg Gly Val Val Gly Val Thr Phe Thr Ser Ser His Cys
    50                  55                  60

Arg Arg Asp Arg Ser Thr Pro Gln Arg Ile Asn Phe Asn Leu Arg Gly
65                  70                  75                  80

His Asn Ser Glu Val Val Leu Val Arg Trp Asn Glu Pro Tyr Gln Lys
                85                  90                  95

Leu Ala Thr Cys Asp Ala Asp Gly Gly Ile Phe Val Trp Ile Gln Tyr
            100                 105                 110

Glu Gly Arg Trp Ser Val Glu Leu Val Asn Asp Arg Gly Ala Gln Val
        115                 120                 125

Ser Asp Phe Thr Trp Ser His Asp Gly Thr Gln Ala Leu Ile Ser Tyr
    130                 135                 140

Arg Asp Gly Phe Val Leu Val Gly Ser Val Ser Gly Gln Arg His Trp
145                 150                 155                 160
```

-continued

```
Ser Ser Glu Ile Asn Leu Glu Ser Gln Ile Thr Cys Gly Ile Trp Thr
                165                 170                 175

Pro Asp Asp Gln Gln Val Leu Phe Gly Thr Ala Asp Gly Gln Val Ile
            180                 185                 190

Val Met Asp Cys His Gly Arg Met Leu Ala His Val Leu Leu His Glu
        195                 200                 205

Ser Asp Gly Val Leu Gly Met Ser Trp Asn Tyr Pro Ile Phe Leu Val
    210                 215                 220

Glu Asp Ser Ser Glu Ser Asp Thr Asp Ser Asp Asp Tyr Ala Pro Pro
225                 230                 235                 240

Gln Asp Gly Pro Ala Ala Tyr Pro Ile Pro Val Gln Asn Ile Lys Pro
                245                 250                 255

Leu Leu Thr Val Ser Phe Thr Ser Gly Asp Ile Ser Leu Met Asn Asn
            260                 265                 270

Tyr Asp Asp Leu Ser Pro Thr Val Ile Arg Ser Gly Leu Lys Glu Val
        275                 280                 285

Val Ala Gln Trp Cys Thr Gln Gly Asp Leu Leu Ala Val Ala Gly Met
    290                 295                 300

Glu Arg Gln Thr Gln Leu Gly Glu Leu Pro Asn Gly Pro Leu Leu Lys
305                 310                 315                 320

Ser Ala Met Val Lys Phe Tyr Asn Val Arg Gly Glu His Ile Phe Thr
                325                 330                 335

Leu Asp Thr Leu Val Gln Arg Pro Ile Ile Ser Ile Cys Trp Gly His
            340                 345                 350

Arg Asp Ser Arg Leu Leu Met Ala Ser Gly Pro Ala Leu Tyr Val Val
        355                 360                 365

Arg Val Glu His Arg Val Ser Ser Leu Gln Leu Leu Cys Gln Gln Ala
    370                 375                 380

Ile Ala Ser Thr Leu Arg Glu Asp Lys Asp Val Ser Lys Leu Thr Leu
385                 390                 395                 400

Pro Pro Arg Leu Cys Ser Tyr Leu Ser Thr Ala Phe Ile Pro Thr Ile
                405                 410                 415

Lys Pro Pro Ile Pro Asp Pro Asn Asn Met Arg Asp Phe Val Ser Tyr
            420                 425                 430

Pro Ser Ala Gly Asn Glu Arg Leu His Cys Thr Met Lys Arg Thr Glu
        435                 440                 445

Asp Asp Pro Glu Val Gly Gly Pro Cys Tyr Thr Leu Tyr Leu Glu Tyr
    450                 455                 460

Leu Gly Gly Leu Val Pro Ile Leu Lys Gly Arg Arg Ile Ser Lys Leu
465                 470                 475                 480

Arg Pro Glu Phe Val Ile Met Asp Pro Arg Thr Asp Ser Lys Pro Asp
                485                 490                 495

Glu Ile Tyr Gly Asn Ser Leu Ile Ser Thr Val Ile Asp Ser Cys Asn
            500                 505                 510

Cys Ser Asp Ser Ser Asp Ile Glu Leu Ser Asp Asp Trp Ala Ala Lys
        515                 520                 525

Lys Ser Pro Lys Ile Ser Arg Ala Ser Lys Ser Pro Lys Leu Pro Arg
    530                 535                 540

Ile Ser Ile Glu Ala Arg Lys Ser Pro Lys Leu Pro Arg Ala Ala Gln
545                 550                 555                 560

Glu Leu Ser Arg Ser Pro Arg Leu Pro Leu Arg Lys Pro Ser Val Gly
                565                 570                 575

Ser Pro Ser Leu Thr Arg Arg Glu Phe Pro Phe Glu Asp Ile Thr Gln
            580                 585                 590
```

-continued

```
His Asn Tyr Leu Ala Gln Val Thr Ser Asn Ile Trp Gly Thr Lys Phe
        595                 600                 605

Lys Ile Val Gly Leu Ala Ala Phe Leu Pro Thr Asn Leu Gly Ala Val
    610                 615                 620

Ile Tyr Lys Thr Ser Leu Leu His Leu Gln Pro Arg Gln Met Thr Ile
625                 630                 635                 640

Tyr Leu Pro Glu Val Arg Lys Ile Ser Met Asp Tyr Ile Asn Leu Pro
                645                 650                 655

Val Phe Asn Pro Asn Val Phe Ser Glu Asp Glu Asp Asp Leu Pro Val
            660                 665                 670

Thr Gly Ala Ser Gly Val Pro Glu Asn Ser Pro Pro Cys Thr Val Asn
        675                 680                 685

Ile Pro Ile Ala Pro Ile His Ser Ser Ala Gln Ala Met Ser Pro Thr
    690                 695                 700

Gln Ser Ile Gly Leu Val Gln Ser Leu Leu Ala Asn Gln Asn Val Gln
705                 710                 715                 720

Leu Asp Val Leu Thr Asn Gln Thr Thr Ala Val Gly Thr Ala Glu His
                725                 730                 735

Ala Gly Asp Ser Ala Thr Gln Tyr Pro Val Ser Asn Arg Tyr Ser Asn
            740                 745                 750

Pro Gly Gln Val Ile Phe Gly Ser Val Glu Met Gly Arg Ile Ile Gln
        755                 760                 765

Asn Pro Pro Pro Leu Ser Leu Pro Pro Pro Pro Gln Gly Pro Met Gln
    770                 775                 780

Leu Ser Thr Val Gly His Gly Asp Arg Asp His Glu His Leu Gln Lys
785                 790                 795                 800

Ser Ala Lys Ala Leu Arg Pro Thr Pro Gln Leu Ala Ala Glu Gly Asp
                805                 810                 815

Ala Val Val Phe Ser Ala Pro Gln Glu Val Gln Val Thr Lys Ile Asn
            820                 825                 830

Pro Pro Pro Pro Tyr Pro Gly Thr Ile Pro Ala Ala Pro Thr Thr Ala
        835                 840                 845

Ala Pro Pro Pro Pro Leu Pro Pro Pro Gln Pro Pro Val Asp Val Cys
    850                 855                 860

Leu Lys Lys Gly Asp Phe Ser Leu Tyr Pro Thr Ser Val His Tyr Gln
865                 870                 875                 880

Thr Pro Leu Gly Tyr Glu Arg Ile Thr Thr Phe Asp Ser Ser Gly Asn
                885                 890                 895

Val Glu Glu Val Cys Arg Pro Arg Thr Arg Met Leu Cys Ser Gln Asn
            900                 905                 910

Thr Tyr Thr Leu Pro Gly Pro Gly Ser Ser Ala Thr Leu Arg Leu Thr
        915                 920                 925

Ala Thr Glu Lys Lys Val Pro Gln Pro Cys Ser Ser Ala Thr Leu Asn
    930                 935                 940

Arg Leu Thr Val Pro Arg Tyr Ser Ile Pro Thr Gly Asp Pro Pro Pro
945                 950                 955                 960

Tyr Pro Glu Ile Ala Ser Gln Leu Ala Gln Gly Arg Gly Ala Ala Gln
                965                 970                 975

Arg Ser Asp Asn Ser Leu Ile His Ala Thr Leu Arg Arg Asn Asn Arg
            980                 985                 990

Glu Ala Thr Leu Lys Met Ala Gln  Leu Ala Asp Ser Pro  Arg Ala Pro
        995                 1000                 1005

Leu Gln  Pro Leu Ala Lys Ser  Lys Gly Gly Pro Gly  Gly Val Val
    1010                 1015                 1020
```

-continued

Thr Gln Leu Pro Ala Arg Pro Pro Pro Ala Leu Tyr Thr Cys Ser
1025 1030 1035

Gln Cys Ser Gly Thr Gly Pro Ser Ser Gln Pro Gly Ala Ser Leu
1040 1045 1050

Ala His Thr Ala Ser Ala Ser Pro Leu Ala Ser Gln Ser Ser Tyr
1055 1060 1065

Ser Leu Leu Ser Pro Pro Asp Ser Ala Arg Asp Arg Thr Asp Tyr
1070 1075 1080

Val Asn Ser Ala Phe Thr Glu Asp Glu Ala Leu Ser Gln His Cys
1085 1090 1095

Gln Leu Glu Lys Pro Leu Arg His Pro Pro Leu Pro Glu Ala Ala
1100 1105 1110

Val Thr Leu Lys Arg Pro Pro Pro Tyr Gln Trp Asp Pro Met Leu
1115 1120 1125

Gly Glu Asp Val Trp Val Pro Gln Glu Arg Thr Ala Gln Thr Ser
1130 1135 1140

Gly Pro Asn Pro Leu Lys Leu Ser Ser Leu Met Leu Ser Gln Gly
1145 1150 1155

Gln His Leu Asp Val Ser Arg Leu Pro Phe Ile Ser Pro Lys Ser
1160 1165 1170

Pro Ala Ser Pro Thr Ala Thr Phe Gln Thr Gly Tyr Gly Met Gly
1175 1180 1185

Val Pro Tyr Pro Gly Ser Tyr Asn Asn Pro Pro Leu Pro Gly Val
1190 1195 1200

Gln Ala Pro Cys Ser Pro Lys Asp Ala Leu Ser Pro Thr Gln Phe
1205 1210 1215

Ala Gln Gln Glu Pro Ala Val Val Leu Gln Pro Leu Tyr Pro Pro
1220 1225 1230

Ser Leu Ser Tyr Cys Thr Leu Pro Pro Met Tyr Pro Gly Ser Ser
1235 1240 1245

Thr Cys Ser Ser Leu Gln Leu Pro Pro Val Ala Leu His Pro Trp
1250 1255 1260

Ser Ser Tyr Ser Ala Cys Pro Pro Met Gln Asn Pro Gln Gly Thr
1265 1270 1275

Leu Pro Pro Lys Pro His Leu Val Val Glu Lys Pro Leu Val Ser
1280 1285 1290

Pro Pro Pro Ala Asp Leu Gln Ser His Leu Gly Thr Glu Val Met
1295 1300 1305

Val Glu Thr Ala Asp Asn Phe Gln Glu Val Leu Ser Leu Thr Glu
1310 1315 1320

Ser Pro Val Pro Gln Arg Thr Glu Lys Phe Gly Lys Lys Asn Arg
1325 1330 1335

Lys Arg Leu Asp Ser Arg Ala Glu Glu Gly Ser Val Gln Ala Ile
1340 1345 1350

Thr Glu Gly Lys Val Lys Lys Glu Ala Arg Thr Leu Ser Asp Phe
1355 1360 1365

Asn Ser Leu Ile Ser Ser Pro His Leu Gly Arg Glu Lys Lys Lys
1370 1375 1380

Val Lys Ser Gln Lys Asp Gln Leu Lys Ser Lys Lys Leu Asn Lys
1385 1390 1395

Thr Asn Glu Phe Gln Asp Ser Ser Glu Ser Glu Pro Glu Leu Phe
1400 1405 1410

Ile Ser Gly Asp Glu Leu Met Asn Gln Ser Gln Gly Ser Arg Lys
1415 1420 1425

-continued

```
Gly Trp  Lys Ser Lys Arg Ser  Pro Arg Ala Ala Gly  Glu Leu Glu
    1430                 1435                 1440

Glu Ala  Lys Cys Arg Arg Ala  Ser Glu Lys Glu Asp  Gly Arg Leu
    1445                 1450                 1455

Gly Ser  Gln Gly Phe Val Tyr  Val Met Ala Asn Lys  Gln Pro Leu
    1460                 1465                 1470

Trp Asn  Glu Ala Thr Gln Val  Tyr Gln Leu Asp Phe  Gly Gly Arg
    1475                 1480                 1485

Val Thr  Gln Glu Ser Ala Lys  Asn Phe Gln Ile Glu  Leu Glu Gly
    1490                 1495                 1500

Arg Gln  Val Met Gln Phe Gly  Arg Ile Asp Gly Ser  Ala Tyr Ile
    1505                 1510                 1515

Leu Asp  Phe Gln Tyr Pro Phe  Ser Ala Val Gln Ala  Phe Ala Val
    1520                 1525                 1530

Ala Leu  Ala Asn Val Thr Gln  Arg Leu Lys
    1535                 1540
```

In another embodiment of this aspect of the present invention, the one or more mutations detected in the patient sample include a mutation in the CBX3 gene encoding chromobox protein homolog 3. This mutation maps to position 26214576 of chromosome 7 of hg 18. The mRNA sequence for human CBX3 (NCBI Accession No. NM_007276) and corresponding amino acid sequence are provided below as SEQ ID NOs: 17 and 18, respectively. A relapse specific mutation in CBX3 results in a cysteine to tyrosine substitution at an amino acid position corresponding to C69 of SEQ ID NO: 18 below. An exemplary mutation in CBX3 encoding this amino acid substitution comprises a G→A change at a nucleotide position corresponding to position 206 of SEQ ID NO: 17.

```
                                                   SEQ ID NO: 17
Human CBX3
atggcctcca acaaaactac attgcaaaaa atgggaaaaa aacagaatgg aaagagtaaa    60

aaagttgaag aggcagagcc tgaagaattt gtcgtggaaa aagtactaga tcgacgtgta   120

gtgaatggga aagtggaata tttcctgaag tggaagggat ttacagatgc tgacaatact   180

tgggaacctg aagaaaattt agattgtcca gaattgattg aagcgtttct taactctcag   240

aaagctggca aagaaaaaga tggtacaaaa agaaaatctt tatctgacag tgaatctgat   300

gacagcaaat caaagaagaa aagagatgct gctgacaaac caagaggatt tgccagaggt   360

cttgatcctg aaagaataat tggtgccaca gacagcagtg gagaattgat gtttctcatg   420

aaatggaaag attcagatga ggcagacttg gtgctggcga aagaggcaaa tatgaagtgt   480

cctcaaattg taattgcttt ttatgaagag agactaactt ggcattcttg tccagaagat   540

gaagctcaat aa                                                       552

                                                   SEQ ID NO: 18
Human Chromobox protein homolog 3
Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
            20                  25                  30

Glu Lys Val Leu Asp Arg Arg Val Val Asn Gly Lys Val Glu Tyr Phe
        35                  40                  45

Leu Lys Trp Lys Gly Phe Thr Asp Ala Asp Asn Thr Trp Glu Pro Glu
    50                  55                  60

Glu Asn Leu Asp Cys Pro Glu Leu Ile Glu Ala Phe Leu Asn Ser Gln
65                  70                  75                  80

Lys Ala Gly Lys Glu Lys Asp Gly Thr Lys Arg Lys Ser Leu Ser Asp
                85                  90                  95

Ser Glu Ser Asp Asp Ser Lys Ser Lys Lys Lys Arg Asp Ala Ala Asp
            100                 105                 110
```

-continued

```
Lys Pro Arg Gly Phe Ala Arg Gly Leu Asp Pro Glu Arg Ile Ile Gly
        115                 120                 125

Ala Thr Asp Ser Ser Gly Glu Leu Met Phe Leu Met Lys Trp Lys Asp
    130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180
```

In another embodiment of this aspect of the present invention, the one or more mutations detected in the patient sample include a mutation in the COBRA1 gene encoding negative elongation factor B. This mutation maps to position 139270653 of chromosome 9 of hg 18. The mRNA sequence for human COBRA1 (NCBI Accession No. NM_015456) and corresponding amino acid sequence are provided below as SEQ ID NOs: 19 and 20, respectively. A relapse specific mutation in COBRA1 results in a methionine to isoleucine substitution at an amino acid position corresponding to M106 of SEQ ID NO:20 below. An exemplary mutation in COBRA1 encoding this amino acid substitution comprises a G→A change at a nucleotide position corresponding to position 318 of SEQ ID NO: 19.

```
                                                      SEQ ID NO: 19
Human COBRA1
atgttcgcgg ggctgcagga cctgggcgtg gccaacggcg aggacctgaa ggagaccctg    60

accaactgca cggagccgct caaggccatc gagcagttcc agacagagaa tggtgtgctg   120

ctgccatctc ttcagtcagc cctccccttc ttggacctgc acgggacgcc gcggctggag   180

ttccaccagt cggtattcga tgagctgcgg gacaagctgc tggagcgagt gtcagccatc   240

gcttcggagg ggaaggctga ggaaaggtac aagaagctgg aagaccttct ggagaagagc   300

ttttctctgg tgaagatgcc gtccctgcag cccgtggtga tgtgcgtcat gaagcacctg   360

cccaaggttc cggagaaaaa actgaagctg gttatggctg acaaggagct gtatcgagcc   420

tgcgccgtgg aggtgaagcg gcagatctgg caagacaacc aggccctctt cggggacgag   480

gtttccccac tcctgaagca gtacatcctg gagaaggaga gcgctctctt cagtacagag   540

ctctctgtcc tgcacaactt tttcagtcct tcccccaaga ccaggcgcca gggcgaggtg   600

gtgcagcggc tgacgcggat ggtggggaag aacgtgaagc tgtacgacat ggtgctgcag   660

tttctgcgca cgctcttcct gcgcacgcgg aatgtgcact actgcacgct gcgggctgag   720

ctgctcatgt ccctgcacga cctggacgtg ggtgaaatct gcaccgtgga cccgtgccac   780

aagttcacct ggtgcctgga cgcctgcatc cgagagcggt tcgtggacag caagagggcg   840

cgggagctgc aggggtttct cgatggcgtc aagaagggcc aggagcaggt gctgggggac   900

ctgtccatga tcctgtgtga ccccttcgcc atcaacacgc tggcactgag cacagtcagg   960

cacctgcagg agctggtcgg ccaggagaca ctgcccaggg acagccccga cctcctgctg  1020

ctgctccggc tgctggcgct gggccaggga gcctgggaca tgatcgacag ccaggtcttc  1080

aaggagccca agatggaggt agagctcatc accaggttcc tcccgatgct catgtccttc  1140

ctggtggatg actacacttt caatgtggat cagaaacttc cggctgagga gaaagcccca  1200

gtctcatatc caaacacact tcccgaaagc ttcactaagt ttctgcagga gcagcgcatg  1260

gcctgcgagg tggggctgta ctacgtcctg cacatcacca agcagaggaa caagaacgcg  1320

ctcctccgcc tgctgcccgg gctggtggag acctttggcg acttggcctt tggcgacatc  1380

ttcctccacc tgctcacggg caaccttgcg ctgctggccg acgaatttgc ccttgaggac  1440

ttctgcagca gcctcttcga tggcttcttc ctcaccgcct ctccaaggaa ggagaacgtg  1500

caccggcacg cgctgcggct cctcattcac ctgcacccca gggtggcccc gtctaagctg  1560
```

-continued

```
gaggcgttgc agaaggccct ggagcctaca ggccagagcg gagaggcagt gaaggagctt  1620

tactcccagc tcggcgagaa gctggaacag ctggatcacc ggaagcccag cccggcacag  1680

gctgcggaga cgccggccct ggagctgccc ctccccagcg tgcccgcccc tgccccgctc  1740

tga                                                                1743
```

SEQ ID NO: 20

Human Negative elongation factor B

```
Met Phe Ala Gly Leu Gln Asp Leu Gly Val Ala Asn Gly Glu Asp Leu
1               5                   10                  15

Lys Glu Thr Leu Thr Asn Cys Thr Glu Pro Leu Lys Ala Ile Glu Gln
            20                  25                  30

Phe Gln Thr Glu Asn Gly Val Leu Leu Pro Ser Leu Gln Ser Ala Leu
        35                  40                  45

Pro Phe Leu Asp Leu His Gly Thr Pro Arg Leu Glu Phe His Gln Ser
    50                  55                  60

Val Phe Asp Glu Leu Arg Asp Lys Leu Leu Glu Arg Val Ser Ala Ile
65                  70                  75                  80

Ala Ser Glu Gly Lys Ala Glu Glu Arg Tyr Lys Lys Leu Glu Asp Leu
                85                  90                  95

Leu Glu Lys Ser Phe Ser Leu Val Lys Met Pro Ser Leu Gln Pro Val
            100                 105                 110

Val Met Cys Val Met Lys His Leu Pro Lys Val Pro Glu Lys Lys Leu
        115                 120                 125

Lys Leu Val Met Ala Asp Lys Glu Leu Tyr Arg Ala Cys Ala Val Glu
    130                 135                 140

Val Lys Arg Gln Ile Trp Gln Asp Asn Gln Ala Leu Phe Gly Asp Glu
145                 150                 155                 160

Val Ser Pro Leu Leu Lys Gln Tyr Ile Leu Glu Lys Glu Ser Ala Leu
                165                 170                 175

Phe Ser Thr Glu Leu Ser Val Leu His Asn Phe Phe Ser Pro Ser Pro
            180                 185                 190

Lys Thr Arg Arg Gln Gly Glu Val Val Gln Arg Leu Thr Arg Met Val
        195                 200                 205

Gly Lys Asn Val Lys Leu Tyr Asp Met Val Leu Gln Phe Leu Arg Thr
    210                 215                 220

Leu Phe Leu Arg Thr Arg Asn Val His Tyr Cys Thr Leu Arg Ala Glu
225                 230                 235                 240

Leu Leu Met Ser Leu His Asp Leu Asp Val Gly Glu Ile Cys Thr Val
                245                 250                 255

Asp Pro Cys His Lys Phe Thr Trp Cys Leu Asp Ala Cys Ile Arg Glu
            260                 265                 270

Arg Phe Val Asp Ser Lys Arg Ala Arg Glu Leu Gln Gly Phe Leu Asp
        275                 280                 285

Gly Val Lys Lys Gly Gln Glu Gln Val Leu Gly Asp Leu Ser Met Ile
    290                 295                 300

Leu Cys Asp Pro Phe Ala Ile Asn Thr Leu Ala Leu Ser Thr Val Arg
305                 310                 315                 320

His Leu Gln Glu Leu Val Gly Gln Glu Thr Leu Pro Arg Asp Ser Pro
                325                 330                 335

Asp Leu Leu Leu Leu Leu Arg Leu Leu Ala Leu Gly Gln Gly Ala Trp
            340                 345                 350

Asp Met Ile Asp Ser Gln Val Phe Lys Glu Pro Lys Met Glu Val Glu
        355                 360                 365

Leu Ile Thr Arg Phe Leu Pro Met Leu Met Ser Phe Leu Val Asp Asp
```

-continued

```
    370                 375                 380

Tyr Thr Phe Asn Val Asp Gln Lys Leu Pro Ala Glu Glu Lys Ala Pro
385                 390                 395                 400

Val Ser Tyr Pro Asn Thr Leu Pro Glu Ser Phe Thr Lys Phe Leu Gln
                405                 410                 415

Glu Gln Arg Met Ala Cys Glu Val Gly Leu Tyr Tyr Val Leu His Ile
                420                 425                 430

Thr Lys Gln Arg Asn Lys Asn Ala Leu Leu Arg Leu Leu Pro Gly Leu
        435                 440                 445

Val Glu Thr Phe Gly Asp Leu Ala Phe Gly Asp Ile Phe Leu His Leu
    450                 455                 460

Leu Thr Gly Asn Leu Ala Leu Leu Ala Asp Glu Phe Ala Leu Glu Asp
465                 470                 475                 480

Phe Cys Ser Ser Leu Phe Asp Gly Phe Phe Leu Thr Ala Ser Pro Arg
                485                 490                 495

Lys Glu Asn Val His Arg His Ala Leu Arg Leu Leu Ile His Leu His
            500                 505                 510

Pro Arg Val Ala Pro Ser Lys Leu Glu Ala Leu Gln Lys Ala Leu Glu
        515                 520                 525

Pro Thr Gly Gln Ser Gly Glu Ala Val Lys Glu Leu Tyr Ser Gln Leu
    530                 535                 540

Gly Glu Lys Leu Glu Gln Leu Asp His Arg Lys Pro Ser Pro Ala Gln
545                 550                 555                 560

Ala Ala Glu Thr Pro Ala Leu Glu Leu Pro Leu Pro Ser Val Pro Ala
                565                 570                 575

Pro Ala Pro Leu
            580
```

In another embodiment of this aspect of the present invention, the one or more mutations detected in the patient sample include a mutation in the SDF2 gene encoding stromal cell-derived factor 2. This mutation maps to position 24006562 of chromosome 17 of hg 18. The mRNA sequence for human SDF2 (NCBI Accession No. NM_006923) and corresponding amino acid sequence are provided below as SEQ ID NOs: 21 and 22, respectively. A relapse specific mutation in SDF2 results in an arginine to glutamine substitution at an amino acid position corresponding to R73 of SEQ ID NO: 22 below. An exemplary mutation in SDF2 encoding this amino acid substitution comprises a G→A change at a nucleotide position corresponding to position 218 of SEQ ID NO: 21.

```
                                                          SEQ ID NO: 21
Human SDF2
atggctgtag tacctctgct gttgttgggg ggtttgtgga gcgctgtggg agcgtccagc    60

ctgggtgtcg ttacttgcgg ctccgtggtg aagctactca atacgcgcca caacgtccga   120

ctgcactcac acgacgtgcg ctatgggtca ggtagtgggc agcagtcagt gacaggtgta   180

acctctgtgg atgacagcaa cagttactgg aggatacggg ggaagagtgc cacagtgtgt   240

gagaggggaa cccccatcaa gtgtggccag cccatccggc tgacacatgt caacactggc   300

cgaaacctcc atagtcacca cttcacttca cctctttctg gaaaccagga agtgagtgct   360

tttggtgagg aaggtgaagg tgattatctg gatgactgga cagtgctctg taatggaccc   420

tactgggtga gagatggtga ggtgcggttc aaacactctt ccactgaggt actgctgtct   480

gtcacaggag aacaatatgg tcgacctatc agtgggcaaa aagaggtgca tggcatggcc   540

cagccaagtc agaacaacta ctggaaagcc atggaaggca tcttcatgaa gcccagtgag   600

ttgttgaagg cagaagccca ccatgcagag ctgtga                              636

                                                          SEQ ID NO: 22
Human Stromal cell-derived factor 2
Met Ala Val Val Pro Leu Leu Leu Leu Gly Gly Leu Trp Ser Ala Val
1               5                   10                  15
```

-continued

```
Gly Ala Ser Ser Leu Gly Val Val Thr Cys Gly Ser Val Val Lys Leu
            20                  25                  30

Leu Asn Thr Arg His Asn Val Arg Leu His Ser His Asp Val Arg Tyr
        35                  40                  45

Gly Ser Gly Ser Gly Gln Gln Ser Val Thr Gly Val Thr Ser Val Asp
    50                  55                  60

Asp Ser Asn Ser Tyr Trp Arg Ile Arg Gly Lys Ser Ala Thr Val Cys
65                  70                  75                  80

Glu Arg Gly Thr Pro Ile Lys Cys Gly Gln Pro Ile Arg Leu Thr His
                85                  90                  95

Val Asn Thr Gly Arg Asn Leu His Ser His His Phe Thr Ser Pro Leu
            100                 105                 110

Ser Gly Asn Gln Glu Val Ser Ala Phe Gly Glu Glu Gly Glu Gly Asp
        115                 120                 125

Tyr Leu Asp Asp Trp Thr Val Leu Cys Asn Gly Pro Tyr Trp Val Arg
    130                 135                 140

Asp Gly Glu Val Arg Phe Lys His Ser Ser Thr Glu Val Leu Leu Ser
145                 150                 155                 160

Val Thr Gly Glu Gln Tyr Gly Arg Pro Ile Ser Gly Gln Lys Glu Val
                165                 170                 175

His Gly Met Ala Gln Pro Ser Gln Asn Asn Tyr Trp Lys Ala Met Glu
            180                 185                 190

Gly Ile Phe Met Lys Pro Ser Glu Leu Leu Lys Ala Glu Ala His His
        195                 200                 205

Ala Glu Leu
210
```

In another embodiment of this aspect of the present invention, the one or more mutations detected in the patient sample include a mutation in the FBXO3 gene encoding isoform 2 of F-box only protein 3. This mutation maps to position 33725250 of chromosome 11 of hg 18. The mRNA sequence for human FBXO3 (NCBI Accession No. NM_033406) and corresponding amino acid sequence are provided below as SEQ ID NOs: 23 and 24, respectively. A relapse specific mutation in FBXO3 results in a valine to glutamic acid substitution at an amino acid position corresponding to V414 of SEQ ID NO: 24 below. An exemplary mutation in FBXO3 encoding this amino acid substitution comprises an T→A change at a nucleotide position corresponding to position 1241 of SEQ ID NO: 23.

```
                                                          SEQ ID NO: 23
Human FBX03
atggcggcca tggagaccga gacggcgccg ctgaccctag agtcgctgcc caccgatccc    60

ctgctcctca tcttatcctt tttggactat cgggatctaa tcaactgttg ttatgtcagt   120

cgaagactta gccagctatc aagtcatgat ccgctgtgga gaagacattg caaaaaatac   180

tggctgatat ctgaggaaga gaaaacacag aagaatcagt gttggaaatc tctcttcata   240

gatacttact ctgatgtagg aagatacatt gaccattatg ctgctattaa aaaggcctgg   300

gatgatctca agaaatattt ggagcccagg tgtcctcgga tggttttatc tctgaaagag   360

ggtgctcgag aggaagacct cgatgctgtg gaagcgcaga ttggctgcaa gcttcctgac   420

gattatcgat gttcataccg aattcacaat ggacagaagt tagtggttcc tgggttattg   480

ggaagcatgg cactgtctaa tcactatcgt tctgaagatt tgttagacgt cgatacagct   540

gccggaggat tccagcagag acagggactg aaatactgtc tcccttttaac tttttgcata   600

catactggtt tgagtcagta catagcagtg gaagctgcag agggccgaaa caaaaatgaa   660

gttttctacc aatgtccaga ccaaatggct cgaaatccag ctgctattga catgtttatt   720

ataggtgcta cttttactga ctggtttacc tcttatgtca aaaatgttgt atcaggtggc   780

ttccccatca tcagagacca aattttcaga tatgttcacg atccagaatg tgtagcaaca   840
```

-continued

```
actggggata ttactgtgtc agtttccaca tcgtttctgc cagaacttag ctctgtacat    900

ccaccccact atttcttcac ataccgaatc aggattgaaa tgtcaaaaga tgcacttcct    960

gagaaggcct gtcagttgga cagtcgctat tggagaataa caaatgctaa gggtgacgtg   1020

gaagaagttc aaggacctgg agtagttggt gaatttccaa tcatcagccc aggtcgggta   1080

tatgaataca caagctgtac cacattctct acaacatcag gatacatgga aggatattat   1140

accttccatt ttctttactt taaagacaag atctttaatg ttgccattcc ccgattccat   1200

atggcatgtc caacattcag ggtgtctata gcccgattgg taagttaa                1248

                                                          SEQ ID NO: 24
Human Isoform 2 of F-box only protein 3
Met Ala Ala Met Glu Thr Glu Thr Ala Pro Leu Thr Leu Glu Ser Leu
1               5                   10                  15

Pro Thr Asp Pro Leu Leu Leu Ile Leu Ser Phe Leu Asp Tyr Arg Asp
            20                  25                  30

Leu Ile Asn Cys Cys Tyr Val Ser Arg Arg Leu Ser Gln Leu Ser Ser
        35                  40                  45

His Asp Pro Leu Trp Arg Arg His Cys Lys Lys Tyr Trp Leu Ile Ser
    50                  55                  60

Glu Glu Glu Lys Thr Gln Lys Asn Gln Cys Trp Lys Ser Leu Phe Ile
65                  70                  75                  80

Asp Thr Tyr Ser Asp Val Gly Arg Tyr Ile Asp His Tyr Ala Ala Ile
                85                  90                  95

Lys Lys Ala Trp Asp Asp Leu Lys Lys Tyr Leu Glu Pro Arg Cys Pro
            100                 105                 110

Arg Met Val Leu Ser Leu Lys Glu Gly Ala Arg Glu Glu Asp Leu Asp
        115                 120                 125

Ala Val Glu Ala Gln Ile Gly Cys Lys Leu Pro Asp Asp Tyr Arg Cys
    130                 135                 140

Ser Tyr Arg Ile His Asn Gly Gln Lys Leu Val Val Pro Gly Leu Leu
145                 150                 155                 160

Gly Ser Met Ala Leu Ser Asn His Tyr Arg Ser Glu Asp Leu Leu Asp
                165                 170                 175

Val Asp Thr Ala Ala Gly Gly Phe Gln Gln Arg Gln Gly Leu Lys Tyr
            180                 185                 190

Cys Leu Pro Leu Thr Phe Cys Ile His Thr Gly Leu Ser Gln Tyr Ile
        195                 200                 205

Ala Val Glu Ala Ala Glu Gly Arg Asn Lys Asn Glu Val Phe Tyr Gln
    210                 215                 220

Cys Pro Asp Gln Met Ala Arg Asn Pro Ala Ala Ile Asp Met Phe Ile
225                 230                 235                 240

Ile Gly Ala Thr Phe Thr Asp Trp Phe Thr Ser Tyr Val Lys Asn Val
                245                 250                 255

Val Ser Gly Gly Phe Pro Ile Ile Arg Asp Gln Ile Phe Arg Tyr Val
            260                 265                 270

His Asp Pro Glu Cys Val Ala Thr Thr Gly Asp Ile Thr Val Ser Val
        275                 280                 285

Ser Thr Ser Phe Leu Pro Glu Leu Ser Ser Val His Pro Pro His Tyr
    290                 295                 300

Phe Phe Thr Tyr Arg Ile Arg Ile Glu Met Ser Lys Asp Ala Leu Pro
305                 310                 315                 320

Glu Lys Ala Cys Gln Leu Asp Ser Arg Tyr Trp Arg Ile Thr Asn Ala
                325                 330                 335

Lys Gly Asp Val Glu Glu Val Gln Gly Pro Gly Val Val Gly Glu Phe
```

-continued

```
        340                 345                 350

Pro Ile Ile Ser Pro Gly Arg Val Tyr Glu Tyr Thr Ser Cys Thr Thr
        355                 360                 365

Phe Ser Thr Thr Ser Gly Tyr Met Glu Gly Tyr Tyr Thr Phe His Phe
    370                 375                 380

Leu Tyr Phe Lys Asp Lys Ile Phe Asn Val Ala Ile Pro Arg Phe His
385                 390                 395                 400

Met Ala Cys Pro Thr Phe Arg Val Ser Ile Ala Arg Leu Val Ser
                405                 410                 415
```

In another embodiment of this aspect of the present invention, the one or more mutations detected in the patient sample include a mutation in the SCARF1 gene encoding isoform 4 of scavenger receptor class F member 1. This mutation maps to position 1490488 of chromosome 17 of hg 18. The mRNA sequence for human SCARF1 (NCBI Accession No. NM_145351) and corresponding amino acid sequence are provided below as SEQ ID NOs: 25 and 26, respectively. A relapse specific mutation in SCARF1 replaces the stop codon with a cysteine residue, thereby introducing a cysteine after the amino acid position corresponding to R337 of SEQ ID NO: 26 below (Cys338). An exemplary mutation in SCARF1 encoding this amino acid substitution comprises a A→T change at a nucleotide position corresponding to position 1014 of SEQ ID NO: 25.

```
                                                      SEQ ID NO: 25
Human SCARF1
atggggctgg ggctgctgct cccgctgctg ctgctctgga ctcgggggac tcaggggtcc    60

gagctggacc ccaaagggca gcacgtctgt gtggccagca gcccctctgc tgagctgcag   120

tgctgcgcag gctggaggca gaaggatcaa gaatgcacca tccccatctg tgaggggccg   180

gacgcctgcc agaaagacga ggtgtgtgtg aagccgggcc tctgtcgatg caagcctgga   240

ttctttgggg cccactgcag ctcccgctgc ccgggccagt actggggccc cgactgccgt   300

gagagctgcc cctgccaccc gcacggccag tgcgagccag ccacgggcgc gtgccagtgc   360

caggccgacc gctggggagc ccgctgcgag ttcccgtgcg cctgcggccc ccacgggcgc   420

tgcgaccccg cgaccggcgt gtgccactgc gaacccggct ggtggtcgtc cacgtgccgc   480

cgcccgtgcc agtgcaacac cgcggcggcg cgctgcgagc aggccacggg cgcctgcgtg   540

tgcaagccgg gctggtgggg gcgccgctgc agcttccgct gcaactgcca cggctccccg   600

tgcgagcagg actccggccg ctgcgcctgc cggccgggct ggtggggtcc cgaatgccag   660

cagcagtgcg agtgtgtgcg gggccgctgc agcgccgcct ccggcgagtg cacctgcccg   720

cccggcttcc gcggagcgcg ctgcgagctg ccctgcccgg caggcagcca cggggtgcag   780

tgcgcacaca gctgtggccg ctgcaaacac aatgagccgt gctctccaga cacaggcagc   840

tgtgagtcct gcgagccggg ctggaacggg acccagtgcc agcagccctg cctgcctggc   900

acctttggcg agagctgcga acagcagtgc cctcactgcc gacatgggga ggcctgtgag   960

ccagatactg gccactgtca gcgctgtgac cctggctggc tggggcccag gtga         1014

                                                      SEQ ID NO: 26
Isoform 4 of Scavenger receptor class F member 1
Met Gly Leu Gly Leu Leu Leu Pro Leu Leu Leu Leu Trp Thr Arg Gly
1               5                   10                  15

Thr Gln Gly Ser Glu Leu Asp Pro Lys Gly Gln His Val Cys Val Ala
            20                  25                  30

Ser Ser Pro Ser Ala Glu Leu Gln Cys Cys Ala Gly Trp Arg Gln Lys
        35                  40                  45

Asp Gln Glu Cys Thr Ile Pro Ile Cys Glu Gly Pro Asp Ala Cys Gln
    50                  55                  60

Lys Asp Glu Val Cys Val Lys Pro Gly Leu Cys Arg Cys Lys Pro Gly
65                  70                  75                  80

Phe Phe Gly Ala His Cys Ser Ser Arg Cys Pro Gly Gln Tyr Trp Gly
```

-continued

```
                85                  90                  95

Pro Asp Cys Arg Glu Ser Cys Pro Cys His Pro His Gly Gln Cys Glu
            100                 105                 110

Pro Ala Thr Gly Ala Cys Gln Cys Gln Ala Asp Arg Trp Gly Ala Arg
        115                 120                 125

Cys Glu Phe Pro Cys Ala Cys Gly Pro His Gly Arg Cys Asp Pro Ala
    130                 135                 140

Thr Gly Val Cys His Cys Glu Pro Gly Trp Trp Ser Ser Thr Cys Arg
145                 150                 155                 160

Arg Pro Cys Gln Cys Asn Thr Ala Ala Ala Arg Cys Glu Gln Ala Thr
                165                 170                 175

Gly Ala Cys Val Cys Lys Pro Gly Trp Trp Gly Arg Arg Cys Ser Phe
            180                 185                 190

Arg Cys Asn Cys His Gly Ser Pro Cys Glu Gln Asp Ser Gly Arg Cys
        195                 200                 205

Ala Cys Arg Pro Gly Trp Trp Gly Pro Glu Cys Gln Gln Gln Cys Glu
    210                 215                 220

Cys Val Arg Gly Arg Cys Ser Ala Ala Ser Gly Glu Cys Thr Cys Pro
225                 230                 235                 240

Pro Gly Phe Arg Gly Ala Arg Cys Glu Leu Pro Cys Pro Ala Gly Ser
                245                 250                 255

His Gly Val Gln Cys Ala His Ser Cys Gly Arg Cys Lys His Asn Glu
            260                 265                 270

Pro Cys Ser Pro Asp Thr Gly Ser Cys Glu Ser Cys Glu Pro Gly Trp
        275                 280                 285

Asn Gly Thr Gln Cys Gln Gln Pro Cys Leu Pro Gly Thr Phe Gly Glu
    290                 295                 300

Ser Cys Glu Gln Gln Cys Pro His Cys Arg His Gly Glu Ala Cys Glu
305                 310                 315                 320

Pro Asp Thr Gly His Cys Gln Arg Cys Asp Pro Gly Trp Leu Gly Pro
                325                 330                 335

Arg
```

In another embodiment of this aspect of the present invention, the one or more mutations detected in the patient sample include a mutation in the NEGR1 gene encoding neuronal growth regulator 1. This mutation maps to position 71849375 of chromosome 1 of hg 18. The mRNA sequence for human NEGR1 (NCBI Accession No. NM_173808) and corresponding amino acid sequence are provided below as SEQ ID NOs: 27 and 28, respectively. A relapse specific mutation in NEGR1 results in a proline to leucine substitution at an amino acid position corresponding to P237 of SEQ ID NO: 28 below. An exemplary mutation in NEGR1 encoding this amino acid substitution comprises a C→T change at a nucleotide position corresponding to position 710 of SEQ ID NO: 27.

```
                                                    SEQ ID NO: 27
Human NEGR1
atggacatga tgctgttggt gcagggtgct tgttgctcga accagtggct ggcggcggtg    60

ctcctcagcc tgtgctgcct gctaccctcc tgcctcccgg ctggacagag tgtggacttc   120

ccctgggcgg ccgtggacaa catgatggtc agaaaagggg acacggcggt gcttaggtgt   180

tatttggaag atggagcttc aaagggtgcc tggctgaacc ggtcaagtat tatttttgcg   240

ggaggtgata agtggtcagt ggatcctcga gtttcaattt caacattgaa taaaagggac   300

tacagcctcc agatacagaa tgtagatgtg acagatgatg gcccatacac gtgttctgtt   360

cagactcaac atacacccag aacaatgcag gtgcatctaa ctgtgcaagt tcctcctaag   420

atatatgaca tctcaaatga tatgaccgtc aatgaaggaa ccaacgtcac tcttacttgt   480

ttggccactg ggaaaccaga gccttccatt tcttggcgac acatctcccc atcagcaaaa   540
```

-continued

```
ccatttgaaa atggacaata tttggacatt tatggaatta caagggacca ggctggggaa   600

tatgaatgca gtgcggaaaa tgatgtgtca ttcccagatg tgaggaaagt aaaagttgtt   660

gtcaactttg ctcctactat tcaggaaatt aaatctggca ccgtgacccc cggacgcagt   720

ggcctgataa gatgtgaagg tgcaggtgtg ccgcctccag cctttgaatg gtacaaagga   780

gagaagaagc tcttcaatgg ccaacaagga attattattc aaaattttag cacaagatcc   840

attctcactg ttaccaacgt gacacaggag cacttcggca attatacctg tgtggctgcc   900

aacaagctag gcacaaccaa tgcgagcctg cctcttaacc ctccaagtac agcccagtat   960

ggaattaccg ggagcgctga tgttcttttc tcctgctggt accttgtgtt gacactgtcc  1020

tctttcacca gcatattcta cctgaagaat gccattctac aataa                 1065

                                                            SEQ ID NO: 28
Human Neuronal growth regulator 1
Met Asp Met Met Leu Leu Val Gln Gly Ala Cys Cys Ser Asn Gln Trp
1               5                   10                  15

Leu Ala Ala Val Leu Leu Ser Leu Cys Cys Leu Leu Pro Ser Cys Leu
            20                  25                  30

Pro Ala Gly Gln Ser Val Asp Phe Pro Trp Ala Ala Val Asp Asn Met
        35                  40                  45

Met Val Arg Lys Gly Asp Thr Ala Val Leu Arg Cys Tyr Leu Glu Asp
    50                  55                  60

Gly Ala Ser Lys Gly Ala Trp Leu Asn Arg Ser Ser Ile Ile Phe Ala
65                  70                  75                  80

Gly Gly Asp Lys Trp Ser Val Asp Pro Arg Val Ser Ile Ser Thr Leu
                85                  90                  95

Asn Lys Arg Asp Tyr Ser Leu Gln Ile Gln Asn Val Asp Val Thr Asp
            100                 105                 110

Asp Gly Pro Tyr Thr Cys Ser Val Gln Thr Gln His Thr Pro Arg Thr
        115                 120                 125

Met Gln Val His Leu Thr Val Gln Val Pro Pro Lys Ile Tyr Asp Ile
    130                 135                 140

Ser Asn Asp Met Thr Val Asn Glu Gly Thr Asn Val Thr Leu Thr Cys
145                 150                 155                 160

Leu Ala Thr Gly Lys Pro Glu Pro Ser Ile Ser Trp Arg His Ile Ser
                165                 170                 175

Pro Ser Ala Lys Pro Phe Glu Asn Gly Gln Tyr Leu Asp Ile Tyr Gly
            180                 185                 190

Ile Thr Arg Asp Gln Ala Gly Glu Tyr Glu Cys Ser Ala Glu Asn Asp
        195                 200                 205

Val Ser Phe Pro Asp Val Arg Lys Val Lys Val Val Val Asn Phe Ala
    210                 215                 220

Pro Thr Ile Gln Glu Ile Lys Ser Gly Thr Val Thr Pro Gly Arg Ser
225                 230                 235                 240

Gly Leu Ile Arg Cys Glu Gly Ala Gly Val Pro Pro Pro Ala Phe Glu
                245                 250                 255

Trp Tyr Lys Gly Glu Lys Lys Leu Phe Asn Gly Gln Gln Gly Ile Ile
            260                 265                 270

Ile Gln Asn Phe Ser Thr Arg Ser Ile Leu Thr Val Thr Asn Val Thr
        275                 280                 285

Gln Glu His Phe Gly Asn Tyr Thr Cys Val Ala Ala Asn Lys Leu Gly
    290                 295                 300

Thr Thr Asn Ala Ser Leu Pro Leu Asn Pro Pro Ser Thr Ala Gln Tyr
305                 310                 315                 320

Gly Ile Thr Gly Ser Ala Asp Val Leu Phe Ser Cys Trp Tyr Leu Val
```

-continued

```
                325                 330                 335

Leu Thr Leu Ser Ser Phe Thr Ser Ile Phe Tyr Leu Lys Asn Ala Ile
            340                 345                 350

Leu Gln
```

In another embodiment of this aspect of the present invention, the one or more mutations detected in the patient sample include a mutation in the DPH5 gene encoding diphthine synthase. This mutation maps to position 101233272 of chromosome 1 of hg 18. The mRNA sequence for human DPH5 (NCBI Accession No. NM_001077394) and corresponding amino acid sequence are provided below as SEQ ID NOs: 29 and 30, respectively. A relapse specific mutation in DPH5 results in a serine to phenylalanine substitution at an amino acid position corresponding to S171 of SEQ ID NO: 30 below. An exemplary mutation in DPH5 encoding this amino acid substitution comprises a C→T change at a nucleotide position corresponding to position 512 of SEQ ID NO: 29.

```
                                                       SEQ ID NO: 29
Human DPH5
atgctttatc tcatcgggtt gggcctggga gatgccaagg acatcacagt caagggcctg    60

gaagttgtta gacgctgcag tcgagtgtat ctggaagcct acacctcagt cctaactgta   120

gggaaggaag ccttggaaga gttttatgga agaaaattgg ttgttgctga tagagaagaa   180

gtggaacaag aagcagataa tattttaaag gatgctgata tcagtgatgt tgcattcctt   240

gtggttggtg atccatttgg ggccacaaca cacagtgatc ttgttctaag agcaacaaag   300

ctgggaattc cttatagagt tattcacaat gcctccataa tgaatgctgt aggctgctgt   360

ggtttacagt tatataagtt tggagagaca gtttctattg ttttttggac agacacttgg   420

agaccagaaa gcttctttga caaagtgaag aagaacagac aaaatggcat gcacacatta   480

tgtttactag acatcaaagt aaaggagcag tctttggaaa atctaatcaa gggaaggaag   540

atctatgaac ctccacggta tatgagtgta aaccaagcag cccagcagct tctggagatt   600

gttcaaaatc aaagaatacg aggagaagaa ccagcagtta ccgaggagac actttgtgtt   660

ggcttagcca gggttggagc cgacgaccag aaaattgcag caggcacttt aaggcaaatg   720

tgcactgtgg acttgggaga accattgcat tccttgatca tcacaggagg cagcatacat   780

ccaatggaga tggagatgct aagtctgttt tccataccag aaaatagctc agaatctcaa   840

agcatcaatg gactttga                                                 858

                                                       SEQ ID NO: 30
Human Diphthine synthase
Met Leu Tyr Leu Ile Gly Leu Gly Leu Gly Asp Ala Lys Asp Ile Thr
1               5                   10                  15

Val Lys Gly Leu Glu Val Val Arg Arg Cys Ser Arg Val Tyr Leu Glu
            20                  25                  30

Ala Tyr Thr Ser Val Leu Thr Val Gly Lys Glu Ala Leu Glu Glu Phe
        35                  40                  45

Tyr Gly Arg Lys Leu Val Val Ala Asp Arg Glu Glu Val Glu Gln Glu
    50                  55                  60

Ala Asp Asn Ile Leu Lys Asp Ala Asp Ile Ser Asp Val Ala Phe Leu
65                  70                  75                  80

Val Val Gly Asp Pro Phe Gly Ala Thr Thr His Ser Asp Leu Val Leu
                85                  90                  95

Arg Ala Thr Lys Leu Gly Ile Pro Tyr Arg Val Ile His Asn Ala Ser
            100                 105                 110

Ile Met Asn Ala Val Gly Cys Cys Gly Leu Gln Leu Tyr Lys Phe Gly
        115                 120                 125

Glu Thr Val Ser Ile Val Phe Trp Thr Asp Thr Trp Arg Pro Glu Ser
    130                 135                 140

Phe Phe Asp Lys Val Lys Lys Asn Arg Gln Asn Gly Met His Thr Leu
```

-continued

```
145                 150                 155                 160

Cys Leu Leu Asp Ile Lys Val Lys Glu Gln Ser Leu Glu Asn Leu Ile
                165                 170                 175

Lys Gly Arg Lys Ile Tyr Glu Pro Pro Arg Tyr Met Ser Val Asn Gln
            180                 185                 190

Ala Ala Gln Gln Leu Leu Glu Ile Val Gln Asn Gln Arg Ile Arg Gly
        195                 200                 205

Glu Glu Pro Ala Val Thr Glu Glu Thr Leu Cys Val Gly Leu Ala Arg
    210                 215                 220

Val Gly Ala Asp Asp Gln Lys Ile Ala Ala Gly Thr Leu Arg Gln Met
225                 230                 235                 240

Cys Thr Val Asp Leu Gly Glu Pro Leu His Ser Leu Ile Ile Thr Gly
                245                 250                 255

Gly Ser Ile His Pro Met Glu Met Glu Met Leu Ser Leu Phe Ser Ile
            260                 265                 270

Pro Glu Asn Ser Ser Glu Ser Gln Ser Ile Asn Gly Leu
        275                 280                 285
```

In another embodiment of this aspect of the present invention, the one or more mutations detected in the patient sample include a mutation in the SMEK2 gene encoding isoform 3 of serine/threonine-protein phosphatase 4 regulatory subunit 3B. This mutation maps to position 55648886 of chromosome 2 of hg 18. The mRNA sequence for human SMEK2 (NCBI Accession No. NM_020463) and corresponding amino acid sequence are provided below as SEQ ID NOs: 31 and 32, respectively. A relapse specific mutation in SMEK2 results in an arginine to glutamine substitution at an amino acid position corresponding to R543 of SEQ ID NO: 32 below. An exemplary mutation in SMEK2 encoding this amino acid substitution comprises a G→A change at a nucleotide position corresponding to position 1628 of SEQ ID NO: 31.

```
                                                   SEQ ID NO: 31
Human SMEK2
atgtcggata cgcggcggcg agtgaaggtc tataccctga acgaagaccg gcaatgggac    60

gaccgaggca ccgggcacgt ctcctccact tacgtggagg agctcaaggg gatgtcgctg   120

ctggttcggg cagagtccga cggatcacta ctcttggaat caaagataaa tccaaatact   180

gcatatcaga aacaacagga tacattaatt gtttggtcag aagcagagaa ctatgatttg   240

gctctgagtt ttcaggagaa agctggctgt gatgagatct gggaaaaaat ttgtcaggtt   300

caaggtaaag acccatcagt ggaagtcaca caggacctca ttgatgaatc tgaagaagaa   360

cgatttgaag aaatgcctga aactagtcat ctgattgacc tgcccacatg tgaactcaat   420

aaacttgaag agattgctga cttagttacc tcagtgctct cctcacctat ccgtagggaa   480

aagctggctc tcgccttgga aaatgaaggc tatattaaaa aactattgca gctgttccaa   540

gcttgcgaga acctagaaaa cactgaaggc ttacaccatt tgtatgaaat tattagagga   600

atcttattcc taaataaggc aactcttttt gaggtaatgt tttctgatga gtgtatcatg   660

gatgtcgtgg gatgccttga atatgaccct gctttggctc agccaaaaag acatagagaa   720

ttcttgacca aaactgcaaa gttcaaggaa gttataccaa taacagactc tgaactaagg   780

caaaaaatac atcagactta cagggtacag tacattcagg acatcatttt gcccacacca   840

tctgtttttg aagagaattt tctttctact cttacgtctt ttattttctt caacaaagtt   900

gagatagtca gcatgttgca ggaagatgag aagtttttgt ctgaagtttt tgcacaatta   960

acagatgagg ctacagatga tgataaacgg cgtgaattgg ttaatttttt caaggagttt  1020

tgtgcatttt ctcagacatt acaacctcaa aacagggatg catttttcaa aacattggca  1080

aaattgggaa ttcttcctgc tcttgaaatt gtaatgggca tggatgattt gcaagtcaga  1140

tcagctgcta cagatatatt ttcttatcta gtagaattta gtccatctat ggtccgagag  1200
```

-continued

```
tttgtaatgc aagaagctca gcagagtgat gacgatattc ttcttattaa tgtggtaatt  1260

gaacaaatga tctgtgatac tgatcctgag ctaggaggcg ctgttcagtt aatgggactt  1320

cttcgtactc taattgatcc agagaacatg ctggctacaa ctaataaaac cgaaaaaagt  1380

gaatttctaa attttttcta caaccattgt atgcatgttc tcacagcacc acttttgacc  1440

aatacttcag aagacaaatg tgaaaaggat aatatagttg gatcaaacaa aaacaacaca  1500

atttgtcccg gtgcccttcg ctttatgagg cggataattg gacttaaaga tgaattttat  1560

aatcgttaca tcaccaaggg aaatcttttt gagccagtta taaatgcact tctggataat  1620

ggaactcggt ataatctgtt gaattcagct gttattgagt tgtttgaatt tataagagtg  1680

gaagatatca agtctcttac tgcccatata gttgaaaact tttataaagc acttgaatcg  1740

attgaatatg ttcagacatt caaaggattg aagactaaat atgagcaaga aaaagacaga  1800

caaaatcaga aactgaacag tgtaccatct atattgcgta gtaacagatt tcgcagagat  1860

gcaaaagcct tggaagagga tgaagaaatg tggtttaatg aagatgaaga agaggaagga  1920

aaagcagttg tggcaccagt ggaaaaacct aagccagaag atgattttcc agataattat  1980

gaaaagttta tggagactaa aaaagcaaaa gaaagtgaag acaaggaaaa ccttcccaaa  2040

aggacatctc ctggtggctt caaatttact ttctcccact ctgccagtgc tgctaatgga  2100

acaaacagta aatctgtagt ggctcagata ccaccagcaa cttctaatgg atcctcttcc  2160

aaaaccacaa acttgcctac gtcagtaaca gccaccaagg gaagtttggt tggcttagtg  2220

gattatccag atgatgaaga ggaagatgaa gaagaagaat cgtcccccag gaaaagacct  2280

cgtcttggct cataa                                                   2295
```

SEQ ID NO: 32

Human Isoform 3 of Serine/threonine-protein phosphatase 4 regulatory subunit 3B

```
Met Ser Asp Thr Arg Arg Arg Val Lys Val Tyr Thr Leu Asn Glu Asp
1               5                   10                  15

Arg Gln Trp Asp Asp Arg Gly Thr Gly His Val Ser Ser Thr Tyr Val
            20                  25                  30

Glu Glu Leu Lys Gly Met Ser Leu Leu Val Arg Ala Glu Ser Asp Gly
        35                  40                  45

Ser Leu Leu Leu Glu Ser Lys Ile Asn Pro Asn Thr Ala Tyr Gln Lys
    50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Val Gln Gly Lys Asp Pro Ser Val Glu Val Thr Gln Asp
            100                 105                 110

Leu Ile Asp Glu Ser Glu Glu Glu Arg Phe Glu Glu Met Pro Glu Thr
        115                 120                 125

Ser His Leu Ile Asp Leu Pro Thr Cys Glu Leu Asn Lys Leu Glu Glu
    130                 135                 140

Ile Ala Asp Leu Val Thr Ser Val Leu Ser Ser Pro Ile Arg Arg Glu
145                 150                 155                 160

Lys Leu Ala Leu Ala Leu Glu Asn Glu Gly Tyr Ile Lys Lys Leu Leu
                165                 170                 175

Gln Leu Phe Gln Ala Cys Glu Asn Leu Glu Asn Thr Glu Gly Leu His
            180                 185                 190

His Leu Tyr Glu Ile Ile Arg Gly Ile Leu Phe Leu Asn Lys Ala Thr
        195                 200                 205

Leu Phe Glu Val Met Phe Ser Asp Glu Cys Ile Met Asp Val Val Gly
```

-continued

```
    210                 215                 220

Cys Leu Glu Tyr Asp Pro Ala Leu Ala Gln Pro Lys Arg His Arg Glu
225                 230                 235                 240

Phe Leu Thr Lys Thr Ala Lys Phe Lys Glu Val Ile Pro Ile Thr Asp
                245                 250                 255

Ser Glu Leu Arg Gln Lys Ile His Gln Thr Tyr Arg Val Gln Tyr Ile
            260                 265                 270

Gln Asp Ile Ile Leu Pro Thr Pro Ser Val Phe Glu Glu Asn Phe Leu
        275                 280                 285

Ser Thr Leu Thr Ser Phe Ile Phe Phe Asn Lys Val Glu Ile Val Ser
    290                 295                 300

Met Leu Gln Glu Asp Glu Lys Phe Leu Ser Glu Val Phe Ala Gln Leu
305                 310                 315                 320

Thr Asp Glu Ala Thr Asp Asp Asp Lys Arg Arg Glu Leu Val Asn Phe
                325                 330                 335

Phe Lys Glu Phe Cys Ala Phe Ser Gln Thr Leu Gln Pro Gln Asn Arg
            340                 345                 350

Asp Ala Phe Phe Lys Thr Leu Ala Lys Leu Gly Ile Leu Pro Ala Leu
        355                 360                 365

Glu Ile Val Met Gly Met Asp Asp Leu Gln Val Arg Ser Ala Ala Thr
    370                 375                 380

Asp Ile Phe Ser Tyr Leu Val Glu Phe Ser Pro Ser Met Val Arg Glu
385                 390                 395                 400

Phe Val Met Gln Glu Ala Gln Gln Ser Asp Asp Asp Ile Leu Leu Ile
                405                 410                 415

Asn Val Val Ile Glu Gln Met Ile Cys Asp Thr Asp Pro Glu Leu Gly
            420                 425                 430

Gly Ala Val Gln Leu Met Gly Leu Leu Arg Thr Leu Ile Asp Pro Glu
        435                 440                 445

Asn Met Leu Ala Thr Thr Asn Lys Thr Glu Lys Ser Glu Phe Leu Asn
    450                 455                 460

Phe Phe Tyr Asn His Cys Met His Val Leu Thr Ala Pro Leu Leu Thr
465                 470                 475                 480

Asn Thr Ser Glu Asp Lys Cys Glu Lys Asp Asn Ile Val Gly Ser Asn
                485                 490                 495

Lys Asn Asn Thr Ile Cys Pro Gly Ala Leu Arg Phe Met Arg Arg Ile
            500                 505                 510

Ile Gly Leu Lys Asp Glu Phe Tyr Asn Arg Tyr Ile Thr Lys Gly Asn
        515                 520                 525

Leu Phe Glu Pro Val Ile Asn Ala Leu Leu Asp Asn Gly Thr Arg Tyr
    530                 535                 540

Asn Leu Leu Asn Ser Ala Val Ile Glu Leu Phe Glu Phe Ile Arg Val
545                 550                 555                 560

Glu Asp Ile Lys Ser Leu Thr Ala His Ile Val Glu Asn Phe Tyr Lys
                565                 570                 575

Ala Leu Glu Ser Ile Glu Tyr Val Gln Thr Phe Lys Gly Leu Lys Thr
            580                 585                 590

Lys Tyr Glu Gln Glu Lys Asp Arg Gln Asn Gln Lys Leu Asn Ser Val
        595                 600                 605

Pro Ser Ile Leu Arg Ser Asn Arg Phe Arg Arg Asp Ala Lys Ala Leu
    610                 615                 620

Glu Glu Asp Glu Glu Met Trp Phe Asn Glu Asp Glu Glu Glu Glu Gly
625                 630                 635                 640

Lys Ala Val Val Ala Pro Val Glu Lys Pro Lys Pro Glu Asp Asp Phe
```

-continued

```
        645                 650                 655

Pro Asp Asn Tyr Glu Lys Phe Met Glu Thr Lys Lys Ala Lys Glu Ser
            660                 665                 670

Glu Asp Lys Glu Asn Leu Pro Lys Arg Thr Ser Pro Gly Gly Phe Lys
        675                 680                 685

Phe Thr Phe Ser His Ser Ala Ser Ala Ala Asn Gly Thr Asn Ser Lys
    690                 695                 700

Ser Val Val Ala Gln Ile Pro Pro Ala Thr Ser Asn Gly Ser Ser Ser
705                 710                 715                 720

Lys Thr Thr Asn Leu Pro Thr Ser Val Thr Ala Thr Lys Gly Ser Leu
                725                 730                 735

Val Gly Leu Val Asp Tyr Pro Asp Asp Glu Glu Glu Asp Glu Glu Glu
            740                 745                 750

Glu Ser Ser Pro Arg Lys Arg Pro Arg Leu Gly Ser
        755                 760
```

In another embodiment of this aspect of the present invention, the one or more mutations detected in the patient sample include a mutation in the MIER3 gene encoding mesoderm induction early response protein 3. This mutation maps to position 56262281 of chromosome 5 of hg 18. The mRNA sequence for human MIER3 (NCBI Accession No. NM_152622) and corresponding amino acid sequence are provided below as SEQ ID NOs: 33 and 34, respectively. A relapse specific mutation in MIER3 results in a glutamic acid to lysine substitution at an amino acid position corresponding to E266 of SEQ ID NO: 34 below. An exemplary mutation in MIER3 encoding this amino acid substitution comprises a G→A change at a nucleotide position corresponding to position 796 of SEQ ID NO: 33.

```
                                                       SEQ ID NO: 33
Human MIER3
atggcggagg cttcttttgg aagttcgagc ccagttgggt ctttgtcttc tgaggatcat    60

gattttgacc ccactgctga gatgttggtc catgactatg atgatgaaag aactcttgaa   120

gaagaggaaa tgatggatga gggtaaaaac ttcagttcag aaattgaaga cttagaaaag   180

gaaggaacca tgcctctaga agatttactg gcattctatg gctatgaacc tacaattcca   240

gcagttgcaa attccagtgc aaatagttcc ccaagtgaac tggcagatga actaccagac   300

atgacactag acaaagagga aatagcaaaa gacctgttgt caggtgatga cgaggaaact   360

cagtcttctg cggatgatct gacgccatct gtgacttccc atgaaacttc tgatttcttc   420

cctaggcctt tacgatcaaa tactgcatgt gatggtgata aggaatcaga ggttgaagat   480

gttgaaacag acagtggtaa ttcacctgaa gatttgagga aggaaataat gattggttta   540

caatatcagg cagagattcc cccttatctt ggagagtacg atggtaatga gaaagtatat   600

gaaaacgaag accagttact ttggtgtcct gatgtggttt tggagagcaa agttaaggaa   660

taccttgttg agacttcatt aaggactggc agtgaaaaaa taatggatag gatttctgca   720

ggaacacaca caagggacaa tgaacaggca ttatatgaac ttctcaagtg taaccacaat   780

ataaaggaag caatcgaaag atactgctgc aatggaaagg cctctcaagg aatgactgca   840

tggacggaag aagaatgccg aagctttgaa catgcactca tgctttttgg aaaagatttt   900

catcttatac agaagaataa ggtgagaact aggacagttg ctgagtgtgt agcattctac   960

tatatgtgga agaaatctga acgttatgat tactttgctc aacagacaag atttgggaaa  1020

aaaagatata accatcaccc tggagttacg gactatatgg atcgtttagt agatgaaaca  1080

gaagctttgg gtgggacggt aaatgcttca gccttaactt ctaaccggcc tgagcctatt  1140

cctgatcaac agctaaacat tctcaactcc ttcactgcca gtgacttgac agctttgacc  1200

aacagtgtag caaccgtctg cgaccccaca gatgtgaatt gtttggatga tagctttcct  1260

ccactgggca acacaccccg tggacaagtt aatcatgtgc ctgttgtaac agaagagtta  1320
```

-continued

```
ctcaccctgc ccagcaatgg ggaaagtgat tgttttaatt tatttgagac tggattttat  1380

cactcggagc taaaccctat gaacatgtgc agtgaagagt cagagagacc agcaaaaaga  1440

ttgaaaatgg gcattgccgt ccctgaatcc tttatgaatg aagtttctgt aaataacctg  1500

ggtgtggact ttgaaaatca cacacatcac atcaccagtg ccaaaatggc tgtttctgtg  1560

gctgactttg gcagtctctc tgccaacgag accaatggtt tcatcagtgc ccatgctctg  1620

catcagcacg cggccctaca ctctgagtga                                  1650
```

SEQ ID NO: 34

Isoform 3 of Mesoderm induction early response protein 3

```
Met Ala Glu Ala Ser Phe Gly Ser Ser Ser Pro Val Gly Ser Leu Ser
1               5                   10                  15

Ser Glu Asp His Asp Phe Asp Pro Thr Ala Glu Met Leu Val His Asp
            20                  25                  30

Tyr Asp Asp Glu Arg Thr Leu Glu Glu Glu Glu Met Met Asp Glu Gly
        35                  40                  45

Lys Asn Phe Ser Ser Glu Ile Glu Asp Leu Glu Lys Glu Gly Thr Met
    50                  55                  60

Pro Leu Glu Asp Leu Leu Ala Phe Tyr Gly Tyr Glu Pro Thr Ile Pro
65                  70                  75                  80

Ala Val Ala Asn Ser Ser Ala Asn Ser Ser Pro Ser Glu Leu Ala Asp
                85                  90                  95

Glu Leu Pro Asp Met Thr Leu Asp Lys Glu Glu Ile Ala Lys Asp Leu
            100                 105                 110

Leu Ser Gly Asp Asp Glu Glu Thr Gln Ser Ser Ala Asp Asp Leu Thr
        115                 120                 125

Pro Ser Val Thr Ser His Glu Thr Ser Asp Phe Phe Pro Arg Pro Leu
    130                 135                 140

Arg Ser Asn Thr Ala Cys Asp Gly Asp Lys Glu Ser Glu Val Glu Asp
145                 150                 155                 160

Val Glu Thr Asp Ser Gly Asn Ser Pro Glu Asp Leu Arg Lys Glu Ile
                165                 170                 175

Met Ile Gly Leu Gln Tyr Gln Ala Glu Ile Pro Pro Tyr Leu Gly Glu
            180                 185                 190

Tyr Asp Gly Asn Glu Lys Val Tyr Glu Asn Glu Asp Gln Leu Leu Trp
        195                 200                 205

Cys Pro Asp Val Val Leu Glu Ser Lys Val Lys Glu Tyr Leu Val Glu
    210                 215                 220

Thr Ser Leu Arg Thr Gly Ser Glu Lys Ile Met Asp Arg Ile Ser Ala
225                 230                 235                 240

Gly Thr His Thr Arg Asp Asn Glu Gln Ala Leu Tyr Glu Leu Leu Lys
                245                 250                 255

Cys Asn His Asn Ile Lys Glu Ala Ile Glu Arg Tyr Cys Cys Asn Gly
            260                 265                 270

Lys Ala Ser Gln Gly Met Thr Ala Trp Thr Glu Glu Glu Cys Arg Ser
        275                 280                 285

Phe Glu His Ala Leu Met Leu Phe Gly Lys Asp Phe His Leu Ile Gln
    290                 295                 300

Lys Asn Lys Val Arg Thr Arg Thr Val Ala Glu Cys Val Ala Phe Tyr
305                 310                 315                 320

Tyr Met Trp Lys Lys Ser Glu Arg Tyr Asp Tyr Phe Ala Gln Gln Thr
                325                 330                 335

Arg Phe Gly Lys Lys Arg Tyr Asn His His Pro Gly Val Thr Asp Tyr
            340                 345                 350

Met Asp Arg Leu Val Asp Glu Thr Glu Ala Leu Gly Gly Thr Val Asn
```

-continued

```
        355                 360                 365

Ala Ser Ala Leu Thr Ser Asn Arg Pro Glu Pro Ile Pro Asp Gln Gln
    370                 375                 380

Leu Asn Ile Leu Asn Ser Phe Thr Ala Ser Asp Leu Thr Ala Leu Thr
385                 390                 395                 400

Asn Ser Val Ala Thr Val Cys Asp Pro Thr Asp Val Asn Cys Leu Asp
                405                 410                 415

Asp Ser Phe Pro Pro Leu Gly Asn Thr Pro Arg Gly Gln Val Asn His
            420                 425                 430

Val Pro Val Val Thr Glu Glu Leu Leu Thr Leu Pro Ser Asn Gly Glu
        435                 440                 445

Ser Asp Cys Phe Asn Leu Phe Glu Thr Gly Phe Tyr His Ser Glu Leu
    450                 455                 460

Asn Pro Met Asn Met Cys Ser Glu Glu Ser Glu Arg Pro Ala Lys Arg
465                 470                 475                 480

Leu Lys Met Gly Ile Ala Val Pro Glu Ser Phe Met Asn Glu Val Ser
                485                 490                 495

Val Asn Asn Leu Gly Val Asp Phe Glu Asn His Thr His His Ile Thr
            500                 505                 510

Ser Ala Lys Met Ala Val Ser Val Ala Asp Phe Gly Ser Leu Ser Ala
        515                 520                 525

Asn Glu Thr Asn Gly Phe Ile Ser Ala His Ala Leu His Gln His Ala
    530                 535                 540

Ala Leu His Ser Glu
545
```

In another embodiment of this aspect of the present invention, the one or more mutations detected in the patient sample include a mutation in the DOPEY1 gene encoding dopey-1. This mutation maps to position 83912011 of chromosome 6 of hg 18. The mRNA sequence for human DOPEY1 (NCBI Accession No. NM_015018) and corresponding amino acid sequence are provided below as SEQ ID NOs: 35 and 36, respectively. A relapse specific mutation in DOPEY1 results in an arginine to histidine substitution at an amino acid position corresponding to R1864 of SEQ ID NO: 36 below. An exemplary mutation in DOPEY1 encoding this amino acid substitution comprises a G→A change at a nucleotide position corresponding to position 5591 of SEQ ID NO: 35.

```
                                                        SEQ ID NO: 35
Human DOPEY1
atgaacacag aagagctgga gttattgagt gactccaaat acagaaacta tgtagcagca    60

attgacaaag cactaaagaa ttttgaatac tccagtgaat gggcagattt gatatcagca   120

cttggaaaac ttaataaggt tttacaaaat aatgcaaagt accaagtagt acccaaaaag   180

ctgaccatag gcaaacgcct agctcaatgt ctacatccag cattaccagg tggagttcat   240

cggaaggcgc ttgaaacata tgaaattatc ttcaaaataa ttggacctaa gcgacttgcc   300

aaagatcttt ttttatatag ttctggatta tttcctcttc ttgcaaatgc tgccatgtct   360

gtgaaaccaa cattgctcag tttgtatgag atatattatc tgcctttggg taaaacactg   420

aaacctggtc tacagggatt gcttactggt attcttcctg gcttagaaga aggatcagag   480

tactatgaga gaacaaatat gttgttggaa aaggttgctg ctgctgtgga ccagtcagca   540

ttctacagtg ccctgtgggg tagtcttctc accagtcctg ctgtgcgttt acctggaatc   600

acgtatgttc ttgcccattt aaacaggaag ctttctatgg aagatcaact ttatataatt   660

ggcagtgata ttgagctaat ggtagaagca gtaagtactt cagtgcagga ctcaagtgta   720

cttgtacaga gaagcacact ggacctcata ctcttctgtt ttccattcca catgagtcag   780

gccactcgac cggatatgat caggatcttg tcagcagccc ttcatgtagt gctaaggagg   840

gatatgtctc tgaatcgaag actttatgca tggcttcttg gttttgataa caacggtgct   900
```

-continued

```
atcataggac ccagaagcac aagacacagt aatcctgaag aacatgccac ttactatttc   960
actacctttt caaaagaatt attagtccag gcaatggtgg gaatcttaca agtgaatgga  1020
tttggagaag agaacactct aatgcaggat ctaaagcctt ttcgcatttt aatcagttta  1080
ctggacaaac ctgagctagg acctgtaatt ctagaagatg tcctgattga agtgtttaga  1140
acattatatt ctcaatgcaa agcagagttg gatcttcaaa ctgaaccacc cttcagcaag  1200
gatcatgctc agttaagcag taaattaaga gaaaataaga aaacagcaga gctgattaaa  1260
actgctaacc ttctctttaa ttccttcgaa ccttattata tgtgggatta tgttgcacgc  1320
tggtttgaag aatgttgtag gaggacactg catgtgagac ttcagattgg acctggagat  1380
agtaatgact catctgaatt acagctgacc aatttctgct tactggtgga ttttttgttg  1440
gacatagttt ctttgcctac tagaagtatg agggtgctgt gtcaggagac ttacattgaa  1500
atccagacag aacacttgcc ccagttgctg ctcagaatga tttctgcctt gacaagccat  1560
ctccagacat tgcacttatc tgaactcaca gattctctca gactctgctc aaagatcctt  1620
agcaaggttc agcctccact gttatctgct agcactggag gtgttttgca gtttccaagt  1680
gggcagaaca attcagtcaa agagtgggaa gacaaaaagg tatcatcagt ttctcatgaa  1740
aatcctactg aagtgtttga agatggagaa aatccaccaa gtagtcgatc atcagagagt  1800
ggattcactg agtttataca atatcaagca gaccgaactg atgatattga cagagaactg  1860
agtgagggcc agggggcagc tgccatccca attggtagca catcctctga gacagaaaca  1920
gcatccactg tgggatctga agaaaccatc atccagaccc cttccgtagt cactcagggg  1980
acagcaaccc gaagtaggaa gacagcccaa aagactgcaa tgcagtgctg cttggagtat  2040
gtccaacagt ttcttaccag acttatcaac ctctacatca ttcagaataa ctctttttct  2100
cagtctttgg ctacagaaca tcaaggggat cttggtcgag aacaaggaga gacttcaaaa  2160
tgggacagaa attcacaagg agatgtaaaa gagaaaaaca taagtaaaca aaaaacttct  2220
aaagaatacc tgtctgcctt ccttgctgcc tgtcagctct tcctagagtg ctcaagtttc  2280
ccagtttaca ttgctgaggg gaaccataca tcagagttac gttctgaaaa attggagact  2340
gactgtgagc atgtgcagcc tccacagtgg ctccagactc tgatgaatgc ttgcagccaa  2400
gcaagtgatt tcagtgttca gagtgttgct atttcactag ttatggacct ggtgggactg  2460
acacagtctg tggccatggt cactggggaa aacatcaaca gtgtagagcc tgcacaaccc  2520
ttaagtccaa accagggaag agtagctgtg gttattagac ctcccctcac tcagggcaat  2580
ctgaggtaca tagctgagaa gactgaattt ttcaagcatg tagctttaac attgtgggac  2640
cagttgggag atgggacacc tcagcatcac cagaagagtg tggaactatt ttatcaatta  2700
cataacttag ttccttcttc tagcatctgt gaggatgtta taagtcagca gttaacccat  2760
aaagataaga aaataaggat ggaagcacat gccaagtttg cagttctttg gcatctaacg  2820
agagatctcc atataaataa atcttcatct tttgtacgtt cttttgacag gtcactgttc  2880
atcatgttag atagccttaa cagtctcgat ggttctacta gctctgtggg acaagcctgg  2940
ctgaaccaag tcctacaaag acatgatatt gcacgagttt tggaaccatt gctattgctc  3000
ctgcttcatc caaaaactca gagggtttca gtacagcgtg tacaagcaga acgttattgg  3060
aataagtctc cctgttatcc aggagaggag agtgacaagc atttcatgca aaattttgcc  3120
tgcagcaatg tgagccaagt acaactcatc acatcaaaag gaaatggtga aaagccactt  3180
accatggatg aaatagagaa ctttagtctc actgtgaatc cattaagtga cagactttcc  3240
ctcctaagta ccagcagtga gacaattcca atggttgtgt ctgattttga tcttccagac  3300
```

-continued

```
caacagatag aaatacttca gagttctgac tcgggatgtt cacagtcctc tgctggggac  3360
aacttgagtt acgaagttga tcctgaaacc gtgaatgccc aagaggattc tcaaatgccc  3420
aaggaaagct ccccagatga tgatgttcaa caggtagtat ttgacctgat atgtaaagtt  3480
gtaagtggcc tcgaagtgga atctgcatca gttacatctc aattagaaat tgaagctatg  3540
cccccaaagt gcagtgatat agatccagat gaagagacga ttaaaattga agatgactcc  3600
attcaacaga gtcagaatgc tttgctgagt aatgaaagtt ctcagtttct gtctgtgtct  3660
gcagagggag gccatgagtg tgtggcaaat ggaatctcca ggaatagctc ctcaccttgt  3720
atttcaggaa ccacacacac tcttcatgac tcttctgttg cttccataga aaccaaatct  3780
agacaaagga gtcacagtag tattcaattc agcttcaaag aaaaattatc agaaaaagtt  3840
tcggagaagg aaacaatagt taaggagtca ggtaaacaac caggagcaaa acctaaagta  3900
aaacttgcca gaaaaaagga tgatgacaag aaaaaatctt caaatgaaaa actcaaacaa  3960
accagtgtat tcttcagtga tggtctggat ttagagaact ggtatagctg tggagaggga  4020
gacatttctg aaattgagag tgacatgggt tctccaggat ctcgaaaatc tcccaatttc  4080
aacattcatc ctctctatca acatgtgctc ctgtatctcc agttgtatga ttcatccagg  4140
actttgtatg ctttctctgc catcaaagcc atcttgaaaa ctaaccctat agcttttgta  4200
aatgccattt caactactag tgtaaataat gcatatactc ctcagttgtc tctccttcag  4260
aatctattgg ccagacaccg gatttctgtt atgggcaaag atttttatag tcacattcca  4320
gtggactcaa atcataactt ccggagttct atgtacatag aaattcttat ttctctctgc  4380
ttatattaca tgcgtagcca ttacccaact catgtcaagg ttactgcaca agatttaata  4440
ggcaatcgaa acatgcaaat gatgagcata gaaattctga cactactctt cactgagctg  4500
gcaaaagtaa tagaaagctc agcgaagggt ttccctagtt ttatttctga tatgttatct  4560
aagtgcaaag ttcagaaagt gattcttcat tgtttgctgt catctatctt tagtgctcag  4620
aaatggcata gtgaaaaaat ggcaggtaag aacctggttg ctgtggaaga aggtttctca  4680
gaggacagcc ttattaattt ctcagaggat gaatttgaca atggcagcac gttgcagtca  4740
caacttctta aggtgcttca gaggctgatt gttctagaac acagagtaat gactattcct  4800
gaagagaatg aaacaggttt tgattttgtt gtatctgact tagaacacat cagtccccat  4860
caacccatga cttctcttca gtatttgcat gctcagccaa tcacatgtca aggcatgttc  4920
ctctgtgcag tgatacgagc tttgcatcag cactgtgcat gtaagatgca cccacaatgg  4980
attggtttaa tcacatctac tctgccttac atgggaaaag ttctgcagag agtggttgtt  5040
tctgtgacac tacaactgtg cagaaattta gataatctaa ttcagcagta caaatacgaa  5100
acaggattat ctgatagtag gcctctgtgg atggcatcaa ttattccacc agatatgatt  5160
cttactcttt tggaagggat tacagccatt atccattact gtttgttgga tccaactaca  5220
cagtatcacc aacttttggt cagtgtagac cagaaacact tgtttgaagc acgcagtgga  5280
atcctctcaa tccttcatat gatcatgtcc tctgtgacac tgctttggag catactgcat  5340
caagctgatt cttcagaaaa gatgactatt gccgcatccg catctcttac cactattaat  5400
cttggagcta caaagaactt gagacaacag attcttgaat tgttgggccc catttcaatg  5460
aatcatggtg ttcactttat ggctgccatt gcatttgtgt ggaatgaaag aagacagaat  5520
aaaacaacca ccaggaccaa ggtcattcct gcagccagtg aagaacagct tttattagtg  5580
gaattggttc gttcaatcag tgtcatgaga gcagaaactg ttatccagac tgtaaaagaa  5640
gttttaaagc agccaccagc catagccaag gacaagaaac atctttcttt ggaagtctgc  5700
atgcttcagt ttttctatgc ttatattcaa agaattccag tgcccaattt agtggatagc  5760
```

-continued

```
tgggcgtcac tgttgatact tctgaaagac tctatacaac tgagtcttcc agctccaggg  5820
cagtttctta tacttggggt tctgaatgag tttattatga aaaaccctag tttggaaaat  5880
aaaaaagacc aaagagacct tcaggatgta actcacaaaa tagtggatgc aattggtgca  5940
attgctggtt cttctctgga acagacaaca tggctgcgac gaaatcttga agttaagcct  6000
tctcccaaaa taatggtaga tggaaccaat ttggaatctg atgttgaaga tatgttatca  6060
cctgcaatgg aaaccgcaaa cataactcct tctgtatata gtgtccatgc attgacatta  6120
ctctctgagg ttttggctca tcttttggat atggttttct atagtgatga aaaggagcgg  6180
gttattcctt tacttgtaaa tattatgcat tatgttgtgc cctacctcag aaatcacagt  6240
gcacataatg cccctagtta tcgagcttgt gtccagctgc tcagcagtct tagtgggtat  6300
cagtacacac ggagagcttg gaaaaaagaa gcttttgacc tctttatgga tcccagtttc  6360
tttcagatgg atgcctcttg tgttaatcat tggagagcaa ttatggacaa tctgatgaca  6420
catgataaaa caacatttag agatttgatg actcgtgtag cagtggctca aagcagttca  6480
cttaatctct ttgcaaaccg tgatgtggag ctagaacaga gagctatgct tcttaaaaga  6540
ttagcatttg ctatttttag cagtgaaatt gaccagtacc agaaatatct tccagatata  6600
caagagagat tggttgagag tctccgtttg ccacaggtgc caactctcca ttctcaagtg  6660
ttcctgtttt tcagagtgtt acttttaaga atgtctcccc aacatcttac ctcactctgg  6720
cctaccatga ttacagaact tgtacaagta tttttactga tggagcagga actcactgct  6780
gatgaagata tttcacggac ttcagggccc tctgtggctg gtctggagac aacgtacaca  6840
ggaggtaatg gcttctctac ttcatataac agccagcggt ggttaaacct ctatctctct  6900
gcttgcaaat tttggatttt ggctctcgca ttgccctctg aaaaccttcc tcagtttcag  6960
atgtaccgat gggcctttat tccagaagcc tcagatgatt caggtttgga agtcagaagg  7020
cagggtatac atcaacgaga atttaaacct tacgtggtac gactagcaaa acttcttcgg  7080
aaaagagcaa agaaaaatcc agaggaagac aactcaggga gaacattggg ttgggagcca  7140
gggcacttgc tgctcaccat ctgcaccgtg cgcagtatgg agcagctcct gccgttcttc  7200
aatgtgctca gtcaagtctt caacagcaaa gtcacaagcc gatgtggagg acactcaggg  7260
agtcctatcc tctactcaaa tgccttccct aataaggaca tgaaactgga gaaccacaaa  7320
ccatgttcca gcaaagccag gcaaaaaata gaagagatgg tagaaaaaga ttttctggaa  7380
gggatgataa aaacttga                                                 7398
```

SEQ ID NO: 36

```
Human Protein dopey-1
Met Asn Thr Glu Glu Leu Glu Leu Leu Ser Asp Ser Lys Tyr Arg Asn
1               5                   10                  15

Tyr Val Ala Ala Ile Asp Lys Ala Leu Lys Asn Phe Glu Tyr Ser Ser
            20                  25                  30

Glu Trp Ala Asp Leu Ile Ser Ala Leu Gly Lys Leu Asn Lys Val Leu
        35                  40                  45

Gln Asn Asn Ala Lys Tyr Gln Val Val Pro Lys Lys Leu Thr Ile Gly
    50                  55                  60

Lys Arg Leu Ala Gln Cys Leu His Pro Ala Leu Pro Gly Gly Val His
65                  70                  75                  80

Arg Lys Ala Leu Glu Thr Tyr Glu Ile Ile Phe Lys Ile Ile Gly Pro
                85                  90                  95

Lys Arg Leu Ala Lys Asp Leu Phe Leu Tyr Ser Ser Gly Leu Phe Pro
            100                 105                 110

Leu Leu Ala Asn Ala Ala Met Ser Val Lys Pro Thr Leu Leu Ser Leu
```

-continued

```
        115                 120                 125

Tyr Glu Ile Tyr Tyr Leu Pro Leu Gly Lys Thr Leu Lys Pro Gly Leu
    130                 135                 140

Gln Gly Leu Leu Thr Gly Ile Leu Pro Gly Leu Glu Glu Gly Ser Glu
145                 150                 155                 160

Tyr Tyr Glu Arg Thr Asn Met Leu Leu Glu Lys Val Ala Ala Ala Val
                165                 170                 175

Asp Gln Ser Ala Phe Tyr Ser Ala Leu Trp Gly Ser Leu Leu Thr Ser
            180                 185                 190

Pro Ala Val Arg Leu Pro Gly Ile Thr Tyr Val Leu Ala His Leu Asn
        195                 200                 205

Arg Lys Leu Ser Met Glu Asp Gln Leu Tyr Ile Ile Gly Ser Asp Ile
    210                 215                 220

Glu Leu Met Val Glu Ala Val Ser Thr Ser Val Gln Asp Ser Ser Val
225                 230                 235                 240

Leu Val Gln Arg Ser Thr Leu Asp Leu Ile Leu Phe Cys Phe Pro Phe
                245                 250                 255

His Met Ser Gln Ala Thr Arg Pro Asp Met Ile Arg Ile Leu Ser Ala
            260                 265                 270

Ala Leu His Val Val Leu Arg Arg Asp Met Ser Leu Asn Arg Arg Leu
        275                 280                 285

Tyr Ala Trp Leu Leu Gly Phe Asp Asn Asn Gly Ala Ile Ile Gly Pro
    290                 295                 300

Arg Ser Thr Arg His Ser Asn Pro Glu Glu His Ala Thr Tyr Tyr Phe
305                 310                 315                 320

Thr Thr Phe Ser Lys Glu Leu Leu Val Gln Ala Met Val Gly Ile Leu
                325                 330                 335

Gln Val Asn Gly Phe Gly Glu Glu Asn Thr Leu Met Gln Asp Leu Lys
            340                 345                 350

Pro Phe Arg Ile Leu Ile Ser Leu Leu Asp Lys Pro Glu Leu Gly Pro
        355                 360                 365

Val Ile Leu Glu Asp Val Leu Ile Glu Val Phe Arg Thr Leu Tyr Ser
    370                 375                 380

Gln Cys Lys Ala Glu Leu Asp Leu Gln Thr Glu Pro Pro Phe Ser Lys
385                 390                 395                 400

Asp His Ala Gln Leu Ser Ser Lys Leu Arg Glu Asn Lys Lys Thr Ala
                405                 410                 415

Glu Leu Ile Lys Thr Ala Asn Leu Leu Phe Asn Ser Phe Glu Pro Tyr
            420                 425                 430

Tyr Met Trp Asp Tyr Val Ala Arg Trp Phe Glu Glu Cys Cys Arg Arg
        435                 440                 445

Thr Leu His Val Arg Leu Gln Ile Gly Pro Gly Asp Ser Asn Asp Ser
    450                 455                 460

Ser Glu Leu Gln Leu Thr Asn Phe Cys Leu Leu Val Asp Phe Leu Leu
465                 470                 475                 480

Asp Ile Val Ser Leu Pro Thr Arg Ser Met Arg Val Leu Cys Gln Glu
                485                 490                 495

Thr Tyr Ile Glu Ile Gln Thr Glu His Leu Pro Gln Leu Leu Leu Arg
            500                 505                 510

Met Ile Ser Ala Leu Thr Ser His Leu Gln Thr Leu His Leu Ser Glu
        515                 520                 525

Leu Thr Asp Ser Leu Arg Leu Cys Ser Lys Ile Leu Ser Lys Val Gln
    530                 535                 540

Pro Pro Leu Leu Ser Ala Ser Thr Gly Gly Val Leu Gln Phe Pro Ser
```

-continued

```
545                 550                 555                 560

Gly Gln Asn Asn Ser Val Lys Glu Trp Glu Asp Lys Lys Val Ser Ser
                565                 570                 575

Val Ser His Glu Asn Pro Thr Glu Val Phe Glu Asp Gly Glu Asn Pro
            580                 585                 590

Pro Ser Ser Arg Ser Ser Glu Ser Gly Phe Thr Glu Phe Ile Gln Tyr
        595                 600                 605

Gln Ala Asp Arg Thr Asp Asp Ile Asp Arg Glu Leu Ser Glu Gly Gln
    610                 615                 620

Gly Ala Ala Ala Ile Pro Ile Gly Ser Thr Ser Ser Glu Thr Glu Thr
625                 630                 635                 640

Ala Ser Thr Val Gly Ser Glu Glu Thr Ile Ile Gln Thr Pro Ser Val
                645                 650                 655

Val Thr Gln Gly Thr Ala Thr Arg Ser Arg Lys Thr Ala Gln Lys Thr
            660                 665                 670

Ala Met Gln Cys Cys Leu Glu Tyr Val Gln Gln Phe Leu Thr Arg Leu
        675                 680                 685

Ile Asn Leu Tyr Ile Ile Gln Asn Asn Ser Phe Ser Gln Ser Leu Ala
    690                 695                 700

Thr Glu His Gln Gly Asp Leu Gly Arg Glu Gln Gly Glu Thr Ser Lys
705                 710                 715                 720

Trp Asp Arg Asn Ser Gln Gly Asp Val Lys Glu Lys Asn Ile Ser Lys
                725                 730                 735

Gln Lys Thr Ser Lys Glu Tyr Leu Ser Ala Phe Leu Ala Ala Cys Gln
            740                 745                 750

Leu Phe Leu Glu Cys Ser Ser Phe Pro Val Tyr Ile Ala Glu Gly Asn
        755                 760                 765

His Thr Ser Glu Leu Arg Ser Glu Lys Leu Glu Thr Asp Cys Glu His
    770                 775                 780

Val Gln Pro Pro Gln Trp Leu Gln Thr Leu Met Asn Ala Cys Ser Gln
785                 790                 795                 800

Ala Ser Asp Phe Ser Val Gln Ser Val Ala Ile Ser Leu Val Met Asp
                805                 810                 815

Leu Val Gly Leu Thr Gln Ser Val Ala Met Val Thr Gly Glu Asn Ile
            820                 825                 830

Asn Ser Val Glu Pro Ala Gln Pro Leu Ser Pro Asn Gln Gly Arg Val
        835                 840                 845

Ala Val Val Ile Arg Pro Pro Leu Thr Gln Gly Asn Leu Arg Tyr Ile
    850                 855                 860

Ala Glu Lys Thr Glu Phe Phe Lys His Val Ala Leu Thr Leu Trp Asp
865                 870                 875                 880

Gln Leu Gly Asp Gly Thr Pro Gln His His Gln Lys Ser Val Glu Leu
                885                 890                 895

Phe Tyr Gln Leu His Asn Leu Val Pro Ser Ser Ser Ile Cys Glu Asp
            900                 905                 910

Val Ile Ser Gln Gln Leu Thr His Lys Asp Lys Lys Ile Arg Met Glu
        915                 920                 925

Ala His Ala Lys Phe Ala Val Leu Trp His Leu Thr Arg Asp Leu His
    930                 935                 940

Ile Asn Lys Ser Ser Ser Phe Val Arg Ser Phe Asp Arg Ser Leu Phe
945                 950                 955                 960

Ile Met Leu Asp Ser Leu Asn Ser Leu Asp Gly Ser Thr Ser Ser Val
                965                 970                 975

Gly Gln Ala Trp Leu Asn Gln Val Leu Gln Arg His Asp Ile Ala Arg
```

-continued

```
        980                 985                 990

Val Leu Glu Pro Leu Leu Leu Leu Leu Leu His Pro Lys Thr Gln Arg
        995                 1000                1005

Val Ser Val Gln Arg Val Gln Ala Glu Arg Tyr Trp Asn Lys Ser
    1010                1015                1020

Pro Cys Tyr Pro Gly Glu Glu Ser Asp Lys His Phe Met Gln Asn
    1025                1030                1035

Phe Ala Cys Ser Asn Val Ser Gln Val Gln Leu Ile Thr Ser Lys
    1040                1045                1050

Gly Asn Gly Glu Lys Pro Leu Thr Met Asp Glu Ile Glu Asn Phe
    1055                1060                1065

Ser Leu Thr Val Asn Pro Leu Ser Asp Arg Leu Ser Leu Leu Ser
    1070                1075                1080

Thr Ser Ser Glu Thr Ile Pro Met Val Val Ser Asp Phe Asp Leu
    1085                1090                1095

Pro Asp Gln Gln Ile Glu Ile Leu Gln Ser Ser Asp Ser Gly Cys
    1100                1105                1110

Ser Gln Ser Ser Ala Gly Asp Asn Leu Ser Tyr Glu Val Asp Pro
    1115                1120                1125

Glu Thr Val Asn Ala Gln Glu Asp Ser Gln Met Pro Lys Glu Ser
    1130                1135                1140

Ser Pro Asp Asp Asp Val Gln Gln Val Val Phe Asp Leu Ile Cys
    1145                1150                1155

Lys Val Val Ser Gly Leu Glu Val Glu Ser Ala Ser Val Thr Ser
    1160                1165                1170

Gln Leu Glu Ile Glu Ala Met Pro Pro Lys Cys Ser Asp Ile Asp
    1175                1180                1185

Pro Asp Glu Glu Thr Ile Lys Ile Glu Asp Asp Ser Ile Gln Gln
    1190                1195                1200

Ser Gln Asn Ala Leu Leu Ser Asn Glu Ser Ser Gln Phe Leu Ser
    1205                1210                1215

Val Ser Ala Glu Gly Gly His Glu Cys Val Ala Asn Gly Ile Ser
    1220                1225                1230

Arg Asn Ser Ser Ser Pro Cys Ile Ser Gly Thr Thr His Thr Leu
    1235                1240                1245

His Asp Ser Ser Val Ala Ser Ile Glu Thr Lys Ser Arg Gln Arg
    1250                1255                1260

Ser His Ser Ser Ile Gln Phe Ser Phe Lys Glu Lys Leu Ser Glu
    1265                1270                1275

Lys Val Ser Glu Lys Glu Thr Ile Val Lys Glu Ser Gly Lys Gln
    1280                1285                1290

Pro Gly Ala Lys Pro Lys Val Lys Leu Ala Arg Lys Lys Asp Asp
    1295                1300                1305

Asp Lys Lys Lys Ser Ser Asn Glu Lys Leu Lys Gln Thr Ser Val
    1310                1315                1320

Phe Phe Ser Asp Gly Leu Asp Leu Glu Asn Trp Tyr Ser Cys Gly
    1325                1330                1335

Glu Gly Asp Ile Ser Glu Ile Glu Ser Asp Met Gly Ser Pro Gly
    1340                1345                1350

Ser Arg Lys Ser Pro Asn Phe Asn Ile His Pro Leu Tyr Gln His
    1355                1360                1365

Val Leu Leu Tyr Leu Gln Leu Tyr Asp Ser Ser Arg Thr Leu Tyr
    1370                1375                1380

Ala Phe Ser Ala Ile Lys Ala Ile Leu Lys Thr Asn Pro Ile Ala
```

-continued

```
    1385                1390                1395

Phe Val Asn Ala Ile Ser Thr Thr Ser Val Asn Asn Ala Tyr Thr
    1400                1405                1410

Pro Gln Leu Ser Leu Leu Gln Asn Leu Leu Ala Arg His Arg Ile
    1415                1420                1425

Ser Val Met Gly Lys Asp Phe Tyr Ser His Ile Pro Val Asp Ser
    1430                1435                1440

Asn His Asn Phe Arg Ser Ser Met Tyr Ile Glu Ile Leu Ile Ser
    1445                1450                1455

Leu Cys Leu Tyr Tyr Met Arg Ser His Tyr Pro Thr His Val Lys
    1460                1465                1470

Val Thr Ala Gln Asp Leu Ile Gly Asn Arg Asn Met Gln Met Met
    1475                1480                1485

Ser Ile Glu Ile Leu Thr Leu Leu Phe Thr Glu Leu Ala Lys Val
    1490                1495                1500

Ile Glu Ser Ser Ala Lys Gly Phe Pro Ser Phe Ile Ser Asp Met
    1505                1510                1515

Leu Ser Lys Cys Lys Val Gln Lys Val Ile Leu His Cys Leu Leu
    1520                1525                1530

Ser Ser Ile Phe Ser Ala Gln Lys Trp His Ser Glu Lys Met Ala
    1535                1540                1545

Gly Lys Asn Leu Val Ala Val Glu Glu Gly Phe Ser Glu Asp Ser
    1550                1555                1560

Leu Ile Asn Phe Ser Glu Asp Glu Phe Asp Asn Gly Ser Thr Leu
    1565                1570                1575

Gln Ser Gln Leu Leu Lys Val Leu Gln Arg Leu Ile Val Leu Glu
    1580                1585                1590

His Arg Val Met Thr Ile Pro Glu Glu Asn Glu Thr Gly Phe Asp
    1595                1600                1605

Phe Val Val Ser Asp Leu Glu His Ile Ser Pro His Gln Pro Met
    1610                1615                1620

Thr Ser Leu Gln Tyr Leu His Ala Gln Pro Ile Thr Cys Gln Gly
    1625                1630                1635

Met Phe Leu Cys Ala Val Ile Arg Ala Leu His Gln His Cys Ala
    1640                1645                1650

Cys Lys Met His Pro Gln Trp Ile Gly Leu Ile Thr Ser Thr Leu
    1655                1660                1665

Pro Tyr Met Gly Lys Val Leu Gln Arg Val Val Val Ser Val Thr
    1670                1675                1680

Leu Gln Leu Cys Arg Asn Leu Asp Asn Leu Ile Gln Gln Tyr Lys
    1685                1690                1695

Tyr Glu Thr Gly Leu Ser Asp Ser Arg Pro Leu Trp Met Ala Ser
    1700                1705                1710

Ile Ile Pro Pro Asp Met Ile Leu Thr Leu Leu Glu Gly Ile Thr
    1715                1720                1725

Ala Ile Ile His Tyr Cys Leu Leu Asp Pro Thr Thr Gln Tyr His
    1730                1735                1740

Gln Leu Leu Val Ser Val Asp Gln Lys His Leu Phe Glu Ala Arg
    1745                1750                1755

Ser Gly Ile Leu Ser Ile Leu His Met Ile Met Ser Ser Val Thr
    1760                1765                1770

Leu Leu Trp Ser Ile Leu His Gln Ala Asp Ser Ser Glu Lys Met
    1775                1780                1785

Thr Ile Ala Ala Ser Ala Ser Leu Thr Thr Ile Asn Leu Gly Ala
```

-continued 1790 1795 1800

Thr Lys Asn Leu Arg Gln Gln Ile Leu Glu Leu Leu Gly Pro Ile
1805 1810 1815

Ser Met Asn His Gly Val His Phe Met Ala Ala Ile Ala Phe Val
1820 1825 1830

Trp Asn Glu Arg Arg Gln Asn Lys Thr Thr Thr Arg Thr Lys Val
1835 1840 1845

Ile Pro Ala Ala Ser Glu Glu Gln Leu Leu Leu Val Glu Leu Val
1850 1855 1860

Arg Ser Ile Ser Val Met Arg Ala Glu Thr Val Ile Gln Thr Val
1865 1870 1875

Lys Glu Val Leu Lys Gln Pro Pro Ala Ile Ala Lys Asp Lys Lys
1880 1885 1890

His Leu Ser Leu Glu Val Cys Met Leu Gln Phe Phe Tyr Ala Tyr
1895 1900 1905

Ile Gln Arg Ile Pro Val Pro Asn Leu Val Asp Ser Trp Ala Ser
1910 1915 1920

Leu Leu Ile Leu Leu Lys Asp Ser Ile Gln Leu Ser Leu Pro Ala
1925 1930 1935

Pro Gly Gln Phe Leu Ile Leu Gly Val Leu Asn Glu Phe Ile Met
1940 1945 1950

Lys Asn Pro Ser Leu Glu Asn Lys Lys Asp Gln Arg Asp Leu Gln
1955 1960 1965

Asp Val Thr His Lys Ile Val Asp Ala Ile Gly Ala Ile Ala Gly
1970 1975 1980

Ser Ser Leu Glu Gln Thr Thr Trp Leu Arg Arg Asn Leu Glu Val
1985 1990 1995

Lys Pro Ser Pro Lys Ile Met Val Asp Gly Thr Asn Leu Glu Ser
2000 2005 2010

Asp Val Glu Asp Met Leu Ser Pro Ala Met Glu Thr Ala Asn Ile
2015 2020 2025

Thr Pro Ser Val Tyr Ser Val His Ala Leu Thr Leu Leu Ser Glu
2030 2035 2040

Val Leu Ala His Leu Leu Asp Met Val Phe Tyr Ser Asp Glu Lys
2045 2050 2055

Glu Arg Val Ile Pro Leu Leu Val Asn Ile Met His Tyr Val Val
2060 2065 2070

Pro Tyr Leu Arg Asn His Ser Ala His Asn Ala Pro Ser Tyr Arg
2075 2080 2085

Ala Cys Val Gln Leu Leu Ser Ser Leu Ser Gly Tyr Gln Tyr Thr
2090 2095 2100

Arg Arg Ala Trp Lys Lys Glu Ala Phe Asp Leu Phe Met Asp Pro
2105 2110 2115

Ser Phe Phe Gln Met Asp Ala Ser Cys Val Asn His Trp Arg Ala
2120 2125 2130

Ile Met Asp Asn Leu Met Thr His Asp Lys Thr Thr Phe Arg Asp
2135 2140 2145

Leu Met Thr Arg Val Ala Val Ala Gln Ser Ser Ser Leu Asn Leu
2150 2155 2160

Phe Ala Asn Arg Asp Val Glu Leu Glu Gln Arg Ala Met Leu Leu
2165 2170 2175

Lys Arg Leu Ala Phe Ala Ile Phe Ser Ser Glu Ile Asp Gln Tyr
2180 2185 2190

Gln Lys Tyr Leu Pro Asp Ile Gln Glu Arg Leu Val Glu Ser Leu

-continued

```
    2195                2200                2205

Arg Leu Pro Gln Val Pro Thr Leu His Ser Gln Val Phe Leu Phe
    2210                2215                2220

Phe Arg Val Leu Leu Leu Arg Met Ser Pro Gln His Leu Thr Ser
    2225                2230                2235

Leu Trp Pro Thr Met Ile Thr Glu Leu Val Gln Val Phe Leu Leu
    2240                2245                2250

Met Glu Gln Glu Leu Thr Ala Asp Glu Asp Ile Ser Arg Thr Ser
    2255                2260                2265

Gly Pro Ser Val Ala Gly Leu Glu Thr Thr Tyr Thr Gly Gly Asn
    2270                2275                2280

Gly Phe Ser Thr Ser Tyr Asn Ser Gln Arg Trp Leu Asn Leu Tyr
    2285                2290                2295

Leu Ser Ala Cys Lys Phe Leu Asp Leu Ala Leu Ala Leu Pro Ser
    2300                2305                2310

Glu Asn Leu Pro Gln Phe Gln Met Tyr Arg Trp Ala Phe Ile Pro
    2315                2320                2325

Glu Ala Ser Asp Asp Ser Gly Leu Glu Val Arg Arg Gln Gly Ile
    2330                2335                2340

His Gln Arg Glu Phe Lys Pro Tyr Val Val Arg Leu Ala Lys Leu
    2345                2350                2355

Leu Arg Lys Arg Ala Lys Lys Asn Pro Glu Glu Asp Asn Ser Gly
    2360                2365                2370

Arg Thr Leu Gly Trp Glu Pro Gly His Leu Leu Leu Thr Ile Cys
    2375                2380                2385

Thr Val Arg Ser Met Glu Gln Leu Leu Pro Phe Phe Asn Val Leu
    2390                2395                2400

Ser Gln Val Phe Asn Ser Lys Val Thr Ser Arg Cys Gly Gly His
    2405                2410                2415

Ser Gly Ser Pro Ile Leu Tyr Ser Asn Ala Phe Pro Asn Lys Asp
    2420                2425                2430

Met Lys Leu Glu Asn His Lys Pro Cys Ser Ser Lys Ala Arg Gln
    2435                2440                2445

Lys Ile Glu Glu Met Val Glu Lys Asp Phe Leu Glu Gly Met Ile
    2450                2455                2460

Lys Thr
    2465
```

In another embodiment of this aspect of the present invention, the one or more mutations detected in the patient sample include a mutation in the ZNF192 gene encoding zinc finger protein 192. This mutation maps to position 28229455 of chromosome 6 of hg 18. The mRNA sequence for human ZNF192 (NCBI Accession No. NM_006298) and corresponding amino acid sequence are provided below as SEQ ID NOs: 37 and 38, respectively. A relapse specific mutation in ZNF192 results in an arginine to proline substitution at an amino acid position corresponding to R473 of SEQ ID NO: 38 below. An exemplary mutation in ZNF192 encoding this amino acid substitution comprises a G→C change at a nucleotide position corresponding to position 1418 of SEQ ID NO: 37.

```
                                                    SEQ ID NO: 37
Human ZNF192
atggctgaag aatcaagaaa gccttcagcc ccatccccac cagaccagac tcctgaagag    60

gatcttgtaa tcgtcaaggt agaggaggat catggttggg accaggaatc tagtctgcat   120

gaaagtaacc ctcttggcca agaaagtgttc cgcctgcgct tcaggcagtt acgctaccag  180

gagacactag gaccccgaga agctctgatc caactacggg ccctttgcca tcagtggctg   240

aggccagatt tgaacaccaa ggaacagatc ctggagctgc tggtgctgga gcagttcttg   300

accatcctac ctgaggagct ccagacactg gttaaggaac atcagctaga gaacggagag   360
```

-continued

```
gaggtggtga ccctattaga ggatttggaa aggcagattg atatactagg acgaccagtc   420
tcagctcgcg tacatggaca tagggtactc tgggaggagg tagtacattc agcatctgca   480
ccagagcctc caaatactca gctccaatct gaggcaaccc aacataaatc tccagtgccc   540
caagagtcac aagagagagc catgtctact tcccagagtc ctactcgttc ccagaaagga   600
agttctggag accaggaaat gacagctaca cttctcacag cagggttcca gactttggag   660
aagattgaag acatggctgt gtcccttatt cgagaggagt ggcttcttga tccatcacag   720
aaggatctgt gtagagataa caggccagaa aatttcagaa acatgttctc cctgggtggt   780
gagaccagga gtgagaacag ggaattagct tcaaaacagg taatatctac tggaatccag   840
ccacatggag agacagctgc caaatgcaac ggggatgtta tcaggggtct tgagcatgaa   900
gaagcccgag accttctggg cagattagag aggcagcggg gaaatcccac acaagagaga   960
cgacataaat gtgatgaatg tgggaaaagc tttgctcaga gctcaggcct tgttcgccac  1020
tggagaatcc acactgggga gaaaccctat cagtgtaatg tgtgtggtaa agccttcagt  1080
tacaggtcag cccttctttc acatcaggat atccacaaca aagtaaaacg ctatcactgt  1140
aaggagtgtg gcaaagcctt cagtcagaac acaggcctga ttctgcacca gagaatccac  1200
actggggaga agccatatca gtgcaatcag tgtgggaagg ctttcagtca gagtgcgggc  1260
cttattctgc accagagaat ccacagtgga gagagaccct atgaatgtaa tgagtgtggg  1320
aaagctttca gtcatagctc acacctcatt ggacatcaga gaatccacac tggggagaag  1380
ccctatgagt gtgatgagtg tgggaaaacc ttcaggcgga gctcacatct tattggtcat  1440
cagaggagcc acactgggga gaaaccctac aaatgcaatg agtgtgggag ggccttcagt  1500
cagaagtcag gccttattga acatcagaga atccacactg gagaaagacc ctataaatgt  1560
aaagaatgtg ggaaagcttt caatgggaac actggtctca ttcaacacct gagaattcac  1620
acaggggaga agccctacca atgtaatgag tgtgggaaag cctttattca gaggtcaagt  1680
ctcattcgac atcagagaat ccacagtggt gaaaaatctg aatccataag cgtttag     1737
```

SEQ ID NO: 38

Human Zinc finger protein 192

```
Met Ala Glu Glu Ser Arg Lys Pro Ser Ala Pro Ser Pro Pro Asp Gln
1               5                   10                  15

Thr Pro Glu Glu Asp Leu Val Ile Val Lys Val Glu Glu Asp His Gly
            20                  25                  30

Trp Asp Gln Glu Ser Ser Leu His Glu Ser Asn Pro Leu Gly Gln Glu
        35                  40                  45

Val Phe Arg Leu Arg Phe Arg Gln Leu Arg Tyr Gln Glu Thr Leu Gly
    50                  55                  60

Pro Arg Glu Ala Leu Ile Gln Leu Arg Ala Leu Cys His Gln Trp Leu
65                  70                  75                  80

Arg Pro Asp Leu Asn Thr Lys Glu Gln Ile Leu Glu Leu Leu Val Leu
                85                  90                  95

Glu Gln Phe Leu Thr Ile Leu Pro Glu Glu Leu Gln Thr Leu Val Lys
            100                 105                 110

Glu His Gln Leu Glu Asn Gly Glu Glu Val Val Thr Leu Leu Glu Asp
        115                 120                 125

Leu Glu Arg Gln Ile Asp Ile Leu Gly Arg Pro Val Ser Ala Arg Val
    130                 135                 140

His Gly His Arg Val Leu Trp Glu Glu Val Val His Ser Ala Ser Ala
145                 150                 155                 160

Pro Glu Pro Pro Asn Thr Gln Leu Gln Ser Glu Ala Thr Gln His Lys
                165                 170                 175
```

-continued

```
Ser Pro Val Pro Gln Glu Ser Gln Glu Arg Ala Met Ser Thr Ser Gln
            180                 185                 190

Ser Pro Thr Arg Ser Gln Lys Gly Ser Ser Gly Asp Gln Glu Met Thr
        195                 200                 205

Ala Thr Leu Leu Thr Ala Gly Phe Gln Thr Leu Glu Lys Ile Glu Asp
    210                 215                 220

Met Ala Val Ser Leu Ile Arg Glu Glu Trp Leu Leu Asp Pro Ser Gln
225                 230                 235                 240

Lys Asp Leu Cys Arg Asp Asn Arg Pro Glu Asn Phe Arg Asn Met Phe
                245                 250                 255

Ser Leu Gly Gly Glu Thr Arg Ser Glu Asn Arg Glu Leu Ala Ser Lys
            260                 265                 270

Gln Val Ile Ser Thr Gly Ile Gln Pro His Gly Glu Thr Ala Ala Lys
        275                 280                 285

Cys Asn Gly Asp Val Ile Arg Gly Leu Glu His Glu Glu Ala Arg Asp
    290                 295                 300

Leu Leu Gly Arg Leu Glu Arg Gln Arg Gly Asn Pro Thr Gln Glu Arg
305                 310                 315                 320

Arg His Lys Cys Asp Glu Cys Gly Lys Ser Phe Ala Gln Ser Ser Gly
                325                 330                 335

Leu Val Arg His Trp Arg Ile His Thr Gly Glu Lys Pro Tyr Gln Cys
            340                 345                 350

Asn Val Cys Gly Lys Ala Phe Ser Tyr Arg Ser Ala Leu Leu Ser His
        355                 360                 365

Gln Asp Ile His Asn Lys Val Lys Arg Tyr His Cys Lys Glu Cys Gly
    370                 375                 380

Lys Ala Phe Ser Gln Asn Thr Gly Leu Ile Leu His Gln Arg Ile His
385                 390                 395                 400

Thr Gly Glu Lys Pro Tyr Gln Cys Asn Gln Cys Gly Lys Ala Phe Ser
                405                 410                 415

Gln Ser Ala Gly Leu Ile Leu His Gln Arg Ile His Ser Gly Glu Arg
            420                 425                 430

Pro Tyr Glu Cys Asn Glu Cys Gly Lys Ala Phe Ser His Ser Ser His
        435                 440                 445

Leu Ile Gly His Gln Arg Ile His Thr Gly Glu Lys Pro Tyr Glu Cys
    450                 455                 460

Asp Glu Cys Gly Lys Thr Phe Arg Arg Ser Ser His Leu Ile Gly His
465                 470                 475                 480

Gln Arg Ser His Thr Gly Glu Lys Pro Tyr Lys Cys Asn Glu Cys Gly
                485                 490                 495

Arg Ala Phe Ser Gln Lys Ser Gly Leu Ile Glu His Gln Arg Ile His
            500                 505                 510

Thr Gly Glu Arg Pro Tyr Lys Cys Lys Glu Cys Gly Lys Ala Phe Asn
        515                 520                 525

Gly Asn Thr Gly Leu Ile Gln His Leu Arg Ile His Thr Gly Glu Lys
    530                 535                 540

Pro Tyr Gln Cys Asn Glu Cys Gly Lys Ala Phe Ile Gln Arg Ser Ser
545                 550                 555                 560

Leu Ile Arg His Gln Arg Ile His Ser Gly Glu Lys Ser Glu Ser Ile
                565                 570                 575

Ser Val
```

In another embodiment of this aspect of the present invention, the one or more mutations detected in the patient sample include a mutation in the EVI2A gene encoding human protein EVI2A isoform 2 precursor. This mutation maps to position 26669778 of chromosome 17 of hg 18. The mRNA sequence for human EVI2A and corresponding amino acid sequence are provided below as SEQ ID NOs: 39 and 40, respectively. A relapse specific mutation in EVI2A results in an alanine to valine substitution at an amino acid position corresponding to A127 of SEQ ID NO: 40 below. An exemplary mutation in EVI2A encoding this amino acid substitution comprises a C→T change at a nucleotide position corresponding to position 449 of SEQ ID NO. 39.

```
                                                          SEQ ID NO: 39
Human ecotropic viral integration site 2A (EVI2A), transcript variant 2
atgcccacgg acatggaaca cacaggacat tacctacatc ttgcctttct gatgacaaca   60

gtttttcttt tgtctcctgg aacaaaagca aactataccc gtctgtgggc taacagtact  120

tcttcctggg attcagttat tcaaaacaag acaggcagaa accaaaatga aaacattaac  180

acaaacccta taactcctga agtagattat aaaggtaatt ctacaaacat gcctgaaaca  240

tctcacatcg tagctttaac ttctaaatct gaacaggagc tttatatacc ttctgtcgtc  300

agcaacagtc cttcaacagt acagagcatt gaaaacacaa gcaaaagtca tggtgaaatt  360

ttcaaaaagg atgtctgtgc ggaaaacaac aacaacatgg ctatgctaat ttgcttaatt  420

ataattgcag tgctttttct tatctgtacc tttctatttc tatcaactgt ggttttggca  480

aacaaagtct cttctctcag acgatcaaaa caagtaggca agcgtcagcc tagaagcaat  540

ggcgattttc tggcaagcgg tctatggccc gctgaatcag acacttggaa aagaacaaaa  600

cagctcacag gacccaacct agtgatgcaa tctactggag tgctcacagc tacaagggaa  660

agaaaagatg aagaaggaac tgaaaaactt actaacaaac agataggtta g           711

                                                          SEQ ID NO: 40
Human ectropic integration site 2A
Met Pro Thr Asp Met Glu His Thr Gly His Tyr Leu His Leu Ala Phe
1               5                   10                  15

Leu Met Thr Thr Val Phe Ser Leu Ser Pro Gly Thr Lys Ala Asn Tyr
            20                  25                  30

Thr Arg Leu Trp Ala Asn Ser Thr Ser Ser Trp Asp Ser Val Ile Gln
        35                  40                  45

Asn Lys Thr Gly Arg Asn Gln Asn Glu Asn Ile Asn Thr Asn Pro Ile
    50                  55                  60

Thr Pro Glu Val Asp Tyr Lys Gly Asn Ser Thr Asn Met Pro Glu Thr
65                  70                  75                  80

Ser His Ile Val Ala Leu Thr Ser Lys Ser Glu Gln Glu Leu Tyr Ile
                85                  90                  95

Pro Ser Val Val Ser Asn Ser Pro Ser Thr Val Gln Ser Ile Glu Asn
            100                 105                 110

Thr Ser Lys Ser His Gly Glu Ile Phe Lys Lys Asp Val Cys Ala Glu
        115                 120                 125

Asn Asn Asn Asn Met Ala Met Leu Ile Cys Leu Ile Ile Ile Ala Val
    130                 135                 140

Leu Phe Leu Ile Cys Thr Phe Leu Phe Leu Ser Thr Val Val Leu Ala
145                 150                 155                 160

Asn Lys Val Ser Ser Leu Arg Arg Ser Lys Gln Val Gly Lys Arg Gln
                165                 170                 175

Pro Arg Ser Asn Gly Asp Phe Leu Ala Ser Gly Leu Trp Pro Ala Glu
            180                 185                 190

Ser Asp Thr Trp Lys Arg Thr Lys Gln Leu Thr Gly Pro Asn Leu Val
        195                 200                 205

Met Gln Ser Thr Gly Val Leu Thr Ala Thr Arg Glu Arg Lys Asp Glu
    210                 215                 220

Glu Gly Thr Glu Lys Leu Thr Asn Lys Gln Ile Gly
225                 230                 235
```

In another embodiment of this aspect of the present invention, the one or more mutations detected in the patient sample include a mutation in the GSPT2 gene encoding eukaryotic peptide chain release factor GTP-binding subunit ERF3B. This mutation maps to position 51505138 of chromosome X of hg 18. The mRNA sequence for human GSPT2 (NCBI Accession No. NM_018094) and corresponding amino acid sequence are provided below as SEQ ID NOs: 41 and 42, respectively. A relapse specific mutation in GSPT2 results in a serine to cysteine substitution at an amino acid position corresponding to S559 of SEQ ID NO: 42 below. An exemplary mutation in GSPT2 encoding this amino acid substitution comprises a C→G change at a nucleotide position corresponding to position 1676 of SEQ ID NO: 41.

```
                                                         SEQ ID NO: 41
G1 to S phase transition 2 (GSPT2)
atggattcgg gcagcagcag cagcgactcg gcgcccgatt gctgggacca ggtggacatg    60

gaatccccgg ggtcggcccc gagcggggat ggagtctcct ctgcggtggc cgaggcccag   120

cgcgagcccc tcagctcggc tttcagccgt aagctcaacg tcaacgccaa gcccttcgtg   180

cctaacgtac acgccgcgga gttcgtgccg tccttcctgc ggggcccgac tcagccgccc   240

accctcccgg ccggctccgg cagcaacgat gaaacctgca ccggcgcggg ataccctcaa   300

ggtaaaagga tgggacgggg ggcacctgtg gaaccttccc gagaggaacc gttagtgtcg   360

cttgaaggtt ccaattcagc cgttaccatg gaactttcag aacctgttgt agaaaatgga   420

gaggtggaaa tggccctaga agaatcatgg gagcacagta aagaagtaag tgaagccgag   480

cctgggggtg gttcctcggg agattcaggg cccccagaag aaagtggcca ggaaatgatg   540

gaggaaaaag aggaaataag aaaatccaaa tctgtgatcg taccctcagg tgcacctaag   600

aaagaacacg taaatgtagt attcattggc catgtagacg ctggcaagtc aaccatcgga   660

ggacagataa tgtttttgac tggaatggtt gacaaaagaa cactggagaa atatgaaaga   720

gaagctaagg aaaaaaacag agaaacctgg tatttgtcct gggccttaga tacaaatcag   780

gaggaacgag acaagggtaa aacagtcgaa gtgggtcgtg cctattttga aacagaaagg   840

aaacatttca caattttaga tgcccctggc cacaagagtt ttgtcccaaa tatgattggt   900

ggtgcttctc aagctgattt ggctgtgctg gtcatctctg ccaggaaagg agagtttgaa   960

actggatttg aaaaaggtgg acagacaaga gaacatgcga tgttggcaaa aacggcaggg  1020

gtaaaacatt taatagtgct tattaataag atggatgatc ccacagtaaa ttggagcatc  1080

gagagatatg aagaatgtaa agaaaaactg gtgccctttt tgaaaaaagt aggcttcagt  1140

ccaaaaaagg acattcactt tatgccctgc tcaggactga ccggagcaaa tattaaagag  1200

cagtcagatt tctgcccttg gtacactgga ttaccattta ttccgtattt ggataacttg  1260

ccaaacttca acagatcaat tgatggacca ataagactgc caattgtgga taagtacaaa  1320

gatatgggca ccgtggtcct gggaaagctg gaatccgggt ccatttttaa aggccagcag  1380

ctcgtgatga tgccaaacaa gcacaatgta gaagttcttg gaatactttc tgatgatact  1440

gaaactgatt ttgtagcccc aggtgaaaac ctcaaaatca gactgaaggg aattgaagaa  1500

gaagagattc ttccaggatt catactttgt gatcctagta acctctgcca ttctggacgc  1560

acgtttgatg ttcagatagt gattattgag cacaaatcca tcatctgccc aggttataat  1620

gcggtgctgc acattcatac ttgtattgag gaagttgaga taacagcgtt aatctccttg  1680

gtagacaaaa aatcaggaga aaaaagtaag acacgacccc gcttcgtgaa acaagatcaa  1740

gtatgcattg ctcgtttaag gacagcagga accatctgcc tcgagacgtt caaagatttt  1800

cctcagatgg gtcgttttac tttaagagat gagggtaaga ccattgcaat tggaaaagtt  1860

ctgaaattgg tcccagagaa ggactaa                                      1887

                                                         SEQ ID NO: 42
Eukaryotic peptide chain release factor GTP-binding subunit ERF3B
Met Asp Ser Gly Ser Ser Ser Ser Asp Ser Ala Pro Asp Cys Trp Asp
1               5                   10                  15
```

-continued

```
Gln Val Asp Met Glu Ser Pro Gly Ser Ala Pro Ser Gly Asp Gly Val
            20                  25                  30

Ser Ser Ala Val Ala Glu Ala Gln Arg Glu Pro Leu Ser Ser Ala Phe
        35                  40                  45

Ser Arg Lys Leu Asn Val Asn Ala Lys Pro Phe Val Pro Asn Val His
    50                  55                  60

Ala Ala Glu Phe Val Pro Ser Phe Leu Arg Gly Pro Thr Gln Pro Pro
65                  70                  75                  80

Thr Leu Pro Ala Gly Ser Gly Ser Asn Asp Glu Thr Cys Thr Gly Ala
                85                  90                  95

Gly Tyr Pro Gln Gly Lys Arg Met Gly Arg Gly Ala Pro Val Glu Pro
            100                 105                 110

Ser Arg Glu Glu Pro Leu Val Ser Leu Glu Gly Ser Asn Ser Ala Val
        115                 120                 125

Thr Met Glu Leu Ser Glu Pro Val Val Glu Asn Gly Glu Val Glu Met
    130                 135                 140

Ala Leu Glu Glu Ser Trp Glu His Ser Lys Glu Val Ser Glu Ala Glu
145                 150                 155                 160

Pro Gly Gly Gly Ser Ser Gly Asp Ser Gly Pro Pro Glu Glu Ser Gly
                165                 170                 175

Gln Glu Met Met Glu Glu Lys Glu Glu Ile Arg Lys Ser Lys Ser Val
            180                 185                 190

Ile Val Pro Ser Gly Ala Pro Lys Lys Glu His Val Asn Val Val Phe
        195                 200                 205

Ile Gly His Val Asp Ala Gly Lys Ser Thr Ile Gly Gly Gln Ile Met
    210                 215                 220

Phe Leu Thr Gly Met Val Asp Lys Arg Thr Leu Glu Lys Tyr Glu Arg
225                 230                 235                 240

Glu Ala Lys Glu Lys Asn Arg Glu Thr Trp Tyr Leu Ser Trp Ala Leu
                245                 250                 255

Asp Thr Asn Gln Glu Glu Arg Asp Lys Gly Lys Thr Val Glu Val Gly
            260                 265                 270

Arg Ala Tyr Phe Glu Thr Glu Arg Lys His Phe Thr Ile Leu Asp Ala
        275                 280                 285

Pro Gly His Lys Ser Phe Val Pro Asn Met Ile Gly Gly Ala Ser Gln
    290                 295                 300

Ala Asp Leu Ala Val Leu Val Ile Ser Ala Arg Lys Gly Glu Phe Glu
305                 310                 315                 320

Thr Gly Phe Glu Lys Gly Gly Gln Thr Arg Glu His Ala Met Leu Ala
                325                 330                 335

Lys Thr Ala Gly Val Lys His Leu Ile Val Leu Ile Asn Lys Met Asp
            340                 345                 350

Asp Pro Thr Val Asn Trp Ser Ile Glu Arg Tyr Glu Glu Cys Lys Glu
        355                 360                 365

Lys Leu Val Pro Phe Leu Lys Lys Val Gly Phe Ser Pro Lys Lys Asp
    370                 375                 380

Ile His Phe Met Pro Cys Ser Gly Leu Thr Gly Ala Asn Ile Lys Glu
385                 390                 395                 400

Gln Ser Asp Phe Cys Pro Trp Tyr Thr Gly Leu Pro Phe Ile Pro Tyr
                405                 410                 415

Leu Asp Asn Leu Pro Asn Phe Asn Arg Ser Ile Asp Gly Pro Ile Arg
            420                 425                 430

Leu Pro Ile Val Asp Lys Tyr Lys Asp Met Gly Thr Val Val Leu Gly
        435                 440                 445
```

-continued

```
Lys Leu Glu Ser Gly Ser Ile Phe Lys Gly Gln Gln Leu Val Met Met
    450                 455                 460

Pro Asn Lys His Asn Val Glu Val Leu Gly Ile Leu Ser Asp Asp Thr
465                 470                 475                 480

Glu Thr Asp Phe Val Ala Pro Gly Glu Asn Leu Lys Ile Arg Leu Lys
                485                 490                 495

Gly Ile Glu Glu Glu Glu Ile Leu Pro Gly Phe Ile Leu Cys Asp Pro
            500                 505                 510

Ser Asn Leu Cys His Ser Gly Arg Thr Phe Asp Val Gln Ile Val Ile
        515                 520                 525

Ile Glu His Lys Ser Ile Ile Cys Pro Gly Tyr Asn Ala Val Leu His
    530                 535                 540

Ile His Thr Cys Ile Glu Glu Val Glu Ile Thr Ala Leu Ile Ser Leu
545                 550                 555                 560

Val Asp Lys Lys Ser Gly Glu Lys Ser Lys Thr Arg Pro Arg Phe Val
                565                 570                 575

Lys Gln Asp Gln Val Cys Ile Ala Arg Leu Arg Thr Ala Gly Thr Ile
            580                 585                 590

Cys Leu Glu Thr Phe Lys Asp Phe Pro Gln Met Gly Arg Phe Thr Leu
        595                 600                 605

Arg Asp Glu Gly Lys Thr Ile Ala Ile Gly Lys Val Leu Lys Leu Val
    610                 615                 620

Pro Glu Lys Asp
625
```

In another embodiment of this aspect of the present invention, the one or more mutations detected in the patient sample include mutations in the MYC gene, encoding v-myc myelocytomatosis viral oncogene homolog. These mutations map to positions 128819862 and 128819863, respectively of chromosome 8 of hg 18. The mRNA sequence for human MYC and corresponding amino acid sequence are provided below as SEQ ID NOs: 43 and 44, respectively. Relapse specific mutations in MYC results in a threonine to proline substitution at an amino acid position corresponding to T58 of SEQ ID NO: 44 below or a threonine to asparagine substitution at an amino acid position corresponding to T58 of SEQ ID NO: 44. Exemplary mutations in MYC encoding these amino acid substitution comprise an A→C change at a nucleotide position corresponding to position 172 of SEQ ID NO: 43 and a C→A change at a nucleotide position corresponding to position 173 of SEQ ID NO: 43. Either one of these mutations alone is also considered predictive of relapse disease.

```
                                                          SEQ ID NO: 43
MYC Homo sapiens v-myc myelocytomatosis viral oncogene homolog
atgcccctca acgttagctt caccaacagg aactatgacc tcgactacga ctcggtgcag    60

ccgtatttct actgcgacga ggaggagaac ttctaccagc agcagcagca gagcgagctg   120

cagcccccgg cgcccagcga ggatatctgg aagaaattcg agctgctgcc caccccgccc   180

ctgtccccta gccgccgctc cgggctctgc tcgccctcct acgttgcggt cacacccttc   240

tcccttcggg gagacaacga cggcggtggc gggagcttct ccacggccga ccagctggag   300

atggtgaccg agctgctggg aggagacatg gtgaaccaga gtttcatctg cgacccggac   360

gacgagacct tcatcaaaaa catcatcatc caggactgta tgtggagcgg cttctcggcc   420

gccgccaagc tcgtctcaga gaagctggcc tcctaccagg ctgcgcgcaa agacagcggc   480

agcccgaacc ccgcccgcgg ccacagcgtc tgctccacct ccagcttgta cctgcaggat   540

ctgagcgccg ccgcctcaga gtgcatcgac ccctcggtgg tcttccccta ccctctcaac   600

gacagcagct cgcccaagtc ctgcgcctcg caagactcca gcgccttctc tccgtcctcg   660

gattctctgc tctcctcgac ggagtcctcc ccgcagggca gccccgagcc cctggtgctc   720

catgaggaga caccgcccac caccagcagc gactctgagg aggaacaaga agatgaggaa   780

gaaatcgatg ttgtttctgt ggaaaagagg caggctcctg gcaaaaggtc agagtctgga   840
```

-continued

```
tcaccttctg ctggaggcca cagcaaacct cctcacagcc cactggtcct caagaggtgc   900

cacgtctcca cacatcagca caactacgca gcgcctccct ccactcggaa ggactatcct   960

gctgccaaga gggtcaagtt ggacagtgtc agagtcctga gacagatcag caacaaccga  1020

aaatgcacca gccccaggtc ctcggacacc gaggagaatg tcaagaggcg aacacacaac  1080

gtcttggagc gccagaggag gaacgagcta aaacggagct tttttgccct gcgtgaccag  1140

atcccggagt tggaaaacaa tgaaaaggcc cccaaggtag ttatccttaa aaaagccaca  1200

gcatacatcc tgtccgtcca agcagaggag caaaagctca tttctgaaga ggacttgttg  1260

cggaaacgac gagaacagtt gaaacacaaa cttgaacagc tacggaactc ttgtgcgtaa  1320
```

SEQ ID NO: 44 v-myc myelocytomatosis viral oncogene homolog

```
Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
            180                 185                 190

Val Val Phe Pro Tyr Pro Leu Asn Asp Ser Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335
```

-continued

```
Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
435
```

As noted above, determining a subject's prognosis (i.e., a subject's risk of developing relapse leukemia) using the methods of the present invention will aid in optimizing the subject's ongoing course of treatment. Therefore, based on the determined prognosis, a suitable therapy can be administered to the subject. For example, when one or more of the above identified mutations is detected in a sample from the subject, that subject has an increased likelihood of developing relapse disease. Accordingly, a suitable therapeutic strategy for that subject involves a more aggressive approach to eradicating the disease, such as bone-marrow transplant in place of the common course of chemotherapy and/or radiotherapy. Alternatively, a suitable therapy involves administering a compound that remedies the protein dysfunction caused by the detected mutation. For example, in the early detection of one or more mutations in the NT5C2 gene, a suitable therapeutic is an agent that inhibits NT5C2 gene activity or NT5C2 encoded enzyme activity, i.e., cN-II enzyme activity, and/or an agent that selectively inhibits mutant NT5C2 gene activity or mutant NT5C2 encoded enzyme activity. Suitable NT5C2 gene inhibitors include inhibitory nucleic acid molecules, such as siRNA, shRNA, antisense molecules, microRNAs, as described in more detail infra. Suitable agents for inhibiting NT5C2 encoded enzyme activity, i.e., cN-II enzyme activity, include peptide and small molecule inhibitors. Exemplary cN-II inhibitors, which are described in more detail below, include for example, and without limitation, ribonucleoside 5'-monophosphate analogues (Gallier et al., "Structural Insights into the Inhibition of Cytosolic 5'-Nucleotidase II (cN-II) by Ribonucleoside 5'-Monophosphate Analogues," *PLOS Computational Biology* 7(12):1-14 (2011), which is hereby incorporated by reference in its entirety), and anthraquinone derivatives (Jordheim et al., "Identification and Characterization of Inhibitors of Cytoplasmic 5'Nucleotidase cN-II Issued from Virtual Screening," Biochem. Pharmacol. 85(4): 497-506 (2013), which is hereby incorporated by reference in its entirety).

Detecting the presence or absence of one or more mutations in the one or more above identified genes in a patient sample can be carried out using methods that are well known in the art. In one embodiment of the present invention, the one or more mutations in the one or more identified genes is detected using a hybridization assay. In a hybridization assay, the presence or absence of a gene mutation is determined based on the hybridization of one or more oligonucleotide probes to one or more nucleic acid molecules in a sample from the subject. The oligonucleotide probe or probes comprise a nucleotide sequence that is complementary to at least the region of the gene that contains the one or more above identified mutations. The oligonucleotide probes are designed to be complementary to the wildtype, non-mutant nucleotide sequence and/or the mutant nucleotide sequence of the one or more genes to effectuate the detection of the presence or the absence of the mutation in the sample from the subject upon contacting the sample with the oligonucleotide probes. A variety of hybridization assays that are known in the art are suitable for use in the methods of the present invention. These methods include, without limitation, direct hybridization assays, such as northern blot or Southern blot (see e.g., Ausabel et al., Current Protocols in Molecular Biology, John Wiley & Sons, NY (1991)). Alternatively, direct hybridization can be carried out using an array based method where a series of oligonucleotide probes designed to be complementary to a particular non-mutant or mutant gene region are affixed to a solid support. A labeled DNA or cDNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array.

Other common genotyping methods include, but are not limited to, restriction fragment length polymorphism assays; amplification based assays such as molecular beacon assays, nucleic acid arrays, allele-specific PCR; primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic Acids Res.* 36(12) e75 (2008), which is hereby incorporated by reference in its entirety), homogeneous primer extension assays, primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier M., "The Invader Assay for SNP Genotyping," *Mutat. Res.* 573 (1-2) 103-10 (2005), which is hereby incorporated by reference in its entirety); 5' nuclease assays, such as the TagMan® assay (see U.S. Pat. No. 5,210,015 to Gelfand et al. and U.S. Pat. No. 5,538,848 to Livak et al., which are hereby incorporated by reference in their entirety); and oligonucleotide ligation assays, such as ligation with rolling circle amplification, homogeneous ligation, OLA (see U.S. Pat. No. 4,988,617 to Landgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Alternatively, the presence or absence of one or more mutations identified supra can be detected by direct sequencing of the genes, or preferably particular gene regions comprising the one or more identified mutations, from the patient sample. Direct sequencing assays typically involve isolating DNA sample from the subject using any suitable method known in the art, and cloning the region of interest to be sequenced into a suitable vector for amplification by growth in a host cell (e.g. bacteria) or direct amplification by PCR or other amplification assay. Following amplification, the DNA can be sequenced using any suitable method. As described in the Examples herein, a preferable sequencing method involves high-throughput next generation sequencing (NGS) to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing, which are well known to those of skill in the art, can be used to carry out the methods of the present invention.

Another aspect of the present invention relates to a method of treating a subject having leukemia. This method involves selecting a subject having leukemia and one or more mutations in one or more genes selected from the group consisting of NT5C2, RGS12, LPHN1, CAND1, PRMT2, NIPSNAP1, USP7, TULP4, CBX3, COBRA1, SDF2, FBXO3, SCARF1, NEGR1, DPH5, SMEK2, MIER3, DOPEY1, ZNF192, EVI2A, GSPT2, and MYC, and administering a therapy suitable for treating relapse leukemia to the selected subject.

The particular mutations in the one or more genes and methods of detecting these mutations are described supra.

In one embodiment of this aspect of the present invention, the subject having leukemia is undergoing treatment for leukemia at the time the one or more mutation in the one or more genes is detected. Following detection of the one or more mutations, the subject's therapy is modified to implement a more aggressive treatment that is suitable for treating relapse leukemia, such as bone-marrow transplant. Alternatively, if none of the above identified mutations are detected in a sample from the subject, the subject's therapy may be maintained or modified in a manner consistent with the absence of the one or more mutations and decreased chance of developing relapse disease.

In another embodiment of this aspect of the present invention, the subject having leukemia is not undergoing treatment for leukemia at the time the one or more mutations in the one or more gene is detected, i.e., the gene mutation(s) are detected at the time of diagnosis. In accordance with this embodiment, a preferable course of treatment is an aggressive form of treatment, such as e.g., a bone-marrow transplant.

Another aspect of the present invention is directed to a method of preventing or treating relapsed leukemia in a subject. This method involves selecting a subject having one or more NT5C2 gene mutations and administering to the selected subject an agent that inhibits NT5C2 gene expression and/or NT5C2 encoded enzyme activity, i.e., cytosolic 5'nucleotidase (cN-II) enzyme activity, under conditions effective to prevent or treat the relapsed leukemia in the subject.

Suitable subjects for treatment in accordance with this method of the present invention include, without limitation, subjects having acute lymphoblastic leukemia, specifically, B-cell acute lymphoblastic leukemia or T-cell acute lymphoblastic leukemia.

Mutations in the NT5C2 gene associated with relapsed leukemia include those described supra. As described herein, these relapse specific mutations in NT5C2 have been mapped and found to cluster in a region on the encoded cytosolic 5'nucleotidase (cN-II) enzyme involved in subunit association/disassociation. These mutations are predicted to alter cN-II enzyme activity rather than completely disrupt activity. Accordingly, in one embodiment of the present invention, the agent administered to the subject to prevent or treat relapsed leukemia in the subject inhibits the expression of a mutant NT52C gene and/or mutant NT5C2 encoded enzyme activity, i.e., the activity of the cN-II protein containing one or more amino acid substitutions. cN-II proteins suitable for inhibition include any of those encoded by the one or more mutant NT52C genes identified supra. In another embodiment of the present invention, the administered agent inhibits the expression of the mutant NT52C gene and/or the enzyme activity encoded by the mutant NT52C gene, but not the expression of the wildtype (i.e., normal) NT52C gene or the activity of the corresponding normal cN-II protein.

Suitable inhibitors of cN-II that can be administered to a subject having leukemia in accordance with the methods of the present invention include ribonucleoside 5'monophosphate analogues such as those described by Gallier et al., "Structural Insights into the Inhibition of Cytosolic 5'Nucleotidase II (cN-II) by Ribonucleoside 5'-Monophosphate Analogues," *PLOS Comp. Biol.* 7(12):e1002295 (2011), which is hereby incorporated by reference in its entirety). The ribonucleoside phosphonates act as bioisosteric analogues of the natural cN-II substrate and contain a chemically and enzymatically stable phosphorus-carbon linkage. The β-hydroxyphosphonate nucleosides (i.e., those possessing a hydroxyl group in the β-position at the 5' carbon of the ribose moiety) are particularly effective cN-II inhibitors. In particular uridine-, cytosine-, hypoxanthine-, and adenine-5'β-hydroxyphosphonate nucleoside analogs are powerful inhibitors of cN-II that can be administered to a subject having leukemia to prevent or treat relapse leukemia.

Another suitable nucleoside analogue cN-II inhibitor is fludarabine (9-β-D-arabinosyl-2-fluoroadenine monophosphate). Fludarabine was originally characterized as a substrate for cN-II (Jordheim et al., "F-ara-AMP is a Substrate of Cytoplasmic 5'Nucleotidase II (cN-II): HPLC and NMR Studies of Enzymatic Dephosphorylation," *Nucleosides, Nucleotides, and Nucleic Acids* 25:289-297 (2006), which is hereby incorporated by reference in its entirety); however, at high concentrations F-ara-AMP is a strong inhibitor of cN-II activity.

Other suitable inhibitors of cN-II activity include anthraquinone derivatives, such as anthraquinone-2,6-disulfonic acid (AdiS), 3-(2-Pyridyl)-5,6-diphenyl-1,2,4-triazine-p,p'-disulfonic acid (PDTdiS), and 7-amino-1,3-naphthalene disulfonic acid (ANdiS) as disclosed by Jordheim et al., "Identification and Characterization of Inhibitors of Cytoplasmic 5'Nucleotidase cN-II Issued from Virtual Screening," *Biochem. Pharmacol.* 85(4): 497-506 (2013), which is hereby incorporated by reference in its entirety.

Other suitable inhibitors of cN-II activity include nucleic acid inhibitors of NT5C2 gene expression, such as e.g., siRNA, shRNA, antisense molecules, microRNAs, etc.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense nucleic acid molecule hybridizes to its corresponding target NT5C2 nucleic acid molecule to form a double-stranded molecule, which interferes with translation of the mRNA, as the cell will not translate a double-stranded mRNA. Antisense nucleic acids suitable for use in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the NT5C2 mRNA molecule (i.e., SEQ ID NO: 1). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Suitable NT5C2 siRNA inhibitors are described by Kulkarni et al., "Suppression of 5'Nucleotidase Enzymes Promote AMP-Activated Protein Kinase (AMPK) Phosphorylation and Metabolism in Human and Mouse Skeletal Muscle," *J. Biol. Chem.* 286(40): 34567-74 (2011), which is hereby incorporated by reference in its entirety. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; and WO1998/39352 to Imanishi et al.; U.S. Patent Application Publication No. 2002/0068708 to Jesper et al.; U.S. Patent Application Publication No. 2002/0147332 to Kaneko et al; and U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. Suitable shRNA NT5C2 inhibitors are described by Careddu et al., "Knockdown of Cytosolic 5'Nucleotidase II (cN-II) Reveals that its Activity is Essential for Survival in Astrocytoma Cells," *Biochim. Biophys. Acta* 1783:1529-35 (2008), which is hereby incorporated by reference in its entirety.

In accordance with this aspect of the invention, NT5C2 or cN-II modulating agents, e g., inhibitors, can be administered to a subject alone or in combination with one or more other anti-leukemia therapies, such as chemotherapy, e.g., predinisolone, dexamethasone, cincristine, asparaginase, daunorubicin, cyclophosphamide, cytarabine, etoposide, thioguanine, mercaptopurine, methotrexate, or radiotherapy, e.g., external beam radiation therapy or brachytherapy.

In accordance with the methods of the present invention, the mode of administering therapeutic agents of the present invention (i.e., NT5C2 or cN-II modulating agents), including the use of suitable delivery vehicles, to a subject at risk of developing relapse disease or having relapse disease will vary depending on the type of therapeutic agent (e.g., nucleic acid molecule, ribonucleoside analogue, or small molecule). For example, ribonucleoside analogues and small molecule inhibitors can be administered directly, preferably systemically. In contrast, inhibitory NT5C2 nucleic acid molecules (i.e., antisense, siRNA, etc.), may be incorporated into a gene therapy vector to facilitate delivery. Suitable gene therapy vectors include, without limitation, adenovirus, adeno-associated virus, retrovirus, lentivirus, or herpes virus.

Adenoviral viral vector gene delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral vector vehicles can be constructed and used to deliver inhibitory nucleic acid molecules as described by Chatterjee et al., "Dual-Target Inhibition of HIV-1 In Vitro by Means of an Adeno-Associated Virus Antisense Vector," Science 258: 1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-Associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver inhibitory nucleic acid molecules to a target cell. One such type of retroviral vector is disclosed in U.S. Pat. No. 5,849,586 to Kriegler et al., which is hereby incorporated by reference.

Gene therapy vectors carrying the therapeutic nucleic acid molecule are administered to a subject by, for example, intravenous injection or local administration (U.S. Pat. No. 5,328,470 to Nabel et al., which is hereby incorporated by reference in its entirety). The pharmaceutical preparation of the vector can include the vector in an acceptable diluent, or can comprise a slow release matrix in which the vector delivery vehicle is imbedded. Alternatively, where the complete delivery vector can be produced intact from recombinant cells, e.g., retroviral vectors, the pharmaceutical preparation can include one or more cells which produce the gene delivery system.

The therapeutic agents of the present invention (i.e., NT5C2 or cN-II modulating agents) can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, intranasal drops). Typically, parenteral administration is the preferred mode of administration.

Therapeutic agents of the present invention are formulated in accordance with their mode of administration. For oral administration, for example, the therapeutic agents of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: *Enzymes as Drugs*, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The therapeutic agents of the present invention may also be delivered systemically, formulated for parenteral administration by injection, e.g., by bolus injection or continuous infusion. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. In all cases, the form must be sterile and must be fluid to the extent that easy syringability exists. It must be stable under the conditions of manufacture and storage and must be preserved against the contaminating action of microorganisms, such as bacteria and fungi.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents of the present invention, for the prevention or treatment of relapse leukemia vary depending upon many different factors, including type and stage of leukemia, mode of administration, target site, physiological state of the patient, other medications or therapies administered, and physical state of the patient relative to other medical complications. Treatment dosages need to be titrated to optimize safety and efficacy.

EXAMPLES

The following examples are provided to illustrate embodiments of the present invention but they are by no means intended to limit its scope Materials and Methods for Examples 1-5

Patient Samples and Sequencing.

Cryopreserved matched pairs of pediatric B lymphoblastic leukemia marrow specimens from diagnosis and relapse were obtained from the Children's Oncology Group (COG) ALL cell bank from ten patients from trials: AALL0232, AALL0331, and COG 9906 (ClinicalTrials.gov: NCT00075725, NCT00103285, NCT00005603 respectively). Patient characteristics are summarized in Table 1. All specimens were Ficoll-enriched prior to cryopreservation and contained >80% blasts measured by flow cytometry.

Time to relapse was calculated from the initial diagnosis date. Samples were chosen based on bone marrow blast percentage at the time of banking submission, as well as by Affymetrix SNP6.0 chip. All samples with less than 20% disparity between the two methods and with >80% blasts in both diagnosis and relapse samples were considered for sequencing.

TABLE 1

Patient Characteristics

| Patient | Gender | Race | Time to Relapse (years) | Age at Diagnosis (years) | Cytogenetics |
|---|---|---|---|---|---|
| 1 | Male | White | 3.8 | 16.0 | Normal |
| 2 | Male | White | 4.3 | 15.8 | Normal |
| 3 | Female | White | 3.1 | 14.3 | Normal |
| 4 | Male | White | 2.6 | 6.0 | Hyperdiploid |
| 5 | Female | Asian | 3.2 | 17.0 | Normal |
| 6 | Female | Unknown | 1.5 | 7.3 | Normal |
| 7 | Male | White | 2.1 | 1.9 | TEL-AML |
| 8 | Male | Unknown | 1.0 | 18.0 | Normal |
| 9 | Female | White | 3.6 | 13.0 | Hyperdiploid |
| 10 | Male | White | 0.6 | 16.0 | Normal |

RNA Sequencing and Analysis.

RNA was extracted from diagnosis and relapse bone marrow samples using RNeasy Mini Kits (Qiagen) and quality verified by an Agilent Bioanalyzer 2100 (Agilent Technologies). Libraries were prepared according to Illumina's mRNA-Seq Sample Prep kit protocol using 1 μg of total cellular RNA. Single end (n=12) and paired end (n=8) 200 base pair and 300 base pair, respectively, cDNA libraries were purified and reamplified by PCR according to protocol. Final cDNA libraries were evaluated for fragment size distribution by 2100 Agilent Bioanalyzer (DNA 1000 chip) and quantified by Quanti-IT Picogreen dsDNA Assay kit (Invitrogen). All libraries were sequenced using 54 base pair reads on the Illumina Genome Analyzer GAIIx. Image collection and analysis was completed using the Illumina CASAVA pipeline. Reads in raw FASTQ files were aligned to the human reference genome (hg18) using the Burroughs-Wheeler Aligner (v0.5.8a) (Li & Durbin, "Fast and Accurate Short Read Alignment with Burrows-Wheeler Transform," *Bioinformatics* 25:1754-60 (2009), which is hereby incorporated by reference in its entirety) allowing up to two mismatches. Data have been deposited at the NCBI Sequence Read Archive (SRA048657). Mapped reads in the raw BAM files were then recalibrated and locally realigned to call single nucleotide variants (SNVs) and insertion/deletions (Indels) using the Genome Analysis Toolkit (GATK) (McKenna et al., "The Genome Analysis Toolkit: a MapReduce Framework for Analyzing Next-Generation DNA Sequencing Data," *Genome Res.* 20:1297-303 (2010), which is hereby incorporated by reference in its entirety). After removing duplicate reads, only those reads with mapping qualities Q≥30 were used to predict SNVs and indels, again using GATK (DePristo et al., "A Framework for Variation Discovery and Genotyping Using Next-Generation DNA Sequencing Data," *Nat. Genet.* 43:491-8 (2011), which is hereby incorporated by reference in its entirety). Data was subjected to a set of post processing filters: i) a minimum of ≥8× coverage per variant site; ii) reads supporting the variant in ≥20% of the total reads per site; iii) bidirectional sequence support of variant reads; iv) no more than 1 variant within 5 bp distance; v) minimum of 8× wild type (WT) coverage at the corresponding site in the paired diagnosis sample. Variants were filtered for known SNPs from the most current dbSNP database, dbSNP 135, and 1000 Genomes Project (1000 Genomes Project Consortium "A Map of Human Genome Variation From Population-Scale Sequencing," *Nature* 467:1061-73 (2010), which is hereby incorporated by reference in its entirety). Finally, only those variants present in genes with the most conservative annotation by RefSeq were considered (removal of all XM_annotations). All predicted variants were then manually inspected on the paired BAM files using the Integrative Genomics Viewer (IGV) (Robinson et al., "Integrative Genomics Viewer," *Nat Biotechnol* 29:24-6 (2011), which is hereby incorporated by reference in its entirety). SNVs were compared to COSMIC v55 database (Forbes et al., "COSMIC: Mining Complete Cancer Genomes in the Catalogue of Somatic Mutations in Cancer," *Nucleic Acids Res.* 39:D945-D950 (2011), which is hereby incorporated by reference in its entirety), and processed using PolyPhen-2 prediction program and SIFT (Adzhubei et al., "A Method and Server for Predicting Damaging Missense Mutations," *Nat. Methods* 7:248-9 (2010) and Kumar et al., "Predicting the Effects of Coding Non-Synonymous Variants on Protein Function Using the SIFT Algorithm," *Nat. Protocols* 4:1073-81 (2009), which are hereby incorporated by reference in their entirety). A schematic of the filtering process for SNV detection is outlined in FIG. 1. A schematic for indel detection is outlined in FIG. 2.

To predict variants that showed a clonal expansion at relapse: each site was required to have ≥40× coverage at diagnosis and all SNVs to be present in ≥5% of the total reads. In the matched relapse sample, SNVs were required to have ≥8× reads and show a 40% change in the number of total reads per mutation site to preferentially discover those mutations that became the predominate clone as relapse (>45% of total reads per site).

Figure 3:
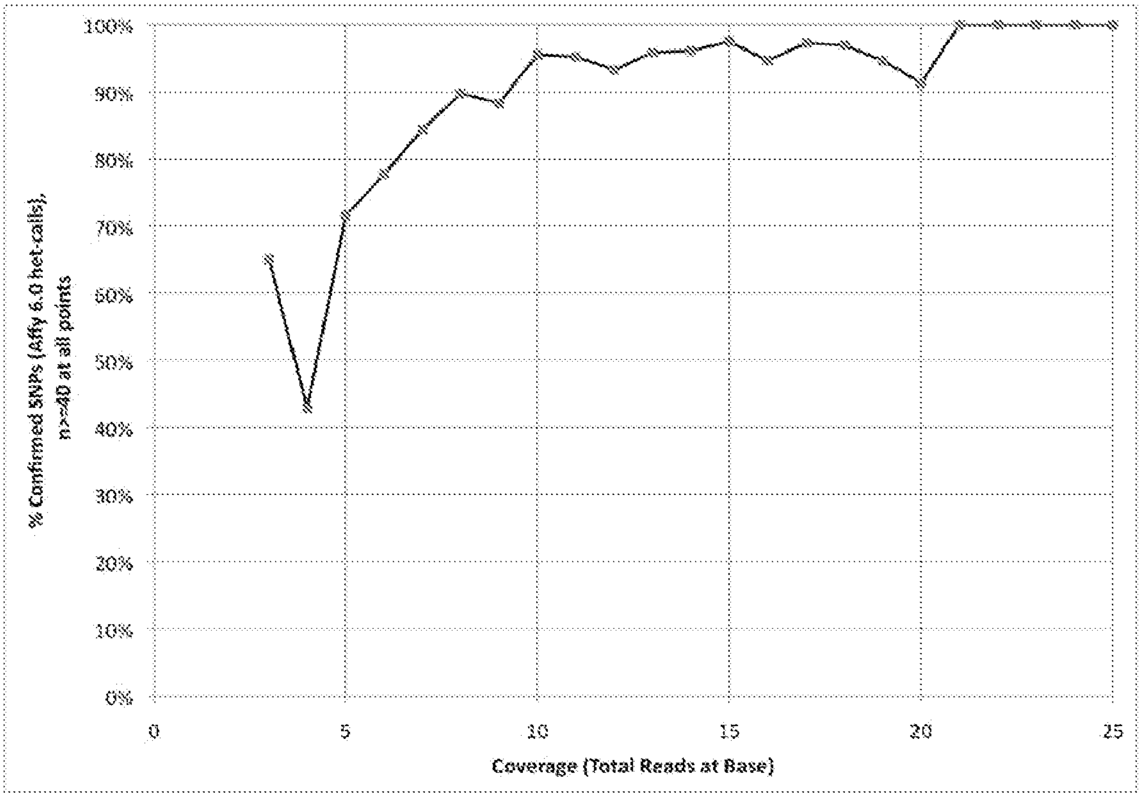
FIG. 3 is a chart showing the concordance of heterozygous SNP calls. Confirmation rate of genotype calls to heterozygous SNPs called from Affymetrix 6.0 Genotyping arrays. A very high concordance was seen at 8× coverage, and >90% concordance with any site beyond 10× coverage.

Correlation between sequencing sites was determined by log 2 expression counts comparing the same sample sequenced at both institutions (Pearson correlation=0.902). Each sample was sequenced in 7 lanes (single end libraries) or 2 lanes (pair-end libraries) using 54 base pair sequencing. After applying the default filter for clusters that pass filter (PF) and removing duplicate reads, an average of 84 million high-quality reads per sample were obtained (Tables 2 and 3, below). Sequencing data was compared to previously called heterozygous single nucleotide polymorphisms (SNP) from Affymetrix 6.0 genotyping arrays, and 90% concordance was observed at 8× coverage and 96% concordance at 10× coverage (FIG. 3) (Hogan et al., "Integrated Genomic Analysis of Relapsed Childhood Acute Lymphoblastic Leukemia Reveals Therapeutic Strategies," *Blood* 118(19): 5218-26 (2011), which is hereby incorporated by reference in its entirety).

TABLE 2

| Summary of Library Sequencing | | |
|---|---|---|
| | Total | Average per Sample |
| Reads Passed Filter | 1,890,814,154 | 94,540,708 |
| Aligned Reads | 1,689,615,798 | 84,480,790 |
| Gene Coverage (of 29,427 genes) | | |
| 1X | 82% | (16,289) 70% |
| 8X | 51% | (11,528) 40% |
| 10X | 47% | (11,060) 38% |
| 20X | 28% | (5,468) 19% |
| 30X | 21% | (2,634) 9% |

Total column show genome coverage for all patients. Number of genes covered is based on reads aligned to human genome build hg18.

TABLE 3

Sequencing Summary per Sample Aligned to hg18

| Sample | Total Reads | Aligned Reads | % of Aligned Reads out of Total Reads |
|---|---|---|---|
| 1D | 114566026 | 104490537 | 91.21% |
| 1R | 119356414 | 106772001 | 89.46% |
| 2D | 67429232 | 62085952 | 92.08% |
| 2R | 66728602 | 58226811 | 87.26% |
| 3D | 75758846 | 66223741 | 87.41% |
| 3R | 66918290 | 58228949 | 87.01% |
| 4D | 108777132 | 98851362 | 90.88% |
| 4R | 86243015 | 78183686 | 90.66% |
| 5D | 102775901 | 92965927 | 90.45% |
| 5R | 102584737 | 92264090 | 89.94% |
| 6D | 85074576 | 74243617 | 87.27% |
| 6R | 88044774 | 76752180 | 87.17% |

TABLE 3-continued

Sequencing Summary per Sample Aligned to hg18

| Sample | Total Reads | Aligned Reads | % of Aligned Reads out of Total Reads |
|---|---|---|---|
| 7D | 72799452 | 64993143 | 89.28% |
| 7R | 85248846 | 73220499 | 85.89% |
| 8D | 108892892 | 97289998 | 89.34% |
| 8R | 100726420 | 94737031 | 90.08% |
| 9D | 109094096 | 99011101 | 90.76% |
| 9R | 107347885 | 94415898 | 87.95% |
| 10D | 117280311 | 105413909 | 89.88% |
| 10R | 105166707 | 91245366 | 90.59% |

Fusion Detection.

Paired end data (n=8) was processed using an in-house pipeline BEGAT. Results were filtered to remove candidates that: i) were covered by fewer than 8 reads; ii) were in a region less than 10 Kb away from each other; iii) represented mapping errors between gene iosformal and paralogs as determined with a homologous gene filter; and iv) were fusions that mapped to repetitive regions.

Validation.

Variant validation was completed in eight out of ten discovery specimens, for which matched germline, diagnosis, remission, and relapse genomic DNA were available. Primers were designed within 400 base pairs of the variant site and amplified by PCR. PCR products were sequenced using Sanger sequencing and trace files were manually inspected for variation from the reference genome using the Mutation Surveyor program (Softgenetics). All validated mutations were reconfirmed with a second PCR and Sanger reaction. Full exon sequencing of NT5C2 was completed by Sanger sequencing using exon specific primers (Genewiz Inc.). NT5C2 sequencing primers are provided below.

| Exon | Forward Primer | Sequence 5' to 3' | Reverse Primer | Sequence 5' to 3' |
|---|---|---|---|---|
| 1 | NT5C2-1F | TTATCTTTCCGGATTGAAATTACC (SEQ ID NO: 45) | NT5C2-1R | CCATGTACTAGACATACGATCTGGG (SEQ ID NO: 46) |
| 2 | NT5C2-2F | AAGGTAACTGTATGGGATAATGGG (SEQ ID NO: 47) | NT5C2-2R | AATTGAATTGCCTACTGTGAACC (SEQ ID NO: 48) |
| 3 | NT5C2-3F | ACAGAACATGGAGTTTGAGGG (SEQ ID NO: 49) | NT5C2-3R | AAGTGGGTCTTCCTCAGTTGC (SEQ ID NO: 50) |
| 4 | NT5C2-4F | ACAAAGCTTGAATTAAATGAGGTTG (SEQ ID NO: 51) | NT5C2-4R | AACTAACCTTATGTAAGGGAATTTGC (SEQ ID NO: 52) |
| 5 | NT5C2-5F | TTCTGTCTTGCACATAGCCATC (SEQ ID NO: 53) | NT5C2-5R | ACTAGGCAGGCCAACAGGTAG (SEQ ID NO: 54) |
| 6 | NT5C2-6F | ACTGATGCTTTCCCTTCTGTG (SEQ ID NO: 55) | NT5C2-6R | CTGGTGCTGTCCCATCTCTC (SEQ ID NO: 56) |
| 7 | NT5C2-7F | AGCCATTTCTGGTGGTCAAAG (SEQ ID NO: 57) | NT5C2-7R | TTGGAAAGTTAATGCCACGC (SEQ ID NO: 58) |
| 8 | NT5C2-8F | ACTCTAGCATGGGCAACAGG (SEQ ID NO: 59) | NT5C2-8R | CCCGACACATACTATGCCAAG (SEQ ID NO: 60) |

-continued

| Exon | Forward Primer | Sequence 5' to 3' | Reverse Primer | Sequence 5' to 3' |
|---|---|---|---|---|
| 9 | NT5C2-9F | TCCTGTTGTGGACAGAAATCC (SEQ ID NO: 61) | NT5C2-9R | AAATTTGAGAACCACTGTTATCCTG (SEQ ID NO: 62) |
| 10 | NT5C2-10F | TAATTTCTGGCTTCCACTGCC (SEQ ID NO: 63) | NT5C2-10R | GGTTCTGACCAATTCTTTCCC (SEQ ID NO: 64) |
| 11 | NT5C2-11F | TGTGCCTGGCTGACACAATAC (SEQ ID NO: 65) | NT5C2-11R | GCCAAATGAATGGCACTTACTC (SEQ ID NO: 66) |
| 12 | NT5C2-12F | CTGTCTGGCCAAGTAGCACTG (SEQ ID NO: 67) | NT5C2-12R | AACTGCTCAAACCCAGACTCC (SEQ ID NO: 68) |
| 13 | NT5C2-13F | GTCAGCACAGTGGAGCTGAAG (SEQ ID NO: 69) | NT5C2-13R | TTGACCACCTCTGACTTCCTG (SEQ ID NO: 70) |
| 14 | NT5C2-14F | TGTTGTCAGACTCCAAGCAGG (SEQ ID NO: 71) | NT5C2-14R | GGGATTACTGGCCTGGAAAG (SEQ ID NO: 72) |
| 15 | NT5C2-15F | GCTAATTAGGGTGGCTGAGGC (SEQ ID NO: 73) | NT5C2-15R<br>NT5C2-16R | AAACAGGCTTCCCATCATCC (SEQ ID NO: 74) |
| 16 | NT5C2-16F | CGTCCAGACATCAGTTCCATC (SEQ ID NO: 75) | NT5C2-17R | GTGCCATCTCACAAAGGTGG (SEQ ID NO: 76) |
| 17 | NT5C2-17F | AGATGTAATTGCATGGCCACC (SEQ ID NO: 77) | | AGGGACCTCGTTTGTTCCTG (SEQ ID NO: 78) |

Roche 454 Amplicon Sequencing.

Targeted amplicon sequencing was performed using the Roche 454 Genome Sequencer FLX+ deep sequencing platform. PCR amplicons spanning the mutated sites were tagged using Roche 454 adaptor-multiplex identifier (MID) tags primer sets and added to PCR primers designed for bidirectional sequencing. Amplicons were then purified with AMPure XP beads (Beckman Coulter) to remove excess primer and quantified by fluorometry using the Quant-iT PicoGreen dsDNA Assay kit. A titration test was performed on the amplicon libraries using a low-volume emulsion PCR amplicon kit according to the Roche 454 protocol, which was followed by emulsion-based clonal amplification (emPCR amplification; Lib-A). Libraries were sequenced on the Roche 454 Genome Sequencer FLX+sequencing system (454 Life Sciences) at ultra-deep coverage (17,000-50,000×) using a two-region 70-mm×75-mm Titanium PicoTiterPlate, and mutation analysis was performed using the Roche 454 Amplicon Variant Analyzer package.

Mutation Modeling.

Molecular graphics of NT5C2 were rendered with ICM-Pro (Molsoft, LLC). Molecular surface rendering and exact-boundary electrostatic mapping onto that surface were calculated as previously described (Totrov & Abagyan, "The Contour-Buildup Algorithm to Calculate the Analytical Molecular Surface," *J. Struct. Biol.* 116:138-43 (1996) and Totrov & Abagyan, "Rapid Boundary Element Solvation Electrostatics Calculations in Folding Simulations: Successful Folding of a 23-Residue Peptide," *Biopolymers* 60:124-33 (2001), which are hereby incorporated by reference in their entirety).

cN-II Protein Expression and 5'-Nucleotidase Assay.

Full-length NT5C2 cDNA for wild-type and mutant (Arg238Trp, Arg367Gln and Ser445Phe) (purchased from Genewiz) was cloned into the pET30a expression vector using NdeI and HindIII restriction sites. pET30a expression vectors were transformed into BL21 DE3 pLysS chemically competent *E. coli* (Invitrogen). NT5C2 expression was induced using 1 mM IPTG with 5 h of incubation at 37° C. Cells were pelleted at 8,000 g for 2 min at 4° C. and resuspended in lysis buffer (50 mM NaH2PO4, 300 mM NaCl and 10 mM imidazole) with 1× protease inhibitors (GE Healthcare). Lysozyme (1 mg/ml) was added, and samples were incubated on ice for 30 min. Lysates were centrifuged at 15,000 g for 10 min at 4° C. Protein was subjected to electrophoresis on 9% SDS-Tris acrylamide gels and transferred to PVDF membranes. Membranes were incubated with a 1:5,000 dilution of rabbit polyclonal antibody to cN-II (ab96084, Abcam), incubated with a 1:10,000 dilution of horseradish peroxidase (HRP)-conjugated secondary antibody to rabbit (GE Healthcare) and developed using enhanced chemiluminescence (ECL; GE Healthcare). Purified protein extract (10 ml) was used to assess the enzymatic activity of wild-type and mutant proteins using the 5'-Nucleotidase Enzymatic Test kit (Diazyme) according to the provided protocol. Data are represented as the mean±s.d. from three independent experiments.

Cell Culture and Drug Treatment.

Reh cells obtained from the American Type Culture Collection (ATCC) were grown in RPMI1640 supplemented with 10% FBS, 10 mM HEPES and 1% penicillin-streptomycin under 5% $CO_2$ at 37° C. 293T cells (ATCC) were grown in DMEM supplemented with 10% FBS and 1% penicillin-streptomycin under 5% $CO_2$ at 37° C. 6-mercaptopurine, 6-thioguanine, cytarabine, doxorubicin, gemcitabine and prednisolone (Sigma) were serially diluted in RPMI before use at the indicated concentrations.

Transient Transfection and Lentivirus Gene Transfer.

NT5C2 DNA for wild-type and mutant (Arg238Trp, Arg367Gln and Ser445Phe) was cloned into the lentiviral vector pLenti using SalI and XbaI restriction sites. All plasmids were sequence verified. cDNA constructs were transfected into 293T cells along with helper plasmids using the calcium phosphate method to produce replication-defective virus. Supernatant was harvested 48 h later and used to transduce Reh cells (whose NT5C2 sequence was verified as wild type) supplemented with 8 mg/ml polybrene (Sigma). Virus-containing medium was replaced 24 h after infection. Cells were monitored 72 h after infection for infection efficiency by the detection of GFP-positive cells using a FACScan (BD). Infected cells were plated (200,000 cells per well in 200 ml of medium) in triplicate for drug treatment with 6-mercaptopurine, 6-thioguanine, cytarabine, doxorubicin, gemcitabine and prednisolone (Sigma). Cells were incubated for 24-72 h and then assayed for apoptosis by Annexin V-PE and 7-AAD staining (Annexin V-PE Apoptosis Detection kit, BD Pharmingen) followed by flow cytometry analysis using a FACScan. The percentages of cells positive and negative for Annexin V and/or 7-AAD staining were analyzed with FlowJo software (version 7.6.1, Tree Star). Data were plotted relative to results obtained with no chemotherapy treatment, and error bars represent the standard deviation from three independent determinations. Cells ($1\times10^6$) were harvested for protein at the time of plating. Briefly, cells were pelleted at 200 g for 5 min and resuspended in 100 ml of RIPA buffer with 1× protease inhibitors (GE Healthcare), incubated on ice for 15 min and centrifuged at 15,000 g for 10 min at 4° C. Protein was subjected to electrophoresis on 9% SDS-Tris acrylamide gels and transferred to PVDF membranes. Membranes were incubated with a 1:5,000 dilution of antibody to Flag (F3165, Sigma), incubated with a 1:10,000 dilution of HRP-conjugated secondary antibody to mouse (GE Healthcare) and developed using ECL (GE Healthcare).

HPLC Determination of Nucleotides.

Reh cells were transiently infected with NT5C2 constructs. After infection, cells were treated with 10 mM 6-mercaptopurine for 24 h in duplicate. After 24 h, $5\times10^6$ cells were washed twice with PBS, and cell pellets were frozen at −80° C. Intraceullar accumulation of thioguanine nucleotides (6-mercaptopurine active metabolites) was determined by a reversed-phase liquid chromatography assay as described previously (Dervieux et al., "HPLC Determination of Thiopurine Nucleosides and Nucleotides In Vivo in Lymphoblasts Following Mercaptopurine Therapy," *Clin. Chem.* 48: 61-68 (2002), which is hereby incorporated by reference in its entirety).

Statistical Analysis.

Statistical analysis of enzymatic and chemoresistance assays was performed using the two-sided unpaired Student's t test. Statistical analysis of the clinical and biological characteristics of study subjects with NT5C2 mutations was performed using Fisher's exact test. $P<0.05$ was considered to be statistically significant.

Example 1—Indel Analysis

Figure 2:
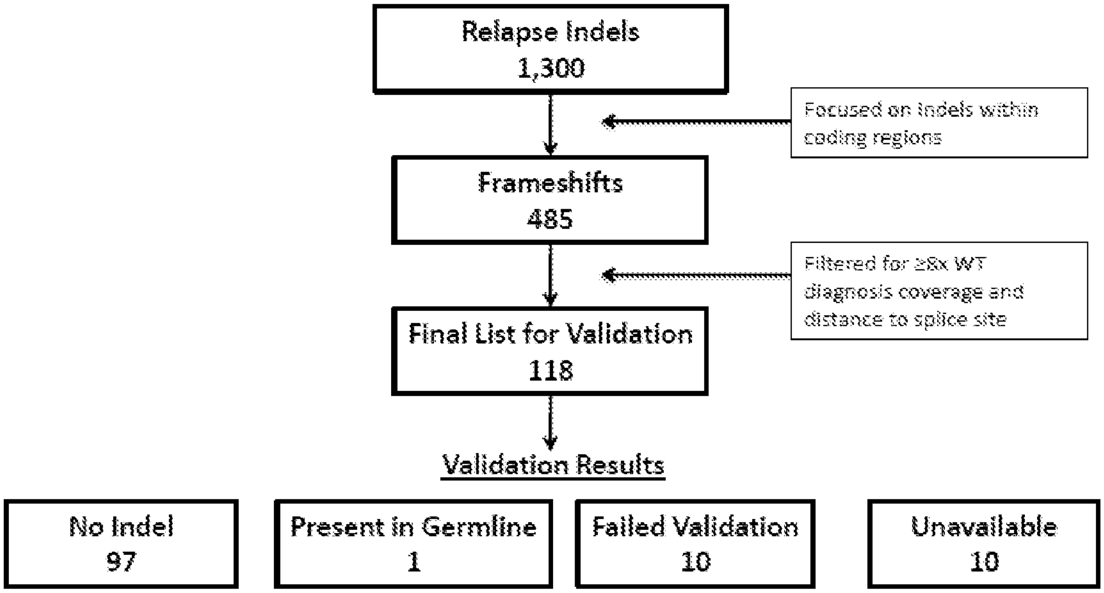
FIG. 2 is flow diagram showing the prioritization scheme for validation of relapse specific indels.

In total 1,300 insertion/deletions were predicted to be relapse specific (FIG. 2). Filtering for those that were located in coding regions and caused frameshifts resulted in 485 that were then subjected to manual review using IGV to view BAM alignment files for WT diagnosis coverage. Of these, 118 were determined to have at ≥8×WT coverage in the corresponding diagnosis sample. Based on sample availability, 108 indels were sent for validation from germline, diagnosis, and relapse genomic DNA based on sample availability. After validation by Sanger Sequencing, 97 sites examined had WT sequence and one site was validated as a private SNP.

Example 2—Fusion Detection

To explore for the potential of new fusion genes within the samples, all paired end sample data was processed using an in-house pipeline. The fusion prediction software generated a list of candidates that were then filter based on the following criteria: i) coverage, ii) region size, iii) homologous gene filter, and iv) genome location and repetitive regions. To determine the likelihood of filtering for true fusion genes versus mapping errors, one patient previously identified with the known fusion gene, ETV6-RUNX1 was included. After processing all four pairs and considering all criteria in the filtering process, the only fusion candidate that remained was the previously identified ETV6-RUNX1 fusion.

Example 3—Mutation Prediction and Validation

B lymphoblastic leukemia patient specimens (Table 1) subjected to next-generation transcriptome sequencing generated an average of 84 million reads per specimen (Tables 2 and 3) and showed very strong correlation (>90% genotype concordance for >8× coverage) to previously analyzed heterozygous SNP calls from Affymetrix SNP 6.0 arrays of the same specimens (FIG. 3) (Hogan et al., "Integrated Genomic Analysis of Relapsed Childhood Acute Lymphoblastic Leukemia Reveals Therapeutic Strategies," *Blood* 118(19):5218-26 (2011), which is hereby incorporated by reference in its entirety). Reads were mapped to human reference genome sequence (hg18) and variants were predicted. To preferentially discover genome-wide somatic changes that evolved during therapy that were associated with relapsed disease, events that occurred specifically at relapse compared to diagnosis were focused on. All variants were required to have ≥8× coverage, reads supporting the lesion in both sequencing directions, and be present in at least 20% or more of the reads at relapse. All relapse specific variants were then cross-referenced against the human SNP database, dbSNP135, and against those events that were identified in the 1000 Genomes project (1000 Genomes Project Consortium, "A Map of Human Genome Variation From Population-Scale Sequencing," *Nature* 467:1061-73 (2010), which is hereby incorporated by reference in its entirety). To further narrow the list, those events resulting in non-synonymous substitutions or frameshifts were chosen for further analysis. Also, to reduce false positive events including private SNPs, each site was required to have a minimum of ≥8× wild type coverage in the corresponding diagnosis specimen, with no evidence of an alternative allele (FIG. 1 and FIG. 2). Based on this filtering process 55 putative non-synonymous relapse-specific SNVs in 10 paired specimens were identified. In total, 50 variants were subjected to validation by Sanger sequencing from corresponding germline, diagnosis, and relapse genomic DNA specimens based on specimen availability.

Twenty missense mutations were validated that were specifically found in the relapse specimens, but absent from both germline and diagnosis DNA (see Table 4 below).

Figure 4:
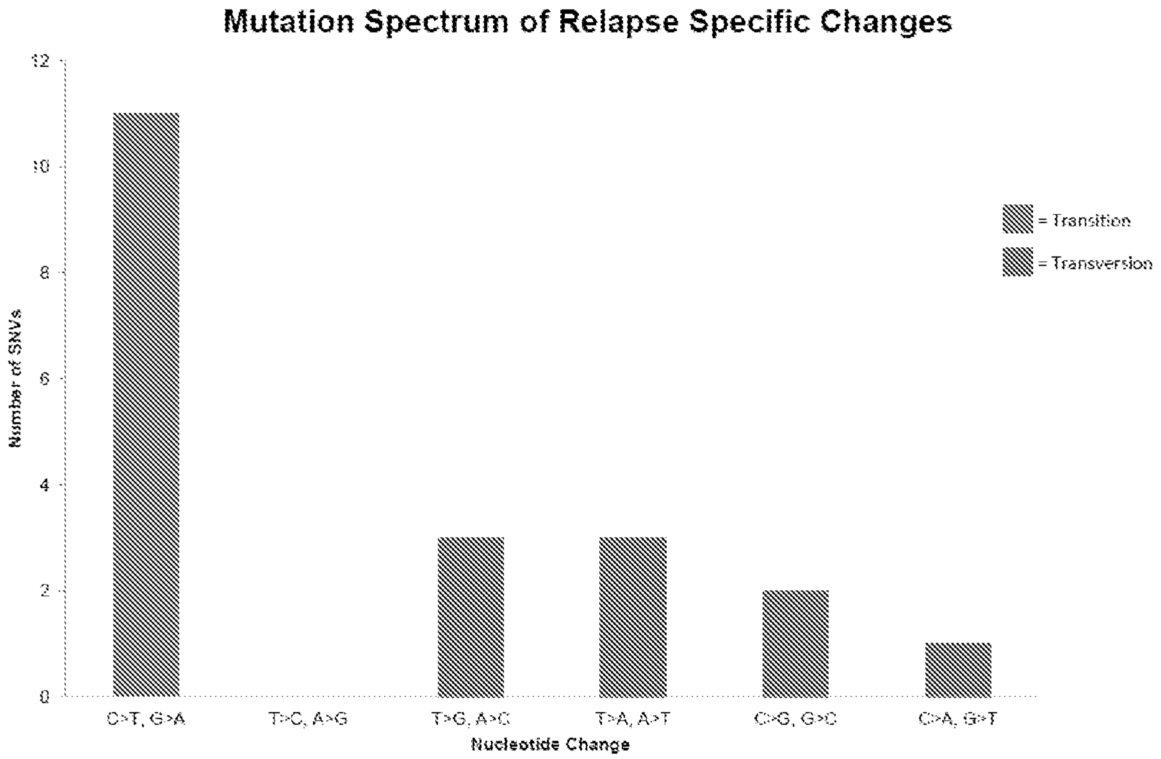
FIG. 4 is a bar graph showing the spectrum of relapse specific mutations. The transition to transversion ratio is 1.22.

Patients harbored between 1-6 relapse specific mutations. Predominate nucleotide changes were those causing C:G>T:A transitions resulting in a transition-to-transversion ratio of 1.22 (FIG. 4) similar to other studies (Ding et al., "Genome Remodelling in a Basal-Like Breast Cancer Metastasis and Xenograft," *Nature* 464:999-1005 (2010), which is hereby incorporated by reference in its entirety). In addition, the proportion of reads supporting each mutation was variable ranging from 22-67% of the total number of reads per site.

TABLE 4

Validated Replase Specific Mutations

| Subject | Gene | Chromosome | Position | Function | Nucleotide change | Protein change | PolyPhen-2 prediction | SIFT prediction | In COSMIC database? | Encoded protein |
|---|---|---|---|---|---|---|---|---|---|---|
| 1 | RGS.12 | 4 | 3287853 | Missense | c.158C > T | pAla53Val | Damaging | Damaging | Yes | Regulator of G protein signaling 12 |
| 1 | LPHN1 | 19 | 14134808 | Missense | c.822C > G | p.Glu274Gln | Damaging | Damaging | Yes | Latrophilin 1 |
| 2 | CAND1 | 12 | 65985593 | Missense | c.1878A > C | p.Leu626Phe | Damaging | Damaging | Yes | Cullin-associated and neddylation-dissociated 1 |
| 2 | PRMT2 | 21 | 46903160 | Missense | c.730A > C | p.Met244Leu | Benign | Tolerated | Yes | Protein arginine methyltransferase 2 |
| 2 | NIPSNAP1 | 22 | 28287562 | Missense | c.512G > T | p.Ser171Ile | Damaging | Damaging | Yes | Nipsnap homolog 1 |
| 3 | USP7 | 16 | 8902368 | Missense | c.2188A > T | p.Thr730Ser | Damaging | Tolerated | Yes | Ubiquitin-specific peptidase 7 |
| 4 | TULP4 | 6 | 158844705 | Missense | c.4022T > G | p.Leu1341Arg | Damaging | Tolerated | Yes | Tubby-like protein 4 |
| 4 | CBX3 | 7 | 26214576 | Missense | c.206G > A | p.Cys69Tyr | Damaging | Damaging | Yes | Chromobox homolog 3 |
| 4 | COBRA1 | 9 | 139270653 | Missense | c.318G > A | p.Met106Ile | Benign | Tolerated | Yes | Cofactor of BRCAl |
| 4 | SDF2 | 17 | 24006562 | Missense | c.218G > A | p.Arg73Gln | Damaging | Tolerated | No[a] | Stromal cell-derived factor 2 |
| 5 | FBX03 | 11 | 33725250 | Missense | c.1241T > A | p.Val414Glu | Damaging | Tolerated | Yes | F-box protein 3 |
| 5 | SCARF1 | 17 | 1490488 | Nonsense | c.1014A > T | p.Cys338* | Isoform change | Tolerated | Yes | Scavenger receptor class F, member 1 |
| 6 | NEGR1 | 1 | 71649375 | Missense | c.710C > T | p.Pro237Leu | Benign | Tolerated | Yes | Neuronal growth regulator 1 |
| 7 | NT5C2 | 10 | 104847097 | Missense | c.712C > T | p.Arg238Trp | Damaging | Damaging | No[a] | 5'-nucleotidase, cytosolic II |
| 8 | DPH5 | 1 | 101233272 | Missense | c.512C > T | p.Ser171Phe | Damaging | Damaging | Nod | DPH5 homolog |
| 8 | SMEK2 | 2 | 55648886 | Missense | c.1628G > A | p.Arg54Gln | Damaging | Damaging | Yes | SMEK homolog 2, suppressor of mek 1 |
| 8 | MIER3 | 5 | 56262281 | Missense | c.796G > A | p.Glu266Lys | Benign | Tolerated | No[a] | Mesoderm induction early response 1, family member 3 |
| 8 | DOPEY1 | 6 | 83912011 | Missense | c.5591G > A | p.Arg1864His | Damaging | Tolerated | Yes | Dopey family member 1 |
| 8 | ZNF192 | 6 | 28229455 | Missense | c.1418G > C | p.Arg473Pro | Damaging | Tolerated | No[a] | Zinc-finger protein 192 |
| 8 | NT5C2 | 10 | 104840473 | Missense | c.13340 > T | p.Ser445Phe | Damaging | Tolerated | No[a] | 5'-nucleotidase, cytosolic II |

Mutations were validated using remission, diagnosis and relapse genomic DNA.

Chromosome postions are in reference to hg18 alignment.

Nucleotide changes are in reference to the start of the coding sequences.

Prediction of the structural and functional consequences of the mutation were completed using PolyPhen-2 and SIFT.

[a]Preseant in the Catalogue of Somatic Mutations in Cancer (COSMIC) database after July 2012.

Figures 5A, 5B:
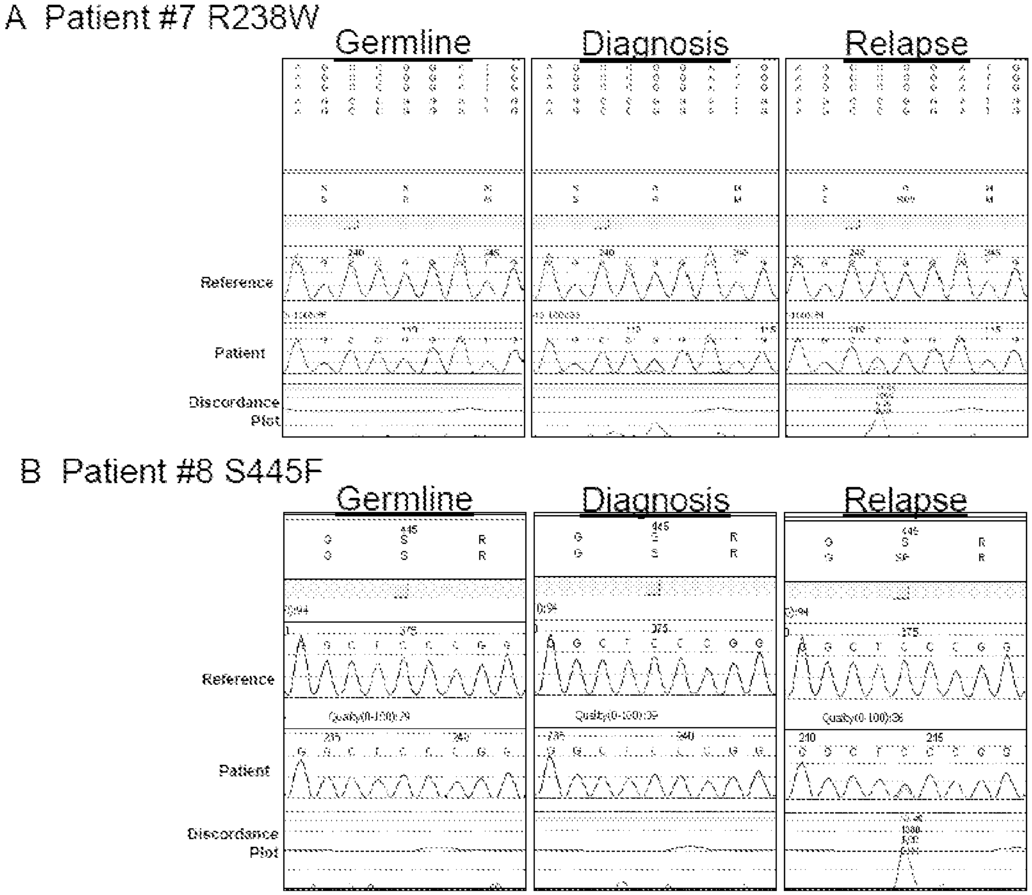
FIGS. 5A-5D are exemplary NT5C2 diagnosis and relapse sequencing traces generated using Mutation Surveyor (Softgenetics).
Figure 5C:
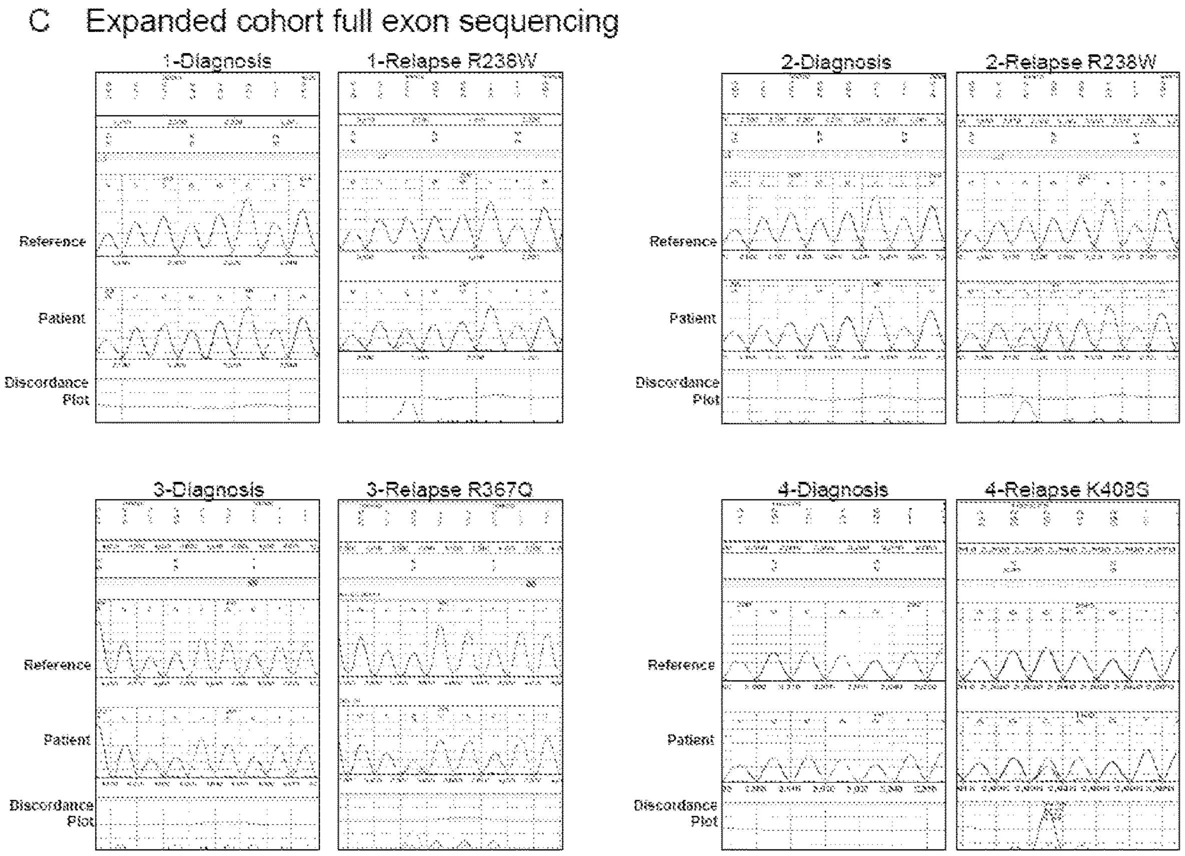
Figure 5D:
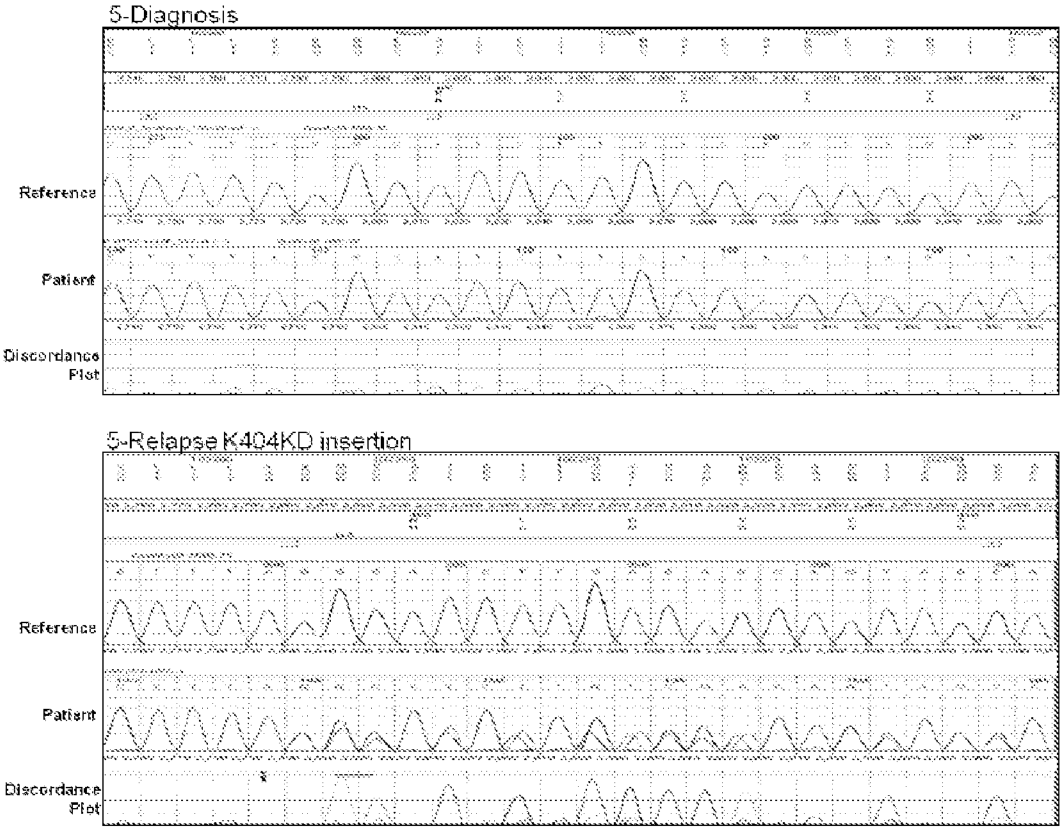

While more than half of the mutations were found in genes recently identified to be mutated in cancer genome sequencing projects from head/neck, melanoma, and ovarian carcinomas (Stransky et al., "The Mutational Landscape of Head and Neck Squamous Cell Carcinoma," *Science* 333: 1157-60 (2011); Forbes et al., "COSMIC: Mining Complete Cancer Genomes in the Catalogue of Somatic Mutations in Cancer," *Nucleic Acids Res.* 39:D945-50 (2011); Wei et al., "Exome Sequencing Identifies GRIN2A as Frequently Mutated in Melanoma," *Nat. Genet.* 43:442-6 (2011); and Cancer Genome Atlas Research Network, "Integrated Genomic Analyses of Ovarian Carcinoma," *Nature* 474:609-15 (2011), which are hereby incorporated by reference in their entirety), none of the relapse specific mutations were observed in previous targeted sequencing projects from pediatric ALL (Mullighan et al., "CREBBP Mutations in Relapsed Acute Lymphoblastic Leukaemia," *Nature* 471: 235-9 (2011) and Greenman et al., "Patterns of Somatic Mutation in Human Cancer Genomes," *Nature* 446:153-8 (2007), which are hereby incorporated by reference in their entirety). Sequencing was completed in an additional 62 B-cell precursor ALL diagnosis-relapse specimen pairs to look for additional mutations at or near the validated site in 9 of the 14 genes associated with cancer genomes (CAND1, CBX3, COBRA1, FBXO3, PRMT2, RGS12, SMEK2, TULP4, and USP7) as well as for one novel gene, SDF2. One additional mutation (R1338W) was found in TULP4, a gene with WD repeats thought to be a substrate recognition component of a SCF-E3 ubiquitin ligase complex (Li et al., "Molecular Cloning and Characterization of the Mouse and Human TUSP Gene, a Novel Member of the Tubby Superfamily," *Gene* 273:275-84 (2001), which is hereby incorporated by reference in its entirety). However further sequencing of the diagnostic sample also showed this substitution indicating a shared mutation or a SNP Example 4—NT5C2 Mutations Present at Relapse Two different mutations were observed and validated in NT5C2, which encodes for a 5'-nucleotidase enzyme active in the cell cytoplasm, in two of the relapse patients profiled by RNA sequencing. Both mutations were confirmed at the DNA level and were specific to the relapse specimens (FIG. 5). To determine the frequency of mutations in NT5C2 in ALL patients, full exon resequencing was completed in an additional 61 relapse specimens. Among the 61 patients, 5 additional NT5C2 somatic mutations were found. Further sequencing of the corresponding diagnosis specimens revealed that the mutations were in fact relapse specific (FIGS. 5C-5D). Thus, 7 out of 71 patients (10 RNA sequenced plus 61 full exon sequenced) patients harbored NT5C2 relapse specific mutations for an overall occurrence rate of 10%. Two of the 5 additional mutations were located at the same amino acid site and coded for the missense change, R238W. In addition, mutations were also found at R367Q, S408R, S445F, and a single amino acid insertion resulting in K404insKD was observed (see FIG. 6A-6B).

Coverage at diagnosis at the two NT5C2 mutated sites identified by RNA sequencing was 96× and 112×. Taking into consideration this depth of sequencing, a subclone at diagnosis would have to be present in less than 1% of the bulk leukemia cells to be missed by this sequencing technique. To assess whether mutations in NT5C2 were present at diagnosis as a rare subclone, backtracking using ultra-deep sequencing was performed. Amplicon resequencing of DNA from diagnosis and relapse specimens identified two cases where a rare clone indeed existed at diagnosis in 0.01% and 0.02% of the total reads (with 25,000× and 32,000× coverage, respectively) (Table 5). In the remaining five cases, no mutation could be detected at diagnosis. These data suggest that the emergence of clones containing mutations in NT5C2 is driven by powerful selective pressures presumably due to drug resistance.

TABLE 5

Deep Amplicon Sequencing of NT5C2 Mutations

| NT5C2 exon | Nucleotide change | Protein change | Mutant allele frequency (coverage) Diagnosis | Relapse |
|---|---|---|---|---|
| 9 | c.712C > T | p.Arg238Trp | 0.01% (25,000×) | 27% (17,000×) |
| 9 | c.712C > T | p.Arg238Trp | 0 (22,000×) | 18% (16,000×) |
| 9 | c.712C > T | p.Arg238Trp | 0 (49,000×) | 31% (18,000×) |
| 13 | c.1100G > A | p.Arg367Gln | 0.02% (32,000×) | 25% (28,000×) |
| 15 | c.1212insAGAC | p.Lys404ins | 0 (26,000×) | 55% (29,000×) |
| 15 | c.1224C > A | p.Ser408Arg | 0 (31,000×) | 50% (22,000×) |
| 16 | c.1334C > T | p.Ser445Phe | 0 (42,000×) | 25% (45,000×) |

Figures 6A, 6B, 6C, 6D:
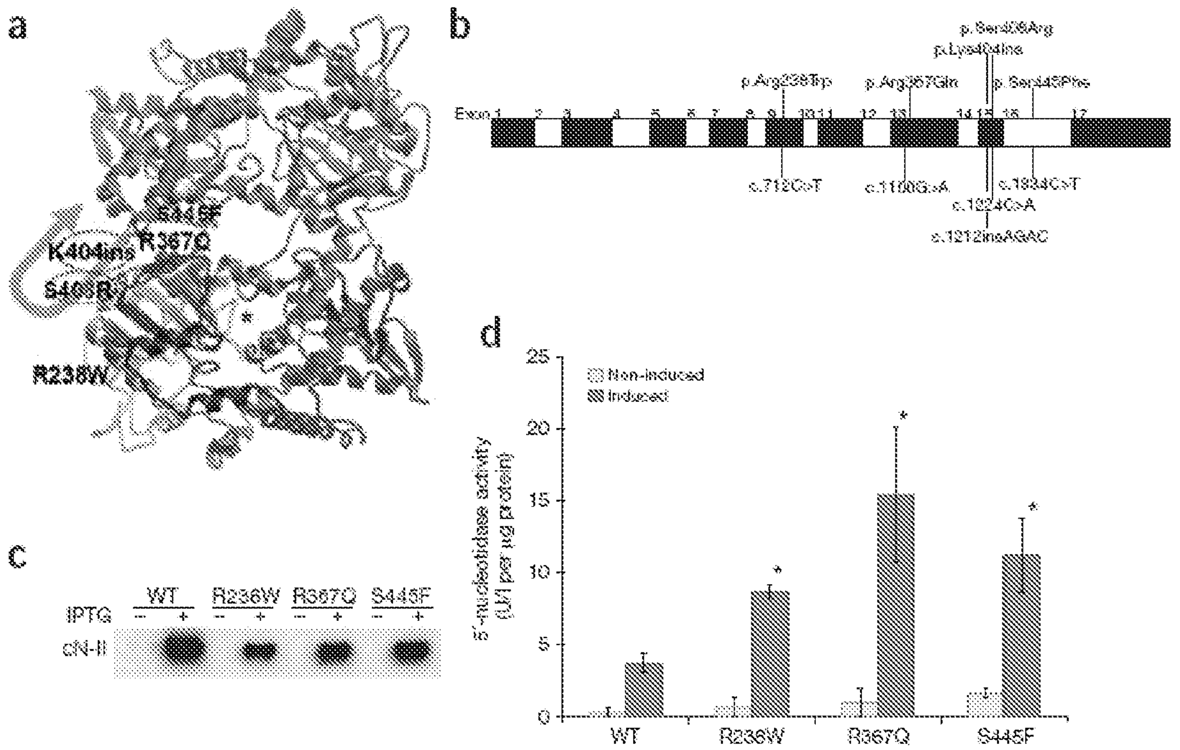
FIGS. 6A-6D demonstrate that relapse-specific mutations in NT5C2 alter enzymatic activity.
Figure 9:
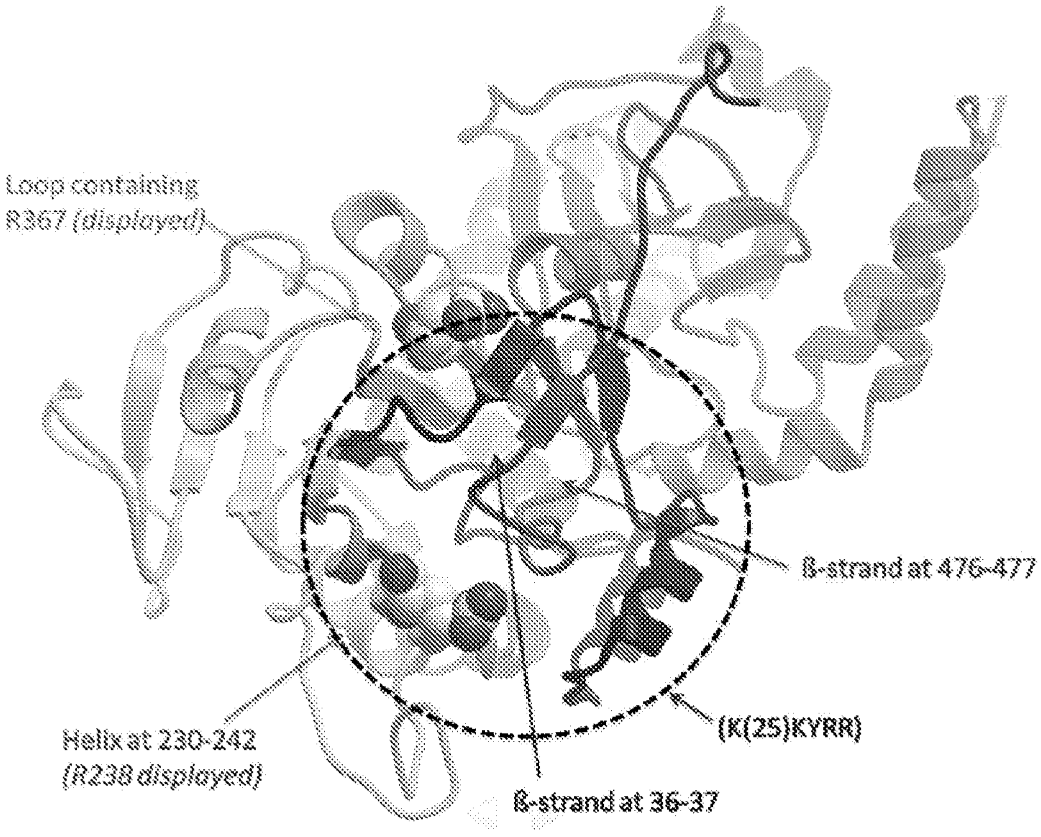
FIG. 9 is a three-dimensional representation of the human cytosolic 5'nucleotidase II monomer structure viewed face on into the positively charged molecular surface (dashed circle) formed by the helix at amino acid positions 21-29, (K(25)KYRR (SEQ ID NO:79)), the small beta sheet formed by amino acid residues 36-37 and 476-477, the helix at amino acid residues 230-242, and the loop containing R367. The single molecular surface formed by disparate elements has been hypothesized to interact with the enzyme's acidic C-terminal tail and contains two of the mutations described infra.

Mutations in NT5C2 were mapped onto the previously published crystal structure (Wallden et al., "Crystal Structure of Human Cytosolic 5'-Nucleotidase II: Insights Into Allosteric Regulation and Substrate Recognition," *J. Biol. Chem.* 282:17828-36 (2007), which is hereby incorporated by reference in its entirety). All the mutations clustered in a region thought to be involved in subunit association/dissociation through the acidic C-terminal tail of the enzyme (FIGS. 6A-6B and FIG. 9) (Spychala et al., "ATP and Phosphate Reciprocally Affect Subunit Association of Human Recombinant High Km 5'-Nucleotidase. Role for the C-Terminal Polyglutamic Acid Tract in Subunit Association and Catalytic Activity," *Eur. J. Biochem.* 259:851-8 (1999), which is hereby incorporated by reference in its entirety). Part of this region, a positively charged helix at (K(25) KYRR (SEQ ID NO: 79)), forms a subdomain of segments with the helix at amino acid positions 230-242, a short anti-parallel beta sheet between amino acid positions 36-37 at the N-terminus and amino acid positions 476-477 at the C-terminus and the loop containing R367 (FIG. 9). The (K(25)KYRR) helix has been hypothesized to interact specifically with the acidic C-terminal tail (Spychala et al., "ATP and Phosphate Reciprocally Affect Subunit Association of Human Recombinant High Km 5'-Nucleotidase. Role for the C-Terminal Polyglutamic Acid Tract in Subunit Association and Catalytic Activity," *Eur. J. Biochem.* 259: 851-8 (1999), which is hereby incorporated by reference in its entirety). The R238W and R367Q mutations result in the removal of positive charges from the molecular surface of this assembly, presumably perturbing interactions with the C-terminal tail (FIGS. 6A-6B). K404insKD and S408R introduce negative and positive charges respectively into a disordered loop that lies directly over this region (FIG. 6A-6B). S445F is also located in this region, directly underneath the stems of the disordered loop in contact with a region known to be an allosteric site for phosphates previously termed "effector site 2" (Spychala et al., "ATP and Phosphate Reciprocally Affect Subunit Association of Human Recombinant High Km 5'-Nucleotidase. Role for the C-Terminal Polyglutamic Acid Tract in Subunit Association and Catalytic Activity," *Eur. J. Biochem.* 259:851-8 (1999), which is hereby incorporated by reference in its entirety). All of the mutations are located a significant distance from the active site of the enzyme, but S445F and R367Q are located at the periphery of another phosphate binding allosteric site at the dimer interface termed "effector site 1". However the focal locations of the observed mutations suggest the acquisition of novel biological properties rather than complete disruption of enzymatic activity.

Therefore, to test the functional impact of the mutations on enzyme activity, NT5C2 cDNA for wild-type protein and the Arg238Trp, Arg367Gln and Ser445Phe mutants were expressed in BL21 *Escherichia coli* cells. Protein expression was induced by isopropyl b-D-thiogalactoside (IPTG), and extracts were analyzed for expression by immunoblot (FIG. 6C). Equal volumes of fresh protein extracts were then assayed for 5'-nucleotidase activity by monitoring the hydrolysis of inosine monophosphate compared against a standard curve. Significantly higher enzymatic activity was observed for all mutants—Arg238Trp, Arg367Gln and Ser445Phe compared to wild-type protein ($P \leq 0.01$; FIG. 6D). No activity above background was observed with matched non-induced samples. It was hypothesized that mutations in NT5C2 allow for resistance to chemotherapy treatment, in particular, nucleoside analogs, given their effects on enzymatic function. In addition, the early emergence of NT5C2 mutations correlates with the introduction of the maintenance phase of ALL therapy in which nucleoside analogs assume a predominant role in treatment. Therefore, whether mutant forms of cN-II could provide protection from the apoptosis induced by treatment with various chemotherapeutic agents used clinically for childhood ALL was investigated.

Figures 7A, 7B, 7C, 7D, 7E, 7F, 7G:
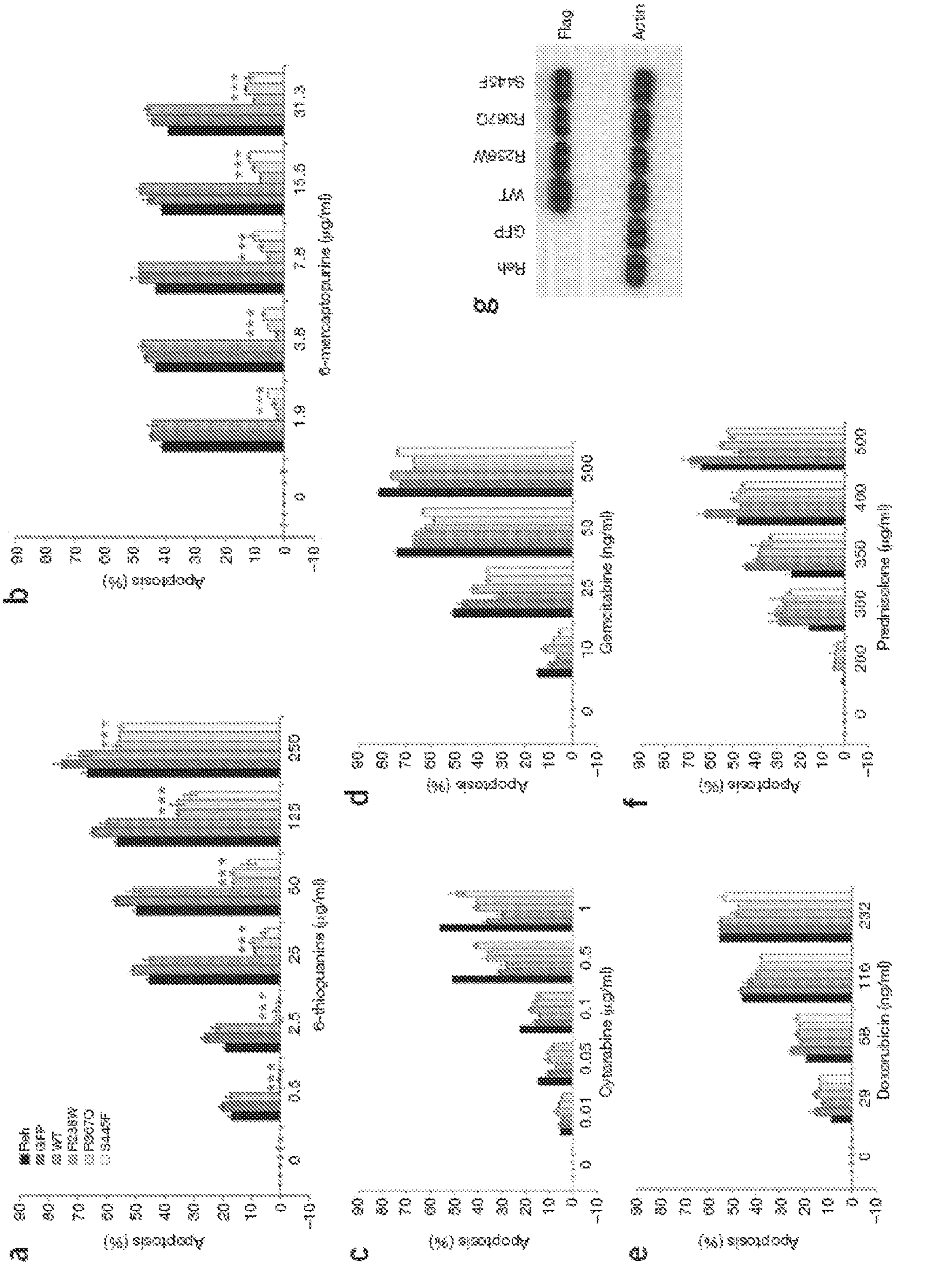
FIGS. 7A-7G show that NT5C2 mutations confer chemoresistance to purine nucleoside analog treatment.
Figure 8:
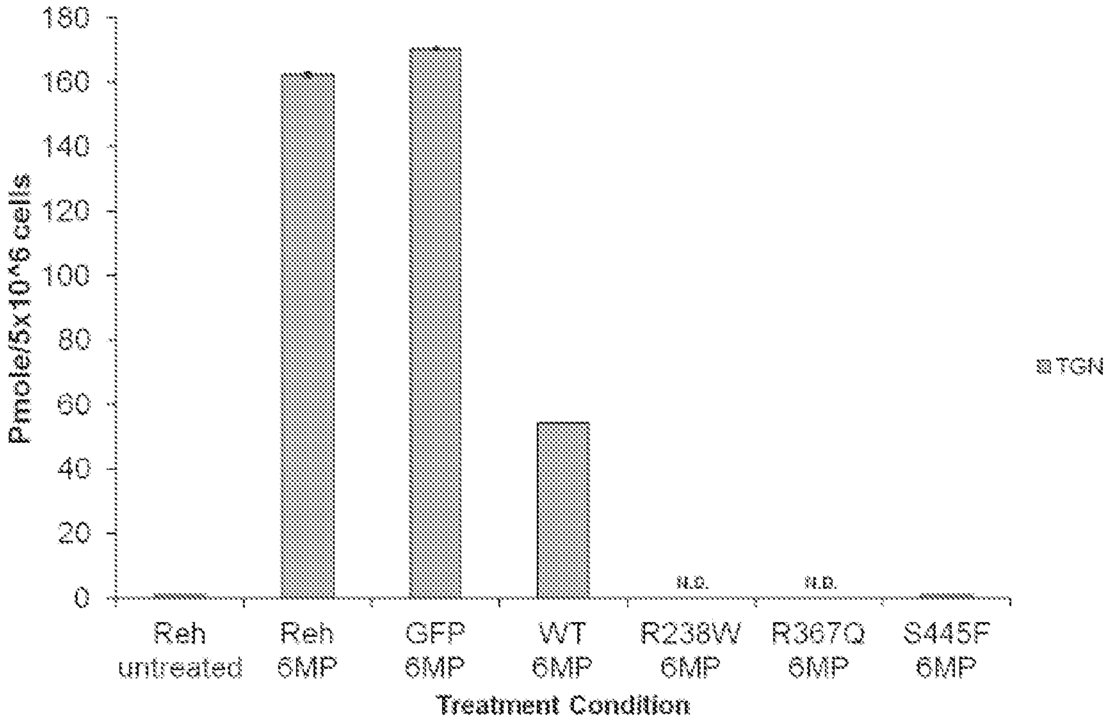
FIG. 8 is a graph showing HPLC determination of thioguanine nucleotide (TGN) levels post-treatment with 6-MP. Reh cells transiently infected with wildtype (WT), mutant, or control GFP lentivirus were treated with 10 uM 6-MP for 24 hr. Reh cells not treated with 6-MP were included as a control. Cells of each condition ($5\times10^6$) were then subjected to HPLC. Columns show a mean of two independent determinations ±s.d. from a representative experiment. Samples with non-detectable signals labeled as N.D.

The B-lymphoblastic leukemia cell line Reh was transduced with lentiviruses encoding wild-type or mutant (Arg238Trp, Arg367Gln or Ser445Phe) cN-II and assayed for apoptosis after incubation with various chemotherapeutic agents for 24-72 h (FIGS. 7A-7F). Compared to cells expressing wild-type protein, cells expressing mutant forms of cN-II were significantly more resistant to apoptosis after treatment with the purine analogs 6-mercaptopurine and 6-thioguanine (FIGS. 7A and 7B). As expected, no resistance was seen when the experiment was repeated with cytarabine, doxorubicin, gemcitabine or prednisolone (FIGS. 7C-7F). To further understand the mechanistic basis of cN-II-mediated chemoresistance, the effects of the NT5C2 mutations on the intracellular accumulation of thiopurine nucleotides, which are active metabolites of 6-mercaptopurine, were examined After treatment with 6-mercaptopurine, Reh cells transduced with lentiviruses expressing mutant forms of cN-II showed reduction in the level of thioguanine nucleotides compared to control cells expressing wild-type protein or GFP (FIG. 8), consistent with the thiopurine resistance resulting from the NT5C2 mutations noted at relapse.

Figure 10:
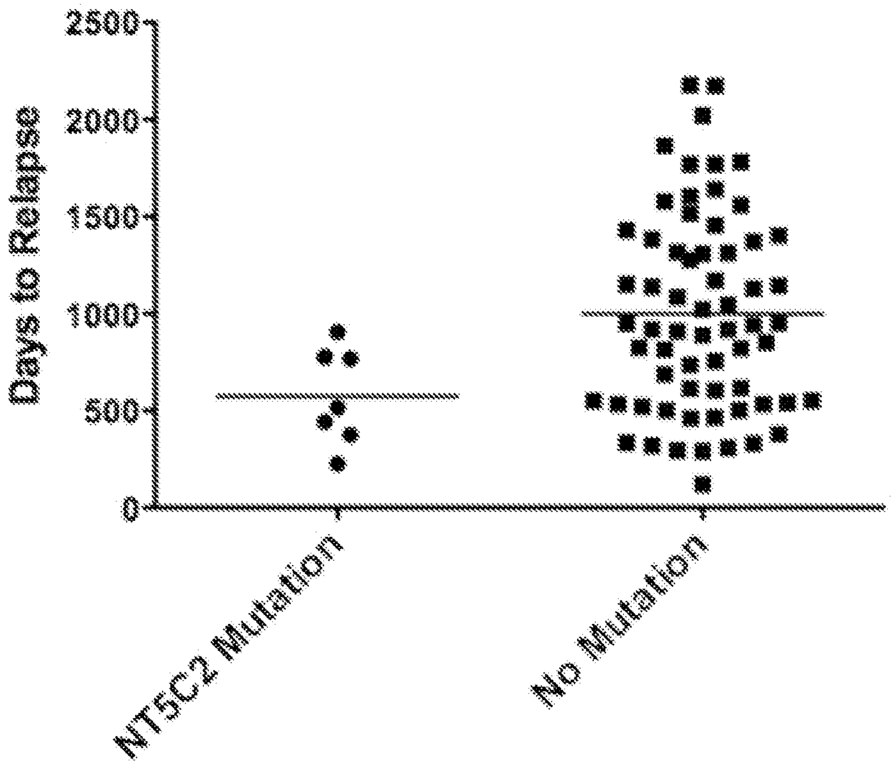
FIG. 10 is a graph showing the time (days) to relapse based on the presence or absence of NT5C2 mutation in patient samples. Bar indicates median number of days: 516 days for mutated and 930 for non-mutated patients. Chi-squared p-value 0.003.
Figures 11A, 11B:
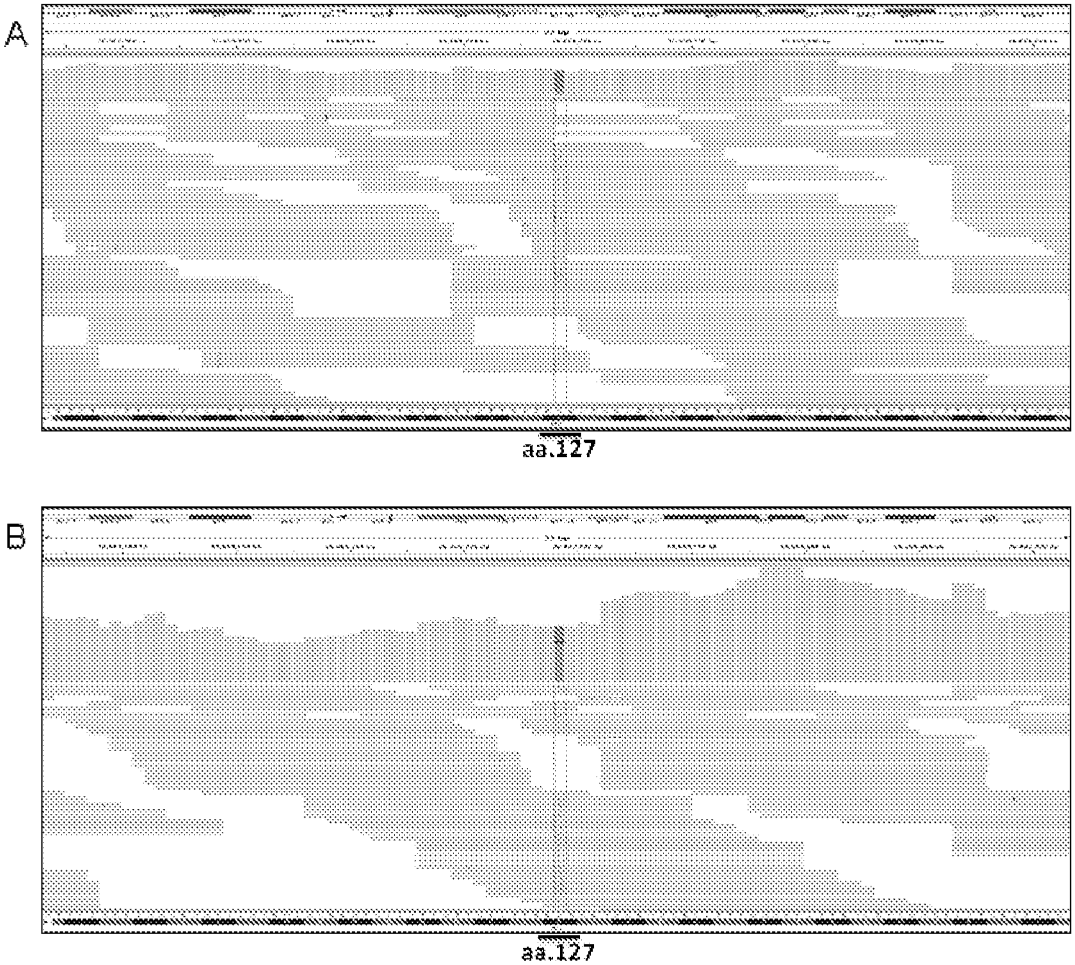
FIGS. 11A-11D are mapped sequence reads for clonal outgrowth mutations.
Figure 11C:
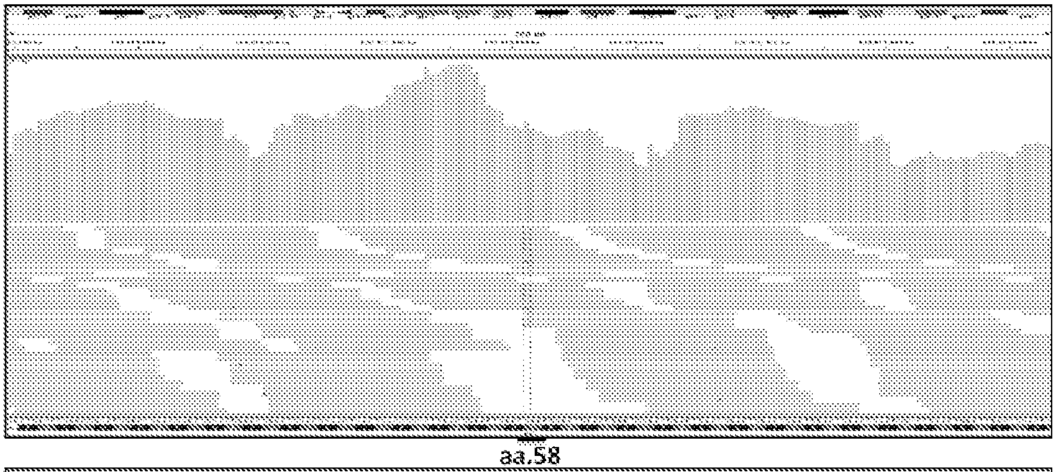
Figure 11D:
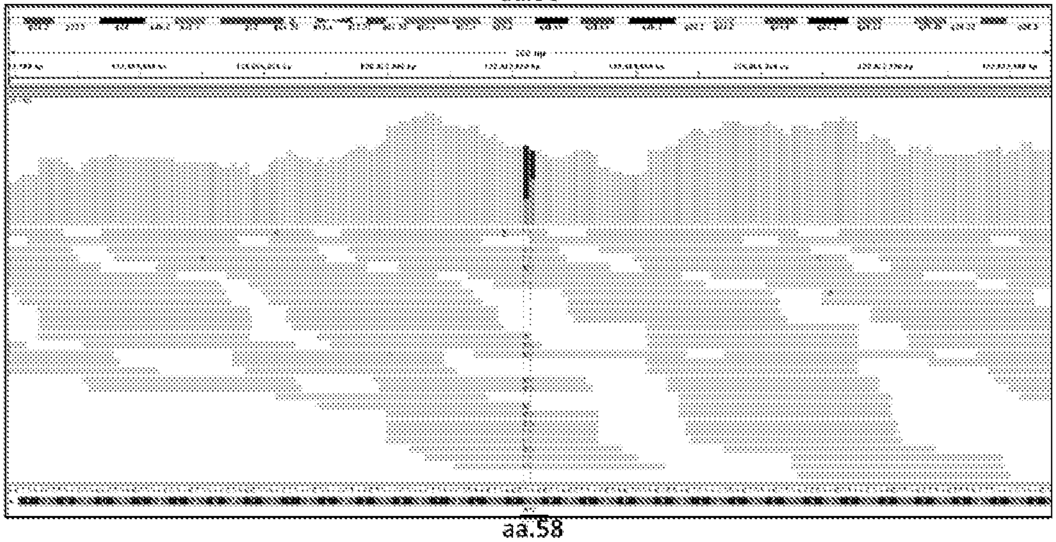

The characteristics of patients with and without NT5C2 mutations are presented in Table 6 below. Interestingly, all patients who acquired mutations relapsed early, or within 36 months of initial diagnosis (p=0.03). Median time to relapse for those with NT5C2 mutation was 516 days compared to 930 for those without a NT5C2 mutation (FIG. 10). This finding is consistent with previous data indicating potential differences in biological pathways that mediate early vs. late relapse (Hogan et al., "Integrated Genomic Analysis of Relapsed Childhood Acute Lymphoblastic Leukemia Reveals Therapeutic Strategies," *Blood* 118(19):5218-26 (2011), which is hereby incorporated by reference in its entirety).

TABLE 6

Characteristics of Patients According to NT5C2 Mutation Status

| Variable | | Mutated NT5C2 (n = 7) | Non-mutated NT5C2 (n = 64) | P value |
|---|---|---|---|---|
| Age at diagnosis | Less than 10 years | 4 | 39 | 0.57 |
| | At least 10 years | 3 | 25 | |
| Ancestry | European | 3 | 47 | 0.11[a] |
| | African | 1 | 6 | |
| | Asian | 1 | 3 | |
| | Other | 1 | 5 | |
| | Unknown | 1 | 3 | |
| Sex | Female | 2 | 27 | 0.39 |
| | Male | 5 | 37 | |
| Cytogenetics | ETV6/RUNX1 | 1 | 13 | 0.12[b] |
| | Hyperdiploid | 0 | 15 | |
| | E2aPBX1 | 0 | 1 | |
| | Normal | 6 | 35 | |
| Time to relapse | Early | 7 | 37 | 0.03 |
| | Late | 0 | 27 | |
| Risk group[c] | Standard | 2 | 25 | 0.46 |
| | High | 5 | 39 | |

[a]Fisher's exact test P value of all other ancestry groups compared to individuals of European ancestry.
[b]Fisher's exact test P value of normal compared to all other cytogenetic groups.
[c]National Cancer Institute (NCI) risk group[33].

Example 5—Clonal Outgrowth of Mutations Present at Diagnosis

B lymphoblastic leukemia is a very heterogeneous disease and it has been shown through clonal analysis of antigen receptor genes and copy number abnormalities that clonal expansion can be found in up to 93% of relapse cases (Mullighan et al., "Genomic Analysis of the Clonal Origins of Relapsed Acute Lymphoblastic Leukemia," *Science* 322: 1377-80 (2008); Szczepanski et al., "Comparative Analysis of Ig and TCR Gene Rearrangements at Diagnosis and at Relapse of Childhood Precursor-B-ALL Provides Improved Strategies for Selection of Stable PCR Targets for Monitoring of Minimal Residual Disease," *Blood* 99:2315-23 (2002); Germano et al., "Clonality Profile in Relapsed Precursor-B-ALL Children by GeneScan and Sequencing Analyses. Consequences on Minimal Residual Disease Monitoring," *Leukemia* 17:1573-82 (2003), which are hereby incorporated by reference in their entirety). Therefore mutations that may have been present at low levels of detection at diagnosis that showed allele-specific expansion at relapse were searched and identified. Only two novel missense SNVs, EVI2A p.A127V and GSPT2 p.S559C and one adjacent double mutation, MYC p.T58H, were identified that demonstrated this pattern of development. Two out of the three mutations, EVI2A and MYC were validated in the corresponding genomic DNA as somatic mutations (Table 7 and FIGS. 11A-11D). The mutation in EVI2A showed a shift in expression from 23% of the total reads at diagnosis to 71% of the reads by RNA sequencing at relapse. This gene has been shown to be part of a cell surface receptor and is located within an intron of NF1 (Cawthon et al., "Identification and Characterization of Transcripts From the Neurofibromatosis 1 Region: The Sequence and Genomic Structure of EVI2 and Mapping of Other Transcripts," *Genomics* 7:555-65 (1990), which is hereby incorporated by reference in its entirety). Mutations in MYC at amino acid 58, required for MYC degradation by FBXW7, have been seen before and are found in a majority of patients with Burkitt's lymphoma but have not been documented in ALL (Bhatia et al., "Point Mutations in the c-Myc Transactivation Domain are Common in Burkitt's Lymphoma and Mouse Plasmacytomas," *Nat. Genet.* 5:56-61 (1993), which is hereby incorporated by reference in its entirety).

TABLE 7

Validated Shared Mutations that Show Shift in Expression from Diagnosis to Relapse

| Patient | Gene | Chromosome | Position | Function | Protein Change | % Mutant Reads out of Total Diagnosis | %Mutant Reads out of Total Relapse |
|---|---|---|---|---|---|---|---|
| 3 | EVI2A | 17 | 25669778 | missense | p.A127V | 23 | 71 |
| 4 | MYC | 8 | 128819862 | missense | p.T58P | 15 | 68 |
| 4 | MYC | 8 | 128819863 | missense | p.T58N | 13 | 61 |

Each mutation was validated in both diagnosis and relapse sample per specific patient, and not present in germline by Sanger sequencing.

Discussion of Examples 1-5

There has been a remarkable improvement in outcome for children with ALL over the past 5 decades, with stepwise increments in survival concordant with ongoing efforts to refine therapy (Carroll & Raetz, "Clinical and Laboratory Biology of Childhood Acute Lymphoblastic Leukemia," *J. Pediatr.* 160(1):10-8 (2012), which is hereby incorporated by reference in its entirety). In sharp contrast to the favorable prognosis of newly diagnosed ALL, most children who experience bone marrow relapse eventually succumb to the disease. Given the fact that ALL is the most common cancer in children, relapsed ALL is one of the leading causes of childhood cancer death. While a number of clinical and laboratory variables correlate with prognosis at initial diagnosis, only immunophenotype and site and time to relapse are the best known predictors of survival (Chessells et al., "Long-Term Follow-Up of Relapsed Childhood Acute Lymphoblastic Leukaemia," *Br. J. Haematol.* 123:396-405 (2003); Raetz et al., "Reinduction Platform for Children With First Marrow Relapse in Acute Lymphoblastic Lymphoma," *J. Clin. Oncol.* 26:3971-8 (2008); and Rivera et al., "Bone Marrow Recurrence After Initial Intensive Treatment for Childhood Acute Lymphoblastic Leukemia," *Cancer* 103:368-76 (2005), which are hereby incorporated by reference in their entirety). Patients whose time from initial diagnosis to relapse is under thirty six months (mostly but not all on therapy) and those with bone marrow relapse fare particularly poorly. Treatment failure is due to the intrinsic resistance of the relapsed blast compared to diagnosis as evidenced by in vitro drug insensitivity, lower remission-induction rates and higher rates of detectable end induction minimal residual disease compared to initial diagnosis and early second relapse (Raetz et al., "Reinduction Platform for Children With First Marrow Relapse in Acute Lymphoblastic Lymphoma," *J. Clin. Oncol.* 26:3971-8 (2008) and Klumper et al., "In Vitro Cellular Drug Resistance in Children With Relapsed/Refractory Acute Lymphoblastic Leukemia," *Blood* 86:3861-8 (1995), which are hereby incorporated by reference in their entirety). These differences suggest that relapsed blasts have acquired additional biological properties that contribute to drug resistance.

As described herein, a sequencing approach was taken to discover somatic mutations that might drive drug resistance in vivo. The results indicate that relapse is associated with the acquisition of a small number of non-synonymous mutations. Twenty (20) such mutations were validated. These acquired mutations were hemizygous with expression of the wild type allele suggesting that the mutation conferred a dominant phenotype. In most cases the mutations were predicted to have a deleterious effect on protein structure that would indicate a dominant negative property or a state of haploinsufficiency. An expanded cohort of relapse specimens was screened to determine whether similar mutations might be shared among patients for 9 of the 20 mutations observed. The failure to detect shared relapse specific mutations in these genes indicates that some of the observed variants may be peripheral to drug resistance (so called passengers) and/or that escape mechanisms may be unique for individual patients, a finding similar to what is observed for metastasis in breast cancer (Shah et al., "Mutational Evolution in a Lobular Breast Tumour Profiled at Single Nucleotide Resolution," *Nature* 461:809-13 (2009), which is hereby incorporated by reference in its entirety).

Multiple relapse specific mutations were identified in NT5C2, a gene not previously associated with somatic mutations in cancer. Mutations were found in 10% of patients profiled in this study, and were found to be significantly enriched within the early relapse group with 16% of such cases harboring mutations. This gene encodes for cytosolic 5'-nucleotidase II (cN-II), a member of a family of seven enzymes that regulate nucleotide levels. cN-II dephosphorylates purine nucleotides to produce nucleosides that are shuttled out of the cell via nucleoside transporters. The enzyme also displays phosphotransferase activity (Bianchi & Spychala, "Mammalian 5'-Nucleotidases," *J. Biol. Chem.* 278:46195-8 (2003) and Tozzi et al., "Cytosolic 5'-Nucleotidase/Phosphotransferase of Human Colon Carcinoma," *Adv. Exp. Med. Biol.* 309B:173-6 (1991), which are hereby incorporated by reference in their entirety).

Mutations affecting cN-II were mapped onto the previously published crystal structure (Walldén et al. "Crystal Structure of Human Cytosolic 5'-Nucleotidase II: Insights into Allosteric Regulation and Substrate Recognition," *J. Biol. Chem.* 282: 17828-17836 (2007), which is hereby incoporated by reference in its entirety). All five mutations found in this study mapped to a single functional unit clustered in a region thought to be involved in subunit association/dissociation through the acidic C-terminal tail of the enzyme (FIGS. 6A and 9) (Spychala et al., "ATP and Phosphate Reciprocally Affect Subunit Association of Human Recombinant High Km 5'-Nucleotidase. Role for the C-terminal Polyglutamic Acid Tract in Subunit Association and Catalytic Activity," *Eur. J. Biochem.* 259:851-858 (1999), which is hereby incorporated by reference in its entirety). In addition, the focal nature of the observed mutations suggested the acquisition of novel biological properties rather than disruption of enzymatic activity. Indeed, the data suggest a direct relationship between acquired somatic mutations and chemoresistance to a specific class of drugs used in treatment, purine analogs, as opposed to defects in pathways shared across classes of cytotoxic agents. A previous study did not correlate cytosolic 5'-nucleotidase activity with in vitro resistance to 6-thioguanine in blasts from children at diagnosis with ALL, although a weak correlation was seen with the total amount of enzyme (Pieters et al. "Relation of 5'-Nucleotidase and Phosphatase Activities with Immunophenotype, Drug Resistance and Clinical Prognosis in Childhood Leukemia," *Leuk. Res.* 16: 873-880 (1992), which is hereby incorporated by reference in its entirety). However these studies focused on cases at diagnosis, and, presumably, these cases all contained wild-type NT5C2. In addition, previous studies have correlated high NT5C2 mRNA levels with resistance to cytarabine in patients with acute myeloid leukemia (Galmarini et al., "Expression of High Km 5'-Nucleotidase in Leukemic Blasts is an Independent Prognostic Factor in Adults with Acute Myeloid Leukemia," *Blood* 98:1922-1926 (2001), and Galmarini et al., "Deoxycytidine Kinase and cN-II Nucleotidase Expression in Blast Cells Predict Survival in Acute Myeloid Leukaemia Patients Treated with Cytarabine," *Br. J. Haematol.* 122:53-60 (2003), which are hereby incorporated by reference in their entirety), whereas other studies showed that the purified enzyme does not hydrolyze araC monophosphate (Mazzon et al., "Cytosolic and Mitochondrial Deoxyribonucleotidases: Activity with Substrate Analogs, Inhibitors and Implications for Therapy," *Biochem. Pharmacol.* 66: 471-479 (2003), which is hereby incorporated by reference in its entirety). The results described here for ALL are in agreement with the later finding. It is hypothesized that the emergence of clones containing NT5C2 mutations early in maintenance, after completing phases of rotational multiagent chemotherapy, correlates with a greater reliance on these agents. Additional genes whose expression might have a role in resistance to purine analogs have been identified (Yang et al., "Genome-Wide Copy Number Profiling Reveals Molecular Evolution From Diagnosis to Relapse in Childhood Acute Lymphoblastic Leukemia," *Blood* 112: 4178-4183 (2008), and Diouf et al., "Somatic Deletions of Genes Regulating MSH2 Protein Stability Cause DNA Mismatch Repair Deficiency and Drug Resistance in Human Leukemia Cells," *Nat. Med.* 17:1298-1303 (2011), which are hereby incorporated by reference in their entirety). However, the discovery of acquired mutations in NT5C2 in individuals with early relapse, a group with a uniformly poor outcome, provides a focal point to develop insight into major biological pathways that mediate drug resistance in vivo and potentially to develop new therapies targeting NT5C2 to prevent the emergence of resistant clones during maintenance therapy and/or to treat relapsed ALL. Inhibitors of 5'-nucleotidase have already been developed, given their potential usefulness in cancer therapy and the prevention of drug resistance to anti-retroviral treatment (Gallier et al. "Structural Insights into the Inhibition of Cytosolic 5'-Nucleotidase II (cN-II) by Ribonucleosidse 5'-Monophosphate Analogues," *PLOS Comput. Biol.* 7-e1002295 (2011), and Jordheim et al., "Identification and Characterization of Inhibitors of Cytoplasmic 5'-Nucleotidase cN-II Issued From Virtual Screening," *Biochem. Pharmacol.* 85:497-506 (2013), which are hereby incorporated by reference in their entirety). Taken together, the data herein demonstrates that discovery-based approaches can identify recurrent mutations in individuals with cancer who relapse after cytotoxic chemotherapy.

Although the invention has been described in detail for the purpose of illustration, it is understood that such detail is solely for that purpose, and variations can be made therein by those skilled in the art without departing from the spirit and scope of the invention which is defined in the following claims.

What is claimed is:

1. A method of inhibiting thiopurine resistance in a human subject comprising:

administering, to a human subject in need of thiopurine therapy and having one or more 5'nucleotidase, cytosolic II (NT5C2) gene mutations, an agent that inhibits mutant or wildtype NT5C2 gene expression or mutant or wildtype NT5C2 encoded enzyme activity under conditions effective to inhibit thiopurine resistance in the subject, wherein said one or more NT5C2 gene mutations is selected from the group consisting of (i) a mutation encoding a substitution at the amino acid position corresponding to R367 of SEQ ID NO: 2, (ii) a mutation encoding a substitution at the amino acid position corresponding to R238 of SEQ ID NO: 2, (iii) a mutation encoding substitution at the amino acid position corresponding to S408 of SEQ ID NO: 2, (iv) a mutation encoding a substitution at the amino acid position corresponding to S445 of SEQ ID NO: 2, and (v) a mutation encoding an amino acid residue insertion at the amino acid position corresponding to lysine 404 of SEQ ID NO:2.

2. The method of claim 1, wherein the agent inhibits mutant NT5C2 gene expression or mutant NT5C2 encoded enzyme activity.

3. The method of claim 1, wherein the human subject has acute lymphoblastic leukemia.

4. The method of claim 3, further comprising administering to the human subject one or more anti-leukemia therapies in conjunction with said agent that inhibits mutant or wildtype NT5C2 gene expression or mutant or wildtype NT5C2 encoded enzyme activity.

5. The method of claim 1, wherein the agent comprises a ribonucleoside 5'-monophosphate analogue.

6. The method of claim 1, wherein said one or more NT5C2 gene mutations are within a region of the encoded cN-II protein that is involved in cN-II enzyme subunit association and dissociation.

7. The method of claim 1, wherein the one or more NT5C2 gene mutations encode an arginine to tryptophan substitution at the amino acid position corresponding to R238 of SEQ ID NO: 2.

8. The method of claim 1, wherein the one or more NT5C2 gene mutations encode an arginine to glutamine substitution at the amino acid position corresponding to R367 of SEQ ID NO: 2.

9. The method of claim 1, wherein the one or more NT5C2 gene mutations encode a serine to arginine substitution at the amino acid position corresponding to 5408 of SEQ ID NO: 2.

10. The method of claim 1, wherein the one or more NT5C2 gene mutations encode a serine to phenylalanine substitution at the amino acid position corresponding to 5445 of SEQ ID NO: 2.

11. The method of claim 1, wherein the amino acid residue insertion comprises an aspartic acid residue insertion at the position corresponding to lysine 404 of SEQ ID NO:2.

12. The method of claim 3, wherein the human subject has B-cell acute lymphoblastic leukemia.

13. A method of treating a human subject having leukemia comprising:

administering, to the human subject having leukemia and having one or more 5'nucleotidase, cytosolic II (NT5C2) gene mutations, a non-thiopurine based anti-leukemic therapeutic, wherein said one or more NT5C2 gene mutations is selected from the group consisting of (i) a mutation encoding a substitution at the amino acid position corresponding to R367 of SEQ ID NO: 2, (ii) a mutation encoding a substitution at the amino acid position corresponding to R238 of SEQ ID NO: 2, (iii) a mutation encoding a substitution at the amino acid position corresponding to S408 of SEQ ID NO: 2, (iv) a mutation encoding a substitution at the amino acid position corresponding to 5445 of SEQ ID NO: 2, and (v) a mutation encoding an amino acid residue insertion at the position corresponding to lysine 404 of SEQ ID NO:2.

14. The method of claim 13, wherein the non-thiopurine based anti-leukemic therapeutic is a chemotherapeutic selected from the group consisting of vincristine, asparaginase, daunorubicin, cyclophosphamide, cytarabine, etoposide, and methotrexate.

15. The method of claim 13, wherein the non-thiopurine based anti-leukemic therapeutic is radiotherapy.

16. The method of claim 13, wherein the non-thiopurine based anti-leukemic therapeutic is a bone-marrow transplant.

17. The method of claim 13, wherein the subject has acute lymphoblastic leukemia.

* * * * *

UNITED STATES PATENT AND TRADEMARK OFFICE

CERTIFICATE OF CORRECTION

PATENT NO. : 10,745,759 B2
APPLICATION NO. : 14/399467
DATED : August 18, 2020
INVENTOR(S) : Carroll and Meyer It is certified that error appears in the above-identified patent and that said Letters Patent is hereby corrected as shown below:

In the Claims

Claim 9 at Column 295, Line 26 delete "5408" insert --"S408"--
Claim 10 at Column 295, Line 31 delete "5445" insert --"S445"--
Claim 13 at Column 296, Line 18 delete "5445" insert --"S445"--

Signed and Sealed this
First Day of December, 2020

Andrei Iancu
*Director of the United States Patent and Trademark Office*